(12) United States Patent
Storer et al.

(10) Patent No.: US 8,044,091 B2
(45) Date of Patent: *Oct. 25, 2011

(54) PHOSPHO-INDOLES AS HIV INHIBITORS

(75) Inventors: Richard Storer, Kent (GB); Cyril Dousson, Montpellier (FR); Francois-Rene Alexandre, Montpellier (FR); Arlene Roland, Montpellier (FR)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 104 days.

This patent is subject to a terminal disclaimer.

(21) Appl. No.: 12/275,510

(22) Filed: Nov. 21, 2008

(65) Prior Publication Data

US 2009/0163444 A1  Jun. 25, 2009

Related U.S. Application Data

(63) Continuation of application No. 11/229,150, filed on Sep. 16, 2005, now Pat. No. 7,534,809.

(60) Provisional application No. 60/611,061, filed on Sep. 17, 2004, provisional application No. 60/711,445, filed on Aug. 25, 2005, provisional application No. 60/711,565, filed on Aug. 26, 2005.

(51) Int. Cl.
*A61K 31/40* (2006.01)
*C07F 9/28* (2006.01)
(52) U.S. Cl. .................. 514/419; 548/111; 548/492
(58) Field of Classification Search .................. 514/419; 548/492, 111
See application file for complete search history.

(56) References Cited

U.S. PATENT DOCUMENTS

| | | | |
|---|---|---|---|
| 4,866,084 A | 9/1989 | Gunasekera et al. |
| 5,124,327 A | 6/1992 | Greenlee et al. |
| 5,424,329 A | 6/1995 | Boschelli et al. |
| 5,489,685 A | 2/1996 | Houpis et al. |
| 5,527,819 A | 6/1996 | Williams et al. |
| 5,565,446 A | 10/1996 | Boschelli et al. |
| 5,703,069 A | 12/1997 | Connor et al. |
| 5,830,894 A | 11/1998 | Pevear et al. |
| 5,852,011 A | 12/1998 | Matsunaga et al. |
| 5,929,114 A | 7/1999 | Domagala et al. |
| 5,935,982 A | 8/1999 | Dykstra et al. |
| 5,945,440 A | 8/1999 | Kleinschroth et al. |
| 5,981,525 A | 11/1999 | Farina et al. |
| 6,017,903 A | 1/2000 | Slusher et al. |
| 6,025,345 A | 2/2000 | Jackson et al. |
| 6,025,390 A | 2/2000 | Farina et al. |

(Continued)

FOREIGN PATENT DOCUMENTS

EP   1 961 757 A1   8/2008

(Continued)

OTHER PUBLICATIONS

EPO, Communication pursuant to Article 96(2) EPC, dated Nov. 16, 2007 for European patent application No. 05850774.0.

(Continued)

*Primary Examiner* — Rei-tsang Shiao
(74) *Attorney, Agent, or Firm* — Jones Day

(57) ABSTRACT

3-phosphoindole compounds for the treatment of retroviral infections, and particularly for HIV, are described. Also included are compositions comprising the 3-phosphoindole derivatives alone or in combination with one or more other anti-retroviral agents, processes for their preparation, and methods of manufacturing a medicament incorporating these compounds.

25 Claims, 3 Drawing Sheets

(A)

(B)

(C)

U.S. PATENT DOCUMENTS

| | | | |
|---|---|---|---|
| 6,506,787 | B2 | 1/2003 | Fujishita et al. |
| 6,710,068 | B2 | 3/2004 | La Colla et al. |
| 6,716,605 | B2 | 4/2004 | Fujishita et al. |
| 6,825,201 | B2 | 11/2004 | Wang et al. |
| 6,900,206 | B2 | 5/2005 | Kadow et al. |
| 7,534,809 | B2 * | 5/2009 | Storer et al. .................. 514/419 |
| 2002/0019434 | A1 | 2/2002 | Fujishita et al. |
| 2003/0096825 | A1 | 5/2003 | Wang et al. |
| 2003/0236277 | A1 | 12/2003 | Kadow et al. |
| 2004/0006090 | A1 | 1/2004 | Kadow et al. |
| 2004/0063746 | A1 | 4/2004 | Regueiro-Ren et al. |
| 2006/0074054 | A1 | 4/2006 | Storer et al. |
| 2008/0213217 | A1 | 9/2008 | Storer et al. |

FOREIGN PATENT DOCUMENTS

| | | |
|---|---|---|
| EP | 1 799 696 B1 | 11/2008 |
| WO | WO 94/19321 | 9/1994 |
| WO | WO 96/29077 | 9/1996 |
| WO | WO 97/48399 | 12/1997 |
| WO | WO 97/48400 | 12/1997 |
| WO | WO 97/48409 | 12/1997 |
| WO | WO 98/13046 | 4/1998 |
| WO | WO 98/38332 | 9/1998 |
| WO | WO 98/53812 | 12/1998 |
| WO | WO 99/52915 | 10/1999 |
| WO | WO 01/02388 | 1/2001 |
| WO | WO 03/068221 | 8/2003 |
| WO | WO 03/090690 | 11/2003 |
| WO | WO 03/090691 | 11/2003 |
| WO | WO 03/091264 | 11/2003 |
| WO | WO 2004/014364 | 2/2004 |
| WO | WO 2006/054182 | 3/2007 |

OTHER PUBLICATIONS

ISA/EP, International Search Report, dated Apr. 1, 2008 for International Application No. PCT/US2007/020900.

ISA/EP, PCT International Preliminary Report on Patentability, dated Mar. 31, 2009 for International Application No. PCT/US2007/020900.

EPO, Communication under Rule 71(3) EPC of intent to grant an European patent, dated Feb. 2, 2010, for European Patent Application No. 08075531.7 (division of European Application Patent No. 05850774.0).

EPO, Communication pursuant to Article 94(3) EPC, dated Feb. 11, 2010, for European Patent Application No. 07838974.9.

USPTO, non-final Office Action, mailed Dec. 11, 2009, for U.S. Appl. No. 11/906,095.

USPTO, Final Office Action, mailed Jul. 22, 2010, for U.S. Appl. No. 11/906,095.

ISA/EP International Search Report dated Nov. 23, 2006, for International Application No. PCT/IB2005/004063, filed Sep. 16, 2005.

ISA/EP Written Opinion of the International Searching Authority dated Nov. 23, 2006, for International Application No. PCT/IB2005/004063, filed Sep. 16, 2005.

EPO Communication pursuant to Article 96(2) EPC dated Jul. 6, 2007, for European Patent Application No. 05 850 774.0-2117, with attached Beilstein Crossfire Search per Section V. 2.5 of the Written Opinion.

European Search Report dated Jul. 25, 2008, for European Application No. 08075531.7 (division of European Application No. 05850774.0), filed Sep. 16, 2005.

Singapore Written Opinion dated Jul. 7, 2008, referencing Australian Patent Office Written Opinion dated Jun. 27, 2008, for Singapore Patent Application No. 200702002-7 (based on International Application No. PCT/IB2005/004063), filed Sep. 16, 2005.

Abdou et al., 2004, "Phosphono-Substituted Isoindolines and Indoles from 2,3- and 2,4- Benzoxazin-1-1 ones," Heteroatom Chemistry, vol. 15:77-84.

Abousaoude and Collignon, 1985, "Dialkyl Formyl-1 Methylphosphonates α-Fonctionnels-II," Tetrahedron, vol. 41(2):427-433.

Alexandre et al., 2007, "Synthesis and Antiviral Activity of Phospho-Indoles as Novel NNRTI with Potent Anti-HIV Activity and Enhanced Barrier to Resistance," Poster presented at ASMC07, St. Petersburg, Russia (Aug. 28-31, 2007).

Alexandre et al., 2007, "IDX 12899; A Novel and Highly Potent anti-HIV Non-Nucleosidic-Reverse-Transcriptase-Inhibitor with Enhanced Barrier to Resistance Profile," Poster 21 presented at $14^{th}$ SCI-RSC Medicinal Chemistry Symposium, Cambridge, UK (Sep. 23-26, 2007).

Aoyagi et al., 1974, "Studies on Chromogenic and Fluorogenic Substrates for Detection of Enzymatic Activities," J. Fac. Eng. Chiba Univ., 26(49):185-191.

Artico et al., 1996, "2-Sulfonyl-4-Chloroanilino Moiety: A Potent Pharmacophore for the Anti-Human Immunodeficiency Virus Type 1 Activity of Pyrrolyl Aryl Sulfones," J. Med. Che., 39:522-530.

Artico et al., 1997, "1-Arylsulfonyl-3-(α-hydroxybenzyl)-1H-Pyrroles, a Novel Class of Anti-HIV-1 Reverse Transcriptase Inhibitors," Bioorganic & Med. Chem. Letters 7:1931-1936.

Artico et al., 2000, "Strucure-Based Design, Synthesis, and Biological Evaluation of Novel Pyrrolyl Aryl Sulfones: HIV-1 Non-Nucleoside Reverse Transcriptase Inhibitors Active at Nanomolar Concentrations," J. Med. Chem., 43:1886-1891.

Asadov et al., 2003, "Synthesis of 3-Phosphorylated Indoles from α-Chloro Aldehydes," Chemistry of Heterocyclic Compounds, vol. 39(11):1521-1522.

Baba et al., 1992, "Highly Potent and Selective Inhibition of HIV-1 Replication by 6-Phenylthiouracil Derivatives," Antiviral Res., 17:245-264.

Balzarini et al., 1992, "2'5'-Bis-O-(tert-Butyldimethylsilyl)-3'-Spiro5"-(4"-Amino-1",2"-Oxathiole-2",2"-Dioxide) Pyrimidine (TSAO) Nucleoside Analogues: Highly Selective Inhibitors of Human Immunodeficiency Virus Type 1 that are Targeted at the Viral Reverse Transcriptase," PNAS, 89:4392-4396.

Beilstein Registry No. 284968, Chemical Name "di-indol-3-yl-phosphinic acid," Beilstein Entry Date: Jun. 27, 1988.

Bell et al., 1995, "Phenethylthiazolethiourea (PETT) Compounds, a New Class of HIV-1 Reverse Transcriptase Inhibitors. 1. Synthesis and Basic Structure—Activity Relationship Studies of PETT Analogs," J. Med. Chem., 38:4929-4936.

Benincori et al., 2000, "3,3"-Bis(diphenylphosphino)-1,1"-disubstituted-2-2"-biindoles: Easily Accessible, Electron-Rich, Chiral Diphosphine Ligands for Homogeneous Enantioselective Hydrogenation of Oxoesters," J. Org. Chem., vol. 65:8340-8347.

Blechert, 1985, "Hetero-Cope-Rearrangements. Regio-Controlled Synthesis of Indoles," Helvetica Chimica Acta., vol. 68:1835-1843.

Cantrell et al., 1996, "Phenethylthiazolylthiourea (PETT) Compounds as a New Class of HIV-1 Reverse Transcriptase Inhibitors. 2. Synthesis and Further Structure—Activity Relationship Studies of PETT Analogs," J. Med. Chem., 39:4261-4274.

Chen et al., 1997, "Synthesis of Indoles via a Palladium-Catalyzed Annulation between Iodoanilines and Ketones," J. Org. Chem., 62(9):2676-2677.

Danel et al., 1996, "Synthesis of Potent Anti-HIV-1 Activity of Novel 6-Benzyluracil Analogues of 1-[(2- Hydroxyethoxy)methyl]-6-(phenylthio)thymine," J. Med. Chem., 39:2427-2431.

Danel et al., 1997, "Anti-HIV Active Naphthyl Analogues of HEPT and DABO," Acta Chemica Scandinavica, 51:426-430.

Declercq, 1992, "HIV Inhibitors Targeted at the Reverse Transcriptase," Aids Research and Human Retroviruses, 8(2):119-134.

Gonda et al., 1987, "2-Isothiocyanatobenzyltriphenyphosphonium Bromides—New Type of Functionalized Heterocumulenes Suitable for Synthesis of Indole Derivatives," Collection Czechoslovak Chem. Commun., vol. 52:2508-2520.

Gray, et al., 1996, "Carbanion-Mediated Heterocyclizations: Regiospecific, General Route to Dibenzo-[b. e]phosphininones by Synthetic Anionic Equivalents of Friedel-Crafts Reactions and Remote Fries Rearrangement," Angew. Chem. Int. Ed. Engl., vol. 35(13/14):1558-1560.

Greene, 1991, "The Molecular Biology of Human Immunodeficiency Virus Type 1 Infection," New England Journal of Medicine, 324:308-317.

Gribble and Conway, 1992, "Palladium-Catalyzed Coupling of 3-Indolyl Triflate. Syntheses of 3-Vinyl and 3-Alkynylindoles," Synthetic Communications, vol. 22(15):2129-2141.

Gurevich et al., 1984, "Quaternization of N,N,N',N'-Tetraalkyl-P-(Indol-1-YL)-Phosphonous Diamides," The Journal of General Chemistry of the USSR, vol. 54(12):2510.

Gurevich et al., 1985, "Phosphorylation of Indoles with Phosphorus (III) Acid Chlorides," J. Gen. Chem. USSR (Engl. Transl.), 55(5):1121-1125.

Gurevich et al., 1984, "Phosphorylated 3-Thioindoles," Pharmaceut. Chem. J. (Engl. Transl.), 18(7):431-512.

Gurevich et al., 1978, "1-3 Isomerization of Phosphorylated Indoles," The Journal of General Chemistry of the USSR, vol. 48(7), Part 2, pp. 1513.

Haake and Ossip, 1971, "Reactions of Phosphinates in Sulfuric Acid and Oleum," Journal of the American Chemical Society, pp. 6919-6924.

Haelters et al.,1988, "Synthese D'Indole Phosphonates PAR Cyclisation Selon Fischer D'Arylhydrazones Phosphonates," Phosphorus and Sulfur, vol. 37:41-63.

Haikal, 1996, "Synthesis of Guanosine-3'-(5-Bromo-4-Chloroindol-3-YL)-Phosphate (G-3'-BCIP)," Collection of Czechoslovak Chemical Communications, 61(3):427-431.

Horwitz et al., 1966, "Substrates for Cytochemical Demonstration of Enzyme Activity II. Some Dihalo-3-Indolyl Phosphates and Sulfates," Journal of Medicinal Chemistry, 447 (May 1966).

Horwitz et al., 1970, "Substrates for Cytochemical Demonstration of Enzyme Activity V. Thymidine 3'-and 5'-(5-Bromo-4-Chloro-3-Indolyl) Phosphates," Journal of Medicinal Chemistry, 13(5):1024-1025.

Jakubik et al., 2007, "IDX 12899 anti-HIV-1 Activity and Resistance Profile is Superior to Efavirenz," Poster 1657 presented at the XVI International HIV Drug Resistance Workshop, Barbados, West Indies (Jun. 12-16, 2007).

Kohlstaedt et al., 1992, "Crystal Structure at 3.5 Angst Resolution of HIV-1 Reverse Transcriptase Complexed with an Inhibitor," Science, 256(5065):1783-1790.

Mai et al., 1997, "Dihydro(alkylthio)(naphthylmethyl)oxopyrimidines: Novel Non-Nucleoside Reverse Transcriptase Inhibitors of the S-DABO Series," J. Med. Chem., 40:1447-1454.

March et al., 1970, "The Synthesis of Ribonucleotide-5'-(5-Iodoindol-3-ol) and (4-Methylcoumarin-7-ol) Esters for the Histochemical Demonstration of Nucleases (1A)," Journal of Heterocyclic Chemistry, 7(4):885-889.

Mingoia, 1932, "Su alcuni nuovi fosfossidi ed acidi fosfonici a nucleo pirrolico e indolico," Gazzetta Chimica Italiana, vol. 62:333-337.

Mingoia, 1930, "Su alcune fosfine indoliche," Gazzetta Chimica Italiana, vol. 60:144-147.

Mitsuya et al., 1990, "Molecular Targets for AIDS Therapy," Science, 249(4976):1533-1544.

Pauwels et al., 1990, "Potent and Selective Inhibition of HIV-1 Replication in vitro by a Novel Series of TIBO Derivatives," Nature, 343:470-474.

Pauwels et al., 1993, "Potent and highly Selective Human Immunodeficiency Virus Type 1 (HIV-1) Inhibition by a Series of α-anilinophenylacetamide Derivates Targeted at HIV-1 Reverse Transcriptase," PNAS, 90:1711-1715.

Pontikis et al., 1997, "Synthesis and Anti-HIV Activity of Novel N-1 Side Chain-Modified Analogs of 1-[(2-Hydroxyethoxy)methyl]-6-(phenylthio)thymine (HEPT)," J. Med. Chem., 40:1845-1854.

Powers, 1966, "Chloroindoles," The Journal of Organic Chemistry, vol. 31(8):2627-2631.

Rabiger et al., 1970, "Synthesis of 5-Iodo and 5-Nitro-3-indolyl Phosphates as Cytochemical Substrates for Acid Phosphatase," Journal of Heterocyclic Chemistry, 7:307-311.

Razumov et al., 1980, "Phosphorylation of Indoles with Phosphoramidites," J. General Chemistry, USSR (Engl. Transl.) 50(4):618-624.

Razumov et al., 1974, "Phosphorylated (Aminomethyl) Indoles," The Journal of General Chemistry of the USSR, vol. 44(II) Part 2. pp. 2545.

Razumov et al., 1974, "[Hydroxy(Indol-3-Yl)Methyl]Phosphonic EST ERS," The Journal of General Chemistry of the USSR, vol. 44(II) Part 2. pp. 2546.

Razumov et al., 1974, "Synthesis of 3-Phosphorylated Indoles," The Journal of General Chemistry of the USSR, vol. 44(II) Part 2. pp. 2547.

Romero et al., 1993, "Bis(heteroaryl)piperazine (BHAP) Reverse Transcriptase Inhibitors: Structure—Activity Relationships of Novel Substituted Indole Analogues and the Identification of 1-[(5-Methanesulfonamido-1H-indol-2-yl)-carbonyl]-4-[3-[(I-methylethyl)amino]-pyridinyl]piperazine Monomethanesulfonate (U-90152S), a Second-Generation Clinical Candidate," J. Med. Chem., 36:1505-1508.

Russell and Yao, 1992, "Reactions of Ethyl Phosphites with β-Nitrostyrenes. The Role of Nitrosoalkenes as Intermediates," The Journal of Organic Chemistry, vol. 57(24):6508-6513.

Silvestri et al., 2000, "Computer-Assisted Design, Synthesis and Biological Evaluation of Novel Pyrrolyl Heteroaryl Sulfones Targeted at HIV-1 Reverse Transcriptase as Non-Nucleside Inhibitors," Bioorganic & Med. Chem., 8:2305-2309.

Silvestri et al., 2002, "Anti-HIV-1 NNRT Agents: Acylamino Pyrryl Aryl Sulfones (APASs) as Truncated Analogues of Tricyclic PBTDs," Med. Chem. Research 11:195-218.

Silvestri et al., 2003, "Novel Indolyl Sulfones Active Against HIV-1 Carrying NNRTI Resistance Mutations: Synthesis and SAR Studies," J. Med. Chem., 46:2482-2493.

Sundberg, 1965, "Deoxygenation of Nitro Groups by Trivalent Phosphorus. Indoles from o-Nitrostyrenes," The Journal of Organic Chemistry, vol. 30:3604-3610.

Tanaka et al., 1991, "A New Class of HIV-1-Specific 6-Substituted Acyclouridine Derivatives: Synthesis and Anti-HIV-1 Activity of 5- or 6-Substituted Analogues of 1-[(2-Hydroxyethoxy)methyl]-6-(phenylthio)thymine (HEPT)," J. Med. Chem, 34:349-357.

Tolmachev et al., 1990, "Phosphorylation of 1,2-Dimethylinode with Phosphorus Tribomide and Diphenylchlorophosphine," J. Chem. USSR (Engl. Transl.), 60(7):1488-1489.

Tolmachev et al., 1996, "3-Phosphorylated N-Alkylindoles," Heteroatom Chemistry, 7(6):525-531.

Tsou et al., 1967, "Synthesis of 3-Indolyl and 5-Bromo-3-Indolyl Phosphate for Histochemical Demonstration of Alkaline Phosphatase," Journal of Medicinal Chemistry, 10(4):662-664.

Tsou et al., 1970, "Synthesis of 5-Iodo-3-Indolylphosphodiesters of 5-Fluorodeoxyuridine as Possible Chromogenic Cancer Chemotherapeutic Agents," Journal of Medicinal Chemistry, 13(4):765-768.

Tsou et al., 1972, "Indigogenic Phosphodiesters as Potential Chromogenic Cancer Chemotherapeutic Agents," Journal of Medicinal Chemistry, 15(12):1221-1224.

Williams et al., 1993, "5-Chloro-3-(phenylsulfonyl)indole-2-carboxamide: A Novel, Non-Nucleoside Inhibitor of HIV-1 Reverse Transcriptase," J. Med. Chem., 36(9):1291-1294.

Yaroshevskaya et al., 2001, "Reaction of $CoS_4C_4Ph_4$ with (3-Indolyl)phosphonites by ESR Data," Russian Journal of General Chemistry, vol. 71(7):1036-1037.

Yaroshevskaya et al., 2001 "Sorption Properties of Phosphorylated Indoles," Russian Journal of General Chemistry, vol. 71(7):1033-1035.

Yuan et al., 1993, "New Synthetic Methods for Carbocyclic and Heterocyclic Compounds Bearing Phosphonate Moiety with Biological Significances," Phosphorus, Sulfur, and Silicon, vol. 75:147-150.

Zbiral and Berner-Fenz, 1967, "Über die Umsetzung von Triphenyldibromphosphin mit nucleophilen Substraten Von," Reaktionen mit phosphororganichen Verbindungen, 11. Mitt., pp. 667-678.

Zhang et al., 1990, "A Facile One-Pot Synthesis of 3-dialkoxyphosphoryl- and 3-[alkoxy(phenyl)phosphoryl]-1-hydroxyindoles," Synthesis, 9:801-802.

Richman et al., "IDX 12899 and IDX 12989, Novel NNRTIs with Potent anti-HIV Activity, Enhanced Barrier to Resistance and Favorable Pharmacokinetic Profile," Abstract of Poster 489 presented at Session 87, 14th Conference on Retroviruses and Opportunistic Infections, Feb. 25-28, 2007, Los Angeles, California (Abstract only provided).

USPTO, Notice of Allowance, mailed Jan. 28, 2011, for U.S. Appl. No. 11/906,095.

* cited by examiner (A)

(B)

(C)

(I), (II), (III), (IV), (V), (VI), (VII), (VIII), (IX), and (X)

PHOSPHO-INDOLES AS HIV INHIBITORS

CROSS REFERENCE TO RELATED APPLICATIONS

This application is a continuation of U.S. application Ser. No. 11/229,150, filed Sep. 16, 2005 now U.S. Pat. No. 7,534,809, which claims the benefit of U.S. Provisional Application Nos. 60/611,061, filed Sep. 17, 2004, 60/711,445, filed Aug. 25, 2005, and 60/711,565, filed Aug. 26, 2005, all entitled "Phospho-Indoles as HIV Inhibitors", and each of these applications is incorporated by reference herein in its entirety.

FIELD OF THE INVENTION

The present invention provides new human immunodeficiency virus (HIV) reverse transcriptase inhibitory compounds and their pharmaceutically acceptable salts, prodrugs, analogs and derivatives. Also included are methods of using these compounds for the prophylaxis and treatment of HIV infection and AIDS, and pharmaceutical compositions that contain the compounds.

BACKGROUND OF THE INVENTION

Numerous compounds have been synthesized to combat the human immunodeficiency virus (HIV) since it was discovered to be the etiological cause of the acquired immunodeficiency syndrome (AIDS) in 1983. A focal point of AIDS research efforts has been and continues to be the development of inhibitors of human immunodeficiency virus (HIV-1) reverse transcriptase, the enzyme responsible for the reverse transcription of the retroviral RNA to proviral DNA (W. C. Greene, *New England Journal of Medicine* (1991), 324:308-17; Mitsuya et al., *Science* (1990), 249:1533-44; E. J. DeClercq, *Retrovirus* (1992), 8:119-34). Inhibitors include non-nucleoside reverse transcriptase inhibitors or NNRTIs that bind to a specific allosteric site of the HIV reverse transcriptase near the polymerase site and interfere with reverse transcription by either altering the conformation or the mobility of the reverse transcriptase, thus leading to noncompetitive inhibition of the enzyme (Kohlstaedt et al., *Science* (1992), 256:1783-90).

Several classes of compounds have been identified as NNRTIs of HIV. Examples of these include:
1) 1-[(2-hydroxyethoxy)methyl]-6-phenylthio)thymines (HEPT) (Tanaka et al., *J. Med. Chem.* (1991), 34:349-57; Pontikis et al., *J. Med. Chem.* (1997), 40:1845-54; Danel et al., *J. Med. Chem.* (1996), 39:2427-31; Baba et al., *Antiviral Res.* (1992), 17:245-64);
2) bis(heteroaryl)piperazines (BHAP) (Romero et al., *J. Med. Chem.* (1993), 36:1505-8);
3) dihydroalkoxybenzyloxopyrimidine (DABO) (Danel et al., *Acta Chemica Scandinavica* (1997), 51:426-30; Mai et al., *J. Med. Chem.* (1997), 40:1447-54);
4) 2',5'-bis-O-(tertbutyldimethylsilyl)-3'-spiro-5"-(4"-amino-1", 2"-oxathiole-2", 2"-dioxide)pyrimidines (TSAO) (Balzarini et al., *PNAS USA* (1992), 89:4392-96);
5) phenylethylthiazolylthiourea (PETT) derivatives (Bell et al., *J. Med. Chem.* (1995), 38:4929-36; Cantrell et al., *J. Med. Chem.* (1996), 39:4261-74);
6) tetrahydro-imidazo[4,5,1-jk][1,4]-benzodiazepine-2(1H)-one and -thione (TIBO) derivatives (Pauwels et al., *Nature* (1990), 343:470-4);
7) phosphorus-substituted imidazole derivatives (PCT Publication No. WO 03/091264 A2 to Gilead Sciences, Inc.);
8) alpha-anilinophenylacetamide (alpha-APA) derivatives (Pauwels et al., *PNAS USA* (1993), 90:1711-15); and
9) indole derivatives (U.S. Pat. No. 5,527,819 to Merck & Co. and counterpart PCT Publication No. WO 94/19321).

Indole derivatives described in U.S. Pat. No. 5,527,819 assigned to Merck & Co. have been shown to be inhibitors of HIV reverse transcriptase. Some of these compounds exhibited $IC_{50}$ values against HIV reverse transcriptase at concentrations of from 3-35 ηM. A process for synthesizing optionally substituted indoles by a palladium-catalyzed annulation between a ketone and an iodoaniline was also developed at Merck & Co. (Chen et al., *J. Org. Chem.* (1997), 62(9):2676-77).

The compounds disclosed in the '819 patent are generally represented by the following broad structural Formula (III):

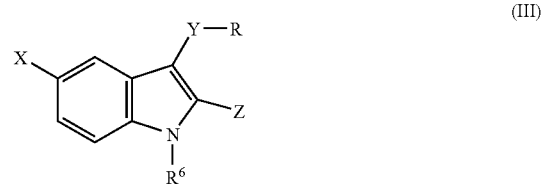

(III)

in which the variables X, Y, Z, R and $R^6$ are broadly defined.

U.S. Pat. No. 5,124,327 to Merck & Co. discloses a class of optionally substituted sulfonylphenyl indole compounds. The patent reports that the compounds are active as reverse transcriptase inhibitors and could be useful in the treatment of HIV infection and AIDS.

U.S. Pat. No. 6,710,068 to Idenix Pharmaceuticals, Ltd., discloses a class of phenylindoles substituted with at least two moieties other than hydrogen on either or both rings. See also PCT Publication No. WO 02/083126.

PCT Publication No. WO 2004/014364 to Idenix Pharmaceuticals discloses another class of phenylindoles that displays enhanced anti-HIV activity. These compounds are also substituted with at least two moieties other than hydrogen on either or both rings. In addition, these compounds incorporate a number of different substituents with a carboxamide functionality at position-2 on the indole, the position shown in formula (II) above as "Z". Typical placement of substituents is at the 3" and 5" positions on the phenyl ring, and at the 4' and 5', 5' and 6', or 5' and 7' positions on the benzo ring of the indole moiety.

Bristol Myers Squibb disclose various optionally substituted indoles, azaindoles, piperazines, and pyrrolidines for the treatment of HIV and/or AIDS in several U.S. patents and U.S. and PCT publications. See U.S. Publication Nos. 2004/0006090; 2004/0063746; 2003/0096825; 2003/0236277; and WO 03/068221.

WO 01/02388 to SmithKline Beecham S.P.A discloses optionally substituted phenylindoles with a carbamyl substituent that are alleged to have utility in the treatment of HIV, AIDS, osteoporosis, cancers, and Alzheimer's disease.

Warner-Lambert Company discloses various indole-thiazepinones, oxazepinones, diazepinones, benzothiophenes, benzofurans, and indole-2-carboxamides for the treatment of HIV in U.S. Pat. Nos. 5,424,329; 5,565,446; 5,703,069; and WO 96/29077.

Shinogi & Co. report optionally substituted indole derivatives that are viral integrase inhibitors useful as anti-HIV drugs in U.S. Publication No. 2002/0019434 and U.S. Pat. Nos. 6,716,605 and 6,506,787.

U.S. Pat. No. 5,945,440 to Kleinschroth et al. discloses a class of indolocarbazole amides for the treatment of a variety of diseases including cancer, viral diseases (including HIV), cardiac and vascular diseases, bronchopulmonary diseases, inflammatory disorders, degenerative diseases of the central nervous system, and other diseases.

U.S. Pat. No. 4,866,084 to Gunasekera et al. teaches certain bisindole alkaloid compounds that have antiviral and antitumor activity, including HSV (herpes simplex virus). U.S. Pat. No. 5,935,982 to Dykstra et al. reports a different class of bisindoles that have utility versus retroviral infections and especially HIV.

U.S. Pat. No. 5,852,011 to Matsunaga et al. discloses a class of indole derivatives substituted by a heteroaryl function and an amide function. The compounds are said to possess antitumor, antiviral, and antimicrobial properties.

U.S. Pat. No. 5,935,982 to Dykstra et al. discloses a class of bis-indoles and specifically propose their use for treating retroviral infections, and especially infection by HIV.

U.S. Pat. No. 5,929,114 to Domagala et al. discloses a class of arylthio and bithiobisarylamide compounds, including indole derivative, that reportedly have antibacterial and antiviral activity.

U.S. Pat. No. 5,830,894 to Pevear et al. discloses a class of triazinoindole derivatives that reportedly have anti-pestivirus activity, most notably BVDV activity.

Indoles have been used in the treatment of diseases other than HIV. U.S. Pat. No. 5,981,525 to Farina et al. discloses a complex array of indoles for use in the treatment of osteoporosis based on their ability to inhibit osteoclast H+-ATPase and thus reduce bone resorption. U.S. Pat. No. 6,025,390, also to Farina et al., teaches another group of indole derivatives, termed heteroaromatic pentadienoic acid derivatives, also for the treatment of osteoporosis. U.S. Pat. No. 5,489,685 to Houpis et al. discloses a series of compounds that are furo(2,3-b) pyridine carboxylic acid esters, allegedly useful in the treatment of HIV.

It is known that over a period of time, antiviral agents that are active against HIV induce mutations in the virus that reduce the efficacy of the drug. This was apparently the problem exhibited by the Merck indoles in U.S. Pat. No. 5,527,819 (Williams et al., *J. Med. Chem.*, 1993, 36(9), 1291-94). Drug resistance most typically occurs by mutation of a gene that encodes an enzyme used in viral replication, and most typically in the case of HIV, reverse transcriptase, protease, or DNA integrase. It has been demonstrated that the efficacy of a drug against HIV infection can be prolonged, augmented, or restored by administering the compound in combination or alternation with a second, and perhaps third, antiviral compound that induces a different mutation from that caused by the principal drug. Alternatively, the pharmacokinetics, biodistribution, or other parameters of a drug can be altered by such combination or alternation therapy. In general, combination therapy is typical rather than alternation therapy since combination therapy induces multiple simultaneous pressures on the virus. However, one cannot predict which mutations will be induced in the HIV-1 genome by a given drug, whether the mutations are permanent or transient, or how an infected cell with a mutated HIV-1 sequence will respond to therapy with other agents in combination or alternation. These factors are exacerbated by the fact that there is a paucity of data on the kinetics of drug resistance in long-term cell cultures treated with modern antiretroviral agents.

Therefore, there is a need to provide new compounds and methods for the treatment of HIV.

It is thus an object of the present invention to provide new compounds, compositions, methods and uses for the treatment of patients infected with HIV.

It is yet another object of the present invention to provide new compositions and methods for the treatment of patients infected with HIV that exhibit activity against drug-resistant forms of the virus.

SUMMARY OF THE INVENTION 3-phosphoindole compounds display antiviral activity against HIV, in particular against strains of HIV that have developed cross resistance to other anti-HIV drugs. Compounds, compositions and methods for treatment of HIV infection are disclosed that include the 3-phosphoindole compounds. The 3-phosphoindoles can be in the form of a wide variety of moieties, including, but not limited to, phosphates, phosphonates, a phosphorthioate, including .thiophosphates, thiophosphonates, phosphate, and a phosphoramidate, including .iminiophosphates and iminophosphonates.

In one embodiment, the compounds that can have anti-HIV activity are of Formula (A) below. These compounds include an phosphorus-linked substituent at position-3 and particular substituents at position-2 on the indole, and a monosubstitution at position $R^{5'}$ or a disubstitution at positions $R^{4'}$ and $R^{5'}$, $R^{5'}$ and $R^{6'}$, or $R^{5'}$ and $R^{7'}$ on the benzo ring.

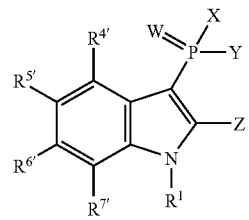

(A)

In one particular embodiment, substituent "X" represents a phenyl ring that is unsubstituted or is substituted by one or more halogens or lower alkyl groups such as methyl or ethyl. Particular substituents at position 2 on the indole moiety include, for example, hydrogen, hydroxy, halogen, alkyl, aryl, heteroaryl, and especially substituents having a carboxamide or carboxamide moiety shown as "Z" in Formula (A). Substituents for the benzo ring of the indole moiety include but are not limited to chlorine, fluorine, bromine, iodine, $CF_3$, CN, $NO_2$, and methoxy.

The active compound may be a salt or prodrug that, upon administration, provides directly or indirectly the parent compound or that itself exhibits a desired activity. In another embodiment, the compound of Formula A includes a charged heteroatom, and in a particular embodiment, the compound includes an N-oxide group. Modifications affecting the biological activity of the compounds of the present invention also are included here, as are any changes that produce increased activity over that of the parent compounds.

DETAILED DESCRIPTION OF THE INVENTION

Figure 1:
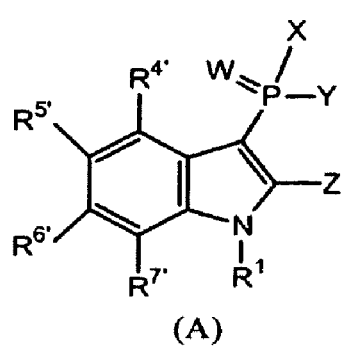
FIG. 1 is an illustration of three (3) general structures of the present invention given as Formula (A), Formula (B), and Formula (C).
Figure 1:
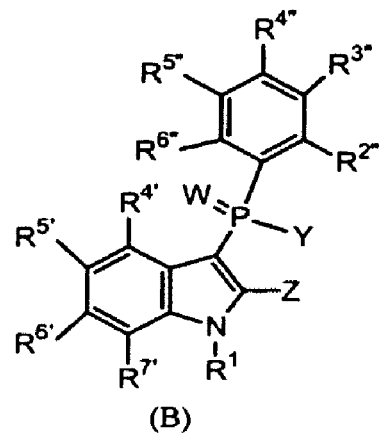
Figure 1:
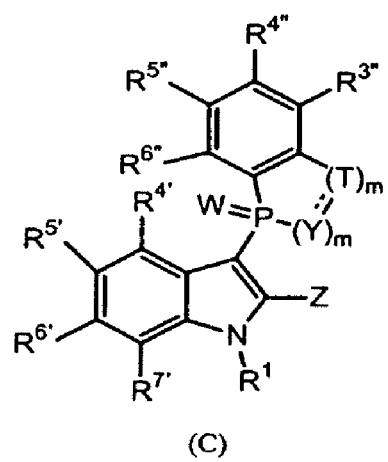
Figure 2:
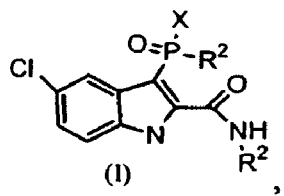
FIG. 2 is an illustration of phosphorylated compounds (I)-(X) of the general Formulae (A) and (B).
Figure 2:
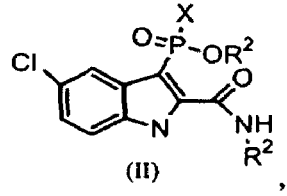
Figure 2:
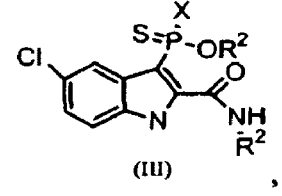
Figure 2:
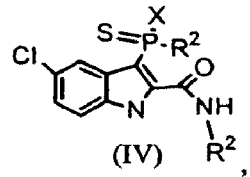
Figure 2:
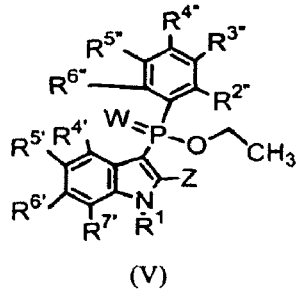
Figure 2:
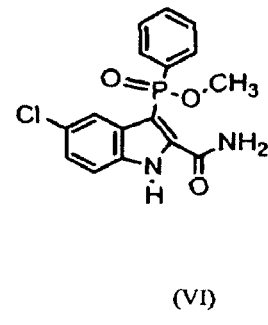
Figure 2:
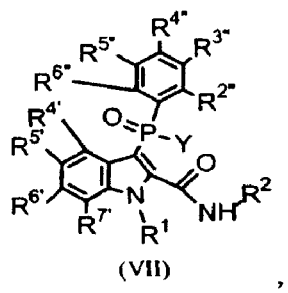
Figure 2:
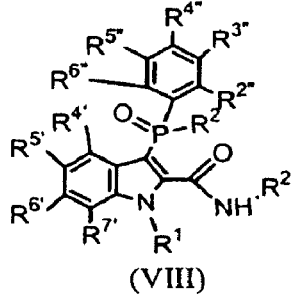
Figure 2:
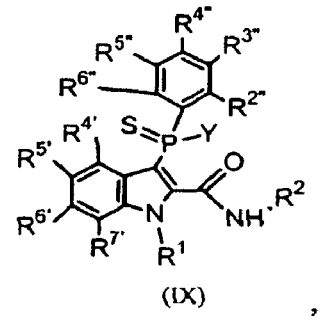
Figure 2:
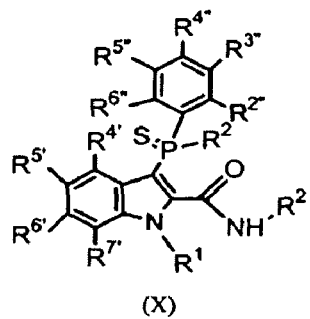
Figure 3:
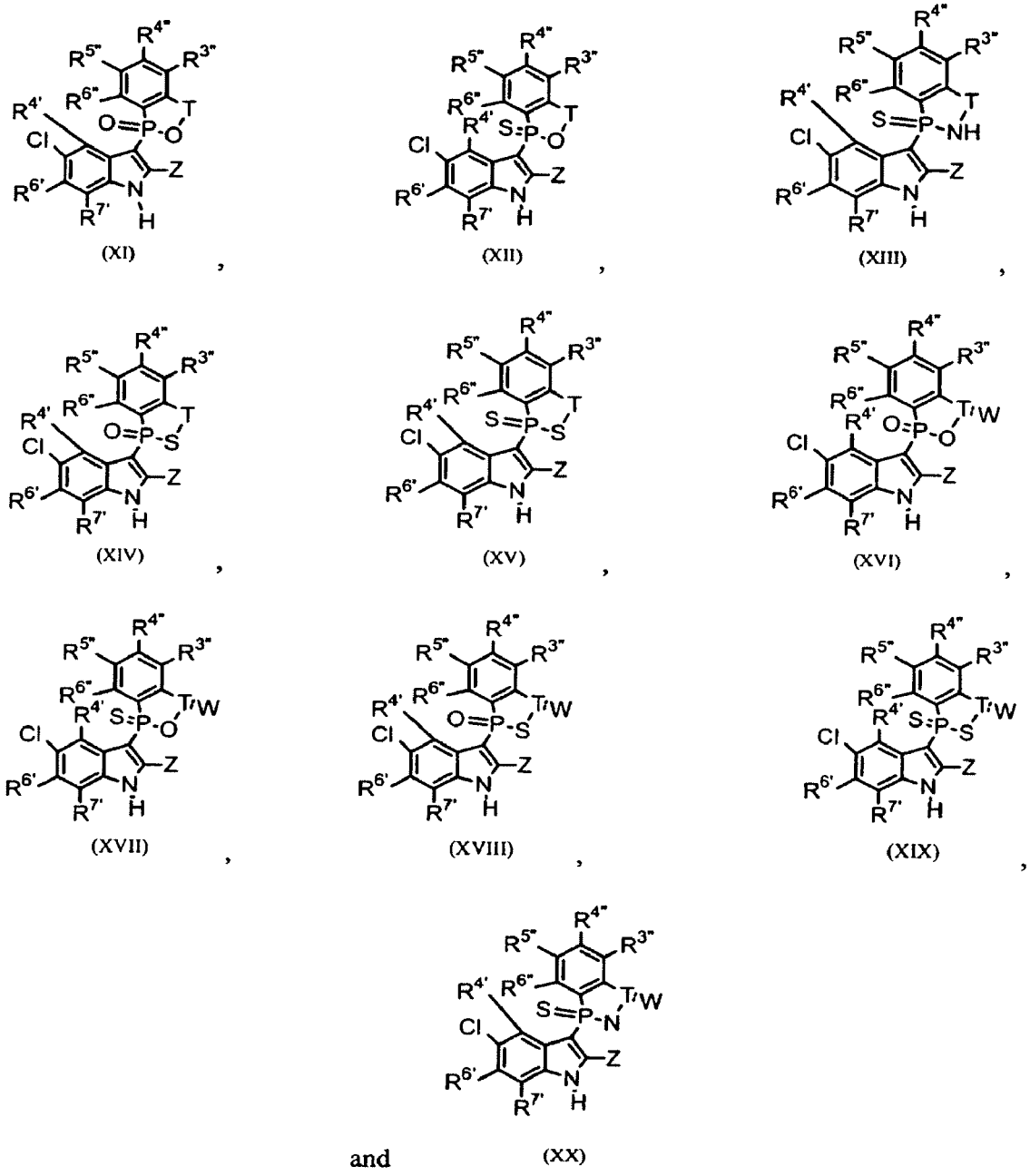
FIG. 3 is an illustration of 9- and 10-membered bicyclic phosphorylated compounds (XI)-(XX) of the general Formula (C).

Provided are a composition of matter, method of use and a pharmaceutical composition for the treatment of retroviral infections in mammals and, in particular, HIV in humans. Included within the present invention are the following features:

- 3-phosphoindoles and pharmaceutically acceptable salts and prodrugs thereof as described herein, optionally substantially free of other chemical entities;
- 3-phosphoindoles of Formulas A-C and pharmaceutically acceptable salts and prodrugs thereof as described herein, optionally substantially free of other chemical entities;
- 3-phosphoindoles and pharmaceutically acceptable salts and prodrugs thereof as described herein that are effective against HIV in a host;
- 3-phosphoindoles and pharmaceutically acceptable salts and prodrugs thereof as described herein that are effective against drug-resistant strains of HIV in a host, and, in certain embodiments, where the drug-resistant strains of HIV is due to a reverse transcriptase mutation, such as lysine 103→asparagine and/or tyrosine 181→cysteine;
- 3-phosphoindoles and pharmaceutically acceptable salts and prodrugs thereof as described herein for use in the treatment or prophylaxis of an HIV infection in a host, or in the manufacture of a medicament for the treatment or prophylaxis of an HIV infection in a host, especially in individuals diagnosed as having an HIV infection or being at risk for such infection;
- 3-phosphoindoles and pharmaceutically acceptable salts and prodrugs thereof as described herein for use in the treatment or prophylaxis of an HIV infection, or in the manufacture of a medicament for the treatment or prophylaxis of an HIV infection, which is resistant to one or more reverse transcriptase inhibitors, in a host;
- 3-phosphoindoles and their pharmaceutically acceptable salts and prodrugs therefor as described herein for use in the treatment or prophylaxis of an HIV infection as a form of salvage therapy in a host, or in the manufacture of a medicament for the treatment or prophylaxis of an HIV infection as a form of salvage therapy in a host, especially in individuals diagnosed as having an HIV infection or being at risk for such infection;
- 3-phosphoindoles and their pharmaceutically acceptable salts and prodrugs therefor as described herein for use in the treatment or prophylaxis, or in the manufacture of a medicament for the treatment or prophylaxis, of an HIV infection that is resistant to one or more reverse transcriptase inhibitors due to a reverse transcriptase mutation, such as lysine 103→asparagine and/or tyrosine 181→cysteine, in a host, especially in individuals diagnosed as having an HIV infection or being at risk for such infection;
- processes for the preparation of 3-phosphoindoles, optionally substantially isolated from other chemical entities;
- pharmaceutical compositions comprising an effective anti-HIV treatment amount of a 3-phosphoindole or its pharmaceutically acceptable salt or prodrug thereof, together with a pharmaceutically acceptable carrier or diluent;
- pharmaceutical compositions comprising an effective anti-HIV treatment amount of a 3-phosphoindole or its pharmaceutically acceptable salt or prodrug thereof, in combination with one or more other anti-HIV agents, optionally with a pharmaceutically acceptable carrier or diluent;
- pharmaceutical compositions for the treatment or prophylaxis of an HIV infection that is resistant to one or more reverse transcriptase inhibitors, in a host, comprising an effective anti-HIV treatment amount of a 3-phosphoindole or its pharmaceutically acceptable salt or prodrug, optionally in combination with at least one other anti-HIV agent, optionally with a pharmaceutically acceptable carrier or diluent;
- pharmaceutical compositions for the treatment or prophylaxis of an HIV infection in a host as a form of salvage therapy comprising an effective anti-HIV treatment amount of a 3-phosphoindole or its pharmaceutically acceptable salt or prodrug, optionally in combination with at least one other anti-HIV agent, and optionally with a pharmaceutically acceptable carrier or diluent;
- pharmaceutical compositions for the treatment or prophylaxis of an HIV infection that is resistant to one or more reverse transcriptase inhibitors due to a reverse transcriptase mutation, such as lysine 103→asparagine and/or tyrosine 181→cysteine, in a host comprising an effective anti-HIV treatment amount of a 3-phosphoindole or its pharmaceutically acceptable salt or prodrug, optionally in combination with at least one other anti-HIV agent, and optionally with a pharmaceutically acceptable carrier or diluent;
- methods for the treatment or prophylaxis of an HIV infection in a host, wherein the HIV can be resistant to one or more reverse transcriptase inhibitors, comprising administering to said host an effective anti-HIV treatment amount of a 3-phosphoindole or its pharmaceutically acceptable salt or prodrug, optionally in combination or alternation with at least one other anti-HIV agent, and optionally with a pharmaceutically acceptable carrier or diluent;
- methods for the treatment or prophylaxis of an HIV infection in a host as a form of salvage therapy comprising administering to said host an effective anti-HIV treatment amount of a 3-phosphoindole or its pharmaceutically acceptable salt or prodrug, optionally in combination or alternation with at least one other anti-HIV agent, and optionally with a pharmaceutically acceptable carrier or diluent;
- methods for the treatment or prophylaxis of an HIV infection, which is resistant to one or more reverse transcriptase inhibitors due to a reverse transcriptase mutation, such as lysine 103→asparagine and/or tyrosine 181→cysteine, in a host comprising administering to said host an effective anti-HIV treatment amount of a 3-phosphoindole or its pharmaceutically acceptable salt or prodrug, optionally in combination or alternation with at least one other anti-HIV agent, and optionally with a pharmaceutically acceptable carrier or diluent;
- use of a 3-phosphoindole or its pharmaceutically acceptable salt or prodrug, optionally in combination or alternation with at least one other anti-HIV agent, and optionally with a pharmaceutically acceptable carrier or diluent, for the treatment or prophylaxis of an HIV infection in a host;
- use of a 3-phosphoindole or its pharmaceutically acceptable salt or prodrug, optionally in combination or alternation with at least one other anti-HIV agent, and optionally with a pharmaceutically acceptable carrier or diluent, for the treatment or prophylaxis of an HIV infection, or in the manufacture of a medicament for the treatment or prophylaxis of an HIV infection, which is resistant to one or more reverse transcriptase inhibitors, which can be due to a reverse transcriptase mutation, such as lysine 103→asparagine and/or tyrosine 181→cysteine, in a host. This use can be a form of salvage therapy; and any or all of the foregoing in which the host is a human.

I. Active Compounds of the Present Invention

In a general embodiment of the invention, a 3-phosphoindole or a pharmaceutically acceptable salt, prodrug, N-oxide, quaternary amine, stereochemical isomer or tautomer thereof is provided. The 3-phosphoindole can be in the form of a phosphate, phosphonate, thiophosphate, thiophosphonate, iminiophosphate or iminophosphonate.

In a first embodiment of the present invention, the compound is represented generally by the following chemical Formula (A):

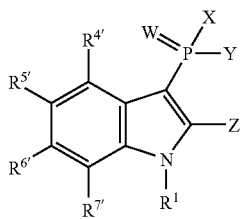

(A)

or a pharmaceutically acceptable salt, prodrug, N-oxide, quaternary amine, stereochemical isomer or tautomer thereof, wherein:

each X and Y independently is
  a) H;
  b) halogen (F, Cl, Br, or I), typically F;
  c) $R^3$;
  d) $CF_3$;
  e) $C_{1-6}$, alkyl;
  f) $C_{2-6}$ alkenyl;
  g) $C_{2-6}$ alkynyl;
  h) alkylheterocycle;
  i) 3-14 membered carbocycle, aryl, heterocycle, any of which may comprise a monocyclic, bicyclic, tricyclic or spiro structure;
  j) OH;
  k) $OR^2$;
  l) O-alkyl;
  m) O-alkenyl;
  n) O-alkynyl;
  o) O-alkylaryl;
  p) O-aryl;
  q) O-heterocycle;
  r) O-aralkyl;
  s) O-carbocycle;
  t) SH;
  u) $SR^2$;
  v) S-alkyl;
  w) S-alkenyl;
  x) S-alkynyl;
  y) S-alkylaryl;
  z) S-aryl;
  aa) S-heterocycle;
  bb) S-aralkyl;
  cc) S-carbocycle;
  dd) $NH_2$;
  ee) $NHR^2$;
  ff) $NR^2R^2$;
  gg) NH-alkyl;
  hh) N-dialkyl;
  ii) NH-aryl;
  jj) N-alkaryl;
  kk) N-aralkyl;
  ll) NH-heterocycle;
  mm) N-alkyl-heterocycle;
  nn) N-alkenyl-heterocycle;
  oo) N-alkynyl-heterocycle; or
  alternatively, X and Y may come together to form an optionally substituted bicyclic or tricyclic phosphorylated heterocycle wherein each ring comprises 3-7 members;

Z is:
  a) H;
  b) CN;
  c) $NO_2$;
  d) $C_{1-6}$ alkyl;
  e) $C_{2-6}$ alkenyl;
  f) $C_{2-6}$ alkynyl;
  g) alkaryl;
  h) aralkyl;
  i) heterocycle;
  j) alkyl-heterocycle;
  k) aryl;
  l) alkoxy;
  m) $OR^2$;
  n) $SR^2$;
  o) $S(O)_n R^2$;
  p) $S(O)_n$—$NR^2R^3$;
  q) $N(R^2)(R^3)$;
  r) carboxamido;
  s) amido;
  t) acyl;
  u) C(=W)—$R^3$;
  v) C(=W)NH—C($R^3$)($R^3$)—C(=W)—N($R^2$)($R^2$);
  w) C(=W)NH—P(=W)($R^3$)-A-$R^3$;
  x) C(=W)NH-A-S(O)$_n$—$NR^2$;
  y) C(=W)NH—C$R^3R^3$—S(O)$_n NR^2R^2$;
  z) C(=W)—NH-A-C(=W)—N($R^2$)($R^2$);
  aa) C(=W)—N($R^2$)($R^2$);
  bb) C(=W)—NH-A-$R^3$;
  cc) C(=W)—NH—NH—$R^3$;
  dd) C(=W)—NH—C($R^3$)($R^3$)—C(=W)NH—C($R^3$)($R^3$)C(=W)—N($R^2$)($R^2$);
  ee) C(=W)—NH—$R^2$;
  ff) C(=W)—NH-A-C(=W)—NH-A-C(=W)—$NH_2$;
  gg) C($R^2$)($R^3$)($R^3$);
  hh) C($R^2$)($R^3$)—NH—$R^2$;
  ii) A-S(O)$_n$—$R^3$;
  jj) C(=W)-A-C(=W)-A-C(=W)$R^3$;
  kk) A-$R^3$;
  ll) C(=W)—(O)$R^2$;
  mm) C(=W)-A-C(=W)—$NH_2$;
  nn) an amino acid residue;
  oo) C(=W)—N($R^2$)-A-(amino acid residue);
  pp) C(=W)—N($R^2$)-A-(amino acid residue)-C(=W)—$R^3$;
  qq) C(=W)-amino acid residue;
  rr) C(=W)—N($R^2$)-A-(amino acid residue)-A-C(=W)—$R^3$;
  ss) C(=W)—$OR^2$;
  tt) C(=W)—S($R^2$);
  uu) C(=W)—NH—NH—$R^2$;
  vv) C(=W)—NH—N($R^2$)-A-C(=W)$R^3$;
  ww) C(=W)—N($R^2$)—C(=W)—$R^3$;

xx) C(=W)-A-NH—C(=W)R$^3$;
yy) C(=W)-A-NH—C(=W)OR$^2$;
zz) C(=W)-A-R$^3$;
aaa) C(=W)—NH—NH—CH$_2$—C(=W)R$^3$;
bbb) P(=W)(R$^3$)(R$^3$); or
ccc) A-P(=W)(R$^3$)(R$^3$).
ddd) C(=W)—NH—C$_{1-10}$alkyl-heteroaryl
eee) C(=W)—NH—C$_{1-4}$alkyl-heteroaryl
fff) C(=W)—NH—CH$_2$-heteroaryl ggg)

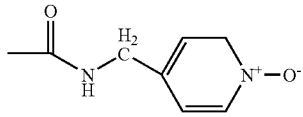

wherein in embodiments (ddd), (eee) and (fff), the heteroaryl can optionally include a charged heteroatom, and in particular can include an N-oxide
wherein each X, Y and Z independently may be unsubstituted or substituted by one or more of C$_{1-4}$ alkyl; alkoxy; OH; oxo; halo (F, Cl, Br, or I); NR$^2$R$^2$; optionally substituted aryl; optionally substituted heterocycle; O—C(=W)-alkyl; C(=W)—OR$^2$; CN; NO$_2$; NH—C(=W)-alkyl; NH—S(O)$_n$-alkyl; NH—S(O)$_n$—NR$^2$R$^2$; or C$_{3-6}$ cycloalkyl;

each W is independently:
  a) O;
  b) S;
  c) NH;
  d) N—N(R$^2$)(R$^2$);
  e) N(R$^2$);
  f) N—OH;
  g) N—O-alkyl; or
  h) N—O—R$^2$;
R$^1$ is:
  a) H;
  b) —R$^2$;
  c) C(=W)—R$^3$;
  d) C(=W)—O(R$^2$);
  e) C(=W)—S(R$^2$);
  f) C(=W)—NH—R$^2$;
  g) C(=W)—N(R$^2$)(R$^2$);
  h) C(=W)—NH-A-(amino acid residue);
  i) A-(amino acid residue)-R$^3$;
  j) S(O)$_n$—R$^3$; or
  k) S(O)$_2$—N(R$^2$)(R$^2$);
  any of which optionally may be substituted by one or more of C$_{1-6}$ alkyl; OH; alkoxy; aryl; halo; CN; NO$_2$; or N(R$^2$)(R$^2$);
each R$^2$ is independently:
  a) H;
  b) CF$_3$;
  c) CN;
  d) optionally substituted, branched or unbranched, alkyl, such as a C$_{1-6}$ alkyl;
  e) optionally substituted, branched or unbranched, alkenyl, such as a C$_{2-6}$ alkenyl;
  f) optionally substituted, branched or unbranched, alkynyl, such as a C$_{2-6}$ alkynyl;
  g) 3-14 membered carbocycle;
  h) optionally substituted aryl;
  i) optionally substituted aralkyl;
  j) optionally substituted alkylaryl;
  k) optionally substituted heterocycle;
  l) optionally substituted alkylheterocycle;
  m) optionally substituted heterocycle-alkyl;
  n) A-heterocycle;
  o) acyl;
  p) alkoxy;
  q) CH$_2$—S(O)$_n$R$^3$;
  r) C(alkyl)$_2$—S(O)$_n$alkyl;
  s) CH(alkyl)-S(O)$_n$alkyl;
  t) CH$_2$NH$_2$;
  u) CH$_2$NH(alkyl);
  v) CH$_2$N(alkyl)$_2$;
  w) CH(alkyl)-NH$_2$;
  x) CH(alkyl)-NH(alkyl);
  y) CH(alkyl)-N(alkyl)$_2$;
  z) C(alkyl)$_2$—NH$_2$;
  aa) C(alkyl)$_2$—NH(alkyl);
  bb) C(alkyl)$_2$—N(alkyl)$_2$;
  cc) CH$_2$—C(=W)H;
  dd) CH$_2$—C(=W)alkyl;
  ee) A-alkyl;
  ff) C(alkyl)$_2$—C(=W)alkyl;
  gg) CH$_2$—C(=W)H;
  hh) CH$_2$—C(=W)alkenyl;
  ii) CH(alkenyl)-C(=W)H;
  jj) A-S(O)alkyl;
  kk) CH(NH)—S(O)$_n$alkyl; or
  ll) A-N(NH)alkyl;
  mm) C(R$^3$)(R$^3$)—S(O)$_n$NH$_2$;
  nn) C(R$^3$)(R$^3$)—S(O)$_n$CF$_3$;
  oo) C(R$^3$)(R$^3$)—NH$_2$;
each R$^3$ is independently:
  a) H;
  b) OH;
  c) halogen (F, Cl, Br, or I);
  d) CF$_3$;
  e) CN;
  f) optionally substituted, branched or unbranched, alkyl, such as a C$_{1-6}$ alkyl;
  g) optionally substituted, branched or unbranched, alkenyl, such as a C$_{2-6}$ alkenyl;
  h) optionally substituted, branched or unbranched, alkynyl, such as a C$_{2-6}$ alkynyl;
  i) 3-14 membered carbocycle;
  j) optionally substituted aryl;
  k) optionally substituted aralkyl;
  l) optionally substituted alkylaryl;
  m) optionally substituted heterocycle;
  n) optionally substituted alkylheterocycle;
  o) optionally substituted heterocycle-alkyl;
  p) A-heterocycle;
  q) acyl;
  r) carboxamido;
  s) carbamoyl;
  t) alkoxy;
  u) OH
  v) OR$^2$;
  w) O-alkyl;
  x) O-alkenyl;
  y) O-alkynyl;
  z) O-alkaryl;
  aa) O-aralkyl;
  bb) O-carbocycle;
  cc) O-heterocycle;
  dd) O-aryl;
  ee) SH
  ff) SR$^2$;

gg) S-alkyl;
hh) S-alkenyl;
ii) S-alkynyl;
jj) S-alkaryl;
kk) S-aralkyl;
ll) S-carbocycle;
mm) S-heterocycle;
nn) S-aryl;
oo) $S(O)_n$—$R^2$;
pp) amino;
qq) $NH^2$;
rr) $NHR^2$.
ss) $N(R^2)(R^2)$;
tt) NH—$S(O)_n$—$R^2$;
uu) NHC(=W)-aryl;
vv) NHC(=W)-alkyl;
ww) NH—C(=W)-heterocycle;
xx) $CH_2$—$S(O)_nR^2$;
yy) $C(=W)R^2$;
zz) C(=W)—$N(R^2)$—$R^2$;
aaa) $C(alkyl)_2$—$S(O)_nR^2$;
bbb) CH(alkyl)-$S(O)_nR^2$;
ccc) $C(alkyl)_2$—$NH_2$;
ddd) CH(alkyl)-N(alkyl)$R^2$;
eee) $C(R^2)(R^2)$—$NR^2R^2$;
fff) $CH_2$N(alkyl)$R^2$;
ggg) CH(alkyl)-$NHR^2$;
hhh) $C(alkyl)_2$—$NHR^2$;
iii) $C(alkyl)_2$—N(alkyl)$R^2$;
jjj) $CH_2$—C(=W)H;
kkk) $CH_2$—C(=W)alkyl;
lll) $CR^2R^2C$(=W)$R^2$;
mmm) A-$R^2$;
nnn) $C(R^2)_2$—C(=W)$R^2$;
ooo) $CH_2$—C(=W)H;
ppp) $CH_2$—C(=W)alkyl;
qqq) CH(alkenyl)-C(=W)H;
rrr) A-$S(O)R^2$;
sss) CH(NH)—$S(O)_nR^2$; or
ttt) A-N(NH)$R^2$;
uuu) $C(R^2)(R^2)$—$S(O)_nNH_2$;
vvv) $C(R^2)(R^2)$—$S(O)_nCF_3$;
www) $C(R^2)(R^2)$—$NH_2$;
wherein the optional substitution comprises one or more of
a) a substituted or unsubstituted heterocycle;
b) C(=W)O-aryl;
c) C(=W)O-alkyl;
d) C(=W)$NH_2$;
e) C(=W)NH-alkyl;
f) C(=W)NH-aryl;
g) C(=W)N-di-alkyl;
h) C(=W)N(alkyl)-aryl;
i) α-amino acid;
j) α-amino ester;
k) α-amino-carboxamide;
l) β-amino acid;
m) β-amino ester; or
n) β-amino-carboxamide;
wherein, when the optional substitution includes a substituted heterocycle, then the heterocycle substitution is selected from the group consisting of:
a) C(=W)O-aryl;
b) C(=W)O-alkyl;
c) C(=W)$NH_2$;
d) C(=W)NH-aryl;
e) C(=W)NH-alkyl;
f) C(=W)N-di-alkyl;
g) C(=W)N(alkyl)-aryl;
h) α-amino acid;
i) α-amino ester;
j) α-amino-carboxamide;
k) β-amino acid;
l) β-amino ester; and
m) β-amino-carboxamide;
n) halo; or
o) cyano,
alone or in any combination;
n independently is 0, 1 or 2;
each A is independently a disubstituted spacer selected from the group consisting of:
a) $C_{1-6}$ alkylene, branched or unbranched, and optionally having one or more heteroatoms, aryl, cycloalkyl or heterocyclyl functions in or attached to the chain;
b) $C_{2-12}$ alkenylene, branched or unbranched, and optionally having one or more heteroatoms, aryl, cycloalkyl or heterocyclyl functions in or attached to the chain;
c) $C_{2-12}$ alkynylene, branched or unbranched, and optionally having one or more heteroatoms, aryl, cycloalkyl or heterocyclyl functions in or attached to the chain;
d) optionally substituted arylene;
e) O-alkylene, branched or unbranched, and optionally having one or more heteroatoms, aryl, cycloalkyl or heterocyclyl functions in or attached to the chain;
f) aralkylene, branched or unbranched, and optionally having one or more heteroatoms, aryl, cycloalkyl or heterocyclyl functions in or attached to the chain;
g) optionally substituted cycloalkyl; and
h) optionally substituted heterocycle;
wherein "A" may be joined by any desired linkage such as, for example, an ether, thioether, amino, carboxamido, ester or carbon-carbon linkage, or any combination thereof;
each $R^{4'}$, $R^{5'}$, $R^{6'}$ and $R^{7'}$ independently is:
a) H;
b) halogen (F, Cl, Br, I);
c) $NO_2$;
d) CN;
e) $CF_3$;
f) OH
g) $OR^2$;
h) SH
i) $SR^2$;
j) $NR^2R^2$;
k) $NHS(O)_nR^2$;
l) NHCO—$C_{1-3}$ alkyl;
m) $S(O)_nR^2$;
n) aryl;
o) heterocycle;
p) $C_{1-6}$ alkyl;
q) $C_{2-6}$ alkenyl;
r) $C_{2-6}$alkynyl;
s) C(=W)—$S(O)_nR^2$;
t) C(=W)—$S(O)_n$—$NR^2R^2$;
u) C(=W)-aryl;
v) C(=W)-alkyl;
w) C(=W)-heterocycle; or
x) C(=W)—$NR^2R^2$;
each of which optionally may be substituted with one or more of:
a) $OR^2$;
b) $S(O)_nR^2$;
c) C(=W)—$S(O)_nR^2$;
d) C(=W)—$S(O)_n$—$NR^2R^2$;
e) C(=W)-aryl;

f) C(=W)-alkyl;
g) C(=W)-heterocycle;
h) C(=W)NR$^2$R$^2$;
i) NO$_2$;
j) CN;
k) CF$_3$;
l) halogen (F, Cl, Br, I);
m) NHS(O)$_n$R$^2$;
n) NHCO—C$_{1-3}$ alkyl;
o) aryl;
p) heterocycle;
q) C$_{1-6}$ alkyl;
r) C$_{2-6}$ alkenyl;
s) C$_{2-6}$ alkynyl; or
t) NR$^2$R$^2$.

In one embodiment of Formula (A), X is an optionally substituted phenyl; Y is any of its definitions; R$^1$, R$^{4'}$, R$^{6'}$, and R$^{7'}$ are all hydrogen; R$^{5'}$ is halogen; and Z is a carboxamide moiety.

In an alternative embodiment, R$^1$ is acyl, alkyl, aryl, alkaryl, or aralkyl.

In yet another alternative embodiment, R$^{4'}$ is fluoro, nitro or cyano, W is oxygen, and Y is O-alkyl.

In a second embodiment of Formula (A), X is an optionally substituted phenyl; Y is any of its definitions; R$^1$, R$^{4'}$, R$^{6'}$, and R$^{7'}$ are all hydrogen; R$^{5'}$ is chlorine; and Z is a carboxamide or carboxamido-heterocyclyl moiety.

In yet another embodiment of Formula (A), X is tolyl, thiazolyl or pyridyl; Y is H, OH, or O-alkyl; R$^1$, R$^{4'}$, R$^{6'}$, and R$^{7'}$ are all hydrogen; R$^{5'}$ is halogen; and Z is carboxamido, acyl, an alkyl-sulphonyl group or a carboxylic acid derivative.

In an alternative to the preceding embodiment, X, Y, R$^1$, R$^{4'}$, R$^{6'}$, R$^{7'}$ and R$^{5'}$ all are as defined above, and Z is a carboxamido-alkylene-heterocycle, typically carboxamido-alkylene-pyridyl; a thioamido-pyridyl wherein the pyridyl is unsubstituted or substituted by OH, OMe or lower alkyl; an imino-nitrile; or an alkylsulphonyl-aryl group.

In yet another embodiment, Z is a carboxamido-alkylene-heterocycle wherein the heterocycle includes at least one N-oxide group.

In a second embodiment, the invention provides a phenylindole for use in the treatment of HIV represented by the following general Formula (B):

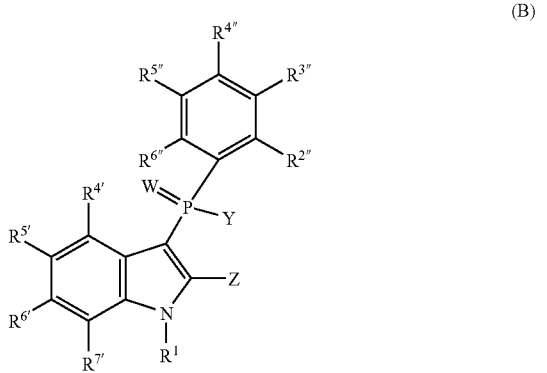

(B)

or a pharmaceutically acceptable salt, prodrug, N-oxide, quaternary amine, stereochemical isomer or tautomer thereof, wherein:

each W, Y, Z, R$^1$, R$^2$, R$^3$, A, n, R$^{4'}$, R$^{5'}$, R$^{6'}$ and R$^{7'}$ is as defined above for Formula (A); and
each R$^{2''}$, R$^{3''}$, R$^{4''}$, R$^{4'''}$, R$^{5''}$, and R$^{6''}$ independently is:
a) H;
b) halogen;
c) NO$_2$;
d) CN;
e) OR$^2$;
f) SR$^2$;
g) NH$_2$;
h) NR$^2$R$^3$;
i) N(R$^2$)—C(=W)—C$_{1-4}$ alkyl;
j) N(R$^2$)—SO$_2$—C$_{1-4}$ alkyl;
k) C$_{1-6}$ alkyl;
l) C$_{2-6}$ alkenyl;
m) C$_{2-6}$ alkynyl;
n) aryl;
o) CF$_3$;
p) CR$^2$R$^2$—S(O)$_n$—R$^3$;
q) CR$^2$R$^2$NR$^2$R$^3$;
r) C—OH;
s) CR$^2$R$^2$—C(=W)R$^2$;
t) acyl;
u) C(=W)R$^2$;
v) C(=W)OR$^2$;
w) C(=W)SR$^2$;
x) C(=W)—NR$^2$R$^3$;
y) C(=W)NH(CH$_2$)$_p$-(amino acid residue);
z) amino residue; or
aa) A-(amino acid residue);
wherein any of the above optionally may be substituted; or
alternatively, R$^{2''}$ or R$^{6''}$ may be joined to Y to form an optionally substituted bicyclic or tricyclic phosphorylated heterocycle wherein each ring comprises 3-14 members.

The following are non-limiting examples of embodiments of Formula (B):
a) Y is alkyl; W is O, S(O)$_n$, or NH; R$^1$, R$^{4'}$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide;
b) Y is aryl; W is O, S(O)$_n$, or NH; R$^1$, R$^{4'}$, R$^{6'}$, R$^{7'}$, R$^{2''}$, R$^{3''}$, R$^{4'''}$, R$^{5''}$, and R$^{6''}$ are all hydrogen; R$^{5'}$ is amino-alkyl, thioamino-alkyl, or aminocarbonyl-alkyl; and Z is carboxamide;
c) Y is —OH or —SR$^2$; W is O, S(O), or N—NH$_2$; R$^1$, R$^{4'}$, R$^{6'}$, R$^{7'}$, R$^{2''}$, R$^{4'''}$, and R$^{6''}$ are all hydrogen; R$^{5'}$ is halogen; R$^{3''}$ and R$^{5''}$ are methyl; and Z is carboxamide;
d) Y is —OH; W is O, S(O)$_n$, or NH; R$^1$, R$^{6'}$, R$^{7'}$, R$^{2''}$, R$^{4'''}$, and R$^{6''}$ are all hydrogen; R$^{4'}$ and R$^{5'}$ are halogen; R$^{3''}$ and R$^{5''}$ are methyl; and Z is carboxamide;
e) Y is —OH; W is O, S(O)$_n$, or N—NR$^2$R$^2$; R$^1$, R$^{4'}$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide;
f) Y is alkenyl; W is O, S(O)$_n$, or NH; R$^1$, R$^{4'}$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide or carboxamide-heterocycle;
g) Y is alkynyl or —NR$^2$R$^3$; W is O, S(O)$_n$, or N—O-alkyl; R$^1$, R$^{4'}$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide;
h) Y is alkenylene; W is O, S(O)$_n$, or NH; R$^1$, R$^{4'}$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide;
i) Y is ethyl; W is O, S(O)$_n$, or N—OH; R$^1$, R$^{4'}$, R$^{6'}$, R$^{7'}$, R$^{2''}$, R$^{3''}$, R$^{4'''}$, R$^{5''}$, and R$^{6''}$ are all hydrogen; R$^{5'}$ is chloro; and Z is carboxamide;

j) Y is —O-methyl; W is O, S(O)$_n$, or NH; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide;

k) Y is —O-ethyl; W is O, S(O)$_n$, or N—NH$_2$; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide-heterocycle;

l) Y is —O-ethyl; W is O, S(O)$_n$, or NH; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is chloro; and Z is carboxamide;

m) Y is —O—H; W is O, S(O)$_n$, or NH; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is a carboxamide alkyl group that is unsubstituted or substituted by one or more —NO$_2$, —NH—C(=O)-alkyl, or —NH—S(O)$_n$-alkyl;

n) Y is —O—H; W is O, S(O)$_n$, or N—NH$_2$; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is a carboxamido-alkylene-heterocyclyl group wherein said heterocycle imidazole, thiazole, pyridyl or furan, and wherein the heterocycle is unsubstituted or further substituted by one or more halo, oxo, —OH, —NO$_2$, -MeOH, —NH—C(=O)-alkyl, or —NH—S(O)$_n$-alkyl;

o) Y is O—H; W is O, S(O)$_n$, or NH; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is carboxamide-cyclopropyl or carboxamide-cyclobutyl;

p) Y is —O-methyl; W is O, S(O)$_n$, or NH; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is a carboxamide-ethyl, carboxamide-ethanol, or carboxamide-ethyl-methoxy;

q) Y is —OH or —NR$^2$R$^3$; W is O, S(O)$_n$, or N—O-alkyl; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is a carboxamide alkyl-phenyl group wherein the phenyl is further substituted by one or more halo, oxo, —OH, —OCH$_3$, —NO$_2$, -MeOH, or —NH—C(=O)-alkyl groups;

r) Y is —OH or —SR$^2$; W is O, S(O)$_n$, or N—NR$^2$R$^2$; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is an isopropanol carboxamide moiety; and s) Y is —OH; W is O, S(O)$_n$, or N—OH; R$^1$, R$^4$, R$^{6'}$, R$^{7'}$, R$^{2''}$, R$^{3''}$, R$^{4'''}$, R$^{5''}$, and R$^{6''}$ are all hydrogen; R$^{5'}$ is halogen; and Z is a thioacetamide group.

In a third embodiment, the present invention provides an optionally substituted 9-11 membered bicyclic 3-phosphoindole for use in the treatment of HIV represented by the following general Formula (C):

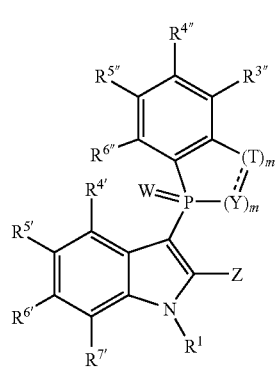

(C)

or a pharmaceutically acceptable salt, prodrug, N-oxide, quaternary amine, stereochemical isomer or tautomer thereof, wherein:

each W, Z, R$^1$, R$^2$, R$^3$, A, n, R$^{4'}$, R$^{5'}$, R$^{6'}$ and R$^{7'}$ is as defined above for Formula (A);

each R$^{3''}$, R$^{4'''}$, R$^{5''}$, and R$^{6''}$ is as defined above for Formula (B);

----indicates the presence of a single or double bond, wherein:

when ---- indicates the presence of a double bond, each Y and T independently is:
 a) CR$^3$;
 b) N; or
 c) S(=W);
 such that at least one of Y and T is CR$^3$; and when ---- indicates the presence of a single bond, then each Y and T independently is:
 a) CHR$^3$;
 b) C(R$^3$)(R$^3$);
 c) O;
 d) S; or
 e) NR$^2$;
 such that at least one of Y and T is C(R$^3$)(R$^3$); and m is 1 or 2, with the proviso that m can only be 2 for T or Y=CR$^2$.

The following are non-limiting examples of embodiments of Formula (C):

a) W is O, Y is CR$^2$, T is (CH$_2$)$_2$, R$^1$, R$^4$, R$^{6'}$, R$^{7'}$, R$^{3''}$, R$^{4'''}$, R$^{5''}$, and R$^{6''}$ are all H; R$^{5'}$ is halogen, and Z is carboxamide;

b) W is S, Y is O, T is CH$_2$, R$^1$, R$^4$, R$^{6'}$, R$^{7'}$, R$^{3''}$, R$^{4'''}$, R$^{5''}$, and R$^{6''}$ are all H; R$^{5'}$ is halogen, and Z is carboxamido-heterocycle wherein said heterocycle is optionally substituted furan, imidazole, thiazole, or pyridyl;

c) W is S, Y is NR$^2$, T is CH$_2$, R$^1$, R$^4$, R$^{6'}$, R$^{7'}$, R$^{3''}$, R$^{4'''}$, R$^{5''}$, and R$^{6''}$ are all H; R$^{5'}$ is halogen, and Z is carboxamide;

d) W is O, Y is SR$^2$, T is CH$_2$, R$^1$, R$^4$, R$^{6'}$, R$^{7'}$, R$^{3''}$, R$^{4'''}$, R$^{5''}$, and R$^{6''}$ are all H; R$^{5'}$ is halogen, and Z is alkyl-carboxamide;

e) W is S, Y is SR$^2$, T is CH$_2$, R$^1$, R$^4$, R$^{6'}$, R$^{7'}$, R$^{3''}$, R$^{4'''}$, R$^{5''}$, and R$^{6''}$ are all H; R$^{5'}$ is halogen, and Z is carboxamide;

f) W is O, Y is CR$^2$, T is C—C(=W)R$^3$, R$^1$, R$^4$, R$^{6'}$, R$^{7'}$, R$^{3''}$, R$^{4'''}$, R$^{5''}$, and R$^{6''}$ are all H; R$^{5'}$ is halogen, and Z is methoxymethyl-carboxamide;

g) W is S, Y is O, T is C—C(=W)R$^3$, R$^1$, R$^4$, R$^{6'}$, R$^{7'}$, R$^{3''}$, R$^{4'''}$, R$^{5''}$, and R$^{6''}$ are all H; R$^{5'}$ is halogen, and Z is carboxamide-cyclobutyl;

h) W is O, Y is SR$^2$, T is C—C(=W)R$^3$, R$^{4'}$, R$^{6'}$, R$^{7'}$, R$^{3''}$, R$^{4'''}$, R$^{5''}$, and R$^{6''}$ are all H; R$^{5'}$ is chloro, and Z is alkyl carboxamide wherein alkyl is optionally substituted by one or more halo, oxo, —OH, —NO$_2$, -MeOH, —NH—C(=O)alkyl, or —NH—S(O)$_n$-alkyl;

i) W is S, Y is NR$^2$, T is CC(=W)R$^3$, R$^4$, R$^{6'}$ R$^{7'}$, R$^{3''}$, R$^{4'''}$, R$^{5''}$, and R$^{6''}$ are all H; R$^{5'}$ is chloro, and Z is carboxamide;

j) W is S, Y is N, T is C—C(=W)R$^3$, R$^1$, R$^4$, R$^{6'}$, R$^{7'}$, R$^{3''}$, R$^{4'''}$, R$^{5''}$, and R$^{6''}$ are all H; R$^{5'}$ is fluoro, and Z is carboxamide;

k) W is NH, Y is CR$^2$, T is NR$_2$, R$^1$, R$^4$, R$^{6'}$, R$^{7'}$, R$^{3''}$, R$^{4'''}$, R$^{5''}$, and R$^{6''}$ are all H; R$^{5'}$ is amino-alkyl, and Z is carboxamide;

l) W is NR$^2$, Y is O, T is (CH$_2$)$_2$, R$^1$, R$^4$, R$^{6'}$, R$^{7'}$, R$^{3''}$, R$^{4'''}$, R$^{5''}$, R$^{6''}$ are all H; R$^{5'}$ is chloro, and Z is carboxamide;

m) W is N—OH, Y is O, T is CH$_2$, R$^1$, R$^4$, R$^{6'}$, R$^{3''}$, R$^{4'''}$, R$^{5''}$, and R$^{6''}$ are all H; R$^{5'}$ is thioamino-alkyl, and Z is alkyl carboxamide;

n) W is S, Y is SR², T is CH₂, R¹, R⁴, R⁶', R⁷', R³'', R⁴'', R⁵'', and R⁶'' are all H; R⁵' is halogen, and Z is a carboxamide-heterocyclyl group wherein the heterocycle is an optionally substituted pyridine, thiazole, imidazole or furan;

o) W is N—O-alkyl, Y is NR², T is CH₂, R¹, R⁴, R⁶', R⁷', R³'', R⁴'', R⁵'', and R⁶'' are all H; R⁵' is halogen, and Z is carboxamide-alkyl group wherein the alkyl is optionally substituted by one or more —NO₂, —NH₂, —NH—C(=W)alkyl, or —NH—S(O)ₙ-alkyl;

p) W is NH, Y is SR², T is (CH₂)₂, R¹, R⁴, R⁶', R⁷', R³'', R⁴'', R⁵'', and R⁶'' are all H; R⁵' is halogen, and Z is carboxamide-alkyl-phenyl wherein phenyl is optionally substituted by one or more halo, oxo, OH, NO₂, MeOH, —NH—C(=O)alkyl or —NH—S(O)ₙ-alkyl groups;

q) W is NR², Y is (CH₂)₂, T is NR₂, R¹, R⁴, R⁶', R⁷', R³'', R⁴'', R⁵'', and R⁶'' are all H; R⁵' is halogen, and Z is a carboxamide-cyclopropyl group;

r) W is N—OH, Y is CH, T is O, R¹, R⁴, R⁶', R⁷', R³'', R⁴'', R⁵'', and R⁶'' are all H; R⁵' is halogen, and Z is a carboxamide-cyclopropyl group;

s) W is N—O-alkyl, Y is O, T is (CH₂)₂, R¹, R⁴, R⁶', R⁷', R³'', R⁴'', R⁵'', and R⁶'' are all H; R⁵' is chloro, and Z is carboxamide-methoxyethyl;

t) W is O, Y is N, T is CH₂, R¹, R⁴, R⁶', R⁷', R³'', R⁴'', R⁵'', and R⁶'' are all H; R⁵' is halogen, and Z is carboxamide-ethanol;

u) W is N—NR²R², Y is NR², T is CH₂, R¹, R⁴, R⁶', R⁷', R³'', R⁴'', R⁵'', and R⁶'' are all H; R⁵' is halogen, and Z is carboxamide; and v) W is O, Y is CR², T is CH₂, R¹, R⁴, R⁶' R⁷', R³'', R⁴'', R⁵'', and R⁶'' are all H; R⁵' is aminocarbonyl-alkyl, and Z is carboxamide.

In one set of embodiments of Formula A, B or C, Z is C(=W)—R³; C(=W)—NH-A-C(=W)—N(R²)(R²); C(=W)—NH-A-R³; C(=W)—NH—R²; or C(=W)-A-R³.

In one embodiment of Formula A, B or C, the compound includes a charged heteroatom. In particular, a charged nitrogen, such as through an N-oxide, is part of the compound. The charged heteroatom can be on a heteroaromatic ring that is attached to the indole, for example through C(O)NH-alkyl, or specifically through C(O)NH—CH₂.

In a particular embodiment of Formula A, B or C, Z is C(=O)—NH—R² wherein R² is an optionally substituted alkylheterocycle, wherein the heterocycle is of the formula

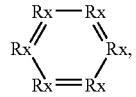

wherein each Rx is independently CH or N⁺—O⁻. In a particular embodiment, one of Rx is N⁺—O⁻. The alkyl group can be C₁₋₁₀ alkyl, or C₁₋₄ alkyl, or can specifically be a methylene or ethylene. In a specific embodiment, R² is of the formula

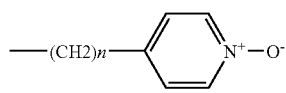

where n is 0, 1 or 2.

In particular embodiments of Formula A, B or C, the compound is:

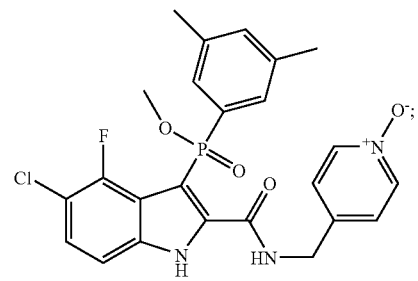
B

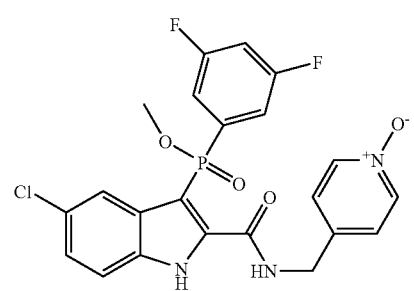
C

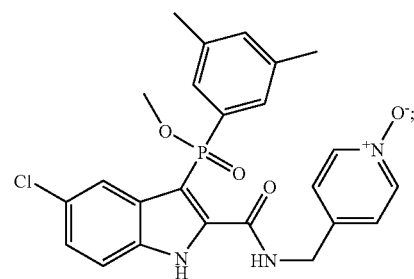
D

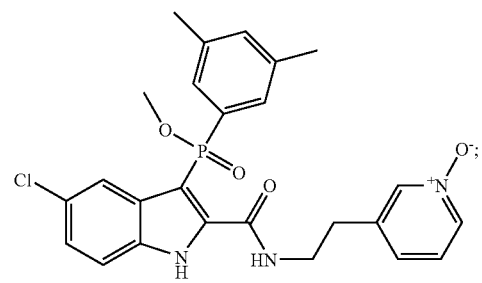
E

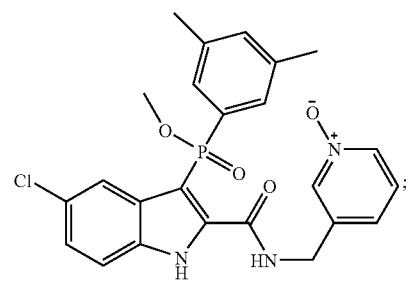
F

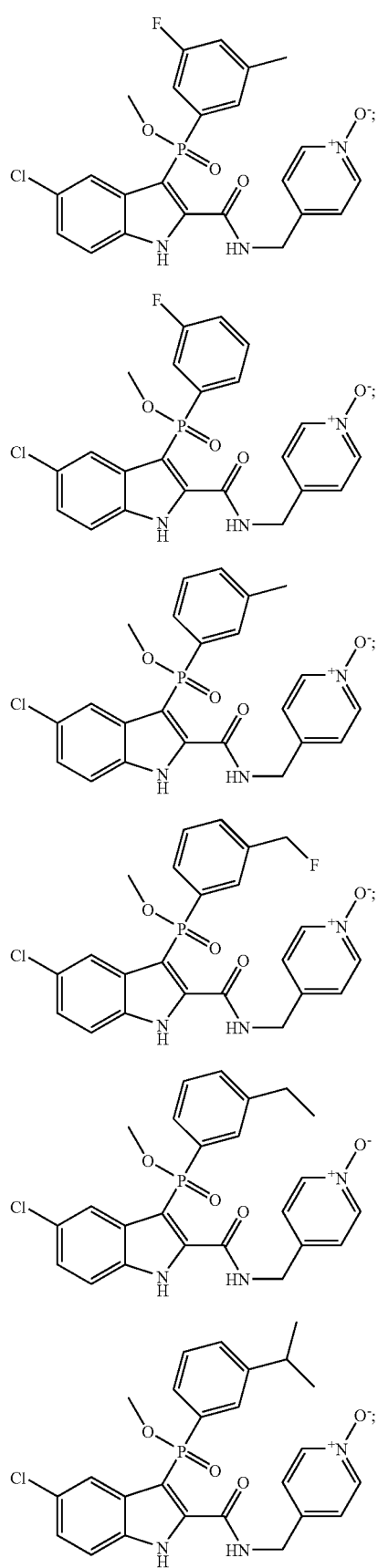
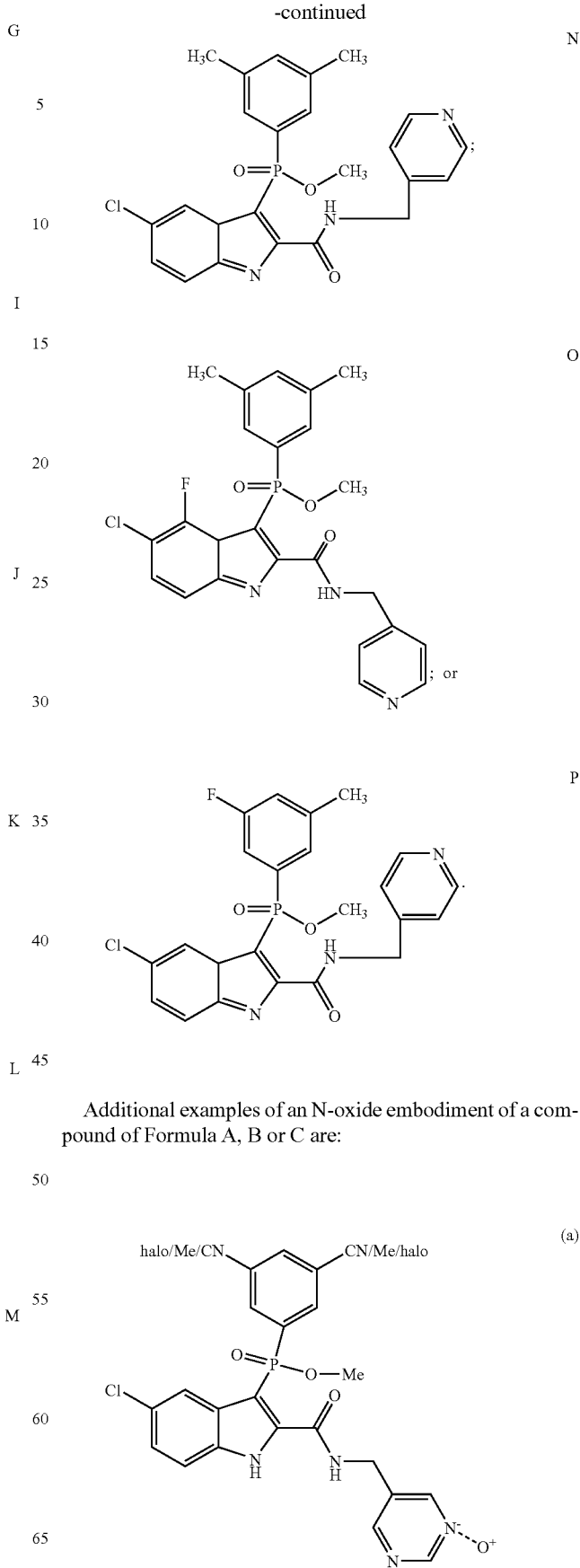
Additional examples of an N-oxide embodiment of a compound of Formula A, B or C are:

-continued (b)

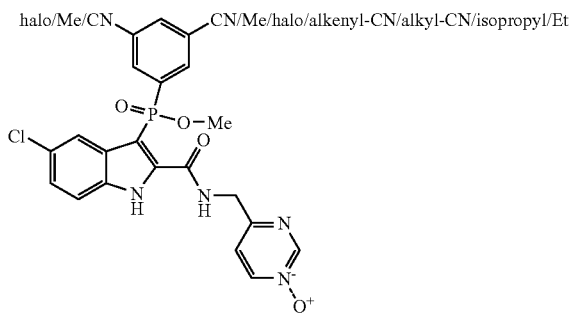

Either substituent on the phenyl ring may be substituted by CN, Me, halo, alkyl, alkenyl, alkynyl, alkyl-CN or alkenyl-CN, as the most commonly synthesized and tested N-oxides in the series to date.

II. Particular Sub-Embodiments of the Present Invention

In the first embodiment of the invention, the compounds are represented generally by the Formula (A):

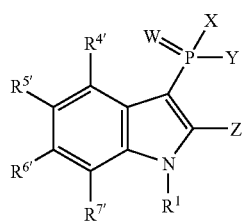

(A)

or a pharmaceutically acceptable salt, prodrug, N-oxide, quaternary amine, stereochemical isomer or tautomer thereof, wherein:

X and Y, each independently, is:
- a) 3-14 membered carbocycle, aryl, heterocycle, any of which may comprise a monocyclic, bicyclic, tricyclic or spiro structure, or optionally may be substituted;
- b) H;
- c) OH;
- d) Cl, Br, I, F;
- e) $CF_3$;
- f) $C_{1-6}$ alkyl;
- g) $C_{2-6}$ alkenyl;
- h) $C_{2-6}$ alkynyl;
- i) alkylheterocycle;
- j) $NH_2$;
- k) NH-alkyl;
- l) N-dialkyl;
- m) NH-aryl;
- n) N-alkaryl;
- o) N-aralkyl;
- p) NH-heterocycle;
- q) N-alkyl-heterocycle;
- r) N-alkenyl-heterocycle;
- s) N-alkynyl-heterocycle;
- t) O-alkyl;
- u) O-alkenyl;
- v) O-alkynyl;
- w) O-alkylaryl;
- x) O-aryl;
- y) O-heterocycle;
- z) O-aralkyl;
- aa) O-carbocycle;
- bb) $SR^2$; or
- cc) $NR^2R^3$;

alternatively, X and Y may be joined to form an optionally substituted bicyclic or tricyclic phosphorylated heterocycle wherein each ring comprises 3-7 members;

Z is:
- a) H;
- b) alkoxy;
- c) $NO_2$;
- d) $N(R^2)(R^3)$;
- e) $OR^2$;
- f) carboxamido;
- g) amido;
- h) acyl;
- i) $S(O)_n R^2$;
- j) $S(O)_n-NR^2R^3$;
- k) $C_{1-6}$ alkyl;
- l) $C_{2-6}$ alkenyl;
- m) $C_{2-6}$ alkynyl;
- n) alkaryl;
- o) aralkyl;
- p) heterocycle;
- q) alkyl-heterocycle;
- r) aryl;
- s) CN;
- t) $C(=W)-R^2$;
- u) $C(=W)NH-C(R^2)(R^2)-C(=W)-N(R^2)(R^2)$;
- v) $C(=W)NH-P(=W)(R^2)-A-R^2$;
- w) $C(=W)NH-A-S(O)_n-NR^2$;
- x) $C(=W)NH-CR^2R^3-S(O)_n-NR^2R^3$;
- y) $C(=W)-NH-A-C(=W)-N(R^2)(R^3)$;
- z) $C(=W)-N(R^2)(R^3)$;
- aa) $C(=W)-NH-A-R^2$;
- bb) $C(=W)-NH-NH-R^2$;
- cc) $C(=W)-NH-C(R^2)(R^2)-C(=W)NH-C(R^2)(R^2)C(=W)-N(R^2)(R^3)$;
- dd) $C(=W)-NH-R^2$;
- ee) $C(=W)-NH-A-C(=W)-NH-A-C(=W)-NH_2$;
- ff) $C(R^2)(R^2)(R^3)$;
- gg) $C(R^2)(R^2)-NH-R^2$;
- hh) $A-S(O)_n-R^2$;
- ii) $C(=W)-A-C(=W)-A-C(=W)R^3$;
- jj) $A-R^2$;
- kk) $C(=W)-(O)R^2$;
- ll) $C(=W)-A-C(=W)-NH_2$;
- mm) an amino acid residue;
- nn) $C(=W)-N(R^2)-A$-(amino acid residue);
- oo) $C(=W)-N(R^2)-A$-(amino acid residue)-$C(=W)-R^2$;
- pp) $C(=W)$-amino acid residue;
- qq) $C(=W)-N(R^2)-A$-(amino acid residue)-$A-C(=W)-R^2$;
- rr) $C(=W)-OR^3$;
- ss) $C(=W)-S(R^2)$;
- tt) $C(=W)-NH-NH-R^2$;
- uu) $C(=W)-NH-N(R^2)-A-C(=W)R^2$;
- vv) $C(=W)-N(R^2)-C(=W)-R^3$;
- ww) $C(=W)-A-NH-C(=W)R^2$;
- xx) $C(=W)-A-NH-C(=W)OR^3$;
- yy) $C(=W)-A-R^3$;
- zz) $C(=W)-NH-NH-CH_2-C(=W)R^2$;
- aaa) $P(=W)(R^2)(R^2)$; or
- bbb) $A-P(=W)(R^2)(R^2)$;

wherein each of the foregoing X, Y and Z independently may be unsubstituted or substituted by one or more of:
a) H;
b) $C_{1-6}$ alkyl;
c) alkoxy;
d) OH;
e) oxo;
f) halo;
g) $NR^2R^2$;
h) optionally substituted aryl;
i) optionally substituted heterocyclyl;
j) O—C(=W)-alkyl;
k) C(=W)—$OR^2$;
l) CN;
m) $NO_2$;
n) NH—C(=W)alkyl;
o) NH—$S(O)_n$-alkyl;
p) NH—$S(O)_n$—$NR^2R^2$; or
q) $C_{3-6}$ cycloalkyl;

W is:
a) O;
b) S;
c) NH;
d) N—$N(R^2)(R^2)$;
e) $N(R^2)$;
f) N—OH; or
g) N—O-alkyl;

$R^1$ is:
a) H;
b) $R^2$;
c) C(=W)—$R^2$;
d) C(=W)—$O(R^2)$;
e) C(=W)—$S(R^2)$;
f) C(=W)—NH—$R^2$;
g) C(=W)—$N(R^2)(R^2)$;
h) C(=W)—NH-A-(amino acid residue);
i) A-(amino acid residue)-$R^2$;
j) $S(O)_n$—$R^3$; or
k) $S(O)_2$—$N(R^2)(R^2)$;
any of which optionally may be substituted by one or more:
a) $C_{1-6}$ alkyl;
b) OH;
c) alkoxy;
d) aryl;
e) halo;
f) CN;
g) $NO_2$; or
h) $N(R^2)(R^2)$;

$R^2$ is:
a) H;
b) OH;
c) halogen;
d) optionally substituted, branched or unbranched alkyl;
e) optionally substituted, branched or unbranched alkenyl;
f) optionally substituted, branched or unbranched alkynyl;
g) 3-14 membered carbocycle;
h) alkylheterocycle;
i) acyl;
j) carboxamido;
k) carbamoyl;
l) alkoxy;
m) optionally substituted aryl;
n) optionally substituted aralkyl;
o) optionally substituted alkylaryl;
p) O-alkyl;
q) O-alkenyl;
r) O-alkynyl;
s) O-alkaryl;
t) O-aralkyl;
u) O-carbocycle;
v) O-heterocycle;
w) O-aryl;
x) $CF_3$;
y) CN;
z) $S(O)_n$—$R^3$;
aa) $N(R^3)(R^3)$;
bb) NH—$S(O)_n$—$R^3$;
cc) NHC(=W)-aryl;
dd) NHC(=W)-alkyl;
ee) NHC(=W)-heterocycle;
ff) $CH_2$—$S(O)_nR^3$;
gg) C(=W)$R^3$;
hh) C(=W)$NR^3R^3$;
ii) $C(alkyl)_2$—$S(O)_nR^3$;
jj) CH(alkyl)-$S(O)_nR^3$;
kk) $C(alkyl)_2$—$NH_2$;
ll) CH(alkyl)-N(alkyl)$R^3$;
mm) $CR^3R^3$—$NR^3R^3$;
nn) $CH_2N(alkyl)R^3$;
oo) CH(alkyl)-$NHR^3$;
pp) $C(alkyl)_2$—$NHR^3$;
qq) $C(alkyl)_2$—N(alkyl)$R^3$;
rr) $CH_2$—C(=W)H;
ss) $CH_2$—C(=W)alkyl;
tt) $CR^3R^3$—C(=W)$R^3$;
uu) A-$R^3$;
vv) $C(R^3)_2$—C(=W)$R^3$;
ww) $CH_2$—C(=W)H;
xx) $CH_2$—C(=W)alkenyl;
yy) CH(alkenyl)C(=W)H;
zz) A-$S(O)R^3$;
aaa) CH(NH)—$S(O)_nR^3$; or
bbb) A-N(NH)$R^3$;
wherein said optional substitution comprises one or more of:
a) a substituted or unsubstituted heterocycle;
b) C(=W)O-aryl;
c) C(=W)O-alkyl;
d) C(=W)$NH_2$;
e) C(=W)NH-alkyl;
f) C(=W)NH-aryl;
g) C(=W)N-di-alkyl;
h) C(=W)N(alkyl)-aryl;
i) α-amino acid;
j) α-amino ester;
k) α-amino-carboxamide;
l) β-amino acid;
m) β-amino ester; or
n) β-amino carboxamide;

$R^3$ is:
a) H;
b) OH;
c) $C_{1-6}$ alkyl;
d) $C_{2-6}$ alkenyl;
e) $C_{2-6}$ alkynyl;
f) alkoxy;
g) $CF_3$;
h) CN;
i) amino;
j) $NR^2R^2$;
k) O-alkyl;
l) O-alkenyl;
m) O-alkynyl;
n) $C(R^2)(R^2)$—$S(O)NH_2$;

o) C(R²)(R²)—S(O)$_n$CF$_3$;
p) C(R²)(R²)—NH$_2$;
q) A-heterocycle;
r) C(R²)(R²)—NR²R²;
s) C(R²)(R²)—C(=W)R²;
t) aryl;
u) carbocycle;
v) heterocycle;
w) cycloalkyl;
x) alkaryl;
y) alkylheterocycle;
z) aralkyl; or
aa) heterocycle-alkyl;
any of which may be unsubstituted or substituted with one or more of the following, taken in any combination:
  a) halo;
  b) OH;
  c) OR²;
  d) SR²;
  e) COOH;
  f) carboxlic acid ester;
  g) C(=W)R²;
  h) C(=W)OR²;
  i) C(=W)OR³;
  j) C(=W)SR²;
  k) A-C(=W)NH$_2$;
  l) C(=W)NR²R³;
  m) NR²R²;
  n) NR²R²;
  o) NR²—S(O)$_n$R³;
  p) NR²—C(=W)—C$_{1-6}$alkyl;
  q) S(O)$_n$R³;
  r) C$_{1-6}$alkoxy;
  s) C$_{1-6}$ thioether;
  t) amino acid residue;
  u) NH-A-(amino acid residue);
  v) C(=W)NH-A-(amino acid residue); and
  wherein when said optional substitution comprises a substituted heterocycle, then substitution is selected from the group consisting of:
    a) C(=W)O-aryl;
    b) C(=W)O-alkyl;
    c) C(=W)NH$_2$;
    d) C(=W)NH-aryl;
    e) C(=W)NH-alkyl;
    f) C(=W)N-di-alkyl;
    g) C(=W)N(alkyl)-aryl;
    h) α-amino acid;
    i) α-amino ester;
    j) α-amino-carboxamide;
    k) β-amino acid;
    l) β-amino ester; or
    m) β-amino-carboxamide;
    n) halo; or
    o) cyano,
  taken alone or in any combination;
n independently is 0, 1 or 2;
each A is independently a disubstituted spacer selected from the group consisting of:
  a) C$_{1-6}$ alkylene, branched or unbranched, and optionally having one or more heteroatoms, aryl, cycloalkyl or heterocyclyl functions in or attached to the chain;
  b) C$_{2-12}$ alkenylene, branched or unbranched, and optionally having one or more heteroatoms, aryl, cycloalkyl or heterocyclyl functions in or attached to the chain;
  c) C$_{2-12}$ alkynylene, branched or unbranched, and optionally having one or more heteroatoms, aryl, cycloalkyl or heterocyclyl functions in or attached to the chain;
  d) optionally substituted arylene;
  e) O-alkylene, branched or unbranched, and optionally having one or more heteroatoms, aryl, cycloalkyl or heterocyclyl functions in or attached to the chain;
  f) aralkylene, branched or unbranched, and optionally having one or more heteroatoms, aryl, cycloalkyl or heterocyclyl functions in or attached to the chain;
  g) optionally substituted cycloalkyl; and
  h) optionally substituted heterocycle;
  wherein "A" may be joined by any desired linkage such as, for example, an ether, thioether, amino, carboxamido, ester or carbon-carbon linkage, or any combination thereof;
Each $R^{4'}$, $R^{5'}$, $R^{6'}$ and $R^{7'}$ independently is:
  a) H;
  b) halogen;
  c) NO$_2$;
  d) CN;
  e) CF$_3$;
  f) OR²;
  g) NR²R²;
  h) NHS(O)$_n$R²;
  i) NHCO—C$_{1-3}$ alkyl;
  j) S(O)$_n$R²;
  k) aryl;
  l) heterocycle;
  m) C$_{1-6}$ alkyl;
  n) C$_{2-6}$ alkenyl;
  o) C$_{2-6}$ alkynyl;
  p) C(=W)—S(O)$_n$R²;
  q) C(=W)—S(O)$_n$—NR²R²;
  r) C(=W)-aryl;
  s) C(=W)-alkyl;
  t) C(=W)-heterocycle; or
  u) C(=W)—NR²R²;
  each of which optionally may be substituted with one or more of:
    a) OR²;
    b) S(O)$_n$R²;
    c) C(=W)—S(O)$_n$R²;
    d) C(=W)—S(O)$_n$—NR²R²;
    e) C(=W)-aryl;
    f) C(=W)-alkyl;
    g) C(=W)-heterocycle;
    h) C(=W)NR²R²;
    i) H;
    j) NO$_2$;
    k) CN;
    l) CF$_3$;
    m) halogen;
    n) NHS(O)$_n$R²;
    o) NHCO—C$_{1-3}$ alkyl;
    p) aryl;
    q) heterocycle;
    r) C$_{1-6}$ alkyl;
    s) C$_{2-6}$ alkenyl;
    t) C$_{2-6}$ alkynyl; or
    u) NR²R².

In one embodiment of Formula (A), X is an optionally substituted phenyl; Y is any of its definitions; $R^1$, $R^{4'}$, $R^{6'}$, and $R^{7'}$ are all hydrogen; $R^{5'}$ is halogen; and Z is a carboxamide moiety.

In an alternative embodiment, $R^1$ is acyl, alkyl, aryl, alkaryl, or aralkyl.

In yet another alternative embodiment, $R^{4'}$ is fluoro, nitro or cyano, W is oxygen, and Y is O-alkyl.

In a second embodiment of Formula (A), X is an optionally substituted phenyl; Y is any of its definitions; $R^1$, $R^{4'}$, $R^{6'}$, and $R^{7'}$ are all hydrogen; $R^{5'}$ is chlorine; and Z is a carboxamide or carboxamido-heterocyclyl moiety.

In yet another embodiment of Formula (A), X is tolyl, thiazolyl or pyridyl; Y is H, OH, or O-alkyl; $R^1$, $R^{4'}$, $R^{6'}$, and $R^{7'}$ are all hydrogen; $R^{5'}$ is halogen; and Z is carboxamido, acyl, an alkyl-sulphonyl group or a carboxylic acid derivative.

In an alternative to the preceding embodiment, X, Y, $R^1$, $R^{4'}$, $R^{6'}$, $R^{7'}$ and $R^{5'}$ all are as defined above, and Z is a carboxamido-alkylene-heterocyclyl wherein the heterocycle typically is imidazole, furan, pyridine, pyrimidine, or thiazole that optionally may be substituted; a thioamido-pyridyl wherein the pyridyl is unsubstituted or substituted by OH, OMe or lower alkyl; an imino-nitrile, or an alkylsulphonyl-aryl group.

A first series of subembodiments of the present invention is given where the Formula (A) is as provided above, and W, X and Y are defined as:

a) W is O, X is alkyl, and Y is —O-alkyl;
b) W is O, X is —O-aryl, and Y is alkyl;
c) W is O, X is —O-aryl, and Y is —$NR^2R^3$;
d) W is O, X is —O-alkyl, and Y is alkyl;
e) W is O, X is —O-alkyl, and Y is halo;
f) W is O, X is —O-heterocycle, and Y is alkyl;
g) W is O, X is aryl, and Y is —O-alkyl;
h) W is O, X is heterocyclyl, and Y is —O-aryl;
i) W is O, X is alkyl, and Y is —O-heterocyclyl;
j) W is —$NR^2R^2$, X is heterocyclyl, and Y is —O-aryl;
k) W is —$NR^2R^2$, X is alkyl, and Y is halo;
l) W is S, X is alkyl, and Y is —O-alkyl;
m) W is S, X is alkyl, and Y is —$NR^2R^3$;
n) W is S, X is —O-aryl, and Y is alkyl;
o) W is S, X is —O-aryl, and Y is C-halo;
p) W is S, X is —O-alkyl, and Y is alkyl;
q) W is S, X is —O-heterocycle, and Y is alkyl;
r) W is S, X is aryl, and Y is —O-alkyl;
s) W is S, X is heterocyclyl, and Y is —O-aryl;
t) W is S, X is alkyl, and Y is —O-heterocyclyl;
u) W is O, X is aryl, and Y is —O-aryl;
v) W is —$NR^2$, X is —O-alkyl, and Y is —$NR^2R^3$;
w) W is O, X is —O-aryl, and Y is —O-aryl;
x) W is O, X is alkyl, and Y is alkyl; and
y) W is —$NR^2$, X is —O-alkyl, and Y is alkyl.

A second series of subembodiments of the present invention is given where Formula (A) is as given, $R^1$ is H, alkyl, acyl, aryl, aralkyl, or alkaryl; and Z is defined as:

a) —C(=W)$NR^2R^3$, $R^2$ is H, and $R^3$ is $NR^2R^2$;
b) —C(=W)$NR^2R^3$, $R^2$ is H, and $R^3$ is $NR^2R^2$, or $R^2$ is $C_{1-5}$ alkyl optionally substituted with OH and $R^3$ is —$NH_2$;
c) —C(=W)$NR^2R^3$, $R^2$ is H, and $R^3$ is $(CH_2)_m C(=W)NR^2R^2$;
d) —C(=W)$NR^2R^3$, $R^2$ is H, and $R^3$ is alkyl substituted by optionally substituted aryl or heterocycle;
e) —C(=W)$R^3$, $R^3$ is an amino acid residue or —NH$(CH_2)_p$-(amino acid residue);
f) —C(=W)NHHC$_2$H$_5$OH;
g) —C(=W)NHCH$_2$C(=W)NH$_2$;
h) —C(=W)NHCH$_2$CONHNH$_2$;
i) —C(=W)NHCH$_2$CH$_2$-(2-NO$_2$, 5-methyl imidazole);
j) —C(=W)NHCH$_2$NHCH(CH$_3$)C(=W)OH;
k) —C(=W)NHCH=CHC(=W)NH$_2$;
l) —C(=W)$NR^2R^5NR^2R^3$, $R^5$ is (=O), $R^2$ and $R^3$ are as defined above;
m) —C(=W)$NR^2NR^2$—C(=W)$R^3$, $R^2$ is H or alkyl, and $R^3$ is aryl;
n) —C(=W)N(—$NR^2R^3$)—N(—$NR^2R^3$)$R^3$, $R^2$ is H, $R^3$ is $R^2$ or alkoxy;
o) —C(=W)NH$R^2$C(=W)-Q, Q is heterocycle, and $R^2$ is as defined above;
p) —C(=W)$NR^2R^3$, $R^2$ is as defined above, and $R^3$ is —OH;
q) —COR$^2R^3$, $R^2$ is amino and $R^3$ is a heterocycle;
r) —C(=W)NHNHC(=W)$R^2$ and $R^2$ is NH$_2$;
s) —C(=W)—$R^2$—CH-A-C(=W)NH$_2$, and $R^2$ is NH;
t) —C(=W)—$R^2$—CH-A-C(=W)H, and $R^2$ is NH;
u) —C(=W)—$R^2$—CH-A-C(=W)OH, and $R^2$ is NH;
v) —C(=W)—$R^2$—CH-A-$R^1$, $R^2$ is NH, and $R^3$ is CH$_1$;
w) —C(=W)NH$R^2$C(=W)NH$_2$, and $R^2$ is optionally substituted, branched chain alkyl;
x) —C(=W)$R^2R^3$, $R^2$ is NH or alkyl, and $R^3$ is NH$_2$;
y) —C(=W)$R^2$—C(=W)O$R^3$, and $R^2$ and $R^3$ are as defined as above;
z) —C(=W)$R^2$—NH—C(=W)C$_{1-4}$ alkoxy, and $R^2$ is as defined above;
aa) —C(=W)$R^2$C(=W)C$_{1-4}$ alkoxy, and $R^2$ is as defined above;
bb) —C(=W)$R^2$, and $R^2$ is NH$_2$;
cc) —C(=W)$R^2$—NH—C(=W)O$R^3$, and $R^2$ and $R^3$ are as defined as above;
dd) —C(=W)$R^2$—C(=W)$R^2$, and $R^2$ is as defined above;
ee) —C(=W)NH$R^2$ where $R^2$ is optionally substituted aryl, cycloalkyl or a heterocyclyl ring;
ff) —C(=W)$R^2$—W—$R^3$, where $R^2$ and $R^3$ are as defined as above;
gg) —C(=W)—NH—CH($R^2$)—C(=W)—NH$_2$, and $R^2$ is as defined above;
hh) —C(=(W)—NH—NH$_2$;
ii) —C(=W)—NH—NH($R^2$), and $R^2$ is as defined above;
jj) —C(=W)—NH—CH(C[=W]NH$_2$)(CH$_2$—C[=W]-O-aryl);
kk) —C(=W)—NH—CH(—[CH$_2$]$_4$—NH—C[=W]-t-BuO)(—C[=W]—NH$_2$);
ll) —C(=W)—NH—CH(—CH$_2$—CH$_2$—C[=W]-t-BuO)(C[=W]—NH$_2$);
mm) —C(=W)—NH—CH($R^3$)(—C[=W]—NH$_2$), and $R^3$ is as defined above;
nn) —C(=W)—NH—CH(—CH$_2$—$R^3$)(—C[=W]—NH$_2$), and $R^3$ is as defined above;
oo) —C(=W)—NH—CH(—CH$_2$OH)(—C[=W]—NH$_2$);
pp) —C(=W)—NH—CH(C[=W]—NH$_2$)(C[=W]—NH$_2$);
qq) —C(=W)—NH$R^2$—C[=W]NH$_2$, and $R^2$ is as defined above;
rr) —C(=W)—NH—CH(—[CH$_2$]$_4$—NH—C[=W]—O—CH$_2$—$R^3$)(—C[=W]—NH$_2$), and $R^3$ is as defined above;
ss) —C(=W)—NH—CH(—CH$_2$—C[=W]—NH$_2$)(—C[=W]—NH$_2$);
tt) —C(=W)—NH—CH(—CH$_2$—$R^3$)(—C[=W]—NH$_2$), where $R^3$ is as defined above;
uu) —C(=W)—NH—CH(—[CH$_2$]$_4$—NH$_2$)(—C[=W]—NH$_2$);
vv) —C(=W)—NH—CH(—CH[$R^2$][OH])(—C[=W]—NH$_2$), and $R^2$ is as defined above;
ww) —C(=W)—NH—CH(—$R^2$)(—C[=W]—NH$_2$), and $R^2$ is as defined above;

xx) —C(=W)—NH—CH(—R²—C[=W]—NH₂)(—C[=W]—NH₂), and R² is as defined above;
yy) —C(=W)—NH—CH(—R²—SCH₃)(—C[=W]—NH₂), and R² is as defined above;
zz) —C(=W)—NH—CH(—C[=N]—NH₂)(—C[=W]—NH₂);
aaa) —C(=W)—NH—CH(—R³)(—C[=W]—NH₂), and R³ is as defined above;
bbb) —C(=W)—NH—CH(—CH₂—R³)(—C[=W]—NH₂), and R³ is as defined above;
ccc) —C(=W)—NH—CH(—R²)(—C[=W]—NH₂), and R² is as defined above;
ddd) —C(=W)—NH—R²—C[=W]R³, and R² is alkylene and R³ is aryl or heteroaryl;
eee) —C(=W)—NH—R²—R³—C[=W]—NH₂, where R² is alkylene and R³ is aryl or heteroaryl;
fff) —C(=W)—NH—NH—R²—R³—C(=W)NH₂, where R² is alkylene and R³ is aryl or heteroaryl;
ggg) —C(=W)NH—NH—CH(R³)—C(=W)R², and R² is NH₂ and R³ is optionally substituted aryl or heteroaryl;
hhh) —C(=W)NHR²(—R³)—C(=W)NH₂, where R² is alkylene and R³ is optionally substituted alkyl, aryl or heteroaryl;
iii) —C(=W)NHR²(—R³)—C(=W)NH—R²—C(=W)OH, where R² is alkylene and R³ is optionally substituted alkyl, aryl or heteroaryl;
jjj) —C(=W)NHR²(—R³)—C(=W)NH—R²—NH₂, where R² is alkylene and R³ is optionally substituted alkyl, aryl or heteroaryl;
kkk) —C(=W)NHR²(—R³)—C(=W)NH—R³, where R² is alkylene and R³ is optionally substituted alkyl, aryl or heteroaryl;
lll) —C(=W)—R²—(CH₂)$_p$-A-C(=W)—NH₂, where R² is —NH, p is 0-10, A is a divalent linker or an optionally substituted aryl or heteroaryl, and W is O or S;
mmm) —C(=W)NH—R³, where R³ is an optionally substituted heterocycle;
nnn) —C(=W)—NH—R²—R⁵—R³, where W is O or S, R² is alkylene, alkenylene or alkynylene, R⁵ is —SO₂, and R³ is —NH₂;
ooo) —C(=W)—NH—NH—R²(R³)—R⁵—NH₂, where W is O or S, R² is alkylene, alkenylene or alkynylene, R³ is aryl, arylene, or heteroaryl, and R⁵ is —SO₂;
ppp) —C(=W)—NH—R³(R⁵—NH₂) where W is O or S, R³ is aryl, arylene or heteroaryl, and R⁵ is SO₂;
qqq) —C(=W)—NH—R²—R³(R⁵—NH₂) where W is O or S, R² is alkylene, alkenylene or alkynylene, R³ is aryl, arylene or heteroaryl, and R⁵ is SO₂;
rrr) —C(=W)—NH—R³(R²R⁵—NH₂) where W is O or S, R² is alkylene, alkenylene or alkynylene, R³ is aryl, arylene or heteroaryl, and R⁵ is SO₂;
sss) —(=W)—NHR²(—R³)—C(=W)NH—R²—C(=W)OH, where R² is an optionally substituted alkylene, alkenylene, or alkynylene, and R³ is any of its definitions as provided above;
ttt) —C(=W)—NHR²(—R³)—C(=W)NH—R²—C(=W)NH₂, where R² is an optionally substituted alkylene, alkenylene, or alkynylene, and R³ is any of its definitions as provided above;
uuu) —C(=W)—NHR²—C(=W)NH—R²—C(=W)OH, where R² is an optionally substituted alkylene, alkenylene, or alkynylene, and R³ is any of its definitions as provided above; or
vvv) —C(=W)—NHR²—C(=W)NH—R²—C(=W)NH₂, where R² is an optionally substituted alkylene, alkenylene, or alkynylene, and R³ is any of its definitions as provided above; and wherein R², R³ and A each is as defined previously.

A third series of subembodiments of the present invention is given for the Formula (A) as provided above where R⁴', R⁵', R⁶' and R⁷' are defined as:

a) R⁶' and R⁷' are both hydrogen, and R⁴' and R⁵' independently are halo; —NO₂; —N; —OR²; —NR²R²; —NH—R⁵—C₁₋₃ alkyl; —NHCO—C₁₋₃ alkyl; oxime; hydrazine; —H(SO₂)C₁₋₃alkyl; —NH—O—C₁₋₃ alkyl; —NHOH; or C₁₋₃ alkyl or alkenyl optionally substituted with one or more —OH, —SR, —C(=W)H, —C(=W)OH, halogen, —NR²R², C₁₋₃ alkoxy, or C₁₋₃ thioether;
b) R⁴' and R⁷' are both hydrogen, and R⁵' and R⁶' independently are halo; —NO₂; —N; —OR²; —NR²R²; —NHSO₂—C₁₋₆ alkyl; —NHCO—C₁₋₆ alkyl; oxime; hydrazine; —H—O—C₁₋₆ alkyl; —NH—OH; or C₁₋₃ alkyl or alkenyl optionally substituted with one or more —OH, —SR, —C(=W)H, —(=W)OH, halogen, —NR²R², C₁₋₃ alkoxy, or C₁₋₃ thioether;
c) R⁴' and R⁶' are both hydrogen, and R⁵' and R⁷' independently are halo; —NO₂; —N; —OR²; —NR²R²; —NHSO₂—C₁₋₆ alkyl; —NHCO—C₁₋₆ alkyl; oxime; hydrazine; —H—O—C₁₋₆ alkyl; —NH—OH; or C₁₋₆ alkyl or alkenyl optionally substituted with one or more —OH, —SR, —C(=W)H, —(=W)OH, halogen, —NR²R², C₁₋₃ alkoxy, or C₁₋₃ thioether;
d) R⁴' and R⁷' are both hydrogen, and R⁵' and R⁶' independently are halo; —NO₂; —N; —OR²; —NR²R²; —NH—O—C₁₋₄ alkyl; —NHOH; or C₁₋₆ alkyl or alkenyl optionally substituted with one or more —OH, —SR, —C(=W)H, —C(=W)OH, halogen or —NH₂;
e) R⁴' and R⁶' are both hydrogen, and R⁵' and R⁷' independently are halo; —NO₂; —N; —OR²; —NR²R²; —NH—O—C₁₋₃ alkyl; —NHOH; or C₁₋₆ alkyl or alkenyl optionally substituted with one or more —OH, —SR, —C(=W)H, —C(=W)OH, halogen or —NH₂;
f) R⁶' and R⁷' are both hydrogen, and R⁴' and R⁵' independently are halo; —C₁₋₆ alkyl, alkenyl or alkynyl optionally substituted with one or more halo;
g) R⁴' and R⁷' are both hydrogen, and R⁵' and R⁶' independently are halo; —C₁₋₆ alkyl, alkenyl or alkynyl optionally substituted with one or more halo;
h) R⁴' and R⁶' are both hydrogen, and R⁵' and R⁷' independently are halo, —C₁₋₆ alkyl, alkenyl or alkynyl optionally substituted with one or more halo;
i) R⁶' and R⁷' are both hydrogen, and R⁴' and R⁵' independently are Cl, F, Br, I, methyl, ethyl or CF₃;
j) R⁴' and R⁷' are both hydrogen, and R⁵' and R⁶' independently are Cl, F, Br, I, methyl, ethyl or CF₃;
k) R⁴' and R⁶' are both hydrogen, and R⁵' and R⁷' independently are Cl, F, Br, I, methyl, ethyl or CF₃; and wherein A is as defined above.

A fourth series of subembodiments for Formula (A) is defined where W, X and Y are as defined in the first series of subembodiments, and Z is as defined in the second series of subembodiments.

A fifth series of subembodiments for Formula (A) is defined where W, X and Y are as defined in the first series of subembodiments, and R⁴', R⁵', R⁶' and R⁷' are as defined in the third series of subembodiments A sixth series of subembodiments for Formula (A) is defined where Z is as defined in the second series of subembodiments, and R⁴', R⁵, R⁶' and R⁷' are as defined in the third series of subembodiments.

Non-limiting species of the first embodiment as given by Formula (A) above are defined when:

1) Z is —C(=W)NHNHC$_2$H$_5$OH, R$^{4'}$, R$^{6'}$ and R$^{7'}$ are H, R$^{5'}$ is Cl, X is H, and Y is H;
2) Z is —C(=W)NHCH$_2$C(=W)NH$_2$, R$^{4'}$ is F or Cl, R$^{6'}$ and R$^{7'}$ are H, R$^{5'}$ is F or Cl, X is H, and Y is OH;
3) Z is —C(=W)NHCH$_2$CONHNH$_2$, R$^{4'}$ is F or Cl, R$^{6'}$ and R$^{7'}$ are H, R$^{5'}$ is F or Cl, X is H, and Y is —O-alkyl;
4) Z is —C(=W)NHCH$_2$CH$_2$-(2-NO$_2$, 5-Me-imidazole), R$^{4'}$ is F or Cl, R$^{6'}$ and R$^{7'}$ are H, R$^{5'}$ is F or Cl, X is H, and Y is —O-alkenyl;
5) Z is —C(=W)NHCH$_2$NHCH(CH$_3$)C(=W)OH, R$^{4'}$ is F or Cl, R$^{6'}$ and R$^{7'}$ are H, R$^{5'}$ is F or Cl, X is H, and Y is —O-alkynyl;
6) Z is —C(=W)CH=CHC(=W)NH$_2$, R$^{4'}$ is F or Cl, R$^{6'}$ and R$^{7'}$ are H, R$^{5'}$ is F or Cl, X is H, and Y is —O-alkaryl;
7) Z is —C(=W)NHNHCH$_2$C(=W)NH$_2$, R$^{4'}$ is F or Cl, R$^{6'}$ and R$^{7'}$ are H, R$^{5'}$ is F or Cl, X is H, and Y is —O-aryl;
8) Z is —C(=W)NHCH$_2$C(=W)R$^2$, where R$^2$ is NH$_2$, R$^{4'}$ is F or Cl, R$^{6'}$ and R$^{7'}$ are H, R$^{5'}$ is F or Cl, X is H, and Y is —O-heterocycle;
9) Z is —C(=W)NHCH$_2$-A-C(=W)NH$_2$, where A is a divalent spacer, R$^{4'}$ is F or Cl, R$^{6'}$ and R$^{7'}$ are H, R$^{5'}$ is F or Cl, X is H, and Y is C$_{1-6}$ alkyl;
10) Z is —C(=W)R$^2$CH-A-C(=W)H, where A is a divalent spacer, R$^2$ is NH, R$^{4'}$ is F or Cl, R$^{6'}$ and R$^{7'}$ are H, R$^{5'}$ is F or Cl, X is H, and Y is C$_{2-6}$ alkynyl;
11) Z is —C(=W)R$^2$CH-A-C(=W)OH, where A is a divalent spacer, R$^2$ is NH, R$^{4'}$ is F or Cl, R$^{6'}$ and R$^{7'}$ are H, R$^{5'}$ is F or Cl, X is H, and Y is C$_{2-6}$ alkynyl;
12) Z is —C(=W)R$^2$—CH-A-R$^3$, where A is a divalent spacer, R$^2$ is NH, R$^3$ is CH$_3$, R$^{4'}$ is F or Cl, R$^{6'}$ and R$^{7'}$ are H, R$^{5'}$ is F or Cl, X is H, and Y is aryl;
13) Z is —C(=W)NHR$^2$—C(=W)R$^2$, where R$^2$ is an optionally substituted, branched chain alkylene or NH, R$^{4'}$ is F or Cl, R$^{6'}$ and R$^{7'}$ are H, R$^{5'}$ is F or Cl, X is H, and Y is heterocycle;
14) Z is —C(=W)R$^2$, where R$^2$ is NH, R$^{4'}$ is F or Cl and R$^{7'}$ are H, R$^{5'}$ is F or Cl, X is OH, and Y is H;
15) Z is —C(=W)R$^2$R$^3$-heterocycle, where R$^2$ is NH, R$^3$ is CH$_2$, heterocycle is optionally substituted morpholine, imidazole or pyrrole, R$^{4'}$ is F or Cl, R$^{6'}$ and R$^{7'}$ are H, R$^{5'}$ is F or Cl, X is C$_{1-6}$ alkyl, and Y is H;
16) Z is —C(=W)R$^2$C(=W)—O—R$^3$, where R$^2$ is optionally substituted alkyl, R$^3$ is benzyloxy, R$^{4'}$ is F or Cl, R$^{6'}$ and R$^{7'}$ are H, R$^{5'}$ is F or Cl, X is —O-alkyl, and Y is H;
17) Z is —C(=W)R$^2$—NH—C(=W)—C$_{1-4}$ alkoxy, where R$^2$ is an optionally substituted alkyl, R$^{4'}$ is F or Cl, R$^{6'}$ and R$^{7'}$ are H, R$^{5'}$ is F or Cl, X is —O-alkenyl, and Y is H;
18) Z is —C(=W)R$^3$—C(=W)R$^2$, where R$^2$ is C$_{1-4}$ alkoxy, R$^3$ is optionally substituted alkyl, R$^{4'}$ is F or Cl, R$^{6'}$ and R$^{7'}$ are H, R$^{5'}$ is F or Cl, X is O-alkynyl, and Y is H;
19) Z is —C(=W)R$^2$R$^3$, where R$^2$ is optionally substituted alkyl, R$^3$ is optionally substituted phenyl, R$^{4'}$ is F or Cl, R$^{6'}$ and R$^{7'}$ are H, R$^{5'}$ is F or Cl, X is O-alkaryl, and Y is H;
20) Z is —C(=W)R$^2$—NH—C(=W)—O—R$^3$, where R$^2$ is optionally substituted alkyl, R$^3$ is benzyl, R$^{4'}$ is F or Cl, R$^{6'}$ and R$^{7'}$ are H, R$^{5'}$ is F or Cl, X is —O-aralkyl, and Y is H;
21) Z is —C(=W)R$^2$C(=W)—NH$_2$, where R$^2$ is optionally substituted alkyl, R$^{4'}$ is F or Cl, R$^{6'}$ and R$^{7'}$ are H, R$^{5'}$ is F or Cl, X is —O-aryl, and Y is H;
22) Z is —C(=W)R$^2$—W—R$^3$, where R$^2$ and R$^3$ are optionally substituted alkyl, R$^{4'}$ is F or Cl, R$^{6'}$ and R$^{7'}$ are H, R$^{5'}$ is F or Cl, X is —O-heterocycle, and Y is H;
23) Z is —C(=W)R$^2$C(=W)—O—R$^3$, where R$^2$ is optionally substituted alkyl, R$^3$ is benzyloxy, R$^{4'}$ is F or Cl, R$^{6'}$ and R$^{7'}$ are H, R$^{5'}$ is F or Cl, X is —C$_{2-6}$-alkenyl, and Y is H;
24) Z is —C(=W)—NH—CH(R$^2$)—C(=W)—NH$_2$, where R$^2$ is NH$_2$, R$^{4'}$ is F or Cl, R$^{6'}$ and R$^{7'}$ are H, R$^{5'}$ is F or Cl, X is —C$_{2-6}$-alkynyl, and Y is H;
25) Z is —C(=W)—NH—NH$_2$, where R$^{4'}$ is F or Cl, R$^{6'}$ and R$^{7'}$ are H, R$^{5'}$ is F or Cl, X is aryl, and Y is H;
26) Z is —C(=W)—NH—NH(R$^2$), where R$^2$ is NH$_2$, R$^{4'}$ is F or Cl, R$^{6'}$ and R$^{7'}$ are H, R$^{5'}$ is F or Cl, X is heterocycle, and Y is H;
27) Z is —C(=W)—NH—CH(C[=W]NH$_2$)CH$_2$—C[=W]—O—CH$_2$-aryl), where R$^{4'}$ and R$^{5'}$ independently are F or Cl, R$^{6'}$ and R$^{7'}$ are H, X is carbocycle, and Y is H;
28) Z is —C(=W)—NH—CH(—[CH$_2$]$_4$—NH—C[=W]-t-BuO)(—C[=W]—NH$_2$), where R$^{4'}$ and R$^{5'}$ independently are F or Cl, R$^{6'}$ and R$^{7'}$ are H, X is —O-alkaryl, and Y is C$_{1-6}$ alkyl;
29) Z is —C(=W)—NH—CH(—CH$_2$—CH$_2$—C[=W]-t-BuO)(—C[=W]—NH$_2$), where R$^{4'}$ and R$^{5'}$ independently are F or Cl, R$^{6'}$ and R$^{7'}$ are H, X is —O-aryl, and Y is —O-alkyl;
30) Z is —C(=W)—NH—CH(—CH$_2$R$^3$)(—C[=W]—NH$_2$), where R$^3$ is CF$_3$, R$^{4'}$ and R$^{5'}$ independently are F or Cl, R$^{6'}$ and R$^{7'}$ are H, X is —C$_{2-6}$ alkenyl, and Y is —OH;
31) Z is —C(=W)—NH—CH(—CH$_2$R$^3$)(—C[=W]—NH$_2$), where R$^3$ is as defined in the first embodiment, R$^{4'}$ and R$^{5'+}$ independently are F or Cl, R$^{6'}$ and R$^{7'}$ are H, X is —C$_{2-6}$ alkynyl, and Y is H;
32) Z is —C(=W)—NH—CH(—CH$_2$OH)(—C[=W]—NH$_2$), where R$^{4'}$ and R$^{5'}$ independently are F or Cl, R$^{6'}$ and R$^{7'}$ are H, X is —O-alkylaryl, and Y is —O-alkyl;
33) Z is —C(=W)—NH—CH(—C[=W]—NH$_2$)(—C[=W]—NH$_2$), where R$^{4'}$ and R$^{5'}$ independently are F or Cl, R$^{6'}$ and R$^{7'}$ are H, X is -heterocycle, and Y is —OH;
34) Z is —C(=W)—NH—CH(—R$^3$)(—C[=W]—NH$_2$), where R$^{4'}$ and R$^{5'}$ independently are F or Cl, R$^{6'}$ and R$^{7'}$ are H, X is —O-alkenyl, and Y is —O-alkyl;
35) Z is —C(=W)—NH—CH(—[CH$_2$]$_4$—NH—C[=W]—O—CH$_2$—R$^3$)(—C[=W]—NH$_2$), where R$^3$ is as defined in the first embodiment, R$^{4'}$ and R$^{5'}$ independently are F or Cl, R$^{6'}$ and R$^{7'}$ are H, X is —OH, and Y is —O-alkylene;
36) Z is —C(=W)—NH—CH(—CH$_2$—C[=W]—NH$_2$)(—C[=W]—NH$_2$), where R$^{4'}$ and R$^{5'}$ independently are F or Cl, R$^{6'}$ and R$^{7'}$ are H, X is carbocycle, and Y is —O-alkyl;
37) Z is —C(=W)—NH—CH(—CH$_2$—R$^3$)(—C[=W]—NH$_2$), where R$^3$ is as defined in the first embodiment, R$^{4'}$ and R$^{5'}$ independently are F or Cl, R$^{6'}$ and R$^{7'}$ are H, X is —O-alkyl, and Y is -heterocycle;
38) Z is —C(=W)—NH—CH(—[CH$_2$]$_4$—NH$_2$)(—C[=W]—NH$_2$), where R$^{4'}$ and R$^{5'}$ independently are F or Cl, R$^{6'}$ and R$^{7'}$ are H, X is —O-alkenyl, and Y is —OH;
39) Z is —C(=W)—NH—CH(—CH[R$^2$][OH])(—C[=W]—NH$_2$), where R$^{4'}$ and R$^{5'}$ independently are F or Cl, R$^{6'}$ and R$^{7'}$ are H, X is —O-alkynyl, and Y is —O-alkyl;
40) Z is —C(=W)—NH—CH(R$^2$)(—C[=W]—NH$_2$), where R$^{4'}$ and R$^{5'}$ independently are F or Cl, R$^{6'}$ and R$^{7'}$ are H, X is —OH, and Y is —O-alkylene;
41) Z is —C(=W)—NH—CH(—R$^2$—C[=W]—NH$_2$)(—C[=W]—NH$_2$), where R$^2$ is NH$_2$, R$^{4'}$ and R$^{5'}$ independently are F or Cl, R$^{6'}$ and R$^{7'}$ are H, X is —C$_{2-6}$ alkylene, and Y is —OH;
42) Z is —C(=W)—NH—CH(C[=NH]—NH$_2$)(—C[=W]—NH$_2$), where R$^{4'}$ and R$^{5'}$ independently are F or Cl, R$^{6'}$ and R$^{7'}$ are H, X is -carbocycle, and Y is —O-alkyl;
43) Z is —C(=W)—NH—CH(—C[=NH]—NH$_2$)(—C[=W]—NH$_2$), where R$^{4'}$ and R$^{5'}$ independently are F or Cl, R$^{6'}$ and R$^{7'}$ are H, X is —OH, and Y is —O-alkylene;

44) Z is —C(=W)—NH—CH(—R³)(—C[=W]—NH₂), where R³ is as defined in the first general embodiment, R⁴' and R⁵' independently are F or Cl, R⁶' and R⁷' are H, X is —O-aryl, and Y is —C₁₋₆ alkyl;
45) Z is —C(=W)—NH—CH(—CH₂—R³)(—C[=W]—NH₂), where R³ is as defined in the first general embodiment, R⁴' and R⁵' independently are F or Cl, R⁶' and R⁷' are H, X is —OH, and Y is —O-alkylene;
46) Z is —C(=W)—NH—CH(—R²)(—C[=W]—NH₂), where R² is NH₂, R⁴' and R⁵' independently are F or Cl, R⁶' and R⁷' are H, X is —C₁₋₆ alkynyl, and Y is —O-aryl;
47) Z is —C(=W)—NH—NH—CH(R³)—C[=W]R², where R² is —NH₂, R³ is optionally substituted aryl or heterocycle, R⁴' and R⁵' independently are F or Cl, R⁶' and R⁷' are H, X is —O-alkylaryl, and Y is —OH;
48) Z is —C(=W)—NHR²(—R³)—C[=W]NH₂, where R² is -alkylene, R³ is optionally substituted alkyl, aryl or heterocycle, R⁴' and R⁵' independently are F or Cl, R⁶' and R⁷' are H, X is —O-alkynyl, and Y is —OH;
49) Z is —C(=W)NHR²(—R³)—C(=W)NH—R²—C(=W)OH, where R² is alkylene, R³ is optionally substituted alkyl, aryl or heterocycle, R⁴' and R⁵' independently are F or Cl, R⁶' and R⁷' are H, X is —O-alkenyl, and Y is —O-alkyl;
50) Z is —C(=W)NHR²(—R³)—C(=W)NH—R²—NH₂, where R² is alkylene, R³ is optionally substituted alkyl, aryl or heterocycle, R⁴' and R⁵' independently are F or Cl, R⁶' and R⁷' are H, X is H, and Y is —O-alkyl;
51) Z is —C(=W)NHR²(—R³)—C(=W)NH—R³—C(=W)OH, where R² is alkylene, R³ is optionally substituted alkyl, aryl or heterocycle, R⁴' and R⁵' independently are F or Cl, R⁶' and R⁷' are H, X is —OH, and Y is —O-alkylene;
52) Z is —C(=W)R²(CH₂)ₚ-A-C(=W)NH₂, where R² is —NH, p is 0-10, A is divalent, optionally substituted aryl or heterocycle, R³ is optionally substituted alkyl, aryl or heterocycle, R⁴' and R⁵' independently are F or Cl, R⁶' and R⁷' are H, X is —C₁₋₆ alkyl, and Y is —O-alkenyl;
53) Z is —C(=W)NH—R³, where R³ is optionally substituted heterocycle, R⁴' and R⁵' independently are F or Cl, R⁶' and R⁷' are H, X is —O-alkyl, and Y is —OH;
54) Z is —C(=W)NH—R²—R⁵—R³, where R² is alkylene, alkenylene or alkynylene, R⁵ is —SO₂, R³ is —NH₂, R⁴' and R⁵' independently are F or Cl, R⁶' and R⁷' are H, X is —O-aryl, and Y is —O-alkyl;
55) Z is —C(=W)NH—NH—R²(R³)—R⁵—NH₂, where R² is alkylene, alkenylene or alkynylene, R³ is aryl, arylene or heterocyclyl, R⁵ is —SO₂, R⁴' and R⁵' independently are F or Cl, R⁶' and R⁷' are H, X is —O-alkynyl, and Y is —OH;
56) Z is —C(=W)NH—R³(R⁵—NH₂), where R³ is aryl, arylene or heterocyclyl, R⁵ is —SO₂, R⁴' and R⁵' independently are F or Cl, R⁶' and R⁷' are H, X is -heterocyclyl, and Y is —O-alkyl;
57) Z is —C(=W)NH—R²R³(R⁵—NH₂), where R² is alkylene, alkenylene or alkynylene, R³ is aryl, arylene or heterocyclyl, R⁵ is —SO₂, R⁴' and R⁵' independently are F or Cl, R⁶' and R⁷' are H, X is -aryl, and Y is —O-alkenyl;
58) Z is —C(=W)NH—R³(R²R⁵—NH₂), where R² is alkylene, alkenylene or alkynylene, R³ is aryl, arylene or heterocyclyl, R⁵ is —SO₂, R⁴' and R⁵' independently are F or Cl, R⁶' and R⁷' are H, X is —OH, and Y is —O-alkylaryl;
59) Z is —C(=W)NHR²(—R³)—C(=W)NH—R²—C(=W)OH, where R² is optionally substituted alkylene, alkenylene or alkynylene, R³ is any of the definitions provided in the first general embodiment, R⁴' and R⁵' independently are F or Cl, R⁶' and R⁷' are H, X is —C₂₋₆ alkynyl, and Y is —O-alkenyl;
60) Z is —C(=W)NHR²(—R³)—C(=W)NH—R²—C(=W)NH₂, where R² is optionally substituted alkylene, alkenylene or alkynylene, R³ is any of the definitions provided in the first general embodiment, R⁴' and R⁵' independently are F or Cl, R⁶' and R⁷' are H, X is —C₂₋₆ alkenyl, and Y is —H;
61) Z is —C(=W)NHR²—C(=W)NH—R²—C(=W)OH, where R² is optionally substituted alkylene, alkenylene or alkynylene, R⁴' and R⁵' independently are F or Cl, R⁶' and R⁷' are H, X is —C₁₋₆ alkyl, and Y is —H;
62) Z is —C(=W)NHR²—C(=W)NH—R²—C(=W)NH₂, where R² is optionally substituted alkylene, alkenylene or alkynylene, R⁴' and R⁵' independently are F or Cl, R⁶' and R⁷' are H, X is —H, and Y is —O-alkyl;
63) Z is —C(=W)NH—R³ where W is O, and R³ is a heterocycle, and in particular pyridyl, pyrimidyl or imidazo that is optionally substituted by one or more halo, cyano, alkyl, alkenyl, alkynyl, or cyanoalkyl groups; R⁴' and R⁵' independently are H, F or Cl, R⁶' and R⁷' are H, X is optionally substituted phenyl, and Y is —O-alkyl; and
wherein W is as defined for Formula (A).

In a second embodiment, the invention provides a phenylindole for use in the treatment of HIV represented by the following general Formula (B):

(B)

or a pharmaceutically acceptable salt, prodrug, N-oxide, quaternary amine, stereochemical isomer or tautomer thereof, wherein:
each W, Y, Z, R¹, R², R³, A, n, R⁴', R⁵', R⁶' and R⁷' is as defined above for Formula (A); and
each R²'', R³'', R⁴'', R⁵'', and R⁶'' independently is:
a) H;
b) halogen;
c) NO₂;
d) CN;
e) OR²;
f) SR²;
g) NH₂;
h) NR²R³;
i) N(R²)—C(=W)—C₁₋₄ alkyl;
j) N(R²)—SO₂—C₁₋₄ alkyl;
k) C₁₋₆ alkyl;
l) C₂₋₆ alkenyl;
m) C₂₋₆ alkynyl;
n) aryl;
o) CF₃;
p) CR²R²—S(O)ₙ—R³;
q) CR²R²NR²R³;
r) C—OH;
s) CR²R²—C(=W)R²;

t) acyl;
u) C(=W)R²;
v) C(=W)OR²;
w) C(=W)SR²;
x) C(=W)—NR²R³;
y) C(=W)NH(CH₂)ₚ-(amino acid residue);
z) amino residue; or
aa) A-(amino acid residue);
bb) cyanoalkyl;
cc) cyanoalkenyl; or
dd) cyanoalkynyl,
wherein any of the above optionally may be substituted; or alternatively, R²″ or R⁶″ may be joined to Y to form an optionally substituted bicyclic or tricyclic phosphorylated heterocycle comprising 4-14 members.

A first series of subembodiments of the Formula (B) include all the subembodiments provided for Formula (A) above.

A second series of subembodiments of the present invention is given for the embodiment of the Formula (B) as provided above where R²″, R³″, R⁴″, R⁵″, and R⁶″ are defined as:
  a) R²″, R⁴″, and R⁶″ are hydrogen, and R³″ and R⁵″ each independently is halogen; —NO₂; —CN; —OR²; —NH—R⁵—C₁₋₄ alkyl; —NHCO—C₁₋₆ alkyl; oxime; hydrazine; —N(OH)C₁₋₆ alkyl; C₁₋₆ alkoxy; —OH; —NR²R²; or —C₁₋₆ alkyl, alkenyl or alkynyl optionally substituted with one or more of —OH, —SR, —CN, -halo, —C(=W)H, —C(=W)OH, halogen, NR²R², —C₁₋₆ thioether, or —C₁₋₆alkoxy;
  b) R²″, R⁴″, and R⁶″ are hydrogen, and R³″ and R⁵″ each independently is halogen, or —C₁₋₆ alkyl, alkenyl, alkynyl optionally substituted with one or more halogen;
  c) R²″, R³″, R⁴″, R⁵″ and R⁶″ are hydrogen;
  d) R²″, R⁴″, and R⁶″ are hydrogen, and R³″ and R⁵ are methyl;
  e) R²″, R⁴″, and R⁶″ are hydrogen, and R³″ and R⁵″ are chloro;
  f) R²″, R⁴″, and R⁶″ are hydrogen, and R³″ and R⁵″ are fluoro;
  g) R²″, R⁴″, and R⁶″ are hydrogen, R³″ is iodo and R⁵″ is bromo;
  h) R²″, R⁴″, and R⁶″ are hydrogen, R³″ is methyl, and R⁵″ is chloro; and
  i) R²″, R⁴″, and R⁶″ are hydrogen, R³″ is chloro, and R⁵″ is methyl.

A third series of subembodiments of the present invention is given for the embodiment of the Formula (B) as provided above where W, Y, R²″, R³″, R⁴″, R⁵″, and R⁶″ are defined as:
  a) W is O, Y is —O-alkyl, R²″, R⁴″, and R⁶″ are hydrogen, and R³″ and R⁵″ each independently is halogen; —NO₂; —CN; —OR²; —NH—R⁵—C₁₋₆ alkyl; —NHCO—C₁₋₆ alkyl; oxime; hydrazine; —N(OH)C₁₋₆ alkyl; C₁₋₆ alkoxy; —OH; —NR²R²; or —C₁₋₆ alkyl, alkenyl or alkynyl optionally substituted with one or more of —OH, —SR, —C(=W)H, —C(=W)OH, halogen, NR²R², —C₁₋₆ thioether, or —C₁₋₆alkoxy;
  b) W is S, Y is OH, R²″, R⁴″, and R⁶″ are hydrogen, and R³″ and R⁵″ each independently is halogen, or —C₁₋₆ alkyl, alkenyl, alkynyl optionally substituted with one or more halogen;
  c) W is O, Y is C₁₋₆ alkyl, R²″, R³″, R⁴″, R⁵″ and R⁶″ are hydrogen;
  d) W is S, Y is C₁₋₆ alkylene, R²″, R⁴″, and R⁶″ are hydrogen, and R³″ and R⁵″ are methyl;
  e) W is NH, Y is —O-alkyl, R²″, R⁴″, and R⁶″ are hydrogen, and R³″ and
  f) R⁵″ are chloro;
  g) W is S, Y is —O-alkenyl, R²″, R⁴″, and R⁶″ are hydrogen, and R³″ and
  h) R⁵″ are fluoro;
  i) W is O, Y is aryl, R²″, R⁴″, and R⁶″ are hydrogen, and R³″ and R⁵″ are fluoro;
  j) W is NH, Y is —O-alkynyl, R²″, R⁴″, and R⁶″ are hydrogen, and R³″ and R⁵″ are fluoro;
  k) W is S, Y is S, R²″, R⁴″, and R⁶′ are hydrogen, and R³″ and R⁵″ are fluoro;
  l) W is O, Y is —O-alkyl, R²″, R⁴″, and R⁶″ are hydrogen, R³″ is iodo and R⁵″ is bromo;
  m) W is O, Y is —O-alkaryl, R²″, R³″, R⁵″ and R⁶″ are hydrogen, and R⁴″ is —OH;
  n) W is S, Y is —NR²R³, R²″, R³″, R⁵″ and R⁶″ are hydrogen, and R⁴″ is —NH₂;
  o) W is S, Y is —SR², R²″, R³″, R⁵″ and R⁶″ are hydrogen, and R⁴″ is —NO₂; and
  p) W is O, Y is —O-aralkyl, ²″, R⁴″, and R⁶″ are hydrogen, R³″ is chloro, and R⁵″ is methyl.

A fourth series of subembodiments are defined when Z is as defined in any one of the second series of subembodiments for Formula (A), R⁴′, R⁵′, R⁶′ and R⁷′ are as defined in the third series of subembodiments for Formula (A), and R²″, R³″, R⁴″, R⁵″ and R⁶″ all are defined as in the second series of subembodiments for Formula (B).

A fifth series of subembodiments are defined where W and Y are as defined in the first series of subembodiments for Formula (A), Z is as defined in any one of the second series of subembodiments for Formula (A), R⁴′, R⁵′, R⁶′ and R⁷′ are as defined in the third series of subembodiments for Formula (A), and R²″, R³″, R⁴″, R⁵″ and R⁶″ all are defined as in the third series of subembodiments for Formula (B).

A sixth series of subembodiments are defined when Z is as defined in any one of the second series of subembodiments for Formula (A), R⁴′, R⁵′, R⁶′ and R⁷′ are as defined in the third series of subembodiments for Formula (A), and W, Y, R²″, R³″, R⁴″, R⁵″ and R⁶″ all are defined as in the third series of subembodiments for Formula (B).

Non-limiting species of the second embodiment as given by Formula (B) above are defined when:
  A) Z is —C(=W)NHNHC₂H₅OH, R⁴′, R⁶′ and R⁷′ are H, R⁵′ is Cl, Y is H, R²″, R⁴″ and R⁶″ are H, and R³″ and R⁵″ are methyl;
  B) Z is —C(=W)NHCH₂C(=W)NH₂, R⁴′ is F or Cl, R⁶′ and R⁷′ are H, R⁵′ is F or Cl, Y is OH, R²″, R⁴″ and R⁶″ are H, and R³″ and R⁵″ are methyl;
  C) Z is —C(=W)NHCH₂CONHNH₂, R⁴′ is F or Cl, R⁶′ and R⁷′ are H, R⁵′ is F or Cl, Y is —O-alkyl, R²″, R⁴″ and R⁶″ are H, and R³″ and R⁵″ are methyl;
  D) Z is —C(=W)NHCH₂CH₂-(2-NO₂, 5-Me-imidazole), R⁴′ is F or Cl, R⁶′ and R⁷′ are H, R⁵′ is F or Cl, Y is —O-alkenyl, R²″, R⁴″ and R⁶″ are H, and R³″ and R⁵″ are methyl;
  E) Z is —C(=W)NHCH₂NHC(=W)OH, R⁴′ is F or Cl, R⁶′ and R⁷′ are H, R⁵′ is F or Cl, Y is —O-alkynyl, R²″, R⁴″ and R⁶″ are H, and R³″ and R⁵″ are methyl;
  F) Z is —C(=W)CH=CHC(=W)NH₂, R⁴′ is F or Cl, R⁶′ and R⁷′ are H, R⁵′ is F or Cl, Y is —O-alkaryl, R²″, R⁴″ and R⁶″ are H, and R³″ and R⁵″ are methyl;
  G) Z is —C(=W)NHNHCH₂C(=W)NH₂, R⁴′ is F or Cl, R⁶′ and R⁷′ are H, R⁵′ is F or Cl, Y is —O-aryl, R²″, R⁴″ and R⁶″ are H, and R³″ and R⁵″ are methyl;
  H) Z is —C(=W)NHCH₂C(=W)R², where R² is NH₂, R⁴′ is F or Cl, R⁶′ and R⁷′ are H, R⁵′ is F or Cl, Y is —O-heterocycle, R²″, R⁴″ and R⁶″ are H, and R³″ and R⁵″ are methyl;

I) Z is —C(=W)NHCH$_2$-A-C(=W)NH$_2$, where A is a divalent spacer, R$^{4'}$ is F or Cl, R$^{6'}$ and R$^{7'}$ are H, R$^{5'}$ is F or Cl, Y is C$_{1-6}$ alkyl, R$^{2''}$, R$^{3''}$, R$^{5''}$ and R$^{6''}$ are H, and R$^{4''}$ is —NH$_2$;

J) Z is —C(=W)R$^2$CH-A-C(=W)H, where A is a divalent spacer, R$^2$ is NH, R$^{4'}$ is F or Cl, R$^{6'}$ and R$^{7'}$ are H, R$^{5'}$ is F or Cl, Y is C$_{2-6}$ alkynyl, R$^{2''}$, R$^{4''}$ and R$^{6''}$ are H, and R$^{3''}$ and R$^{5''}$ are methyl;

K) Z is —C(=W)R$^2$CH-A-C(=W)OH, where A is a divalent spacer, R$^2$ is NH, R$^{4'}$ is F or Cl, R$^{6'}$ and R$^{7'}$ are H, R$^{5'}$ is F or Cl, Y is C$_{2-6}$ alkynyl, R$^{2''}$, R$^{3''}$, R$^{5''}$ and R$^{6''}$ are H, and R$^{4''}$ is —NO$_2$;

L) Z is —C(=W)R$^2$—CH-A-R$^3$, where A is a divalent spacer, R$^2$ is NH, R$^3$ is CH$_3$, R$^{4'}$ is F or Cl, R$^{6'}$ and R$^{7'}$ are H, R$^{5'}$ is F or Cl, Y is aryl, R$^{2''}$, R$^{4''}$ and R$^{6''}$ are H, and R$^{3''}$ and R$^{5''}$ are methyl;

M) Z is —C(=W)NHR$^2$—C(=W)R$^2$, where R$^2$ is an optionally substituted, branched chain alkylene or NH, R$^{4'}$ is F or Cl, R$^{6'}$ and R$^{7'}$ are H, R$^{5'}$ is F or Cl, Y is heterocycle, R$^{2''}$, R$^{4''}$ and R$^{6''}$ are H, and R$^{3''}$ and R$^{5''}$ are methyl;

N) Z is —C(=W)R$^2$, where R$^2$ is NH, R$^{4'}$ is F or Cl, R$^{6'}$ and R$^{7'}$ are H, R$^{5'}$ is F or Cl, Y is H, R$^{2''}$, R$^{3''}$, R$^{5''}$ and R$^{6''}$ are H, and R$^{4''}$ is —OH;

O) Z is —C(=W)R$^2$R$^3$-heterocycle, where R$^2$ is NH, R$^3$ is CH$_2$, heterocycle is optionally substituted morpholine, imidazole or pyrrole, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

P) Z is —C(=W)R$^2$NH—C(=W)—O—R$^3$, where R$^2$ is optionally substituted alkyl, R$^3$ is benzyloxy, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

Q) Z is —C(=W)R$^2$—NH—C(=W)—C$_{1-4}$ alkoxy, where R$^2$ is an optionally substituted alkyl, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

R) Z is —C(=W)R$^3$—C(=W)R$^2$, where R$^2$ is C$_{1-4}$ alkoxy, R$^3$ is optionally substituted alkyl, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

S) Z is —C(=W)R$^2$R$^3$, where R$^2$ is optionally substituted alkyl, R$^3$ is optionally substituted phenyl, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

T) Z is —C(=W)R$^2$—NH—C(=W)—O—R$^3$, where R$^2$ is optionally substituted alkyl, R$^3$ is benzyl, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

U) Z is —C(=W)R$^2$C(=W)—NH$_2$, where R$^2$ is optionally substituted alkyl, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

V) Z is —C(=W)-A-R$^3$, where R$^3$ is an optionally substituted alkyl, A is an alkylene linker, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

X) Z is —C(=W)R$^2$C(=W)—O—R$^3$, where R$^2$ is optionally substituted alkyl, R$^3$ is benzyloxy, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

Y) Z is —C(=W)—NH—CH(R$^2$)—C(=W)—NH$_2$, where R$^2$ is NH$_2$, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

Z) Z is —C(=W)—NH—NH$_2$, where R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

AA) Z is —C(=W)—NH—NH(R$^2$), where R$^2$ is NH$_2$, R$^{4'}$ is F or Cl, R$^{6'}$ and R$^{7'}$ are H, R$^{5'}$ is F or Cl, Y is H, R$^{2''}$, R$^{4''}$ and R$^{6''}$ are H, and R$^{3''}$ and R$^{5''}$ are methyl;

BB) Z is —C(=W)—NH—CH(C[=W]NH$_2$)(CH$_2$—C[=W]—O—NR$^2$R$^2$), where R$^{4'}$ and R$^{5'}$ independently are F or Cl, R$^{6'}$ and R$^{7'}$ are H, R$^2$ is alkyl or aryl, Y is H, R$^{2''}$, R$^{3''}$, R$^{5''}$ and R$^{6''}$ are H, and R$^{4''}$ is —NH$_2$;

CC) Z is —C(=W)—NH—CH(—[CH$_2$]$_4$—NH—C[=W]-t-BuO)(—C[=W]—NH$_2$), where R$^{4'}$ and R$^{5'}$ independently are F or Cl, R$^{6'}$ and R$^{7'}$ are H, Y is C$_{1-6}$ alkyl, R$^{2''}$, R$^{4''}$ and R$^{6''}$ are H, and R$^{3''}$ and R$^{5''}$ are methyl;

DD) Z is —C(=W)—NH—CH(—CH$_2$—CH$_2$—C[=W]-t-BuO)(—C[=W]—NH$_2$), where R$^{4'}$ and R$^{5'}$ independently are F or Cl, R$^{6'}$ and R$^{7'}$ are H, Y is —O-alkyl, R$^{2''}$, R$^{4''}$ and R$^{6''}$ are H, and R$^{3''}$ and R$^{5''}$ are methyl;

EE) Z is —C(=W)—NH—CH(—CH$_2$R$^3$)(—C[=W]—NH$_2$), where R$^3$ is CF$_3$, R$^{4'}$ and R$^{5'}$ independently are F or Cl, R$^{6'}$ and R$^{7'}$ are H, Y is —OH, R$^{2''}$, R$^{4''}$ and R$^{6''}$ are H, and R$^{3''}$ and R$^{5''}$ are methyl;

FF) Z is —C(=W)—NH—CH(—CH$_2$R$^3$)(—C[=W]—NH$_2$), where R$^3$ is as defined in the first embodiment, R$^{4'}$ and R$^{5'}$ independently are F or Cl, R$^{6'}$ and R$^{7'}$ are H, Y is H, R$^{2''}$, R$^{3''}$, R$^{5''}$ and R$^{6''}$ are H, and R$^{4''}$ is —NO$_2$;

GG) Z is —C(=W)—NH—CH(-acyl)(—C[=W]—NH$_2$), where R$^{4'}$ and R$^{5'}$ independently are F or Cl, R$^{6'}$ and R$^{7'}$ are H, Y is —O-alkyl, R$^{2''}$, R$^{4''}$ and R$^{6''}$ are H, and R$^{3''}$ and R$^{5''}$ are methyl;

HH) Z is —C(=W)—NH—CH(—C[=W]—NH$_2$)(—C[=W]—NH$_2$), where R$^{4'}$ and R$^{5'}$ independently are F or Cl, R$^{6'}$ and R$^{7'}$ are H, Y is —OH, R$^{2''}$, R$^{3''}$, R$^{5''}$ and R$^{6''}$ are H, and R$^{4''}$ is —OH;

II) Z is —C(=W)—NH—CH(—R$^3$)(—C[=W]—NH$_2$), where R$^{4'}$ and R$^{5'}$ independently are F or Cl, R$^{6'}$ and R$^{7'}$ are H, Y is —O-alkyl, R$^{2''}$, R$^{4''}$ and R$^{6''}$ are H, and R$^{3''}$ and R$^{5''}$ are methyl;

JJ) Z is —C(=W)—NH—CH(—CH$_2$—R$^3$)(—C[=W]—NH$_2$), where R$^3$ is as defined in the first embodiment, R$^{4'}$ and R$^{5'}$ independently are F or Cl, R$^{6'}$ and R$^{7'}$ are H, Y is -heterocycle, R$^{2''}$, R$^{4''}$ and R$^{6''}$ are H, and R$^{3''}$ and R$^{5''}$ are methyl;

KK) Z is —C(=W)—NH—CH(—[CH$_2$]$_4$—NH$_2$)(—C[=W]—NH$_2$), where R$^{4'}$ and R$^{5'}$ independently are F or Cl, R$^{6'}$ and R$^{7'}$ are H, Y is —OH, R$^{2''}$, R$^{4''}$ and R$^{6''}$ are H, and R$^{3''}$ and R$^{5''}$ are methyl;

LL) Z is —C(=W)—NH—CH(—CR$^2$R$^2$)(—C[=W]—NH$_2$), where R$^{4'}$ and R$^{5'}$ independently are F or Cl, R$^{6'}$ and R$^{7'}$ are H, Y is —O-alkyl, R$^{2''}$, R$^{4''}$ and R$^{6''}$ are H, and R$^{3''}$ and R$^{5''}$ are methyl;

MM) Z is —C(=W)—NH—CH(R$^2$)(—C[=W]—NH$_2$), where R$^{4'}$ and R$^{5'}$ independently are F or Cl, R$^{6'}$ and R$^{7'}$ are H, Y is —O-alkylene, R$^{2''}$, R$^{4''}$ and R$^{6''}$ are H, and R$^{3''}$ and R$^{5''}$ are methyl;

NN) Z is —C(=W)—NH—CH(—R$^3$)(—C[=W]—NH$_2$), where R$^3$ is as defined in the first general embodiment, R$^{4'}$ and R$^{5'}$ independently are F or Cl, R$^{6'}$ and R$^{7'}$ are H, Y is —C$_{1-6}$ alkyl, R$^{2''}$, R$^{4''}$ and R$^{6''}$ are H, and R$^{3''}$ and R$^{5''}$ are methyl;

OO) Z is —C(=W)—NH—CH(—CH$_2$—R$^3$)(—C[=W]—NH$_2$), where R$^3$ is as defined in the first general embodiment, R$^{4'}$ and R$^{5'}$ independently are F or Cl, R$^{6'}$ and R$^{7'}$ are H, Y is —O-alkylene, R$^{2''}$, R$^{4''}$ and R$^{6''}$ are H, and R$^{3''}$ and R$^{5''}$ are methyl;

PP) Z is —C(=W)—NH—CH(—R$^2$)(—C[=W]—NH$_2$), where R$^2$ is NH$_2$, R$^{4'}$ and R$^{5'}$ independently are F or Cl, R$^{6'}$ and R$^{7'}$ are H, Y is —O-aryl, R$^{2''}$, R$^{3''}$, R$^{5''}$ and R$^{6''}$ are H, and R$^{4''}$ is —NH$_2$;

UU) Z is —C(=W)—NH—NH—CH($R^3$)—C[=W]$R^2$, where $R^2$ is —$NH_2$, $R^3$ is optionally substituted aryl or heterocycle, $R^{4'}$ and $R^{5'}$ independently are F or Cl, $R^{6'}$ and $R^{7'}$ are H, Y is —OH, $R^{2''}$, $R^{4''}$ and $R^{6''}$ are H, and $R^{3''}$ and $R^{5''}$ are methyl;

VV) Z is —C(=W)—$NHR^2$(—$R^3$)—C[=W]$NH_2$, where $R^2$ is -alkylene, $R^3$ is optionally substituted alkyl, aryl or heterocycle, $R^{4'}$ and $R^{5'}$ independently are F or Cl, $R^{6'}$ and $R^{7'}$ are H, Y is —OH, $R^{2''}$, $R^{4''}$ and $R^{6''}$ are H, and $R^{3''}$ and $R^{5''}$ are methyl;

WW) Z is —C(=W)$NHR^2$(—$R^3$)—C(=W)NH—$R^2$—C(=W)OH, where $R^2$ is alkylene, $R^3$ is optionally substituted alkyl, aryl or heterocycle, $R^{4'}$ and $R^{5'}$ independently are F or Cl, $R^{6'}$ and $R^{7'}$ are H, Y is —O-alkyl, $R^{2''}$, $R^{4''}$ and $R^{6''}$ are H, and $R^{3''}$ and $R^{5''}$ are methyl;

XX) Z is —C(=W)$NHR^2$(—$R^3$)—C(=W)NH—$R^2$—$NH_2$, where $R^2$ is alkylene, $R^3$ is optionally substituted alkyl, aryl or heterocycle, $R^{4'}$ and $R^{5'}$ independently are F or Cl, $R^{6'}$ and $R^{7'}$ are H, Y is —O-alkyl, $R^{2''}$, $R^{4''}$ and $R^{6''}$ are H, and $R^{3''}$ and $R^{5''}$ are methyl;

YY) Z is —C(=W)$NHR^2$(—$R^3$)—C(=W)NH—$R^3$—C(=W)OH, where $R^2$ is alkylene, $R^3$ is optionally substituted alkyl, aryl or heterocycle, $R^{4'}$ and $R^{5'}$ independently are F or Cl, $R^{6'}$ and $R^{7'}$ are H, Y is —O-alkylene, $R^{2''}$, $R^{4''}$ and $R^{6''}$ are H, and $R^{3''}$ and $R^{5''}$ are methyl;

ZZ) Z is —C(=W)$R^2(CH_2)_p$-A-C(=W)$NH_2$, where $R^2$ is —NH, p is 0-10, A is divalent, optionally substituted aryl or heterocycle, $R^3$ is optionally substituted alkyl, aryl or heterocycle, $R^{4'}$ and $R^{5'}$ independently are F or Cl, $R^{6'}$ and $R^{7'}$ are H, Y is —O-alkenyl, $R^{2''}$, $R^{3''}$, $R^{5''}$ and $R^{6''}$ are H, and $R^{4''}$ is —$NO_2$;

AAA) Z is —C(=W)NH—$R^3$, where $R^3$ is optionally substituted heterocycle, $R^{4'}$ and $R^{5'}$ independently are F or Cl, $R^{6'}$ and $R^{7'}$ are H, Y is —OH, $R^{2''}$, $R^{4''}$ and $R^{6''}$ are H, and $R^{3''}$ and $R^{5''}$ are methyl;

BBB) Z is —C(=W)NH-A-S(O)$_n$—$R^2$, where A is alkylene, alkenylene or alkynylene, $R^2$ is —$NH_2$, $R^{4'}$ and $R^{5'}$ independently are F or Cl, $R^{6'}$ and $R^{7'}$ are H, Y is —O-alkyl, $R^{2''}$, $R^{4''}$ and $R^{6''}$ are H, and $R^{3''}$ and $R^{5''}$ are methyl;

CCC) Z is —C(=W)NH—NH—$R^2(R^3)$-A-C(=W)$NH_2$, where $R^2$ is alkyl, A is alkylene, alkenylene or alkynylene, $R^3$ is aryl, arylene or heterocyclyl, $R^{4'}$ and $R^{5'}$ independently are F or Cl, $R^{6'}$ and $R^{7'}$ are H, Y is —OH, $R^{2''}$, $R^{4''}$ and $R^{6''}$ are H, and $R^{3''}$ and $R^{5''}$ are methyl;

DDD) Z is —C(=W)NH-A-[S(O)$_2$—$NH_2$], where A is alkylene, alkenylene or alkynylene, $R^{4'}$ and $R^{5'}$ independently are F or Cl, $R^{6'}$ and $R^{7'}$ are H, Y is —O-alkenyl, $R^{2''}$, $R^{4''}$ and $R^{6''}$ are H, and $R^{3''}$ and $R^{5''}$ are methyl;

EEE) Z is —C(=W)NH-A-C(=W)NH—$R^2$—C(=W)OH, where $R^2$ and $R^3$ are any of the definitions provided in the first general embodiment, $R^{4'}$ and $R^{5'}$ independently are F or Cl, $R^{6'}$ and $R^{7'}$ are H, Y is —O-alkenyl, $R^{2''}$, $R^{4''}$ and $R^{6''}$ are H, and $R^{3''}$ and $R^{5''}$ are methyl;

FFF) Z is —C(=W)$NHR^2$(—$R^3$)—C(=W)NH—$R^2$—C(=W)$NH_2$, where $R^2$ is optionally substituted alkylene, alkenylene or alkynylene, $R^3$ is any of the definitions provided in the first general embodiment, $R^{4'}$ and $R^{5'}$ independently are F or Cl, $R^{6'}$ and $R^{7'}$ are H, $R^{2''}$, $R^{4''}$ and $R^{6''}$ are H, and $R^{3''}$ and $R^{5''}$ are methyl;

GGG) Z is —C(=W)$NHR^2$—C(=W)NH—$R^2$—C(=W)OH, where $R^2$ is optionally substituted alkylene, alkenylene or alkynylene, $R^{4'}$ and $R^{5'}$ independently are F or Cl, $R^{6'}$ and $R^{7'}$ are H, $R^{2''}$, $R^{4''}$ and $R^{6''}$ are H, and $R^{3''}$ and $R^{5''}$ are methyl;

HHH) Z is —C(=W)$NHR^2$—C(=W)NH—$R^2$—C(=W)$NH_2$, where $R^2$ is optionally substituted alkylene, alkenylene or alkynylene, $R^{4'}$ and $R^{5'}$ independently are F or Cl, $R^{6'}$ and $R^{7'}$ are H, Y is —O-alkyl, $R^{2''}$, $R^{4''}$ and $R^{6''}$ are H, and $R^{3''}$ and $R^{5''}$ are methyl; and wherein W is as defined for Formula (A).

In a third embodiment, the present invention provides an optionally substituted 9-11 membered bicyclic 3-phosphoindole for use in the treatment of HIV represented by the following general Formula (C):

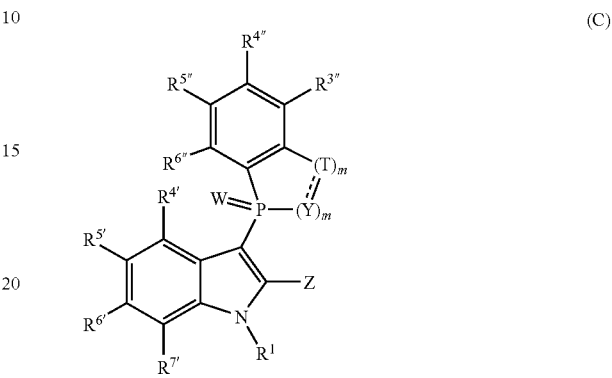

(C)

or a pharmaceutically acceptable salt, prodrug, N-oxide, quaternary amine, stereochemical isomer or tautomer thereof, wherein:

each W, Z, $R^1$, $R^2$, $R^3$, A, n, $R^{4'}$, $R^{5'}$, $R^{6'}$ and $R^{7'}$ is as defined above for Formula (A);

each $R^{3''}$, $R^{4''}$, $R^{5''}$, and $R^{6''}$ is as defined above for Formula (B);

----indicates the presence of a single or double bond, where:
when ----indicates the presence of a double bond, each Y and T independently is:
  a) $CR^2$;
  b) N; or
  c) $SR^2$;
with the caveat that one of Y and T must be $CR^2$;
when ----indicates the presence of a single bond, then each Y and T independently is:
  a) $CR^2$;
  b) O;
  c) $NR^2$; or
  d) $SR^2$;
with the caveat that one of Y and T must be $CR^2$; and
m is 1 or 2, with the proviso that m can only be 2 for T or Y=$CR^2$ A first series of subembodiments of the Formula (C) include all the subembodiments provided for Formula (A) above in which substituent "X" is aryl, heterocyclyl, O-aryl, and O-heterocyclyl.

A second series of subembodiments of the present invention is given for the embodiment of Formula (C) as provided above where Y and T are defined as:

j) T is —$CH_2$ and Y is —O—;
k) T is —C—C(=O)—$OCH_3$ and Y is —O—;
l) T is —O and Y is —$CR^2$;
m) T is (—$CH_2$)$_2$ and Y is —$NR^2$;
n) T is —$CH_2$ and Y is —$SR^2$;
o) T is —O and Y is —C-aryl;
p) T is —$NR^2$ and Y is —C-halo;
q) T is —$SR_2$ and Y is —C-heterocycle;
r) T is —C—$C_{1-6}$ alkyl and Y is —O—;
s) T is —C—C(=S)$CH_2$ and Y is —$CH_2$—;
t) T is —CH—$OCH_3$ and Y is —$SR^2$;
u) T is —C—OH and Y is —$CH_2$—;

v) T is —C—O—$C_{1-6}$ alkyl and Y is —$CH_2$—;
w) T is —C—$NH_2$ and Y is —$CH_2$—;
x) T is —C—NH—$C_{1-6}$ alkyl and Y is —$CH_2$—; and
y) T is (—$CH_2$)$_2$ and Y is (—$CH_2$)$_2$.

A third series of subembodiments of the present invention is given for the embodiment of the Formula (C) as provided above where $R^{3''}$, $R^{4''}$, $R^{5''}$, and $R^{6''}$ are defined as:

a) $R^{4''}$ and $R^{6''}$ are hydrogen, and $R^{3''}$ and $R^{5''}$ each independently is halogen; —$NO_2$; —CN; —$OR^2$; —NH—$R^5$—$C_{1-6}$ alkyl; —NHCO—$C_{1-6}$ alkyl; hydrazine; —N(OH)$C_{1-6}$ alkyl; $C_{1-6}$ alkoxy; —OH; —$NR^2R^2$; or —$C_{1-6}$ alkyl, alkenyl or alkynyl optionally substituted with one or more of —OH, —SR, —C(=W)H, —C(=W)OH, halogen, $NR^2R^2$, —$C_{1-6}$ thioether, or —$C_{1-6}$alkoxy;
b) $R^{4''}$ and $R^{6''}$ are hydrogen, and $R^{3''}$ and $R^{5''}$ each independently is halogen, or —$C_{1-6}$ alkyl, alkenyl, alkynyl optionally substituted with one or more halogen;
c) $R^{3''}$, $R^{4''}$, $R^{5''}$ and $R^{6''}$ are hydrogen;
d) $R^{4''}$ and $R^{6''}$ are hydrogen, and $R^{3''}$ and $R^{5''}$ are methyl;
e) $R^{4''}$ and $R^{6''}$ are hydrogen, and $R^{3''}$ and $R^{5''}$ are chloro;
f) $R^{4''}$ and $R^{6''}$ are hydrogen, and $R^{3''}$ and $R^{5''}$ are fluoro;
g) $R^{4''}$ and $R^{6''}$ are hydrogen, $R^{3''}$ is iodo and $R^{5''}$ is bromo;
h) $R^{3''}$, $R^{4''}$ and $R^{6''}$ are hydrogen, and $R^{5''}$ is chloro;
i) $R^{4''}$ and $R^{6''}$ are hydrogen, $R^{3''}$ is chloro, and $R^{5''}$ is methyl.
i) $R^{3''}$, $R^{5''}$ and $R^{6''}$ are hydrogen, and $R^{4''}$ is halogen; —$NO_2$; —CN; —$OR^2$; —NH—$R^5$—$C_{1-6}$ alkyl; —NHCO—$C_{1-6}$ alkyl; hydrazine; —N(OH)$C_{1-6}$ alkyl; $C_{1-6}$ alkoxy; —OH; —$NR^2R^2$; or —$C_{1-6}$ alkyl, alkenyl or alkynyl optionally substituted with one or more of —OH, —SR, —C(=W)H, —C(=W)OH, $NR^2R^2$, —$C_{1-6}$ thioether, or —$C_{1-6}$alkoxy;
j) $R^{3''}$, $R^{5''}$ and $R^{6''}$ are hydrogen, and $R^{4''}$ is —$NO_2$;
k) $R^{3''}$, $R^{5''}$ and $R^{6''}$ are hydrogen, and $R^{4''}$ is —$OR^2$;
l) $R^{3''}$, $R^{5''}$ and $R^{6''}$ are hydrogen, and $R^{4''}$ is halogen; and
m) $R^{3''}$, $R^{5''}$ and $R^{6''}$ are hydrogen, and $R^{4''}$ is —$NH_2$.

A fourth series of subembodiments for Formula (C) are defined when Z is as defined in any one of the second series of subembodiments for Formula (A), $R^{4'}$, $R^{5'}$, $R^{6'}$ and $R^{7'}$ are as defined in the third series of subembodiments for Formula (A), and $R^{3''}$, $R^{4''}$, $R^{5''}$ and $R^{6''}$ all are defined as in the third series of subembodiments for Formula (C).

A fifth series of subembodiments are defined when Z is as defined in any one of the second series of subembodiments for Formula (A), $R^{4'}$, $R^{5'}$, $R^{6'}$ and $R^{7'}$ are as defined in the third series of subembodiments for Formula (A), and Y and T are as defined as in the second series of subembodiments for Formula (C).

A sixth series of subembodiments for Formula (C) are defined when Z is as defined in any one of the second series of subembodiments for Formula (A), $R^{4'}$, $R^{5'}$, $R^{6'}$ and $R^{7'}$ are as defined in the third series of subembodiments for Formula (A), and $R^{3''}$, $R^{4''}$, $R^{5''}$ and $R^{6''}$ all are defined as in the second series of subembodiments for Formula (B).

Species of the third embodiment as given by Formula (C) above are defined when:

a) Z is —C(=W)N($R^2R^3$)C(=W)$NH_2$, where $R^2$ is NH and $R^3$ is alkyl; $R^1$, $R^{4'}$, $R^{6'}$ and $R^{7'}$ are H; $R^{5'}$ is halo or —$NO_2$; $R^{4''}$ and $R^{6''}$ are H; $R^{3''}$ and $R^{5''}$ independently are —OH or —$NR^2R^2$; Y is O; and T is $CH_2$;
b) Z is —C(=W)—NH—CH(—C[=W]$NH_2$)(—$CH_2$—C[=W]—O—$CH_3$-aryl); $R^1$, $R^{4'}$, $R^{6'}$ and $R^{7'}$ are H; $R^{5'}$ is halo or —CN; $R^{4''}$ and $R^{6''}$ are H; $R^{3''}$ and $R^{5''}$ independently are —$C_{1-5}$ alkoxy or —$C_{1-5}$ alkyl optionally substituted with —$C_{1-5}$ alkoxy; Y is $SR^2$; and T is $CH_2$;
c) Z is —C(=W)NHNH$_2$; $R^1$, $R^{4'}$, $R^{6'}$ and $R^{7'}$ are H; $R^{5'}$ is halo or —$NR^2R^2$; $R^{4''}$ and $R^{6''}$ are H; $R^{3''}$ and $R^{5''}$ independently are —$NO_2$ or —CN; Y is $CH_2$; and T-$R^2$—$R^3$ is $CH_2$;
d) Z is —C(=W)NH—$CH_2$—C(=W)NHNH$_2$; $R^1$, $R^{4'}$, $R^{6'}$ and $R^{7'}$ are H; $R^{5'}$ is halo or —NH—$R^5$—$C_{1-6}$ alkyl, where $R^5$ is —C(O) or —S(O)$_n$ and n is 0, 1 or 2; $R^{4''}$ and $R^{6''}$ are H; $R^{3''}$ and $R^{5''}$ independently are —$OR^2$ or —CN; Y is C—$C_{1-6}$ alkyl; and is T is N;
e) Z is —C(=W)NH—$CH_2$—C(=W)NHNH$_2$; $R^1$, $R^{4'}$, $R^{6'}$ and $R^{7'}$ are H; $R^{5'}$ is halo or —NH—$R^5$—$C_{1-6}$ alkyl, where $R^5$ is —C(O) or —S(O)$_n$ and n is 0, 1 or 2; $R^{4''}$ and $R^{6''}$ are H; $R^{3''}$ and $R^{5''}$ independently are —$OR^2$ or —CN; Y is C—$C_{1-6}$ alkyl; and is T is $SR^2$ and $R^2$ is as defined for Formula (A);
f) Z is —C(=W)NH—CH($R^2$)—C(=W)$NH_2$, where $R^2$ is —$NH_2$ or alkyl; $R^1$, $R^{4'}$, $R^{6'}$ and $R^{7'}$ are H; $R^{5'}$ is halo or —NHCO—$C_{1-6}$ alkyl; $R^{4''}$ and $R^{6''}$ are H; $R^{3''}$ and $R^{5''}$ independently are —NHOH; Y is C-alkenyl; and T is ($CH_2$)$_2$;
g) Z is —C(=W)$NR^2$—C(=W)$R^3$, where $R^2$ is optionally substituted alkyl, alkenyl or alkynyl; $R^3$ is $NH_2$; $R^1$, $R^{4'}$, $R^{6'}$ and $R^{7'}$ are H; $R^{5'}$ is halo or oxime; $R^{4''}$ and $R^{6''}$ are H; $R^{3''}$ and $R^{5''}$ independently are H or —NH—$R^5$—$C_{1-6}$ alkyl, where $R^5$ is —C(O) or —S(O)$_n$ and n is 0, 1 or 2; Y is C-alkynyl; and T is —O;
h) Z is —C(=W)NH—$R^2$—$SR^2$ where $R^2$ is optionally substituted alkyl, alkenyl or alkynyl; $R^1$, $R^{4'}$, $R^{6'}$ and $R^{7'}$ are H; $R^{5'}$ is halo or hydrazine; $R^{4''}$ and $R^{6''}$ are H; $R^{3''}$ and $R^{5''}$ independently are H or —NHCO—$C_{1-6}$ alkyl; Y is C-carbocycle; and T is $NR^2$ where $R^2$ is as defined for Formula (A);
i) Z is —C(=W)—NH—N($R^3$)($R^2$), where $R^2$ is hydroxy or alkoxy, and $R^3$ is H or alkyl; $R^1$, $R^{4'}$, $R^{6'}$ and $R^{7'}$ are H; $R^{5'}$ is halo or $C_{1-6}$ alkyl or alkenyl optionally substituted with one or more —OH, —SR, —C(=W)H, —C(=W)OH, halogen, —$NR^2R^2$, $C_{1-3}$ alkoxy, or $C_{1-13}$ thioether; $R^{4''}$ and $R^{6''}$ are H; $R^{3''}$ and $R^{5''}$ independently are H or —CN; Y is C-aryl; and T is N;
j) Z is —C(=W)NH—$CH_2$NH—CH(CH$_3$)C(=W)OH; $R^1$, $R^{4'}$, $R^{6'}$ and $R^{7'}$ are H; $R^{5'}$ is halo or $CF_3$; $R^{4''}$ and $R^{6''}$ are H; $R^{3''}$ and $R^{5''}$ independently are H or —NH—O—$C_{1-3}$ alkyl; Y is O; and T is $CH_2$;
k) Z is —C(=W)—NH—N($R^2$)—CH($R^2$)—C(=W)$R^2$, where $R^2$ is H or $NH_2$; $R^1$, $R^{4'}$, $R^{6'}$ and $R^{7'}$ are H; $R^{5'}$ is halo or H; $R^{4''}$ and $R^{6''}$ are H; $R^{3''}$ and $R^{5''}$ independently are H or halogen; Y is —$NR^2$ and T is $CR^2$ where $R^2$ is as defined in the first general embodiment;
l) Z is —C(=W)—N($R^2$)—C(=W)$R^3$, where $R^2$ is NH and $R^3$ is $CH_3$; $R^1$, $R^{4'}$, $R^{6'}$ and $R^{7'}$ are H; $R^{5'}$ is halo or H; $R^{4''}$ and $R^{6''}$ are H; $R^{3''}$ and $R^{5''}$ independently are H or halogen; Y is —O; and T is (C—O-alkyl);
m) Z is —C(=W)—NH—CH=CH—C(=W)$R^2$, where $R^2$ is $NH_2$; $R^1$, $R^{6'}$ and $R^{7'}$ are H; $R^{4'}$ and $R^{5'}$ are halo or H; $R^{4''}$ and $R^{6''}$ are H; $R^{3''}$ and $R^{5''}$ independently are H or —$OR^2$ where $R^2$ is as defined in the first general embodiment; Y is —O; and T is (C—$CH_2$—$CH_3$);
n) Z is —C(=W)—NH—CH=CH—C(=W)$R^2$, where $R^2$ is —$NH_2$; $R^1$, $R^{6'}$ and $R^{7'}$ are H; $R^{4'}$ and $R^{5'}$ are halo or —$NO_2$; $R^{4''}$ and $R^{6''}$ are H; $R^{3''}$ and $R^{5''}$ independently are H or —NHOH; Y is —O and T is C—$CH_3$;
o) Z is —C(=W)$R^2$(CH)$_2$—C(=W)$R^2$, where $R^2$ is NH or $NH_2$; $R^1$, $R^{6'}$ and $R^{7'}$ are H; $R^{4'}$ and $R^{5'}$ are halo or —$OR^2$ where $R^2$ is as defined in the first general embodiment; $R^{4''}$ and $R^{6''}$ are H; $R^{3''}$ and $R^{5''}$ independently are H or —$C_{1-3}$ alkyl or alkenyl optionally substituted with one or more —OH, —SR, —C(=W)OH, halogen, or —NH$_2$; Y is —SR$^2$; and T is CH$_2$;

p) Z is —C(=W)—R$^2$—CH$_2$-A-C(=W)R$^2$, where R$^2$ is as defined in the first general embodiment, and A is a divalent linker as defined in the first general embodiment; R$^1$, R$^{6'}$ and R$^{7'}$ are H; R$^{4'}$ and R$^{5'}$ are halo or —CN; R$^{4''}$ and R$^{6''}$ are H; R$^{3''}$ and R$^{5''}$ independently are H or —C$_{1-3}$ alkoxy; Y is —NR$^2$ where R$^2$ is as defined in the first general embodiment; and T is (CH$_2$)$_2$;

q) Z is —C(=W)—R$^2$—CH$_2$-A-C(=W)R$^2$, where R$^2$ is alkyl or —NH$_2$, and A is a divalent linker; R$^1$, R$^{6'}$ and R$^{7'}$ are H; R$^{4'}$ and R$^{5'}$ are halo or —NR$^2$R$^2$, where R$^2$ is as defined in the first general embodiment; R$^{4''}$ and R$^{6''}$ are H; R$^{3''}$ and R$^{5''}$ independently are H or —OH; Y is —CH$_2$ and T is (CH$_2$)$_2$;

r) Z is —C(=W)-A-R$^2$—C(=W)OR$^3$, where R$^2$ is —NH and R$^3$ is —H or alkyl; R$^1$, R$^{6'}$ and R$^{7'}$ are H; R$^{4'}$ and R$^{5'}$ are halo or —NHR$^5$—C$_{1-3}$ alkyl, where R$^5$ is as defined in the first general embodiment; R$^{4''}$ and R$^{6''}$ are H; R$^{3''}$ and R$^{5''}$ independently are H or —NR$^2$R$^2$, where R$^2$ is as defined in the first general embodiment; Y is —C$_{1-6}$ alkyl; and T is CH$_2$;

s) Z is —C(=W)—NH—C(=W)OR$^3$, wherein R$^3$ is as defined for Formula (A); R$^1$, R$^{6'}$ and R$^{7'}$ are H; R$^{4'}$ and R$^{5'}$ are halo or —NHCO—C$_{1-3}$ alkyl; R$^{4''}$ and R$^{6''}$ are H; R$^{3''}$ and R$^{5''}$ independently are halo or H; Y is —C-alkenyl; and T is O;

t) Z is —C(=W)R$^3$—NH—C(=W)—R$^2$, where R$^2$ is —NH$_2$ and R$^3$ is —NH; R$^1$, R$^{6'}$ and R$^{7'}$ are H; R$^{4'}$ and R$^{5'}$ are halo or oxime; R$^{4''}$ and R$^{6''}$ are H; R$^{3''}$ and R$^{5''}$ independently are H or —C$_{1-3}$ alkyl or alkenyl optionally substituted with one or more halogen; Y is —C-alkynyl; and T is (CH$_2$)$_2$;

u) Z is —C(=W)—N(C=O)—N(R$^2$)—R$^3$, where R$^2$ is H or alkyl, R$^3$ is —NH$_2$, R$^1$, R$^{6'}$ and R$^{7'}$ are H; R$^{4'}$ and R$^{5'}$ are halo or hydrazine; R$^{4''}$ and R$^{6''}$ are H; R$^{3''}$ and R$^{5''}$ independently are H; Y is —C-aryl; and T is (CH$_2$)$_2$;

v) Z is —C(=W)—N(R$^2$)—N(R$^2$)—C(=W)R$^3$, where R$^2$ is H or alkyl, and R$^3$ is NH$_2$; R$^1$, R$^{6'}$ and R$^{7'}$ are H; R$^{4'}$ and R$^{5'}$ are halo or —NHS(O)$_2$—C$_{1-3}$ alkyl; R$^{4''}$ and R$^{6''}$ are H; R$^{3''}$ and R$^{5''}$ independently are H or -methyl; Y is —C-heterocycle; and T is O;

w) Z is —C(=W)—N(—N[R$^2$][R$^3$])—R$^3$, where R$^2$ is H or alkyl, and R$^3$ is NH$_2$; R$^1$, R$^{6'}$ and R$^{7'}$ are H; R$^{4'}$ and R$^{5'}$ are halo or —C$_{1-6}$ alkyl or alkenyl optionally substituted with one or more —OH, —SR, —C(=W)H, —C(=W)OH, halogen, NR$^2$R$^2$, C$_{1-3}$ alkoxy, or C$_{1-3}$ thioether, where R$^2$ is as defined in the first general embodiment; R$^{4''}$ and R$^{6''}$ are H; R$^{3''}$ and R$^{5''}$ independently are H or —NR$^2$R$^2$, where R$^2$ is as defined in the first general embodiment; Y is —C-carbocycle; and T is NR$^2$ where R$^2$ is as provided above;

x) Z is —C(=W)R$^2$—C(=W)NH$_2$, where R$^2$ is alkyl; R$^1$, R$^{6'}$ and R$^{7'}$ are H; R$^{4'}$ and R$^{5'}$ are halo or —H; R$^{4''}$ and R$^{6''}$ are H; R$^{3''}$ and R$^{5''}$ independently are H or chlorine; Y is —SR$^2$ and T is CH$_2$;

y) Z is —C(=W)R$^2$—SR$^2$, where R$^2$ is —NH or alkyl; R$^1$, R$^{6'}$ and R$^{7'}$ are H; R$^{4'}$ and R$^{5'}$ are halo or —CF$_3$; R$^{4''}$ and R$^{6''}$ are H; R$^{3''}$ and R$^{5''}$ independently are H or fluorine; Y is —O; and T is (CH$_2$)$_2$;

z) Z is —C(=W)—CH(R$^2$)—C(=NH)R$^2$, where R$^2$ is H or NH$_2$; R$^1$, R$^{4'}$ and R$^{7'}$ are H; R$^{5'}$ and R$^{6'}$ are halo or —H; R$^{4''}$ and R$^{6''}$ are H; R$^{3''}$ and R$^{5''}$ independently are H or —CF$_3$; Y is —NR$^2$; and T is CR$^2$; where R$^2$ is as defined for Formula (A);

aa) Z is —C(=W)—NH-A-NH—C(=W)-A-C—(=W)—R$^2$ where R$^2$ is NH$_2$ and A is a divalent linker; R$^1$, R$^{4'}$ and R$^{7'}$ are H; R$^{5'}$ and R$^{6'}$ are WN or —NO$_2$; R$^{4''}$ and R$^{6''}$ are H; R$^{3''}$ and R$^{5''}$ independently are H or —NO$_2$; Y is —CH$_2$; and T is NR$^2$, where R$^2$ is as defined for Formula (A);

bb) Z is —C(=W)—R$^2$—CH—(-A-C[=W]R$^2$)(—C[=W]—NH$_2$), where R$^2$ is H, alkyl, or NH; A is a divalent spacer linkage as defined for Formula (A); R$^1$, R$^{4'}$, and R$^{7'}$ are H; R$^{5'}$ and R$^{6'}$ are H or —NHCO—C$_{1-6}$ alkyl; R$^{4''}$ and R$^{6''}$ are H; R$^{3''}$ and R$^{5''}$ independently are H or hydrazinyl; Y is (CH$_2$)$_2$; and T is N;

cc) Z is —C(=W)—NH-A(—C[=W]—NH$_2$), where A is an alkylene or arylene divalent spacer linkage; R$^1$, R$^{4'}$ and R$^{7'}$ are H; R$^{5'}$ and R$^{6'}$ are H or —NH(SO$_2$)C$_{1-6}$ alkyl; R$^{4''}$ and R$^{6''}$ are H; R$^{3''}$ and R$^{5''}$ independently are H or —NHOH; Y is —C-alkenyl; and T is N;

dd) Z is —C(=W)—NH—CH(-A-R$^3$)(—C[=W]—NH$_2$), where A is an alkylene or alkenylene spacer; R$^3$ is OH; R$^1$, R$^{4'}$ and R$^{7'}$ are H; R$^{5'}$ and R$^{6'}$ are H or CF$_3$; R$^{4''}$ and R$^{6''}$ are H; R$^{3''}$ and R$^{5''}$ independently are H or —NR$^2$R$^2$ where R$^2$ is as defined for Formula (A); Y is —C-carbocycle; and T is SR$^2$;

ee) Z is —C(=W)—NH—CH(R$^2$)(R$^3$), where R$^2$ and R$^3$ each is C(=W)NH$_2$; R$^1$, R$^{6'}$ and R$^{7'}$ are H; R$^{5'}$ and R$^{4'}$ are H or halo; R$^{4''}$ and R$^{6''}$ are H; R$^{3''}$ and R$^{5''}$ independently are H or —C$_{1-5}$ alkoxy; Y is —O; and T is CH$_2$;

ff) Z is —C(=W)-A-CH(—R$^2$—C[=W]—NH$_2$)(—C[=W]—NH$_2$), where A is a spacer linkage as defined for Formula (A); R$^2$ is NH; R$^1$, R$^{6'}$ and R$^{7'}$ are H; R$^{5'}$ and R$^{4'}$ are H or —NO$_2$; R$^{4''}$ and R$^{6''}$ are H; R$^{3''}$ and R$^{5''}$ independently are H or —OH; Y is —N; and T is CH$_2$;

gg) Z is —C(=W)—NH—CH—(—CH—R$^2$—OH)(—C[=W]—NH$_2$), where R$^2$ is NH or alkylene; R$^1$, R$^{6'}$ and R$^{7'}$ are H; R$^{5'}$ and R$^{4'}$ are H or -halogen; R$^{4''}$ and R$^{6''}$ are H; R$^{3''}$ and R$^{5''}$ independently are H or -halogen; Y is —SR$^2$; and T is CH—OCH$_3$;

hh) Z is —C(=W)—NH—CH(—R$^2$)(—C[=W]—NH$_2$), where R$^2$ is alkyl; R$^1$, R$^{6'}$ and R$^{7'}$ are H; R$^{5'}$ and R$^{4'}$ are H or —NO$_2$; R$^{4''}$ and R$^{6''}$ are H; R$^{3''}$ and R$^{5''}$ independently are H or —CN; Y is —C-aryl; and T is N;

ii) Z is —C(=W)—NH—CH(—R$^2$)(—C[=W]—NH$_2$), where R$^2$ is alkyl; R$^1$, R$^{6'}$ and R$^{7'}$ are H; R$^{5'}$ and R$^{4'}$ are H or —OH; R$^{4''}$ and R$^{6''}$ are H; R$^{3''}$ and R$^{5''}$ independently are H or —CN; Y is —C-heterocycle; and T is (CH$_2$)$_2$;

jj) Z is —C(=W)—NH—CH(—R$^2$—C[=W]—NH$_2$)(—C[=W]—NH$_2$, where R$^2$ is alkylene; R$^1$, R$^{6'}$ and R$^{7'}$ are H; R$^{4'}$ and R$^{5'}$ are H or —NO$_2$; R$^{4''}$ and R$^{6''}$ are H; R$^{3''}$ and R$^{5''}$ independently are H or —NHOH; Y is —O and T is CH$_2$;

kk) Z is —C(=W)—NH—CH(—R$^2$)(—C[=W]—NH$_2$), where R$^2$ is —S(O)R$^3$ and R$^3$ is as defined for Formula (A); R$^1$, R$^{6'}$ and R$^{7'}$ are H; R$^{4'}$ and R$^{5'}$ are H or —OR$^2$, R$^{4''}$ and R$^{6''}$ are H; R$^{3''}$ and R$^{5''}$ independently are H or —C$_{1-3}$ alkoxy; Y is —NR$^2$, where R$^2$ is as defined in the first general embodiment, and T is CH$_2$;

ll) Z is —C(=W)—NH—CH(—C[=NH]—NH$_2$)(—C[=W]—NH$_2$); R$^1$, R$^{6'}$ and R$^{7'}$ are H; R$^{4'}$ and R$^{5'}$ are H or —NR$^2$R$^2$, where R$^2$ is as defined in the first general embodiment; R$^{4''}$ and R$^{6''}$ are H; R$^{3''}$ and R$^{5''}$ independently are H or —OH; Y is —SR$^2$, and T is (CH$_2$)$_2$;

mm) Z is —C(=W)—NH—NH—CH(R$^3$)—C[=W]R$^2$, where R$^2$ is —NH$_2$ and R$^3$ is optionally substituted aryl or heteroaryl; R$^1$, R$^{6'}$ and R$^{7'}$ are H; R$^{4'}$ and R$^{5'}$ are H or —CN; R$^{4''}$ and R$^{6''}$ are H; R$^{3''}$ and R$^{5''}$ independently are H or —NR$^2$R$^2$, where R$^2$ is as defined in the first general embodiment; Y is —C—C$_{1-6}$ alkyl; and T is N;

nn) Z is —C(=W)—NHR$^2$(—R$^3$)—C[=W]NH$_2$, where R$^2$ is alkyl, and R$^3$ is optionally substituted alkyl, aryl or heteroaryl; R$^1$, R$^{6'}$ and R$^{7'}$ are H; R$^{4'}$ and R$^{5'}$ are H or —NH—R$^5$—C$_{1-3}$ alkyl, where R$^5$ is as defined in the first general embodiment; $R^{4''}$ and $R^{6''}$ are H; $R^{3''}$ and $R^{5''}$ independently are H or —$C_{1-6}$ alkyl or alkenyl optionally substituted with one or more —OH, —SR, —C(=W)OH, halogen, or $NH_2$; Y is —C-alkenyl; and T is $SR^2$ where $R^2$ is as defined for Formula (A);

oo) Z is —C(=W)—$NHR^2$(—$R^3$)—C[=W]NH—$R^2$—C(=W)OH, where $R^2$ is alkyl, and $R^3$ is optionally substituted alkyl, aryl or heteroaryl; $R^1$, $R^{6'}$ and $R^{7'}$ are H; $R^{4'}$ and $R^{5'}$ are H or —NHCO—$C_{1-3}$ alkyl; $R^{4''}$ and $R^{6''}$ are H; $R^{3''}$ and $R^{5''}$ independently are H or —$C_{1-6}$ alkyl or alkenyl optionally substituted with one or more halogen; Y is —C-alkynyl; and T is $CH_2$;

pp) Z is —C(=W)—$NHR^2$(—$R^3$)—C[=W]NH—$R^2$ $NH_2$, where $R^2$ is alkyl, and $R^3$ is optionally substituted alkyl, aryl or heteroaryl; $R^1$, $R^{6'}$ and $R^{7'}$ are H; $R^{4'}$ and $R^{5'}$ are H or -oxime; $R^{4''}$ and $R^{6''}$ are H; $R^{3''}$ and $R^{5''}$ independently are H or -halogen; Y is —$CH_2$; and T-$NR^2$ where $R^2$ is as defined for Formula (A);

qq) Z is —C(=W)—$NHR^2$(—$R^3$)—C(=W)NH—$R^3$, where $R^2$ is alkyl, and $R^3$ is optionally substituted alkyl, aryl or heteroaryl; $R^1$, $R^{6'}$ and $R^{7'}$ are H; $R^{4'}$ and $R^{5'}$ are H or -hydrazine; $R^{4''}$ and $R^{6''}$ are H; $R^{3''}$ and $R^{5''}$ independently are H; Y is —$NR^2$ where $R^2$ is as defined in the first general embodiment; and T is $(CH_2)_2$;

rr) Z is —C(=W)—$R^2$-A-C(=W)—$NH_2$, where $R^2$ is —NH, and A is a divalent spacer linkage that is optionally substituted aryl or heteroaryl; $R^1$, $R^{6'}$ and $R^{7'}$ are H; $R^{4'}$ and $R^{5'}$ are H or —NH($SO_2$)$C_{1-6}$ alkyl; $R^{4''}$ and $R^{6''}$ are H; $R^{3''}$ and $R^{5''}$ independently are H or methyl; Y is —C—$C_{1-6}$ alkyl; and T is N;

ss) Z is —C(=W)NH—$R^3$, where $R^3$ is an optionally heterocycle; $R^1$, $R^{6'}$ and $R^{7'}$ are H; $R^{4'}$ and $R^{5'}$ are H or —$C_{1-6}$ alkyl or alkenyl optionally substituted with one or more —OH, —SR, C(=W)H, C(=W)OH, halogen, $NR^2R^2$, $C_{1-3}$ alkoxy, or $C_{1-3}$ thioether; $R^{4''}$ and $R^{6''}$ are H; $R^{3''}$ and $R^{5''}$ independently are H or chloro; Y is —C-alkenyl; and T is $NR^2$ where $R^2$ is as defined for Formula (A);

tt) Z is —C(=W)NH-A-S(O)$_2$—$R^3$, where A is an alkylene, alkenylene or alkynylene divalent spacer linkage, $R^3$ is —$NH_2$, and $R^5$ is —$SO_2$; $R^1$, $R^{6'}$ and $R^{7'}$ are H; $R^{4'}$ and $R^{5'}$ are H; $R^{4''}$ and $R^{6''}$ are H; $R^{3''}$ and $R^{5''}$ independently are H or fluoro; Y is —$(CH_2)_2$; and T is $(CH_2)_2$;

uu) Z is —C(=W)NH—NH-A-($R^3$)—S(O)$_2$—$NH_2$, where A is an alkylene, alkenylene or alkynylene divalent spacer linkage, $R^3$ is aryl, arylene or heteroaryl, and $R^5$ is —$SO_2$; $R^1$, $R^{6'}$ and $R^{7'}$ are H; $R^{4'}$ and $R^{5'}$ are H or $CF_3$; $R^{4''}$ and $R^{6''}$ are H; $R^{3''}$ and $R^{5''}$ independently are H or $CF_3$; Y is —O; and T is $CH_2$;

vv) Z is —C(=W)NH—$R^3$($SO_2$—$NH_2$), where $R^3$ is aryl, arylene or heteroaryl; $R^1$, $R^{4'}$ and $R^{7'}$ are H; $R^{5'}$ and $R^{6'}$ are H or -halo; $R^{4''}$ and $R^{6''}$ are H; $R^{3''}$ and $R^{5''}$ independently are H or —$NO_2$; Y is —O; and T is $CR^2$ where $R^2$ is as defined for Formula (A);

ww) Z is —C(=W)NH-A-($NH_2$), where A is an alkylene, alkenylene or alkynylene divalent spacer linkage; $R^1$, $R^{4'}$ and $R^{7'}$ are H; $R^{5'}$ and $R^{6'}$ are H or —$NO_2$; $R^{4''}$ and $R^{6''}$ are H; $R^{3''}$ and $R^{5''}$ independently are H or -halo; Y is —O—; and T is C-carbocycle;

xx) Z is —C(=W)NH—$R^3$(-A-$SO_2$—$NH_2$), where A is an alkylene, alkenylene or alkynylene divalent spacer linkage; $R^3$ is aryl, arylene or heteroaryl; $R^1$, $R^{4'}$ and $R^{7'}$ are H; $R^{5'}$ and $R^{6'}$ are H or —CN; $R^{4''}$ and $R^{6''}$ are H; $R^{3''}$ and $R^{5''}$ independently are H or —NH—$R^5$—$C_{1-3}$ alkyl, where $R^5$ is as defined in the first general embodiment; Y is —C-carbocycle; and T is $NR^2$ where $R^2$ is as defined for Formula (A);

yy) Z is —C(=W)NH(—$R^3$)—C(=W)NH-A-C(=W)OH, where A is an optionally substituted alkylene, alkenylene or alkynylene divalent spacer linkage, $R^3$ is as defined in the first general embodiment; $R^1$, $R^{4'}$ and $R^{7'}$ are H; $R^{5'}$ and $R^{6'}$ are H or —$OR^2$ where $R^2$ is as defined in the first general embodiment; $R^{4''}$ and $R^{6''}$ are H; $R^{3''}$ and $R^{5''}$ independently are H or —CN; Y is —C-aryl; and T is $CH_2$;

zz) Z is —C(=W)NH(—$R^3$)—C(=W)NH-A-C(=W)$NH_2$, where A is an optionally substituted divalent spacer linkage as defined for Formula (A); $R^3$ is as defined in the first general embodiment; $R^1$, $R^{4'}$ and $R^{7'}$ are H; $R^{5'}$ and $R^{6'}$ are H or —$NR^2R^2$, where $R^2$ is as defined in the first general embodiment; $R^{4''}$ and $R^{6''}$ are H; $R^{3''}$ and $R^{5''}$ independently are H or —NH—$R^5$—$C_{1-6}$ alkyl, where $R^5$ is as defined in the first general embodiment; Y is —C-heterocycle; and T is $SR^2$;

aaa) Z is —C(=W)$NHR^2$—C(=W)NH—$R^2$—C(=W)OH, where $R^2$ is as defined for Formula (A); A is an optionally substituted divalent spacer linkage; $R^1$, $R^{4'}$ and $R^{7'}$ are H; $R^{5'}$ and $R^{6'}$ are H or —$NHSO_2$—$C_{1-6}$ alkyl; $R^{4''}$ and $R^{6''}$ are H; $R^{3''}$ and $R^{5''}$ independently are H or hydrazine; Y is —O and T is $(CH_2)_2$; and bbb) Z is —C(=W)$NHR^2$—C(=W)NH—$R^2$—C(=W)$NH_2$, where $R^2$ is as defined for Formula (A); A is an optionally substituted divalent spacer linkage; $R^1$, $R^{4'}$ and $R^{7'}$ are H; $R^{5'}$ and $R^{6'}$ are H or —NHCO—$C_{1-6}$ alkyl; $R^{4''}$ and $R^{6''}$ are H; $R^{3''}$ and $R^{5''}$ independently are H or —OH; Y is —$NR^2$ where $R^2$ is as defined in the first general embodiment, and T is $CH_2$;

wherein W is as defined above for the first general embodiment of Formula (A).

For all embodiments, subembodiments are defined when:
1) Z is —C(=W)—NH—$R^2$; —C(=W)—$NR^2R^3$; —C—$R^2R^3$; —$CR^2$—C(=W)$R^3$; —$R^2$—C(=W)$R^3$; —$R^2$—C(=W)$R^2$; —$R^2R^3$; $R^3$; or C(=W)—NH—$CR^2R^2$—C(=W)—NH—$CR^2R^3$—C(=W)—$NR^2R^3$;
2) $R^{4'}$, $R^{6'}$ and $R^{7'}$ are H, and $R^{5'}$ is i) halogen, and chlorine in particular; ii) hydrazine; iii) $C_{1-6}$ alkyl, alkenyl, alkynyl, amino-alkyl, thioamino-alkyl, or aminocarbonyl-alkyl, each of which optionally may be substituted with one or more —OH, —C(=W)H, —C(=W)OH, —$NR^2R^3$, —$C_{1-3}$ alkoxy, or —$C_{1-3}$ thioether; or one of the following combinations:
   a) $R^{5'}$, $R^{6'}$ and $R^{7'}$ are hydrogen, and $R^{4'}$ is halogen;
   b) $R^{4'}$, $R^{5'}$ and $R^{7'}$ are hydrogen, and $R^{6'}$ is halogen;
   c) $R^{4'}$, $R^{5'}$ and $R^{6'}$ are hydrogen, and $R^{7'}$ is halogen;
   d) $R^{5'}$, $R^{6'}$ and $R^{7'}$ are hydrogen, and $R^{4'}$ is $CF_3$;
   e) $R^{4'}$, $R^{5'}$ and $R^{7'}$ are hydrogen, and $R^{6'}$ is $CF_3$; and
   f) $R^{4'}$, $R^{5'}$ and $R^{6'}$ are hydrogen, and $R^{7'}$ is $CF_3$.

III. Definitions

The following definitions and term construction are intended, unless otherwise indicated.

Ranges, specific values, and typical values listed for radicals, substituents and derivatives are for illustration only, and do not exclude other defined values or values within defined ranges for the radicals, substituents and derivatives. Whenever a range is described herein, the range independently includes each member of the range. As an illustrative example, when $C_{1-6}$-alkyl are referred to, this listing independently includes $C_1$-alkyl, $C_2$-alkyl, $C_3$-alkyl, $C_4$-alkyl, $C_5$-alkyl and $C_6$-alkyl.

"Halo" is fluoro, chloro, bromo or iodo.

"Alkyl", "alkoxy", "alkenyl", "alkynyl", etc., includes both straight chain and branched groups. However, reference to an individual radical such as "propyl" embraces only that straight-chain radical, whereas a branched chain isomer such as "isopropyl" is specifically termed such.

"Alkyl" as used herein and unless otherwise specified, is a saturated, straight, branched, or cyclic, primary, secondary, or tertiary hydrocarbon of, for example, $C_{1-10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. When the context of this document allows alkyl to be substituted, the moieties with which the alkyl group may be substituted include but not limited to hydroxyl, amino, alkylamino, arylamino, alkoxy, aryloxy, aryl, heterocyclyl, halo, carboxy, acyl, acyloxy, amido, nitro, cyano, sulfonic acid, sulfate, phosphonic acid, phosphate, or phosphonate, either protected or unprotected as needed, as known to those skilled in the art and as taught, for example, in Greene et al., *Protective Groups in Organic Synthesis* John Wiley and Sons, Third Ed., 1999.

The term "lower alkyl" as used herein and unless otherwise specified, includes a $C_{1-4}$ saturated, straight, branched, or if appropriate, cyclic (for example, cyclopropyl) alkyl group, including both substituted and unsubstituted forms. Unless otherwise specifically stated in this application, when alkyl is a suitable moiety, lower alkyl is typical. Similarly, when alkyl or lower alkyl is a suitable moiety, unsubstituted alkyl or lower alkyl is typical.

The terms "alkenyl" and "alkynyl" refer to alkyl moieties, including both substituted and unsubstituted forms wherein at least one saturated C—C bond is replaced by a double or triple bond. Thus, $C_{2-6}$ alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $C_{2-6}$ alkynyl may be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" refers to a saturated, straight chain, divalent alkyl radical of the formula —$(CH_2)_n$—, wherein "n" may be any whole integer from 1 to 10.

As used herein with exceptions as noted, "aryl" is intended to mean any stable monocyclic, bicyclic or tricyclic carbon ring of up to 8 members in each ring, wherein at least one ring is aromatic as defined by the Huckel 4n+2 rule. Examples of aryl ring systems include phenyl, naphthyl, tetrahydronaphthyl, and biphenyl. The aryl group may be substituted with one or more moieties including but not limited to hydroxyl, amino, alkylamino, arylamino, alkoxy, aryloxy, alkyl, heterocyclyl, halo, carboxy, acyl, acyloxy, amido, nitro, cyano, sulfonamido, sulfonic acid, sulfate, phosphonic acid, phosphate, or phosphonate, either protected or unprotected as needed, as known to those skilled in the art and as taught, for example, in Greene et al., *Protective Groups in Organic Synthesis*, John Wiley and Sons, Third Ed., 1999.

The term "heterocycle" or "heterocyclic" as used herein except where noted, refers to a stable 5- to 7-membered monocyclic or stable 8- to 11-membered bicyclic heterocyclic ring which is either saturated or unsaturated, including heteroaryl, and which consists of carbon atom(s) and from one to four heteroatoms including but not limited to O, S, N and P; and wherein the nitrogen and sulfur heteroatoms may optionally be oxidized, and/or the nitrogen heteroatom quaternized, and including any bicyclic group in which any of the above-identified heterocyclic rings is fused to a benzene ring. The heterocyclic ring may be attached at any heteroatom or carbon atom which results in the creation of a stable structure. The heteroaromatic ring may be partially or totally hydrogenated, as desired. For example, dihydropyridine may be used in place of pyridine. Functional oxygen and nitrogen groups on a heteroaryl may be protected as necessary or desired. Suitable protecting groups for oxygen or nitrogen include trimethylsilyl, dimethylhexylsilyl, t-butyldimethylsilyl, t-butyldiphenylsilyl, trityl, substituted trityl, alkyl, methanesulfonyl, p-toluenesulfonyl, or acyl groups such as acetyl and propionyl.

Non-limiting examples of heteroaryl and heterocyclic groups include furyl, pyridyl, pyrimidyl, pyridazinyl, pyrazinyl, piperidinyl, piperazinyl, thienyl, pyrrolyl, pyrrolinyl, pyrrolidinyl, imidazolyl, tetrazolyl, triazolyl, triazinyl, thiazinyl, oxazolyl, purinyl, carbazolyl, quinolinyl, pyrazolyl, morpholinyl, benzimidazolyl, and the like. Any of the heteroaromatic and heterocyclic moieties may be optionally substituted as described above for aryl, including substitution(s) with one or more hydroxyl, amino, alkylamino, arylamino, alkoxy, aryloxy, alkyl, heterocyclyl, halo, carboxy, acyl, acyloxy, amido, nitro, cyano, sulfonic acid, sulfate, phosphonic acid, phosphate, or phosphonate, either protected or unprotected as needed, as known to those skilled in the art and as taught, for example, in Greene et al., *Protective Groups in Organic Synthesis*, John Wiley and Sons, Third Ed., 1999.

The term "acyl" refers to a compound of the formula "RC(O)—", wherein R is substituted or unsubstituted alkyl or aryl as defined herein.

The term "carboxyl" refers to a compound of the formula "RCOOH", wherein R is substituted or unsubstituted alkyl or aryl as defined herein.

The term "aralkyl" as used herein unless otherwise specified, refers to an aryl group as defined above linked to the molecule through an alkyl group as defined above.

The term "alkaryl" as used herein unless otherwise specified, refers to an alkyl group as defined above linked to the molecule through an aryl group as defined above.

The term "alkoxy" as used herein unless otherwise specified, refers to a moiety of the structure "—O-alkyl", where alkyl is as defined above.

The term "amino" as used herein unless otherwise specified, refers to a moiety represented by the structure "—$NR^2$", and includes primary amines, and secondary and tertiary amines optionally substituted by alkyl, aryl, heterocyclyl, and/or sulfonyl groups. Thus, $R_2$ may represent two hydrogens, two alkyl moieties, or one hydrogen and one alkyl moiety.

The term "amido" as used herein unless otherwise specified, refers to a moiety represented by the structure "—C(O)$NR_2$", wherein $R_2$ is an H, alkyl, aryl, acyl, heterocyclyl and/or a sulfonyl group.

As used herein, an "amino acid" or an "amino acid residue" is a natural amino acid or some portion thereof (i.e., Ala, Arg, Asn, Asp, Cys, Glu, Gln, Gly, His, Hyl, Hyp, Ile, Leu, Lys, Met, Phe, Pro, Ser, Thr, Trp, Tyr and Val) in D or L form, or an unnatural amino acid having one or more open valences such as, for example, t-butylglycine, ornithine, hippuric acid and phosphothreonine. Other unnatural amino acids are those represented by the formula "$NH_2(CH_2)_yCOOH$", wherein y is 2-12, and includes aminoalkanoic acids such as ε-amino caproic acid ($H_2N$—$(CH_2)_5$—COOH). The term also comprises natural and unnatural amino acids bearing amino-protecting groups such as acyl, trifluoroacetyl and benzyloxycarbonyl, as well as natural and unnatural amino acids protected at carboxy moieties by protecting groups such as $C_{1-6}$ alkyl, phenyl or benzyl ester and amide, and protecting groups known to those of skill in the art. In all instances where natural and unnatural amino acids contain one or more chiral centers, all possible stereochemical configurations, including both "D" and "L" forms and mixtures thereof, including racemic mixtures, are contained herein.

The term "quaternary amine" as used herein includes quaternary ammonium salts that have a positively charged nitrogen. They are formed by the reaction between a basic nitrogen in the compound of interest and an appropriate quaternizing agent such as, for example, methyliodide or benzyliodide. Appropriate counterions accompanying a quaternary amine include acetate, trifluoroacetate, chloro, bromo and iodo ions.

As used herein, the term "N-oxides" denotes a state of the compounds of the present invention in which one or more nitrogen atoms are oxidized with an oxygen atom.

As used herein, a "retrovirus" includes any virus that expresses reverse transcriptase. Examples of a retrovirus include but are not limited to, HIV-1, HIV-2, HTLV-I, HTLV-II, FeLV, FIV, SIV, AMV, MMTV, and MoMuLV.

As used herein, "reverse transcriptase" or "RT" refers to an enzyme having a non-nucleoside inhibitory binding site similar to that of HIV-1 RT, and to which ligands, which bind the composite binding pocket of the compounds of the present invention, also will bind. One measure of RT activity is viral replication. A measure of HIV-1 viral replication is the automated assay that utilizes MTT, as described earlier in this specification. Another measure is the p24 core antigen enzyme immunoassay, such as, for example, the assay commercially available from Coulter Corporation/Immunotech, Inc.® (Westbrook, Mich.). Another means for measuring RT activity is by assaying recombinant HIV-1 reverse transcriptase activity, such as, for example, by using the Quan-T-RT™ assay system commercially available from Amersham® (Arlington Heights, Ill.) and as described by Bosworth et al., *Nature*, 1989, 341:167-168.

As used herein, a compound that "inhibits replication of human immunodeficiency virus (HIV)" means a compound that, when contacted with HIV-1, for example, via HIV-infected cells, effects a reduction in the amount of HIV-1 as compared with an untreated control. Inhibition of replication of HIV-1 may be measured by any means known to those skilled in the art, such as, for example, by the p24 assay disclosed above.

The reagent denoted "mCPBA" in the synthesis schemes is meta-chloro-peroxybenzoic acid.

The term "salvage therapy" as used herein means a compound that can be taken with any regimen after a patient's initial treatment regimen has failed.

As used herein, the term "host" refers to a multicellular or unicellular organism in which the virus can replicate. Thus, "host" includes a cell line, an mammal and, preferably, a human. Alternatively, a host can be carrying a part of the HIV genome whose replication or function may be altered by the compounds of the present invention. The term host specifically refers to infected cells, cells transfected with all or part of the HIV genome, and mammals, especially primates including chimpanzees and humans. In most mammal applications of the present invention, the host is a human patient. Veterinary applications, however, are clearly anticipated by the present invention, such as, for example, in chimpanzees.

IV. Pharmaceutically Acceptable Salts, Prodrugs, Stereoisomers and Tautomers

An active compound may be administered as a salt or prodrug that, upon administration to the recipient, is capable of providing directly or indirectly the parent compound, or that exhibits activity itself. Nonlimiting examples include a pharmaceutically-acceptable salt, alternatively referred to as a "physiologically-acceptable salt". In addition, modifications made to a compound can affect its biologic activity, in some cases increasing the activity over the parent compound. This activity can be assessed by preparing a salt or prodrug form of the compound, and testing its antiviral activity by using methods described herein or other methods known to those of skill in the art of NNRTIs.

The phrase "pharmaceutically acceptable salt or prodrug" is used throughout the specification to describe any pharmaceutically acceptable form (such as an ester, amide, salt of an ester, salt of an amide or related group) of a compound that, upon administration to a patient, provides an active compound of the invention. The terms "stereoisomer" and "tautomer" as used herein include all possible stereoisomeric and tautomeric forms of the compounds of the present invention, as well as their quaternary amine, salt, solvate, prodrug, derivative, and N-oxide forms. Where the compounds of the general formulae (I) and (II) contain one or more chiral centers, all possible enantiomeric and diastereomeric forms are included.

The term "pharmaceutically acceptable salt" refers to the state of a compound in which the compound carries a counterion that is pharmaceutically acceptable, and wherein the salt retains the desired biological activity of the herein-identified compounds while exhibiting minimal undesired toxicological effects. Such salts are non-toxic, therapeutically useful forms of the compounds of the present invention. Any salt that retains the desired biological activity of the compounds contained herein and that exhibits minimal or no undesired or toxicological effects is intended for inclusion here. Pharmaceutically acceptable salts include those derived from pharmaceutically acceptable organic or inorganic acids and bases. Non-pharmaceutically acceptable acids and bases also find use herein, as for example, in the synthesis and/or purification of the compounds of interest. Thus, all "salts" are intended for inclusion here.

Non-limiting examples of suitable salts include those derived from inorganic acids, such as, for example, hydrochloric acid, hydrobromic acid, sulfuric acid, phosphoric acid, nitric acid, bicarbonic acid, carbonic acid; and salts formed with organic acids, such as, for example, formic acid, acetic acid, oxalic acid, tartaric acid, succinic acid, malic acid, malonic acid, ascorbic acid, citric acid, benzoic acid, tannic acid, palmoic acid, alginic acid, polyglutamic acid, tosic acid, methanesulfonic acid, naphthalenesulfonic acid, naphthalenedisulfonic acid, α-ketoglutaric acid, α-glycerophosphoric acid and polygalacturonic acid. Suitable salts include those derived from alkali metals such as lithium, potassium and sodium, from alkaline earth metals such as calcium and magnesium, as well as from other bases well known to those of skill in the pharmaceutical art. Other suitable salts include those derived from metal cations such as zinc, bismuth, barium, or aluminum, or with a cation formed from an amine, such as ammonia, N,N-dibenzylethylenediamine, D-glucosamine, tetraethylammonium, or ethylenediamine. Moreover, suitable salts include those derived from a combination of acids and bases, such as, for example, a zinc tannate salt.

A pharmaceutically acceptable prodrug refers to a compound that is metabolized (i.e., hydrolyzed or oxidized, for example) in the host to form a compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

The compounds of the present invention either possess antiviral activity against retroviruses and HIV in particular, or are metabolized to a compound that exhibits such activity.

Any of the oxo-pyrimidine compounds described herein may be administered as a prodrug to increase the activity, bioavailability, stability, or otherwise alter the properties of the oxo-pyrimidine. A number of prodrug ligands also are known. In general, acylation, alkylation or other lipophilic modifications of a heteroatom of the oxo-pyrimidine will increase the stability of the compound. Examples of substituent groups that can replace one or more hydrogens on a heterocycle include, but are not limited to, alkyl, aryl, steroidal, carbohydrate including sugars, 1,2-diacylglycerol, phospholipid, phosphotidylcholine, phosphocholine, and/or alcohol. Any of these may be used in combination with the disclosed oxo-pyrimidine compound to achieve a desired effect.

V. Methods of Treatment

In one embodiment, a method of treatment or prophylaxis of an HIV infection in a host is provided, comprising administering a 3-phosphoindole compound to a host in need thereof. In one particular embodiment, the compound is administered orally, parenterally, enterally, intravenously, intradermally, subcutaneously, percutaneously, transdermally, intranasally, topically or by inhalation therapy. The compound may be administered to a host that has been diagnosed with an HIV infection by measurement of a viral load in the host blood or tissue. In other embodiments the host can have been diagnosed by measurement of an anti-HIV antibody titer in blood. In another embodiment, the compounds are administered to reduce or prevent symptoms of AIDS (acquired immune deficiency syndrome) in a host. In yet another embodiment the compounds of the invention are administered to a host at risk of infection with HIV.

In another embodiment, the active compound exhibits activity against drug-resistant forms of HIV, and thus exhibits decreased cross-resistance against currently approved antiviral therapies. The phrase "activity against a drug-resistant form of HIV means that a compound (or its prodrug or pharmaceutically acceptable salt) is active against the mutant strain with an $EC_{50}$ of less than approximately 50, 25, 10 or 1 micromolar concentration. In one embodiment, the non-nucleoside reverse transcriptase inhibitor (NNRTI) displays an $EC_{50}$ (in molar concentration) against a mutant HIV strain of less than approximately 5, 2.5, 1 or 0.1 micromolar. In one non-limiting embodiment, the HIV mutant strain has a reverse transcriptase mutation at lysine 103→asparagine and/or tyrosine 181→cysteine.

The 3-phosphoindoles can be assessed for their ability to inhibit reverse transcriptase activity in vitro according to standard screening methods. The spectrum of activity exhibited by any particular compound is determined by evaluating the compound in assays described in this specification or with other confirmatory assays known to those skilled in the art of anti-HIV compounds. Compounds typically exhibit an $EC_{50}$ of less than 10-15 µM.

In one embodiment, the efficacy of the 3-phosphoindoles is measured by the HIV-specific enzyme-linked immunosorbent assay, p24 ELISA. Drug efficacy is expressed as percent inhibition of the HIV p24 antigen in this rapid and sensitive assay. In a related embodiment useful for specific experiments, the efficacy of the anti-HIV compound is determined by a "plaque reduction assay" which measures the concentration of compound necessary to reduce the plaque number of the virus in vitro, according to the methods set forth more particularly herein, by 50% (i.e., the $EC_{50}$ of the compound). In some embodiments the compound exhibits an $EC_{50}$ of less than 15, or less that 10 micromolar to nanomolar amounts in vitro.

VI. Combination or Alternation Therapy

In a certain embodiments, the 3-phosphoindole compound is administered in combination and/or alternation with one or more other anti-retroviral or anti-HIV agent. In one embodiment, the effect of administering two or more such agents in combination and/or alternation produces a synergistic effect in inhibiting HIV replication. In another embodiment, the effect of administering two or more such agents in combination and/or alternation produces an additive effect in inhibiting HIV replication.

In combination therapy, effective dosages of two or more agents are administered together, whereas during alternation therapy an effective dosage of each agent is administered serially. The dosages will depend upon absorption, inactivation, and excretion rates of the drugs as well as other factors known to those of skill in the art. Dosage values also will vary with the severity of the condition to be alleviated. For any particular individual, specific dosage regimens and schedules should be adjusted over time to meet the needs of the individual and the professional judgment of the person administering or supervising the administration of the compositions.

Drug resistance most typically occurs by mutation of a gene that encodes for an enzyme used in the viral replication cycle, and most typically in the case of HIV, in either the reverse transcriptase or protease genes. It has been demonstrated that the efficacy of an anti-HIV drug can be prolonged, augmented or restored by administering the compound in combination or alternation with a second, and perhaps third, antiviral compound that induces a different mutation(s) from that selected for by the principle drug. Such drug combinations simultaneously reduce the possibility of resistance to any single drug and any associated toxic effects. Alternatively, the pharmacokinetics, biodistribution, or other parameters of the drug can be altered by such combination or alternation therapy. For example, the use of a combination of drugs may permit an individual drug within that combination to be given at a dosage lower than what would be required when the drug is administered as a monotherapeutic. Likewise, when drugs that target different stages of the viral life cycle are combined, there exists the possibility for potentiating their effects. Moreover, use of combinations of drugs could lower or eliminate undesirable side-effects from a single drug while still producing anti-viral activity. In general, combination therapy is typical over alternation therapy because it places multiple, simultaneous pressures on the virus.

The second antiviral agent for the treatment of HIV can be, for example, a protease inhibitor, an HIV-integrase inhibitor, a chemokine inhibitor, or a reverse transcriptase inhibitor ("RTI"), the latter of which can either be a synthetic nucleoside reverse transcriptase inhibitor ("NRTI") or a non-nucleoside reverse transcriptase inhibitor ("NNRTI"). In other embodiments, a second or third compound may be a pyrophosphate analog or a fusion-binding inhibitor. A list compiling resistance data collected in vitro and in vivo for certain antiviral compounds is found in Schinazi et al., Mutations in retroviral genes associated with drug resistance, *International Antiviral News*, 1997, 5(8).

In certain embodiments, the indole compound is administered in combination and/or alternation with FTC (2',3'-dideoxy-3'-thia-5-fluorocytidine); 141W94 (amprenavir, Glaxo Wellcome, Inc.); Viramune (nevirapine); Rescriptor (delavirdine); DMP-266 (efavirenz); DDI (2',3'-dideoxyinosine); 3TC (3'-thia-2',3'-dideoxycytidine); DDC (2',3'-dideoxycytidine), abacavir (1592U89), which is (1S,4R)-4-

[(2-amino-6-cyclopropyl-amino)-9H-purin-9-yl]-2-cyclopentene-1-methanol succinate, Tenofovir DF (Viread), D4T, or AZT.

Other examples of antiviral agents that can be used in combination and/or alternation with the compounds disclosed herein include, but are not limited to, foscarnet; carbovir; acyclovir; interferon; fusion inhibitors such as enfuvirtide; and β-D-dioxolane nucleosides such as β-D-dioxolanylguanine (DXG), β-D-dioxolanyl-2,6-diaminopurine (DAPD), and β-D-dioxolanyl-6-chloropurine (ACP). Interferons that may be used include Schering-Plough's alpha interferon-2b products, Intron® A and PEG-Intron™; and Hoffman La Roche's Co-Pegasus and PEGASYS (pegylated interferon alfa-2a). Combinations with which the 3-phosphoindoles can be administered include Epzicom (ABC+3TC), Trizivir (ABC+3TC+AZT), Truvada (FTC+Viread) and Combivir (AZT+3TC).

Examples of protease inhibitors that can be used in combination and/or alternation with the compounds disclosed herein include, but are not limited to indinavir ({1(1S,2R),5(S)}-2,3,5-trideoxy-N-(2,3-dihydro-2-hydroxy-1H-inden-1-yl)-5-[2-[[(1,1-dimethylethyl)amino]carbonyl]-4-(3-pyridinylmethyl)-1-piperazinyl]-2-(phenylmethyl)-D-erythropentoamide sulfate; Merck & Co., Inc.); nelfinavir (Agouron); ritonavir (Abbott Labs), saquinavir (Roche); Amprenavir; Atazanavir; Fosamprenavir; Kaletra; and DMP-450 {[4R-4(r-a,5-a,6-b,7-6)-hexahydro-5,6-bis(hydroxy)-1,3-bis(3-amino)-phenyl]methyl-4,7-bis(phenylmethyl)-2H-1,3-diazepin-2-one}-bismesylate (Triangle Pharmaceuticals, Inc.).

Other compounds that can be administered in combination or alternation with the phenylindole to augment its anti-viral properties include (1S,4R)-4-[2-amino-6-cyclopropyl-amino-9H-purin-9-yl]-2-cyclopentene-1-methanol succinate (1592U89, a carbovir analog, from GlaxoSmithKline); BILA 1906 (N-{1S-[[[3-[2S-{(1,1-dimethylethyl)amino]carbonyl}-4R-]3-pyridinylmethyl)thio]-1-piperidinyl]-2R-hydroxy-1S-phenylmethyl)propyl]-amino]carbonyl]-2-methylpropyl}-2-quinolinecarboxamide) (Bio Mega/Boehringer Ingelheim); BILA 2185 (N-(1,1-dimethylethyl)-1-[2S-[[[2-2,6-dimethyl-phenoxy]-1-oxoethyl]amino]-2R-hydroxy-4-phenylbutyl]4R-pyridinylthio-2-piperidine-carboxamide) (Bio Mega/Boehringer Ingelheim); BM+51.0836 (triazolo-iso-indolinone derivative) and BMS 186,318 (aminodiol derivative HIV-1 protease inhibitor) (Bristol-Myers Squibb); d4API (9-[2,5-dihydro-5-(phosphonomethoxy)-2-furanyl]-adenine) (Gilead); HBY097 (S-4-isopropoxycarbonyl-6-methoxy-3-[methylthio-methyl]-3,4-dihydroquinoxalin-2(1H)-thione); HEPT (1-[(2-hydroxy-ethoxy)methyl]6-[phenylthio]-thymine); KNI-272 ((2S,3S)-3-amino-2-hydroxy-4-phenylbutyric acid-containing tripeptide); L-697, 593 (5-ethyl-6-methyl-3-(2-phthalimido-ethyl)pyridin-2(1H)-one); L-732,524 (hydroxy-aminopentane amide HIV-1, protease inhibitor) (Merck & Co.); L-697,661 (3-{[(-4,7-dichloro-1,3-benzoxazol-2-yl)methyl]amino}-5-ethyl-6-methyl-pyridin-2(1H)-one); L-FDDC ((−)-β-L-5-fluoro-2', 3'-dideoxycytidine); L-FDOC ((−)-β-L-5-fluoro-dioxolane cytosine); PFA (phosphonoformate; "foscarnet"; Astra); PMEA (9-(2-phosphonylmethoxyethyl)adenine) (Gilead); PMPA ((R)-9-(2-phosphonylmethoxy-propyl)-adenine) (Gilead); Ro 31-8959 (hydroxyethylamine derivative HIV-1 protease inhibitor) (Roche); RPI-3121 (peptidyl protease inhibitor, 1-[(3S)-3-(n-alpha-benzyloxy-carbonyl)-1-asparginyl)-amino-2-hydroxy-4-phenylbutyryl]-n-tert-butyl-1-proline amide); 2720 (6-chloro-3,3-dimethyl-4-(isopropenyloxycarbonyl)-3,4-dihydro-quinoxalin-2(1H)thione); SC-52151 (hydroxyethylurea isostere protease inhibitor) (G. D. Searle); SC-55389A (hydroxyethyl-urea isostere protease inhibitor (G. D. Searle); TIBO R82150 ((+)-(5S)-4,5,6,7-tetrahydro-5-methyl-6-(3-methyl-2-butenyl)-imidazo-[4,5, 1-jk]-[1,4]-benzodiazepin-2(1H)-thione) (Janssen Pharmaceuticals); TIBO 82913 ((+)-(5S)-4,5,6,7-tetrahydro-9-chloro-5-methyl-6-(3-methyl-2-butenyl)imidazo[4,5,1-jk]-[1,4]-benzo-diazepin-2(1H)-thione (Janssen Pharmaceuticals); TSAO-m3T ([2',5'-bis-O-(tert-butyldimethylsilyl)-3'-spiro-5'-(4'-amino-1',2'-oxathiole-2',2'-dioxide)]-β-D-pentofuranosyl-N3-methyl-thymine); U90152 (1-[3-[(1-methylethyl-amino]2-pyridinyl]-4-[[5-[(methylsulphonyl)-amino]-1H-indol-2-yl]-carbonyl]-piperazine); UC (thio-carboxanilide derivatives) (Uniroyal); UC-781 (N-[4-chloro-3-(3-methyl-2-butenyloxy)phenyl]-2-methyl-3-furancarbothioamide); UC-82 (N-[4-chloro-3-(3-methyl-2-butenyloxy)phenyl]-2-methyl-3-thiophenecarbothioamide); VB 11,328 (hydroxyethyl-sulphonamide protease inhibitor) (Vertex/Glaxo Wellcome); XM 323 (cyclic urea protease inhibitor) (Dupont Merck); and penciclovir. In yet another embodiment, the indole compound of the invention is administered in combination with the protease inhibitor LG 1350.

The following drugs have been approved by the FDA or are currently or have been in clinical trials for use in the treatment of HIV infection, and therefore in one embodiment, can be used in combination and/or alternation with the compounds of the present invention.

| Drug Name | Manufacturer |
| --- | --- |
| 3TC, Epivir ® brand lamivudine | GlaxoSmithKline |
| abacavir generic Ziagen ®, ABC, or 1592U89 | GlaxoSmithKline |
| ABC, Ziagen ® brand abacavir, or 1592U89 | GlaxoSmithKline |
| ABT-378/r, or Kaletra ® brand lopinavir/ritonavir | Abbott Laboratories |
| AG-1549, S-1153, or capravirine (CPV) | Pfizer |
| AG1661, Remune ® brand HIV-1 Immunogen, or Salk vaccine | Immune Response Corp. |
| Agenerase ® brand amprenavir (APV), 141W94, or VX-478 | GlaxoSmithKline |
| aldesleukin generic Proleukin ® , or Interleukin-2 (IL-2) | Chiron Corporation |
| amdoxovir, or DAPD | Gilead Sciences |
| amprenavir generic Agenerase ® , APV, 141W94, or VX-478 | GlaxoSmithKline |
| APV, Agenerase ® brand amprenavir, 141W94, or VX-478 | GlaxoSmithKline |
| atazanavir generic Reyataz ™, or BMS-232632 | Bristol-Myers Squibb |
| AZT, Retrovir ® brand zidovudine (ZDV) | GlaxoSmithKline |
| Bis(POC)PMPA, Viread ® brand tenofovir DF | Gilead Sciences |
| BMS-232632, or Reyataz ™ brand atazanavir | Bristol-Myers Squibb |
| BMS-56190, or DPC-083 | Bristol-Myers Squibb |
| calanolide A | Sarawak Medichem |
| capravirine (CPV), AG-1549, or S-1153 | Pfizer |

-continued

| Drug Name | Manufacturer |
|---|---|
| Combivir ® brand zidovudine + lamivudine, or AZT + 3TC | GlaxoSmithKline |
| CPV (capravirine), AG-1549, or S-1153 | Pfizer |
| Crixivan ® brand indinavir (IDV), or MK-639 | Merck & Co. |
| d4T, Zerit ® brand stavudine, or BMY-27857 | Bristol-Myers Squibb |
| DAPD, or amdoxovir | Gilead Sciences |
| ddC, or Hivid ® brand zalcitabine | Hoffmann-La Roche |
| ddI, Videx ® brand didanosine, or BMY-40900 | Bristol-Myers Squibb |
| delavirdine generic Rescriptor ®, DLV, or U-90152S/T | Pfizer |
| didanosine generic Videx ®, ddI, or BMY-40900 | Bristol-Myers Squibb |
| DLV, Rescriptor ® brand delavirdine, or U-90152S/T | Pfizer |
| DPC-083, or BMS-56190 | Bristol-Myers Squibb |
| Droxia ® brand hydroxyurea (HU) | Bristol-Myers Squibb |
| efavirenz generic Sustiva ®, or EFV | Bristol-Myers Squibb |
| EFV, Sustiva ® brand efavirenz | Bristol-Myers Squibb |
| emtricitabine generic Emtriva ™, or FTC | Gilead Sciences |
| Emtriva ® brand emtricitabine, or FTC | Gilead Sciences |
| enfuvirtide generic Fuzeon ™, or T-20 | Trimeris and Hoffmann-La Roche |
| Epivir ® brand lamivudine, or 3TC | GlaxoSmithKline |
| epoetin alfa (erythropoietin) generic Procrit ® | Ortho Biotech |
| erythropoietin (epoetin alfa) generic Procrit ® | Ortho Biotech |
| Fortovase ® brand saquinavir (Soft Gel Cap), or SQV (SGC) | Hoffmann-La Roche |
| fosamprenavir, or GW-433908, or VX-175 | GlaxoSmithKline |
| FTC, or Emtriva ® brand emtricitabine | Gilead Sciences |
| Fuzeon ™ brand enfuvirtide, or T-20 | Trimeris and Hoffmann-La Roche |
| GW-433908, or fosamprenavir, or VX-175 | GlaxoSmithKline |
| HE2000, or alpha-epibromide | HollisEden Pharmaceuticals |
| HIV-1 Immunogen generic Remune ®, Salk vaccine, or AG1661 | Immune Response Corp. |
| Hivid ® brand zalcitabine, or ddC | Hoffmann-La Roche |
| HU, or Droxia ® brand hydroxyurea | Bristol-Myers Squibb |
| hydroxyurea generic Droxia ®, or HU | Bristol-Myers Squibb |
| IDV, Crixivan ® brand indinavir, or MK-639 | Merck & Co. |
| IL-2 (Interleukin-2), or Proleukin ® brand aldesleukin | Chiron Corporation |
| indinavir generic Crixivan ®, IDV, or MK-639 | Merck & Co. |
| Interleukin-2 (IL-2), or Proleukin ® brand aldesleukin | Chiron Corporation |
| Invirase ® brand saquinavir (Hard Gel Cap), SQV (HGC), or Ro-31-8959 | Hoffmann-La Roche |
| Kaletra ® brand lopinavir/ritonavir, or ABT-378/r | Abbott Laboratories |
| lamivudine generic Epivir ®, or 3TC | GlaxoSmithKline |
| lopinavir/ritonavir generic Kaletra ®, or ABT-378/r | Abbott Laboratories |
| MK-639, Crixivan ® brand indinavir (IDV) | Merck & Co. |
| nelfinavir generic Viracept ®, NFV, or AG-1343 | Pfizer |
| nevirapine generic Viramune ®, NVP, or BI-RG-587 | Boehringer Ingelheim |
| NFV, Viracept ® brand nelfinavir, or AG-1343 | Pfizer |
| Norvir ® brand ritonavir (RTV), or ABT-538 | Abbott Laboratories |
| NVP, Viramune ® brand nevirapine, or BI-RG-587 | Boehringer Ingelheim |
| PNU-140690, or tipranavir | Boehringer Ingelheim |
| PRO-542 | Progenics Pharmaceuticals |
| Procrit ® brand epoetin alfa (erythropoietin) | Ortho Biotech |
| Proleukin ® brand aldesleukin, or Interleukin-2 (IL-2) | Chiron Corporation |
| Remune ® brand HIV-1 Immunogen, or Salk vaccine | Immune Response Corp. |
| Rescriptor ® brand delavirdine (DLV), or U-90152S/T | Pfizer |
| Retrovir ® brand zidovudine (ZDV), or AZT | GlaxoSmithKline |
| Reyataz ™ brand atazanavir, or BMS-232632 | Bristol-Myers Squibb |
| ritonavir generic Norvir ®, RTV, or ABT-538 | Abbott Laboratories |
| RTV, Norvir ® brand ritonavir, or ABT-538 | Abbott Laboratories |
| Salk vaccine Remune ® brand HIV-1 Immunogen, or AG1661 | Immune Response Corp. |
| saguinavir (Hard Gel Cap) generic Invirase ®, SQV (HGC), or Ro-31-8959 | Hoffmann-La Roche |
| saquinavir (Soft Gel Cap) generic Fortovase ®, or SQV (SGC) | Hoffmann-La Roche |
| SCH-C | Schering-Plough |
| Serostim ® brand somatropin | Serono Laboratories |
| somatropin generic Serostim ® | Serono Laboratories |
| SQV (HGC), Invirase ® brand saquinavir (Hard Gel Cap), or Ro-31-8959 | Hoffmann-La Roche |
| SQV (SGC), or Fortovase ® brand saquinavir (Soft Gel Cap) | Hoffmann-La Roche |
| stavudine generic Zerit ®, d4T, or BMY-27857 | Bristol-Myers Squibb |
| Sustiva ® brand efavirenz (EFV) | Bristol-Myers Squibb |
| T-1249 | Trimeris and Hoffmann-La Roche |
| T-20, or Fuzeon ™ brand enfuvirtide | Trimeris and Hoffmann-La Roche |
| TDF, tenofovir DF generic Viread ™, or Bis(POC) PMPA | Gilead Sciences |
| tenofovir DF (TDF) generic Viread ™, Bis(POC) PMPA | Gilead Sciences |
| tipranavir, or PNU-140690 | Boehringer Ingelheim |
| TMC-114 | Tibotec-Virco Group |
| TMC-125 | Tibotec-Virco Group |
| Trizivir ® brand abacavir + zidovudine + lamivudine (ABC + AZT + 3TC) | GlaxoSmithKline |
| Videx ® brand didanosine, ddI, or BMY-40900 | Bristol-Myers Squibb |
| Videx ® EC brand didanosine (ddI): delayed-release capsules | Bristol-Myers Squibb |

-continued

| Drug Name | Manufacturer |
|---|---|
| Viracept ® brand nelfinavir (NFV), or AG-1343 | Pfizer |
| Viramune ® brand nevirapine (NVP), or BI-RG-587 | Boehringer Ingelheim |
| Viread ® brand tenofovir DF, or Bis(POC) PMPA | Gilead Sciences |
| VX-175, or fosamprenavir, or GW-433908 | GlaxoSmithKline |
| zalcitabine generic Hivid ®, or ddC | Hoffmann-La Roche |
| ZDV, Retrovir ® brand zidovudine, or AZT | GlaxoSmithKline |
| Zerit ® brand stavudine, d4T, or BMY-27857 | Bristol-Myers Squibb |
| Ziagen ® brand abacavir (ABC), or 1592U89 | GlaxoSmithKline |
| zidovudine generic Retrovir ®, AZT, or ZDV | GlaxoSmithKline |

Additional drugs in clinical trials that can be used in combination and/or alternation with the 3-phosphoindoles include:

| PHASE I | PHASE II | PHASE III |
|---|---|---|
| GW5634 (GSK) | MIV-150 (Medivir/Chiron) | Tipranavir (B-I) |
| RO033-4649 (Roche) | TMC125 (Tibotec) | |
| GW640385 (GSK/Vertex) | TMC114 (Tibotec) | |
| Elvucitabine (Achillion Ph.) | Alovudine (FLT) (B-I) | |
| MIV-210 (GSK/Medivir) | Racivir (Pharmasset) | |
| SPD754 (Shire Pharm.) | Reverset (Incyte Corp.) | |
| FP21399 (Fuji Pharm.) | AMD070 (AnorMed) | |
| GW873140 (GSK) | BMS-488043 (BMS) | |
| Schering C/D (417690) | PRO 542 (Progenics Pharm) | |
| | TAK-220 (Takeda) | |
| | TNX-355 (Tanox) | |
| | UK-427,857 (Pfizer) | |

The following drugs have been approved by the FDA for use in the treatment of complications of HIV infection and AIDS, which can be used in combination and/or alternation with the compounds of the present invention.

| Brand Name | Generic Name | Use | Manufacturer Name |
|---|---|---|---|
| Abelcet, Ambisome | Amphotericin B, ABLC | antifungal for aspergillosis | various |
| Bactrim, Septra | sulfamethoxazole and trimethoprim | antiprotozoal antibiotic for Pneumocystis carinii pneumonia treatment and prevention | various |
| Biaxin, Klacid | clarithromycin | antibiotic for Mycobacterium avium prevention and treatment | Abbott Laboratories |
| Cytovene | ganciclovir, DHPG | antiviral for CMV retinitis | Roche |
| DaunoXome | daunorubicin-liposomal | chemotherapy for Kaposi's sarcoma | Gilead |
| Diflucan | fluconazole | antifungal for candidiasis, cryptococcal meningitis | Pfizer |
| Doxil | doxorubicin hydrochloride-liposomal | chemotherapy for Kaposi's sarcoma | Ortho Biotech |
| Famvir | famciclovir | antiviral for herpes | Novartis |
| Foscarnet | foscavir | antiviral for herpes, CMV retinitis | Astra Pharmaceuticals |
| Gamimune N | immune globulin, gamma globulin, IGIV | immune booster to prevent bacterial infections in children | Bayer Biologicals |
| Intron A | interferon alfa-2b | Karposi's sarcoma, hepatitis C | Schering |
| Marinol | dronabinol | treat appetite loss | Roxane Laboratories |
| Megace | megestrol acetate | treat appetite, weight loss | Bristol Myers-Squibb |
| Mepron | atovaquone | antiprotozoal antibiotic for Pneumocystis carinii pneumonia treatment and prevention | GlaxoSmithKline |
| Mycobutin, Ansamycin | rifabutin | antimycobacterial antibiotic for Mycobacterium avium prevention | Adria Pharmaceuticals |

| Brand Name | Generic Name | Use | Manufacturer Name |
|---|---|---|---|
| NebuPent | pentamidine | antiprotozoal antibiotic for Pneumocystis carinii pneumonia prevention | Fujisawa |
| Neutrexin | trimetrexate glucuronate and leucovorin | antiprotozoal antibiotic for Pneumocystis carinii pneumonia treatment | MedImmune |
| Panretin gel | alitretinoin gel 0.1% | AIDS-related Karposi's sarcoma | Ligand Pharmaceuticals |
| Procrit, Epogen | erythropoetin, EPO | treat anemia related to AZT therapy | Amgen |
| Roferon A | interferon alfa-2a | Karposi's sarcoma and hepatitis C | Roche |
| Serostim | somatropin rDNA | treat weight loss | Serono |
| Sporanox | itraconazole | antifungal for blastomycosis, histoplasmosis, aspergillosis, and candidiasis | Janssen Pharmaceuticals |
| Taxol | paclitaxel | Karposi's sarcoma | Bristol Myers-Squibb |
| Valcyte | valganciclovir | antiviral for CMV retinitis | Roche |
| Vistide | cidofovir, HPMPC | antiviral for CMV retinitis | Gilead |
| Vitrasert implant | ganciclovir insert | antiviral for CMV retinitis | Bausch & Lomb |
| Vitravene intravitreal injectable | fomivirsen sodium injection | antiviral for CMV retinitis | Isis Pharmaceuticals |
| Zithromax | azithromycin | antibiotic for Mycobacterium avium | Pfizer |

Several products have been allowed to proceed as Investigational New Drugs (IND) by the FDA for the treatment of complications of HIV infection and AIDS. Therefore, the following drugs can be used in combination and/or alternation with the compounds of the present invention.

Trimetrexate glucuronate for the treatment of *Pneumocystis carinii* pneumonia in AIDS patients who cannot tolerate standard forms of treatment.

Ganciclovir for the treatment of cytomegalovirus retinitis in AIDS patients.

Aerosolized pentamidine for the prevention of *Pneumocystis carinii* pneumonia in AIDS patients.

Erythropoietin for the treatment of zidovudine-related anemia.

Atovaquone for the treatment of AIDS patients with *Pneumocystis carinii* pneumonia who are intolerant or unresponsive to trimethoprim-sulfamethoxazole.

Rifabutin for prophylaxis against *Mycobacterium avium* complex bacteremia in AIDS patients.

Vistide intravenous cidofovir for HIV-infected persons with relapsing cytomegalovirus (CMV) retinitis that has progressed despite treatment (Hoffmann-La Roche).

Serostim, a mammalian derived recombinat human growth hormone, for the treatment of AIDS-related wasting (Serono Laboratories).

In general, during alternation therapy, an effective dosage of each agent is administered serially. During combination therapy, effective dosages of two or more agents are administered together. Dosages administered depend upon factors such as absorption, biodistribution, metabolism and excretion rates for each drug as well as other factors known to those skilled in the art. It is to be noted that dosage amounts will vary with the severity of the condition to be alleviated, the age, weight, and general physical condition of the subject who receives the drug. It is to be understood further that for any particular subject, specific dosage regimens and schedules should be adjusted over time according to the response of the subject to the drug, the needs of the subject, and the professional judgment of the person administering or supervising the administration of the compositions. Examples of suitable dosage ranges for anti-HIV compounds, including nucleoside derivatives such as, for example, D4T, DDI and 3TC, or protease inhibitors like nelfinavir and indinavir, are to be found in the scientific literature and Physicians' Desk Reference. Suggested ranges for effective dosages of the compounds of the present invention are guidelines only, and are not intended to limit the scope or use of the invention.

The disclosed combination and alternation regimen are useful in the treatment and prevention of retroviral infections and other related conditions, such as, for example, AIDS-related complex (ARC), persistent generalized lymphadenopathy (PGL), AIDS-related neurological conditions, anti-HIV antibody position and HIV-positive conditions, Kaposi's sarcoma, thrombocytopenia purpurea, and opportunistic infections. In addition, these compounds or formulations can be used prophylactically to prevent or retard the progression of clinical illness in individuals who are anti-HIV antibody or HIV-antigen positive, or who have been exposed to HIV.

VII. Pharmaceutical Compositions

The indole compounds of the present invention can be administered to a subject in need thereof, optionally in combination or alternation with another anti-HIV or anti-retroviral agent, and/or with a pharmaceutically acceptable carrier, diluent or excipient. In one embodiment, a subject infected with HIV may be treated by administering to that subject an effective amount of an indole derivative, a salt, prodrug, stereoisomer or tautomer thereof, in the presence of a pharmaceutically acceptable carrier or diluent. For subjects with multiple drug resistance, the oxo-pyrimidine compound is administered either alone or in combination with one or more other anti-retroviral agents or anti-HIV agents. The active compounds may be administered by any appropriate route, for example, orally, parenterally, enterally, intravenously, intradermally, subcutaneously, percutaneously, transdermally, intranasally, topically or by inhalation therapy, and may be in solid, liquid or vapor form.

The active compound(s) are included within the pharmaceutically acceptable carrier, diluent or excipient in an amount sufficient to deliver to a patient a therapeutically effective amount of the active compound in order to inhibit viral replication in vivo, especially HIV replication, without causing serious toxic effects in a treated subject. By an "inhibitory amount" is meant an amount of active ingredient sufficient to halt viral replication as measured by, for example, an assay such as the ones referred to herein.

One dose of the indole compound for all the conditions mentioned is in the range of from about 0.1 to 100 mg/kg of body weight per day, or from about 1 to 75 mg/kg of body weight per day, and even more typically from about 1 to 20 mg/kg of body weight per day. The effective dosage range of the pharmaceutically acceptable derivatives is calculated based on the weight of the parent indole derivative compound to be delivered. If the derivative compound itself exhibits activity, then the effective dosage can be estimated as above using the weight of the derivative, or by other means known to those of skill in the art.

The compounds are conveniently administered in units of any suitable dosage form, including but not limited to one containing from about 7 to 3000 mg, or from about 70 to 1400 mg, and even more typically from about 25 to 1000 mg of active ingredient per unit dosage form. For example, an oral dosage of from about 50 to 1000 mg is usually convenient.

Ideally, the active ingredient is administered to achieve peak plasma concentrations of the active compound of from about 0.02 to 70 µM, and typically of from about 0.5 to 10 µM. For example, this can be achieved by intravenous injection of a 0.1 to 25% solution of active ingredient, optionally in saline, or administered as a bolus of active ingredient. It is to be understood that for any particular subject, specific dosage regimens should be adjusted over time to meet individual needs. The concentrations set forth here are exemplary only and are not intended to limit the scope or practice of the claimed composition. The active ingredient may be administered all at once, or may be divided into a number of smaller doses to be administered at varying intervals of time.

One mode of administration of the active compound is oral. Oral compositions usually include an inert diluent or an edible carrier. They may be enclosed in gelatin capsules, compressed into tablets, or delivered in liquid form. For oral therapeutic administration, the active compound may be incorporated with excipients or formulated as solid dispersions or solid solutions, and used in the form of tablets, troches, or capsules. By a "solid dispersion" is meant a solid state comprising at least two components where one component is dispersed more or less evenly throughout the other component. By "solid solution" is meant a solid state comprising at least two components that are chemically and physically integrated to produce a homogeneous product. A solid solution is typical over a solid dispersion because it more easily forms a liquid solution upon contact with an appropriate liquid medium, thereby increasing the bioavailability of a drug. Pharmaceutically compatible binding agents and/or adjuvant materials also may be included as part of this composition.

The tablets, pills, capsules, troches and the like may contain any of the following ingredients or compounds of a similar nature: a binder such as microcrystalline cellulose, gum tragacanth or gelatin; an excipient such as starch or lactose; a disintegrating agent such as alginic acid, Primogel, or cornstarch; a lubricant such as magnesium stearate or Sterotes; a glidant such as colloidal silicon dioxide; a sweetening agent like sucrose of saccharin; and a flavoring agent, such as peppermint, methyl salicylate, or orange flavoring. When the dosage unit form is a capsule, it may contain a liquid carrier such as a fatty oil in addition to any material of the kinds given above. In addition, dosage unit forms may contain various other materials that modify the physical form of the dosage unit, such as, for example, coatings of sugar, shellac, or other enteric agents.

The indole compounds may be administered as a component of an elixir, suspension, syrup, wafer, chewing gum or the like. A syrup may contain sucrose as a sweetening agent, preservatives, dyes, colorings, and flavorings in addition to the active compounds.

The active compounds or their pharmaceutically acceptable salts or prodrugs can be mixed with other active materials that do not impair the desired action, or with materials that supplement the desired action, such as antibiotics, antifungals, anti-inflammatories, protease inhibitors, or other nucleoside or non-nucleoside antiviral agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates, and agents for the adjustment of tonicity such as sodium chloride or dextrose. A parenteral preparation normally will include sterile water and may be enclosed in ampoules, disposable syringes, or multiple dose vials made of glass or plastic.

If administered intravenously, typical carriers are physiological saline, phosphate buffered saline (PBS), a glucose solution, or a mixed solution comprising glucose and saline. If administration is percutaneous, such as, for example, through the use of a patch or ointment, the associated carrier may comprise a penetration-enhancing agent and/or a suitable wetting agent which are not harmful to the skin. If inhalation or insufflation is the desired route of administration, then the composition of the present invention includes the compound in the form of a solution, suspension or dry powder that can be delivered through the oral and/or nasal orifices.

Liposomal suspensions, which include liposomes targeted to infected cells with monoclonal antibodies to viral antigens, also are typical as pharmaceutically acceptable carriers. These may be prepared according to methods known to those skilled in the art, for example, as described in U.S. Pat. No. 4,522,811, which is incorporated herein by reference in its entirety. For example, liposomal formulations may be prepared by dissolving appropriate lipid(s) such as stearoyl phosphatidyl ethanolamine, stearoyl phosphatidyl choline, arachadoyl phosphatidyl choline, and cholesterol, in an inorganic solvent that later is evaporated, leaving behind a thin film of dried lipid on the surface of the container. An aqueous solution of the active compound, or a salt or prodrug thereof, is then introduced into the container. The container is swirled to free lipid material from its sides and to disperse lipid aggregates, thereby forming the liposomal suspension.

VIII. Processes for Preparing the Active Compounds
General Schemes
Scheme 1:
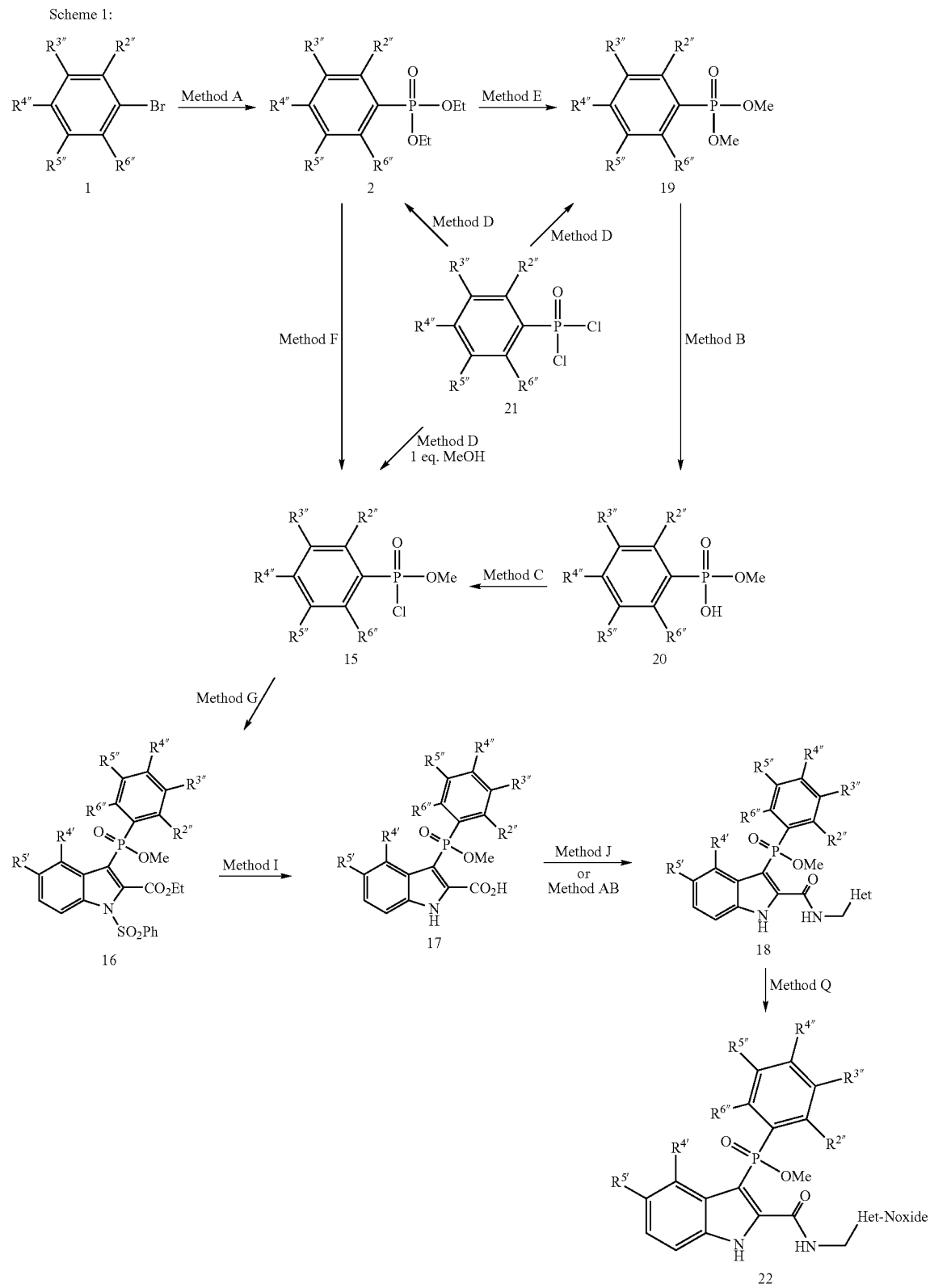

Scheme 2:
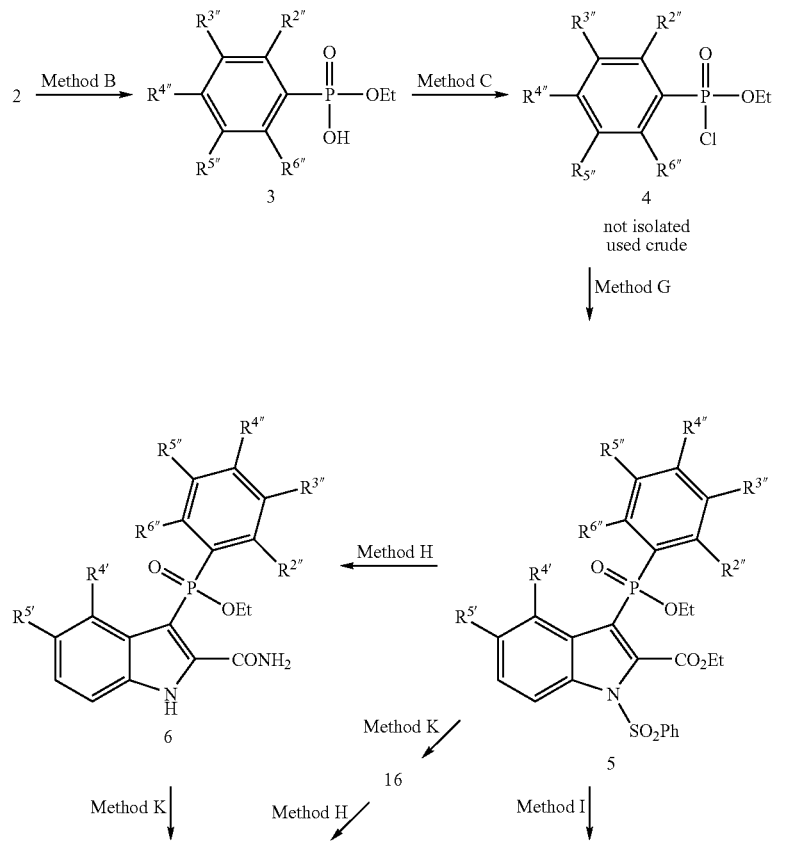
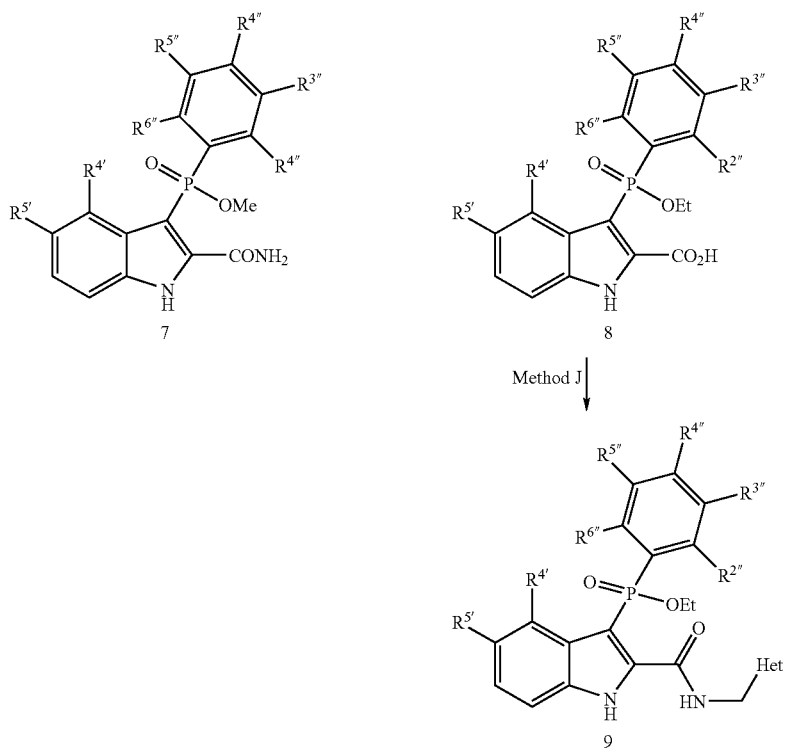

Scheme 3:
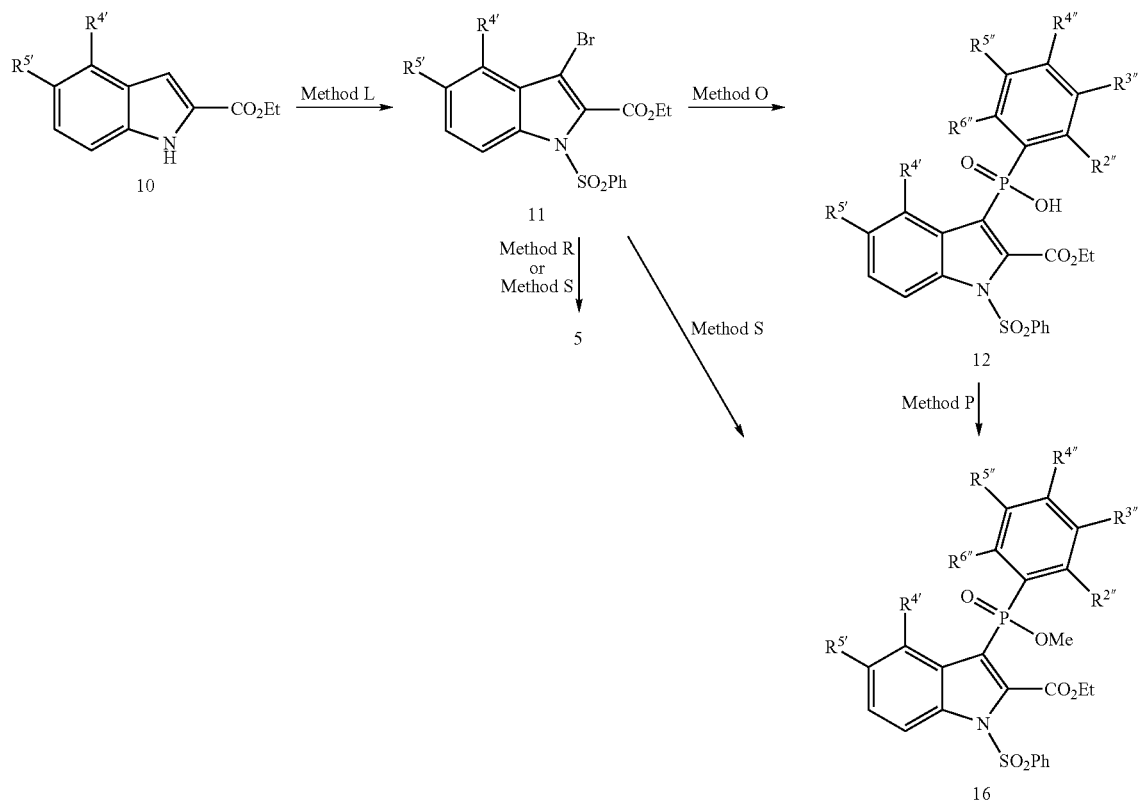
Scheme 4:
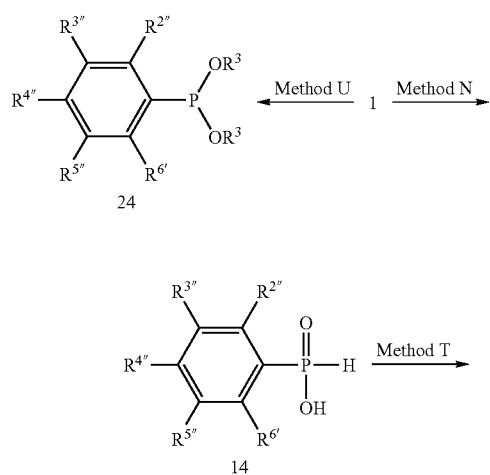
Scheme 5:
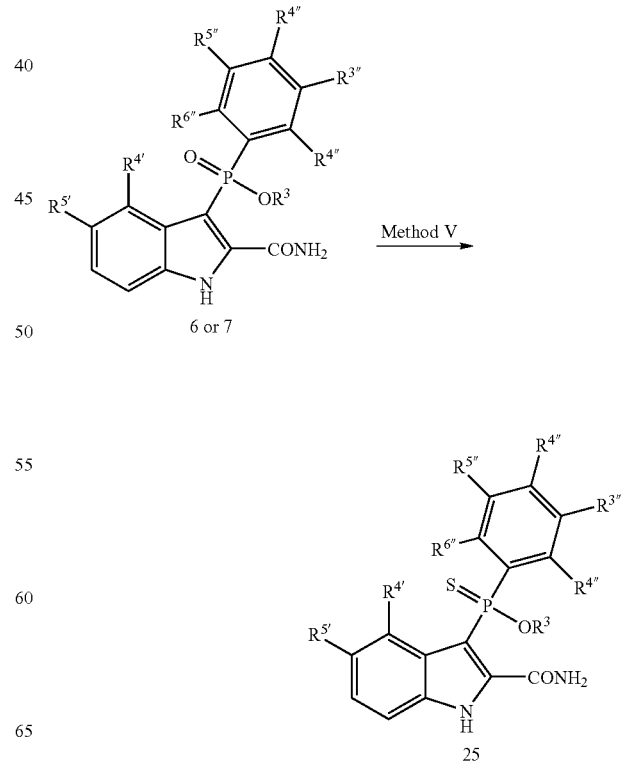

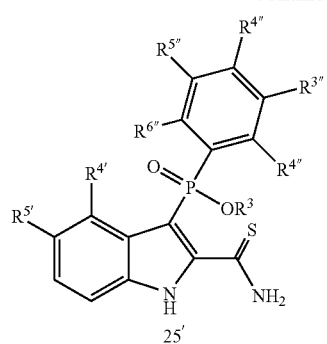
25'
Scheme 6:
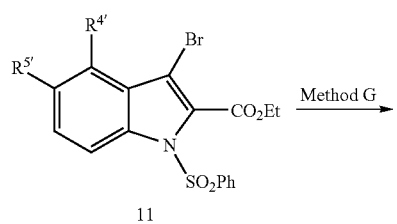
11
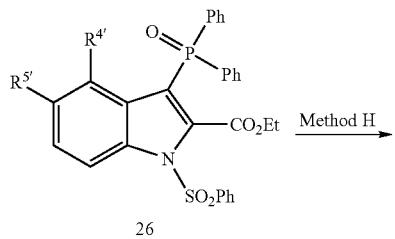
26
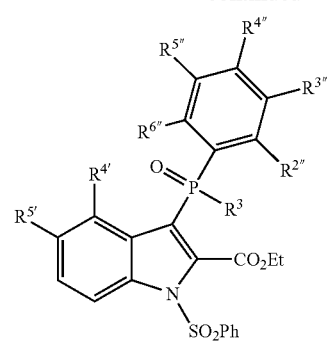
28
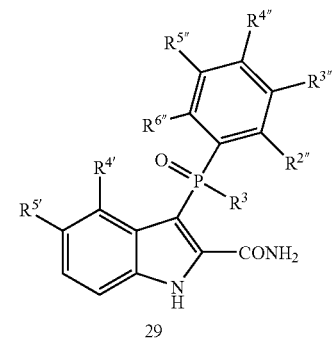
29
Scheme 7:
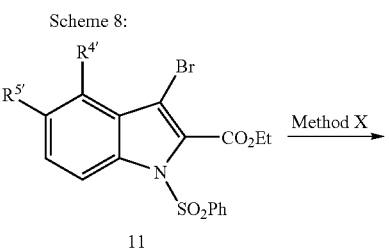
11
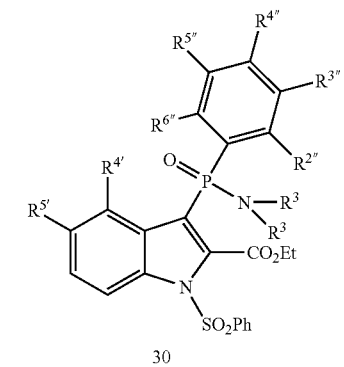
27
Scheme 8:
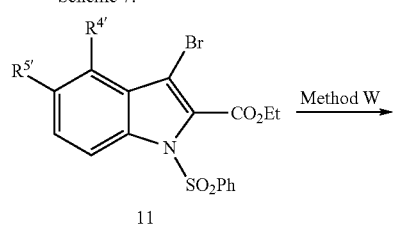
11
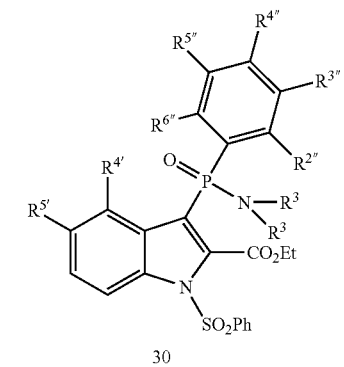
30

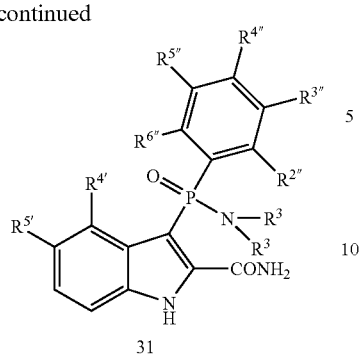
Scheme 9:
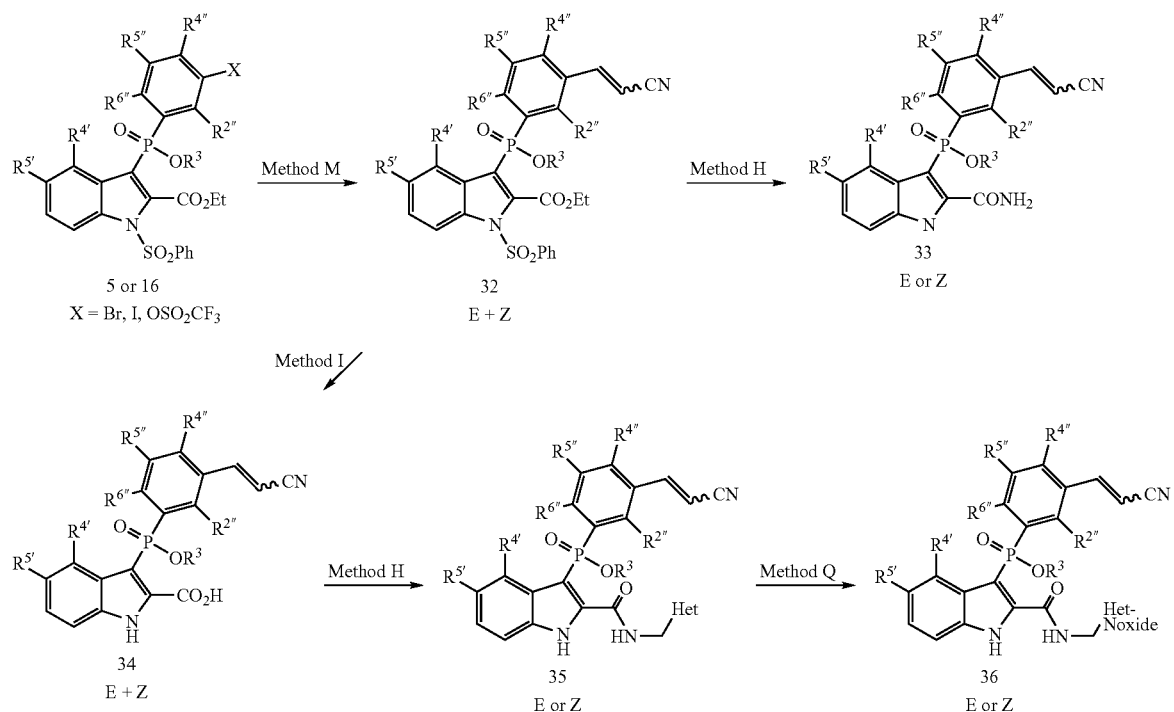
Scheme 10:
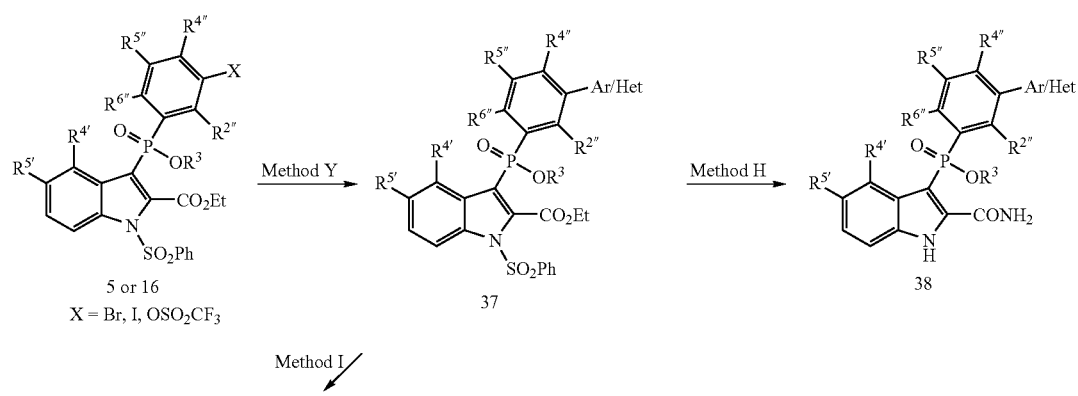

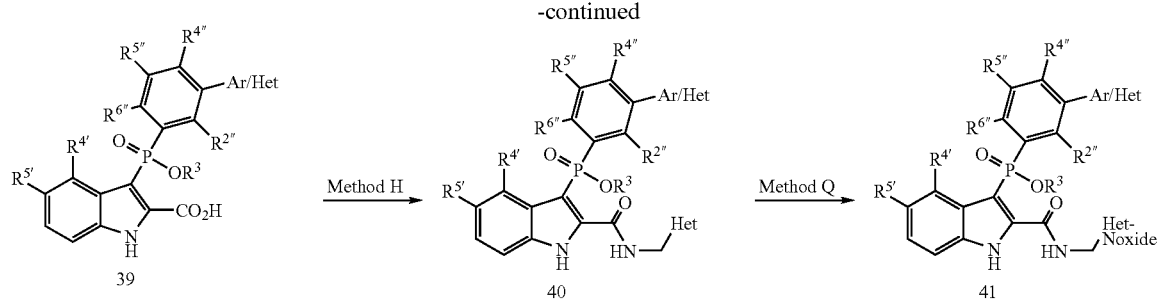
Particularized Schemes
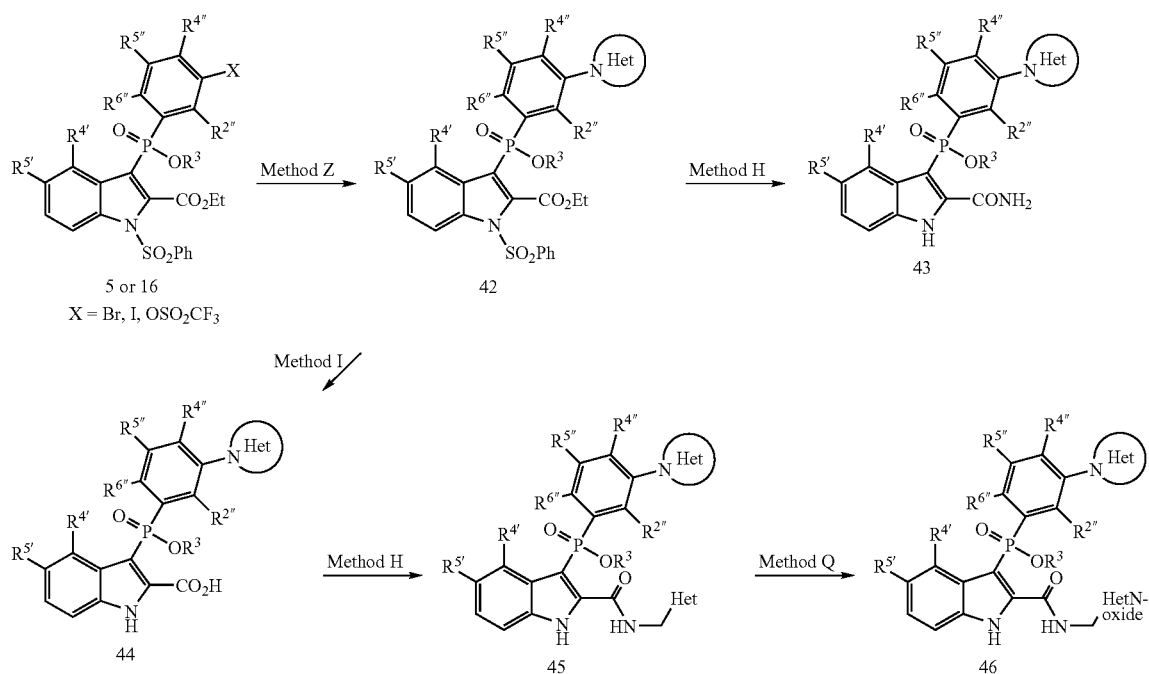
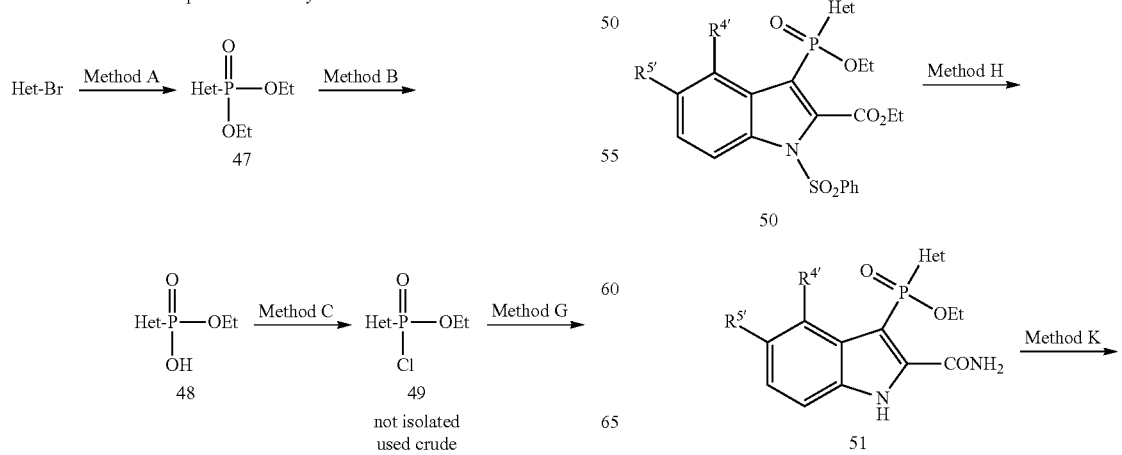

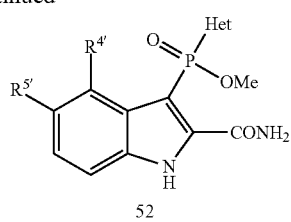
Scheme 13: Alkyl/Alkenyl/Alkynyl Phosphinates
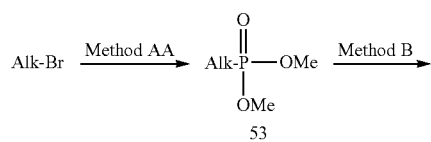
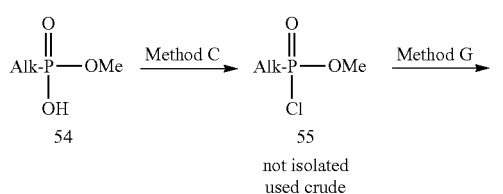
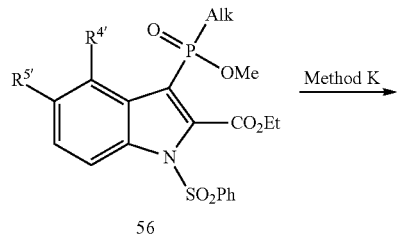
Scheme 14: Alkyl Phosphinates
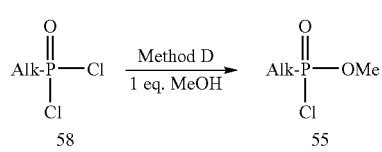
Scheme 15: Alkyl Methyl Carboxamides
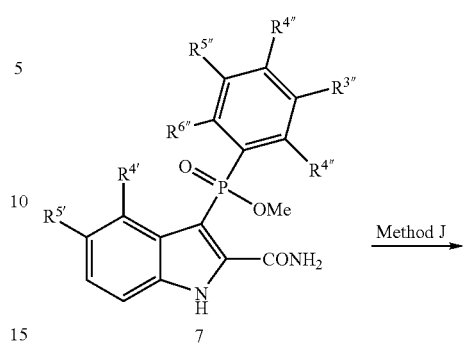
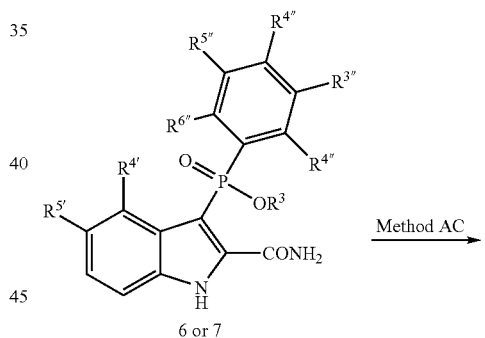
Scheme 16: Phosphinic Acids
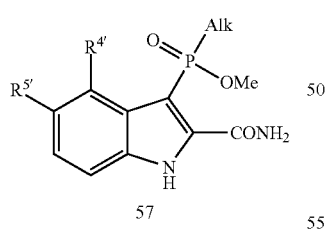
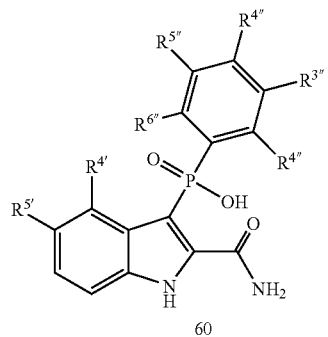
Methods
The following are descriptions of the methodologies used in the foregoing schemes. Numbers in bold print correspond to numbered compounds found in Schemes 1-16. Methods A, B, C, D, F, L, N, T, U and AA are known to those skilled in the art of making this general class of compounds, but have been adapted for preparing the specific compounds of the present invention. This also is true for Methods H, I, J, M, P, Q, Y, Z, AB and AC. Methods E, G, K, O, R, S, W, V and X are new processes for preparing the compounds of the invention.

Method A

Bromobenzene 1 (1 eq) was stirred with diethylphosphite (1.1 eq.) and triethylamine (1.1 eq.) in a pressure tube and the mixture was degased with $N_2$ for about 15 minutes. Then palladium tetrakis (0.05 eq.) was added and the mixture was stirred under pressure at about 85° C. overnight. The next morning, $Et_2O$ was added to the reaction and the mixture was filtered. The filtrate was evaporated and the crude was purified by chromatography on silica gel (eluent:petroleum ether/EtOAc from 8/2 to 6/4). Alternatively, the reaction can be performed using 10 volumes of 1,2-diethoxyethane under the same conditions.

Method B

All the reagents (1 eq. of diethylphosphonate 2 or dimethylphosphonate 19, 6 eq. of sodium hydroxide and ethanol or methanol (3 ml/mmol)) were stirred at room temperature for about 5 hours. Then, ethanol (or methanol) was evaporated in vacuo and the mixture acidified with HCl 2.5N to reach pH=1. Then the mixture was saturated with NaCl and extracted with ethyl acetate. Combined organic layers were dried over $Na_2SO_4$, filtered and concentrated to give the desired products 3 or 20.

Method C

The compound 20 or 3 (1.2 eq.) was stirred at room temperature under $N_2$ with thionyl chloride (3.6 eq.), dichloromethane (5 ml/mmol) and a few drops of dimethylformamide for about 5 hours. An aliquot was taken and put in dry methanol and $Et_3N$ to monitor the reaction. When the reaction was complete, dichloromethane and thionyl chloride, co-evaporated with toluene, were evaporated in vacuo to give an oil which was stored under $N_2$.

Method D

To a solution of arylphosphonyl dichloride 21 (1 mL, 6.35 mmol) in anhydrous dichloromethane (25 mL) ethanol or methanol (1.12 mL, 19.04 mmol) was added dropwise at about 0° C. followed by the addition of triethylamine (2.65 mL, 19.04 mmol). The reaction mixture was stirred at room temperature for about 2 hours, and then was washed with a solution of HCl 1N (50 mL). The aqueous layer was extracted with dichoromethane. Combined organic phases were dried and concentrated under reduced pressure. The crude oil was purified by chromatography on silica gel (eluent: $C_6H_{12}$/EtOAc 6/4) to afford dimethylarylphosphonate 19 or diethylarylphenylphosphonate 2.

Method E

The diethylarylphosphonate 2 (1 eq.) was stirred under $N_2$ at room temperature with bromotrimethylsilane (10 eq.) and dichloromethane (5 ml/mmol) for about 5 hours. Then the bromotrimethylsilane and dichloromethane were evaporated to give a yellow oil. Next, oxalyl chloride, dimethylformamide and dichloromethane were added under $N_2$ and the mixture was stirred at room temperature overnight, following which the oxalyl chloride and solvents were evaporated. The oil in dichloromethane solution was stirred and allowed to cool to about 0° C., and ethanol or methanol (1.12 mL, 19.04 mmol) was added under $N_2$, followed by the dropwise addition of triethylamine. The mixture then was warmed to room temperature. The solvent was evaporated and the resulting product was purified by chromatography on silica gel (eluent: $CH_2Cl_2$/EtOAc:8/2) to afford the compound 14.

Method F

To a stirred solution of diethylarylphosphonate 2 (1 eq.) in dichloromethane (5 ml/mmol) was added bromotrimethylsilane (5 eq.) at room temperature under $N_2$. After about 3 hours of stirring at room temperature, the solvent was evaporated and dichloromethane (5 ml mmol), a few drops of dimethylformamide and oxalyl chloride (2.5 eq) were added. This mixture was stirred at room temperature overnight, and the solvent was evaporated to give an oil. A solution of the oil (1.2 eq.) in diethyl ether (3 ml/mmol) was stirred and cooled to about −17° C., after which anhydrous methanol (1.2 eq.) was added dropwise to remove the double addition components and triethylamine. The resulting mixture was warmed to room temperature, stirred for about 1 hour, and then filtered on autocup under $N_2$ to remove triethylamine salts. The solvent was evaporated to give the compound 15.

Method G n-BuLi (2.5M in hexane, 1.2 eq.) was added dropwise to a stirred and cooled (to about −90° C.) solution of bromoindole 11 (1 eq.) in anhydrous THF (10 ml/mmol) under $N_2$. After keeping the solution at about −90° C. for about 5 minutes, an appropriate chorophosphorus reagent 15, 4 or diphenylphosphonic chloride (1.2 eq.) was added dropwise to the solution at the same temperature. The reaction was allowed to warm slowly to about −40° C. (TLC monitoring, eluent $CH_2Cl_2$/ETOAc 9/1). Water then was added. Extraction with ethyl acetate, drying and evaporation led to a crude oil that was purified by chromatography on silica gel to give the compound 16, 5 or 26.

Method H

A stirred and cooled (to about 0° C.) solution of compound 5, 16, 26, 28 or 30 in methanol in a pressure tube was saturated with $NH_3$ gas for about 10 minutes. Then the mixture was stirred at about 50° C. overnight, and after TLC monitoring, excess ammonia and methanol were evaporated in vacuo and the crude purified by chromatography on silica gel to give the carboxamide 6, 7, 27, 29 or 31.

Method I

Lithium hydroxide (14 eq.) was added to a stirred solution of compound 16 or 5 in tetrahydrofuran (20 ml/mmol) and water (20 ml/mmol). This mixture next was stirred at room temperature and monitored by TLC. If necessary, equivalents of lithium hydroxide were added until the reaction was complete. Then the THF was evaporated and HCL (IN) was added to reach pH 1. The aqueous layer was extracted with ethyl acetate and combined organic phases were dried, filtered and concentrated under reduced pressure to give the compound 17 or 8.

Method J

The compound 17 or 8 (1 eq.) was stirred with dichloromethane (20 ml/mmol) or DMF, and 1-hydroxybenzotriazole (1 eq.) was added followed by the addition of EDCI (1 eq.) followed by the amine (1 eq) were added. This mixture was stirred at room temperature overnight. The next morning the mixture was washed with water (to a pH of 5-6), and organic layers were dried, filtered and concentrated under reduced pressure. The resulting oil was purified by chromatography on silica gel (eluent:$CH_2Cl_2$/EtOAc) to give a powder 18 or 9.

Method K

In a microwave tube, the compound 5 or 6 (1 eq.) was stirred with DMF (5 ml/mmol), and TMSBr (5 eq.) was added. The tube was heated under microwave irradiations under pressure at about 60° C. (maximum power input 100 W, CEM discover apparatus) for about 50 minutes. DMF was evaporated in vacuo, and the mixture was put in a pressure tube. Trimethylphosphite (4 ml/mmol) was added and the mixture was stirred and heated at about 90° C. overnight. The mixture then was cooled in an ice water bath and HCl (1N) was added dropwise. The mixture was extracted with ethyl acetate, and combined organic layers were washed with HCl (1N) until no HP(OMe)$_2$ remained. Next it was dried, filtered and concentrated under reduce pressure to provide an oil, and the resulting oil was purified by chromatography on silica gel to give the compound 16 or 7.

Method L

To a stirred and cooled (to about 0° C.) solution of ethyl indole-2-carboxylate 10 (1 eq.) in DMF (2 ml/mmol) under N$_2$, was added NaH (60% in oil, 1.2 eq.) portionwise. When gas evolution stopped, benzenesulfonyl chloride (1.2 eq.) was added. The reaction mixture was stirred for about 1 hour (TLC monitoring, eluent dichloromethane); a small amount of water then was added carefully and the DMF was evaporated. The crude residue was dissolved in ethyl acetate and washed with water and brine. After drying and evaporation of the solvents, the compound was purified by chromatography on silica gel (eluent:C$_6$H$_{12}$/EtOAc 9/1 to 7/3) to give the ethyl 1-phenylsulfonylindole-2-carboxylate.

To a stirred solution of ethyl 1-phenylsulfonylindole-2-carboxylate (1 eq.) in DMF (2.5 ml/mmol) under N$_2$, was added a solution of bromine (4 eq.) in DMF (0.5 ml/mmol). This reaction mixture was stirred at room temperature for about 4 hours, following which water was added and the mixture was extracted with dichloromethane (×3). The organic layer was washed with a saturated solution of Na$_2$SO$_5$, dried and evaporated to give a crude yellow oil. Purification by chromatography on silica gel (eluent:C$_6$H$_{12}$/EtOAc 9/1) afforded 3-brominated indole 11.

Method M

A mixture of 5 or 16 (1 eq.), acrylonitrile (10 eq.), palladium acetate (20% mol.), triethylamine (1 eq.) and tri-orthotolylphosphine (1 eq.) in degassed acetonitrile (30 mL/mmol) was stirred and heated under microwave irradiation in a pressure tube for about 45 minutes. Next water was added and the aqueous layer was extracted with dichloromethane. The combined organic layers were dried and concentrated and purified by chromatography on silica gel (eluent:Petroleum ether/EtOAc 8/2) to give the compound 32 as a mixture of enantiomers E and Z (which are separated by preparative HPLC).

Method N

Bromobenzene 1 (1 eq.), dimethylformamide (1 ml/mmol), triethylamine (3 eq.) and anilinium salt* (1.25 eq.) were put in a pressure tube and degased with N$_2$ for about 15 minutes. Then palladium tetrakis was added and this mixture was stirred at about 85° C. overnight, following which the solvent was evaporated and water was added to achieve a pH of about 5-6. The mixture was basified with NaHCO$_3$ until a pH 8 was reached, and then extracted with diethyl ether. The aqueous layer was acidified with HCl (1N) to reach a pH=1, and extracted with ethyl acetate. Combined organic layers were dried, filtered and concentrated under reduced pressure to give the compound 14.

Anilinium salt was synthesised according to the procedure of Montchamp et al (J. Am. Chem. Soc., 2001, 123, 510-511).

Method O

Tetramethylorthosilicate (1.2 eq.) was added to a stirred solution of compound 14 (1.2 eq.) in toluene (4 ml/mmol) under N$_2$. This mixture was heated at reflux for about 1.5 hours, and then cooled to room temperature. Next the mixture was degased with N$_2$ before adding triethylamine (3.3 eq.), bromoindole 11 (1 eq.), and palladium tetrakis (0.05 eq.). The mixture was stirred at about 100° C. over a week-end (about 48 hours), after which the reaction was cooled to room temperature and water was added to achieve a pH of about 8-9. The mixture next was extracted with ethyl acetate and the organic phases were washed with KHSO$_4$ (1N) saturated with NaCl. It then was dried, filtered and concentrated under reduced pressure to give an oil, which was purified by chromatography on silica gel (eluent:CH$_2$Cl$_2$/MeOH) to give the compound 12.

Method P

To a stirred solution of compound 12 (1 eq.) in methanol (25 ml/mmol) was added trimethylsilyldiazomethane (13 eq.) in a several fractions at room temperature under N$_2$. This mixture was stirred overnight, after which water was added and the methanol was evaporated under reduce pressure. Then NaHCO$_3$ was added to reach pH 8, and the mixture was extracted with ethyl acetate. The organic phases were dried, filtered and concentrated under reduced pressure. The crude was purified by chromatography on silica gel (eluent:C$_6$H$_{12}$/EtOAc) to give the compound 16.

Method Q

The compound 18 was dissolved in chloroform (or in CH$_2$Cl$_2$) under stirring at room temperature; m-chloroperoxybenzoic acid was added and the reaction allowed to stir overnight (about 15 hours). Then the mixture was diluted with dichloromethane and extracted with a mixture of saturated K$_2$CO$_3$/H$_2$O (1/3). The aqueous layer was extracted three times with dichloromethane. The combined organic layers were dried over Na$_2$SO$_4$, filtered and concentrated under reduced pressure (TLC:dichloromethane/methanol=9/1). The crude product was purified by chromatography on silica gel to give the compound 22.

Method R

In a microwaves sealed tube, the compounds II (1 eq.) and 23 (1.1 eq.) were added to toluene (8 ml/mmol) and triethylamine (3.3 eq.) and degased with N$_2$ for about 10 minutes. Then Pd(PPh$_3$)$_2$ was added and the tube was heated under microwave irradiation under pressure at about 120° C. (maximum power input 200 W, CEM discover apparatus) for about 30 minutes. The reaction was monitored by TLC and the tube was heated for about 30 minutes if necessary. The solvent was evaporated and the crude product was purified by chromatography on silica gel (eluent:C$_6$H$_{12}$/EtOAc:8/2) to give the compound 5.

Method S

In a microwave sealed tube, the compounds 11 (1 eq.) and 24 (2 eq.) were added to toluene (8 ml/mmol) and then degased with N$_2$ over about a 10 minute time period. Next, Pd(OAc)$_2$ in about 20% solution was added, and the tube was under microwave irradiation under pressure at about 150° C. (maximum power input 200 W, CEM discover apparatus) for about 45 minutes. The reaction was monitored by TLC and if any starting material was present, the tube was heated for about another 45 minutes at approximately 170° C. Next HCl (1N) (8 ml/mmol) was added and the solution was extracted with ethyl acetate. The combined organic layers were dried, filtered and concentrated under reduced pressure. The crude product was purified by chromatography on silica gel (eluent: petroleum ether/EtOAc:1/1) to give the compound 5 or 16.

Alternatively the reaction is carried out at about 150° C. in xylene for about 5 hours.

Method T

Pyridine (1 eq.) was carefully added to a vigorously stirred solution of alkyl chloroformate (1 eq.) and arylphosphinic acid (1 eq.) in dichloromethane (2 ml/mmol) at room temperature. Once effervescence stopped, the solution was refluxed for about 15 minutes and then allowed to cool to room temperature. The solution was poured into 0.1M hydrochloric acid (1 ml/mmol) and the organic layer was separated.

After washing with water and drying over $Na_2SO_4$, the solvent was removed in vacuo to give the compound 23.

Method U

Alkyl or aryl bromide (0.15 mol) was added dropwise to a mixture of magnesium (3.6 g) and dry tetrahydrofuran (40 mL) under $N_2$ atmosphere at about 50° C. After this addition, the reaction mixture was stirred at about 50° C. for an additional 1-2 hours to allow the reaction to run to completion. Then the mixture was added dropwise to a solution of triethyl phosphite (0.1 mol) and THF (25 mL) at between 40° C. to 50° C. in $N_2$ atmosphere, and stirred for about 3 hours at about 50° C. After removal of the solvent under reduced pressure, the crude product was distilled from the semisolid residue in vacuo to give the compound 24.

Method V

The compound 6 or 7 (1 eq.) and Lawesson's reagent (4 eq.) were heated in toluene (10 ml/mmol) at about 90° C. under $N_2$ in a pressure tube. The reaction was monitored by TLC and heating continued until no starting material remained (about 5.5 hours). The crude solution was filtered and the filtrate was evaporated to dryness and purified by chromatography on silica gel to give the compound 25 and the compound 25'.

Method W

To a stirred and cooled (to about −90° C.) solution of bromoindole 11 (1 eq.) was added dropwise n-butyllithium (1.2 eq.) under $N_2$. After about 10 minutes, benzenephosphonyl dichloride 21 (1.1 eq.) in tetrahydrofuran (15 ml/mmol) was added dropwise at a temperature of about −70° C., and the temperature then was raised to about −90° C. and maintained for about 15 minutes. This was followed by the addition of methylmagnesium bromide (1.1 eq.), and the mixture was allowed to warm to about −40° C. for about 1 hour, after which it was quenched with water and extracted with ethyl acetate then dichloromethane. The organic layer was dried over $Na_2SO_4$, filtered and concentrated under reduced pressure. The crude product was purified by chromatography on silica gel (eluent:$CH_2Cl_2$/AcOEt:9/1 to 7/3) to give the compound 28.

Method X

Dimethylamine (1 eq.) was added dropwise to a stirred and cooled (to about −55° C.) solution of phenyl phosphonic dichloride 21 (1 eq.) in diethyl ether (1.5 ml/mmol). Then triethylamine was added (1 eq.) and the mixture was allowed to warm to room temperature. The mixture next was filtered and the filtrate was evaporated to give an oil/mixture. To rid the oil/mixture of phenyl phosphonic dichloride, the oil/mixture was dissolved in EtOAc and washed twice with an HCl solution of pH 4-5. The organic phases were dried with $Na_2SO_4$, filtered and concentrated under reduced pressure to give an oil. Then, n-butyllithium (1.2 eq.) was added dropwise to a stirred and cooled (to about −80° C.) solution of bromoindole 11 (1 eq.) in tetrahydrofuran (5 ml/µmol) under $N_2$. At the end of the addition, the mixture was warmed to about −60° C. and tetrahydrofuran (1.2 eq.; 3 ml/mmol) was added dropwise to the oil. Then the mixture was warmed slowly to about −10° C., and the reaction was quenched with water (8 ml/mmol). HCl (1N) was added to achieve a pH of about 5, and the solvent was evaporated in vacuo. The aqueous phase was extracted with ethyl acetate and the combined organic layers were washed with brine, dried over $Na_2SO_4$, filtered and concentrated under reduced pressure. The crude product was purified by chromatography on silica gel (eluent: $C_6H_{12}$/EtOAc:9/1 to 0/10) to give the compound 30.

Method Y Suzuki Cross-coupling $Pd(PPh_3)_4$ (10% mol.), a solution of $Na_2CO_3$ (6 eq.) in $H_2O$ (2M) and a solution of aryl, alkyl or heteroaryl boronic acid (2 eq.) in EtOH (0.3M) were added to a stirred solution of 5 or 16 (bearing an halogeno or triflate substituent) in degassed toluene under $N_2$. The reaction tube was then heated under microwave irradiation at about 110° C. until no starting material remained. Water was added and the reaction media was extracted with EtOAc, dried and concentrated. The crude residue was purified by column chromatography on silica gel (PE/EtOAc 8/2) to afford 37.

Method Z

Under a nitrogen atmosphere, a dry reaction tube was charged with cuprous oxide (10% mol), a ligand (20% mol), a nucleophile (1.5 eq.), cesium carbonate (2 eq.) and the aryl halide 5 or 16 (bearing an halogeno or triflate substituent) (1 eq.), followed by the addition of anhydrous and degassed acetonitrile (0.6 mL per mmol of aryl halide). The tube was sealed and stirring was applied at about 80° C. until the reaction ran to completion. The reaction mixture then was cooled to room temperature, diluted with tert-butylmethyl ether and filtered through a plug of celite, the filter cake being further washed with butylmethyl ether. The filtrate was concentrated in vacuo to remove the acetonitrile and was redissolved in tert-butylmethyl ether. This organic layer filtrate was washed twice with water and once with brine before being dried on $Na_2SO_4$ and filtered. The solvent was removed in vacuo to yield the crude product, which was purified by chromatography on silica gel to give the compound 42.

Method AA

Alkyl halide was heated at about 90° C. overnight in trimethylphosphite (10 mL/mmol). The reaction media was cooled to about 0° C. in an ice bath, and a solution of HCl (IN) was added carefully. The aqueous layer was extracted with EtOAc. The combined organic layers were washed with HCl (IN) and with water, and then dried and concentrated to give compound 53 as a colorless oil.

Method AB

In a microwaves sealed tube, the compounds 17 (1 eq.), formaldehyde (37% wt in water, 1 eq.), and morpholine (1 eq.) were added to t-butyl alcohol (4 m/mmol). The tube was heated under microwave irradiation under pressure at about 170° C. (maximum power input 200 W, CEM discover apparatus) for about 60 minutes. The reaction was monitored by TLC and if any starting material remained, the tube was heated for about 45 minutes at approximately 170° C. The solvents were evaporated in vacuo, and the crude residue was purified by chromatography on silica gel (MeOH/EtOAc:2/98) to give the compound 18.

Method AC

In a microwave tube, the compound 5 or 6 (1 eq.) was stirred with DMF (5 ml/mmol), and TMSBr (5 eq.) was added. The tube was heated under microwave irradiation under pressure at about 60° C. (maximum power input 100 W, CEM discover apparatus) for about 50 minutes. After cooling, water was added and compound 60 was collected by filtration.

IX. Representative Examples of the Active Compounds

Tables 1 and 2 contain a non-limiting list of representative compounds that may be prepared by the methods and according to Schemes 1-16 provided above.

TABLE 1

| Compound | structure | Description |
|---|---|---|
| 2a | [phenyl-P(=O)(OEt)₂] | Colorless oil, $^1$H NMR (CDCl$_3$, 250 MHz) δ 1.33 (t, J = 7.1 Hz, 6H), 4.05-4.25 (m, 4H), 7.46-7.57 (m, 3H), 7.78-7.87 (m, 2H), $^{31}$P NMR (CDCl$_3$, 101.256 MHz) δ 19.3. |
| 2c | [3-ethylphenyl-P(=O)(OEt)₂] | Colorless oil, $^1$H NMR (CDCl$_3$, 300 MHz) δ 1.26 (t, J = 7.5 Hz, 3H), 1.33 (t, J = 7.05 Hz, 6H), 2.7 (q, J = 7.5 Hz, 2H), 4.04-4.19 (m, 4H), 7.37-7.4 (m, 2H), 7.58-7.69 (m, 2H), $^{31}$P NMR (CDCl$_3$, 121.49 MHz) δ 19.53. |
| 2d | [3-CF₃-phenyl-P(=O)(OEt)₂] | Colorless oil, $^1$H NMR (CDCl$_3$, 300 MHz) δ 1.35 (t, J = 7.05 Hz, 6H), 4.05-4.26 (m, 4H), 7.62 (td, J = 3.9 and 7.8 Hz, 1H), 7.8-7.83 (m, 1H), 7.97-8.1 (m, 2H), $^{31}$P NMR (CDCl$_3$, 121.49 MHz) δ 16.4, $^{19}$F NMR (CDCl$_3$, 282.4 MHz) δ 9.27 (s, 3F), MS (ESI, EI$^+$) m/z = 283 (MH$^+$). |
| 2e | [3-CN-phenyl-P(=O)(OEt)₂] | White solid, $^1$H NMR (CDCl$_3$, 300 MHz) δ 1.36 (t, J = 7.05 Hz, 6H), 4.09-4.25 (m, 4H), 7.62 (td, J = 3.9 and 7.8 Hz, 1H), 7.83-7.85 (m, 1H), 8.02-8.12 (m, 2H), $^{31}$P NMR (CDCl$_3$, 121.49 MHz) δ 15.12, MS (ESI, EI$^+$) m/z = 240 (MH$^+$). |
| 2f | [3-Br-phenyl-P(=O)(OEt)₂] | Colorless oil, $^1$H NMR (CDCl$_3$, 300 MHz) δ 1.34 (t, J = 7.05 Hz, 6H), 4.05-4.21 (m, 4H), 7.32-7.38 (m, 1H), 7.66-7.71 (m, 1H), 7.73-7.78 (m, 1H), 7.92-7.97 (m, 1H), $^{31}$P NMR (CDCl$_3$, 121.49 MHz) δ 16.37, MS (ES$^+$) m/z = 292.9/294.8 (MH). |
| 2g | [3,5-diCl-phenyl-P(=O)(OEt)₂] | Colorless oil, $^1$H NMR (CDCl$_3$, 300 MHz) δ 1.35 (t, J = 7.05 Hz, 6H), 4.04-4.23 (m, 4H), 7.53 (t, J = 1.8 Hz, $^1$H), 7.65 (d, J = 1.8 Hz, 1H), 7.7 (d, J = 1.8 Hz, 1H), $^{31}$P NMR (CDCl$_3$, 121.49 MHz) δ 14.74. |
| 2h | [3-(CH₂F)-phenyl-P(=O)(OEt)₂] | Colorless oil, $^1$H NMR (CDCl$_3$, 300 MHz) δ 1.34 (t, J = 7.05 Hz, 6H), 4.06-4.22 (m, 4H), 5.44 (d, J = 47.4 Hz, 2H), 7.51-7.6 (m, 2H), 7.78-7.85 (m, 2H), $^{19}$F NMR (CDCl$_3$, 282.40 MHz) δ -209.67 (t, J = 47.4 Hz, 1F), MS (ES$^+$) m/z = 247 (MH). |
| 2i | [3-(1,3-dioxolan-2-yl)-phenyl-P(=O)(OEt)₂] | Colorless oil, $^1$H NMR (CDCl$_3$, 300 MHz) δ 1.34 (t, J = 7.05 Hz, 6H), 4.04-4.2 (m, 8H), 5.86 (s, 1H), 7.48-7.54 (m, 1H), 7.68-7.7 (m, 1H), 7.8-7.87 (m, 1H), 7.93-7.98 (m, 1H), $^{31}$P NMR (CDCl$_3$, 121.49 MHz) δ 18.45, MS (ES$^+$) m/z = 287 (MH). |
| 2j | [3-Cl-5-Me-phenyl-P(=O)(OEt)₂] | Colorless oil, $^1$H NMR (CDCl$_3$, 300 MHz) & 1.35 (t, J = 7.05 Hz, 6H), 2.39 (s, 3H), 4.05-4.21 (m, 4H), 7.34-7.36 (m, 1H), 7.5-7.6 (m, 2H), $^{31}$P NMR (CDCl$_3$, 121.49 MHz) δ 17.18, MS (ES$^+$) m/z = 263.2 (MH). |

TABLE 1-continued

| Compound | structure | Description |
|---|---|---|
| 2k | (biphenyl-3-yl diethyl phosphonate) | Colorless oil, $^1$H NMR (CDCl$_3$, 300 MHz) δ 1.37 (t, J = 7.05 Hz, 6H), 4.07-4.27 (m, 4H), 7.37-7.65 (m, 6H), 7.78-7.85 (m, 2H), 8.04-8.09 'm, 1H), $^{31}$P NMR (CDCl$_3$, 121.49 MHz) δ 18.84, MS (ES$^+$) m/z = 291.17 (MH). |
| 2l | (2-(acetoxymethyl)phenyl diethyl phosphonate) | Colorless oil, $^1$H NMR (CDCl$_3$, 300 MHz) δ 1.33 (t, J = 7.05 Hz, 6H), 2.15 (s, 3H), 4.06-4.22 (m, 4H), 5.44 (s, 2H), 7.38-7.60 (m, 3H), 7.95-8.03 (m, 1H), $^{31}$P NMR (CDCl$_3$, 121.49 MHz) δ 17.99, MS (ESI, EI$^+$) m/z = 287 (MH$^+$). |
| 2m | (3-methoxyphenyl diethyl phosphonate) | Yellow oil, $^1$H NMR (CDCl$_3$, 300 MHz) δ 1.32 (t, J = 6.9 Hz, 3H), 1.323 (t, J = 6.9 Hz, 3H), 3.84 (s, 3H), 4.03-4.16 (m, 4H), 7.06-7.1 (m, 1H), 7.3-7.4 (m, 3H), $^{31}$P NMR (CDCl$_3$, 121.49 MHz) δ 19.21, MS (ESI, EI$^+$) m/z = 245.13 (MH$^+$). |
| 2q | (3,5-bis(trifluoromethyl)phenyl diethyl phosphonate) | Slight yellow oil, $^1$H NMR (CDCl$_3$, 400 MHz) δ 1.37 (t, J = 7.05 Hz, 6H), 4.11-428 (m, 4H), 8.046-8.048 (m, 1H), 8.237-8.24 (m, 1H), 8.27-8.273 (m, 1H), $^{31}$P NMR (CDCl$_3$, 101.256 MHz) δ 14.36, MS (ESI, EI$^+$) m/z = 351 (MH$^+$). |
| 2r | (3-fluoro-5-(trifluoromethyl)phenyl diethyl phosphonate) | Slight yellow oil, $^1$H NMR (CDCl$_3$, 400 MHz) δ 1.36 (t, J = 7.07 Hz, 6H), 4.08-4.26 (m, 4H), 7.49-7.52 (m, 1H), 7.67-7.73 (m, 1H), 7.85-7.89 (m, 1H), $^{31}$P NMR (CDCl$_3$, 101.256 MHz) δ 14.73 (d, J = 7.8 Hz, 1P), MS (ESI, EI$^+$) m/z = 301 (MH$^+$). |
| 2t | (3-cyano-5-isopropylphenyl diethyl phosphonate) | Colorless oil, $^1$H NMR (d$_6$-DMSO, 300 MHz) δ 1.24 (d, J = 6.9 Hz, 6H), 1.25 (t, J = 7.2 Hz, 6H), 3.07 (heptuplet, J = 6.9 Hz,, 1H), 4.02-4.11 (m, 4H), 7.84-7.94 (m, 2H), 8.04 (brs, 1H), $^{31}$P NMR (d$_6$-DMSO, 121.49 MHz) δ 15.12, MS (ESI, EI$^+$) m/z = 282.3 (MH$^+$). |
| 2u | (4-chloro-3-fluorophenyl diethyl phosphonate) | Yellow pale oil, $^1$H NMR (CDCl$_3$, 300 MHz) δ 1.35 (t, J = 7.05 Hz, 6H), 4.07-4.22 (m, 4H), 7.25-7.29 (m, 1H), 7.37-7.45 (m, 1H), 7.57-7.61 (m, 1H), $^{31}$P NMR (CDCl$_3$, 121.49 MHz) δ 14.82 (d, J = 9.1 Hz, 1P), MS (ES$^+$) m/z = 267.11 (MH$^+$). |
| 2v | (3-propylphenyl diethyl phosphonate) | Colourless oil, $^1$H NMR (CDCl$_3$, 300 MHz) δ 0.94 (t, J = 7.5 Hz, 3H), 1.32 (t, J = 7.2 Hz, 6H), 1.66 (sextuplet, J = 7.5 Hz, 2H), 2.63 (t, J = 7.5 Hz, 2H), 4-4.21 (m, 4H), 7.34-7.41 (m, 2H), 7.58-7.67 (m, 2H), $^{31}$P NMR (CDCl$_3$, 121.49 MHz) δ 19.53, MS (ES$^+$) m/z = 257.37 (MH$^+$). |

TABLE 1-continued

| Compound | structure | Description |
|---|---|---|
| 2w | 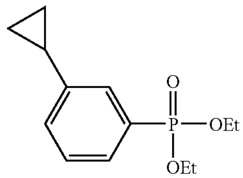 | Colorless oil, $^1$H NMR (d$_6$-DMSO, 300 MHz) δ 0.67-0.73 (m, 2H), 0.97-1.03 (m, 2H), 1.23 (t, J = 7.05 Hz, 6H), 1.97-2.06 (m, 1H), 3.93-4.06 (m, 4H), 7.27-7.31 (m, 1H), 7.38-7.51 (m, 3H), $^{31}$P NMR (d$_6$-DMSO, 121.49 MHz) δ 18.35, MS (ES$^+$) m/z = 255.06 (MH$^+$). |
| 2x | 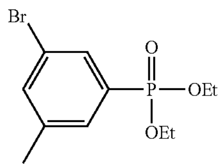 | Colorless oil, $^1$H NMIR (d$_6$-DMSO, 300 MHz) δ 1.23 (t, J = 7.05 Hz, 6H), 2.37 (s, 3H), 3.97-4.09 (m, 4H), 7.49-7.57 (m, 2H), 7.69 (brs, 1H), $^{31}$P NMR (d$_6$-DMSO, 121.49 MHz) δ 15.74, MS (ES$^+$) m/z = 309.24 (MH$^+$). |
| 2y | 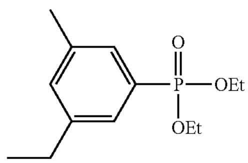 | Colorless oil, $^1$H NMR (d$_6$-DMSO, 300 MHz) δ 1.23 (t, J = 7.05 Hz 6H), 2.34 (s, 3H), 2.63 (q, J = 7.05 Hz, 2H), 3.94-4.05 (m, 4H), 7.29-7.31 (m, 2H), 7.44-7.45 (m, 1H), $^{31}$P NMR (d$_6$-DMSO, 121.49 MHz) δ 18.71, MS (ES$^+$) m/z = 257.4 (MH$^+$). |
| 2z | 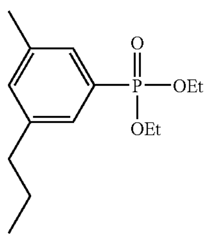 | Colorless oil, $^1$H NMIR (d$_6$-DMSO, 300 MHz) δ 0.88 (t, J = 7.2 Hz, 3H), 1.22 (t, J = 7.05 Hz, 6H), 1.54-1.62 (m, 2H), 2.34 (s, 3H), 2.55-2.6 (m, 2H), 3.94-4.05 (m, 4H), 7.27-7.36 (m, 3H), $^{31}$P NMR (d$_6$-DMSO, 121.49 MHz) δ 18.73, MS (ES$^+$) m/z = 271.36 (MH$^+$). |
| 2aa | 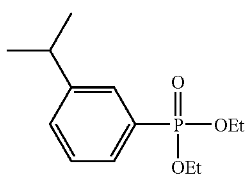 | Colorless oil, $^1$H NMR (CDCl$_3$, 300 MHz) δ 1.28 (d, J = 7.0 Hz, 6H), 1.34 (t, J = 7.2 Hz, 6H), 2.97 (m, 1H), 4.13 (m, 4H), 7.36-7.45 (m, 2H), 7.58-7.75 (m, 2H), MS (ESI, EI$^+$) m/z = 257 (MH$^+$). |
| 2ab | 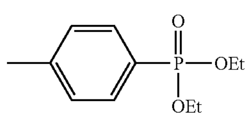 | Brown oil, $^1$H NMR (d$_6$-DMSO, 300 MHz) δ 1.22 (t, J = 7.2 Hz, 6H), 2.37 (s, 3H), 3.92-4.05 (m, 4H), 7.33-7.37 (m, 2H), 7.57-7.64 (m, 2H), $^{31}$P NMR (d$_6$-DMSO, 101.256 MHz) δ 18.62. |
| 2ae | 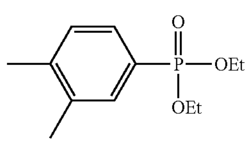 | Yellow oil, $^1$H NMR (d$_6$-DMSO, 400 MHz) δ 1.22 (t, J = 7.3 Hz, 6H), 2.28 (s, 6H), 3.93-4.03 (m, 4H), 7.29-7.32 (m, 1H), 7.4-7.49 (m, 2H), $^{31}$P NMR (d$_6$-DMSO, 101.256 MHz) δ 19.86, MS (ESI, EI$^+$) m/z = 243 (MH$^+$). |
| 2af | 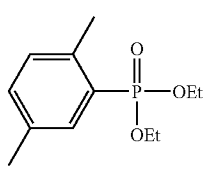 | Yellow oil, MS (ESI, EI$^+$), m/z = 243 (MH$^+$). |
| 2ag | 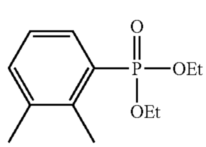 | Yellow oil, $^1$H NMR (d$_6$-DMSO, 300 MHz) δ 1.24 (t, J = 7.05 Hz, 6H), 2.28 (s, 3H), 2.42 (s, 3H), 3.96-4.06 (m, 4H), 7.22 (td, J =, 4.2 and 7.5 Hz, 1H), 7.41 (d, J = 7.5 Hz, 1H), 7.62 (dd, J = 7.5 and 13.8 Hz, 1H), $^{31}$P NMR (d$_6$-DMSO, 121.49 MHz) δ 20.29. |

TABLE 1-continued

| Compound | structure | Description |
|---|---|---|
| 2ah | 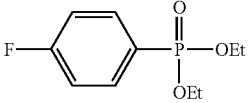 | Oil, $^1$H NMR (CDCl$_3$, 300 MHz) δ 1.32 (t, J = 7.05 Hz, 6H), 4.04-4.19 (m, 4H), 7.12-7.19 (m, 2H), 7.78-7.87 (m, 2H), $^{19}$F NMR (CDCl$_3$, 282.4 MHz) δ −109.18, $^{31}$P NMR (CDCl$_3$, 101.256 MHz) δ 18.33. |
| 2ai | 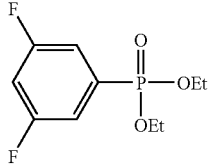 | Pale yellow oil, $^1$H NMR (CDCl$_3$, 300 MHz) δ 1.36 (t, J = 6.9 Hz, 6H, 4.08-4.23 (m, 4H), 6.96-7.04 (m, 1H), 7.30-7.38 (m, 2H), $^{31}$P NMR (CDCl$_3$, 101 MHz) δ 14.77-15.3 (m, 1P), $^{19}$F NMR (CDCl$_3$, 235.36 MHz) δ −107.56 (m, 2F), MS (ESI, EI$^+$) m/z = 251 (MH$^+$). |
| 2ao | 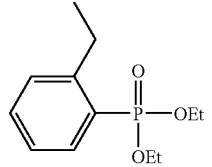 | Yellow oil, $^1$H NMR (d$_6$-DMSO, 300 MHz) δ 1.19 (t, J = 7.5 Hz, 3H), 1.24 (t, J = 7.05 Hz, 6H), 2.89 (q, J = 7.5 Hz, 2H), 3.97-4.07 (m, 4H), 7.29-7.41 (m, 2H), 7.53-7.58 (m, 1H), 7.74 (ddd, J = 1.2 and 7.5 and 13.8 Hz, 1H), $^{31}$P NMR (d$_6$-DMSO, 121.49 MHz) δ 18.71, MS (ESI, EI$^+$) m/z = 243 (MH$^+$). |
| 2ap | 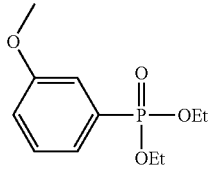 | Yellow oil, $^1$H NMR (d$_6$-DMSO, 300 MHz) δ 1.23 (t, J = 7.05 Hz, 6H), 3.81 (s, 3H), 3.96-4.06 (m, 4H), 7.15-7.32 (m, 3H), 7.44-7.51 (m, $^1$H), $^{31}$P NMR (d$_6$-DMSO, 121.49 MHz) δ 17.71; MS (ESI, EI$^+$) m/z = 245 (MH$^+$) |
| 2aq | 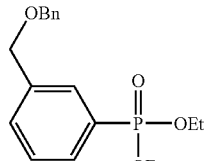 | Oil, $^1$H NMR (d$_4$-DMSO, 300 MHz) δ 1.22 (t, J = 7.05 Hz, 6H), 3.94-4.07 (m, 4H), 4.56 (s, 2H), 4.61 (s, 2H), 7.28-7.37 (m, 5H), 7.5-7.72 (m, 4H), $^{31}$P NMR (d$_6$-DMSO, 121.49 MHz) δ 17.97; MS (ES$^+$) m/z = 335 (MH$^+$) |
| 2ar | 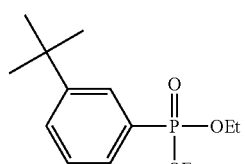 | Colorless oil, $^1$H NMR (d$_6$-DMSO, 300 MHz) δ 1.22 (t, J = 7.2 Hz, 6H), 3.97-4.03 (m, 4H), 7.43-7.56 (m, 2H), 7.65-7.7 (m, 2H), $^{31}$P NMR (d$_6$-DMSO, 121.49 MHz) δ 18.6; MS (ES$^+$) m/z = 271.2 (MH$^+$) |
| 2as | 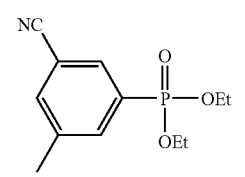 | Oil, $^1$H NMR (d$_6$-DMSO, 300 MHz) δ 1.24 (t, J = 7.05 Hz, 6H), 2.42 (s, 3H), 3.99-4.1 (m, 4H), 7.82-7.94 (m, 3H), $^{31}$P NMR (d$_6$-DMSO, 121.49 MHz) δ 15.09, MS (ES$^+$) m/z = 254 (MH$^+$). |
| 2at | 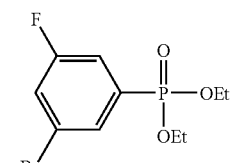 | Yellow oil, $^1$H NMR (d$_6$-DMSO, 300 MHz) δ 1.25 (t, J = 7.2 Hz, 6H), 4.01-4.13 (m, 4H), 7.49-7.57 (m, 1H), 7.65-7.7 (m, 1H), 7.88-7.92 (m, 1H), $^{31}$P NMR (d$_6$-DMSO, 121.49 MHz) δ 13.5 (d, J = 8.7 Hz, 1P), $^{19}$F NMR (d$_6$-DMSO, 282.4 MHz) δ -108.43 (m, 1F). |
| 2au | 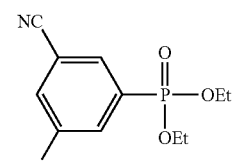 | Orange oil, $^1$H NMR (d$_6$-DMSO, 300 MHz) δ 1.25 (t, J = 7.2 Hz, 6H), 4.04-4.13 (m, 4H), 7.82-7.90 (m, 1H), 7.96-8.01 (m, 1H), 8.15-8.18 (m, 1H), $^{31}$P NMR (d$_6$-DMSO, 121.49 MHz) δ 12.83 (d, J = 8.02 Hz, 1P), $^{19}$F NMR (d$_6$-DMSO, 282.4 MHz) −108.7 (q, J = 8.2 Hz, 1F),. MS (ES$^+$) m/z = 258.2 (MH$^+$). |

TABLE 1-continued

| Compound | structure | Description |
|---|---|---|
| 2aw | 2-chlorophenyl-P(=O)(OEt)₂ | Oil, ¹H NMR (d₆-DMSO, 300 MHz) δ 1.25 (t, J = 7.05 Hz, 6H), 3.97-4.13 (m, 4H), 7.46-7.53 (m, 1H), 7.57-7.66 (m, 2H), 7.84-7.96 (m, 1H), ³¹P NMR (d₆-DMSO, 121.49 MHz) δ 13.64, MS (ESI, EI⁺) m/z = 249.05 (MH⁺). |
| 3a | phenyl-P(=O)(OEt)(OH) | Colorless oil, ¹H NMR (CDCl₃, 300 MHz) δ 1.32 (t, J = 7.3 Hz, 3H), 4.08 (q, J = 7.3 Hz, 2H), 7.42-7.56 (m, 3H), 7.79-7.86 (m, 2H), 10.67 (brs, 1H), ³¹P NMR (CDCl₃, 101.256 MHz) δ 21.3. |
| 3b | 3,5-dimethylphenyl-P(=O)(OEt)₂ | Colorless oil, ¹H NMR (CDCl₃, 300 MHz) δ 1.3 (t, J = 7.05 Hz, 3H), 2.32 (s, 6H), 4.03-4.15 (m, 2H), 7.15 (s, 1H), 7.42 (d, J = 13.8 Hz, 2H), 9.64 (brs, 1H), ³¹P NMR (CDCl₃, 101.256 MHz) δ 22.36, MS (ESI, EI⁺) m/z = 215 (MH⁺). |
| 3c | 4-fluorophenyl-P(=O)(OEt)(OH) | Colorless oil, ¹H NMR (CDCl₃, 300 MHz) δ 1.3 (t, J = 7.05 Hz, 3H), 4.02-4.11 (m, 2H), 7.09-7.16 (m, 2H), 7.76-7.85 (m, 2H), 8.37 (brs, 1H), ¹⁹F NMR (CDCl₃, 282.4 MHz) δ −106 (m, 1F), ³¹P NMR (CDCl₃, 101.256 MHz) δ 20, MS (ESI, EI⁺) m/z = (MH⁺). |
| 3d | 3-(trifluoromethyl)phenyl-P(=O)(OEt)(OH) | Colorless oil, ¹H NMR (CDCl₃, 300 MHz) δ 1.32 (t, J = 7.05 Hz, 3H), 4.11 (quintuplet, J = 7.05 Hz, 2H), 7.55-7.61 (m, 1H), 7.78-7.8 (m, 1H), 7.95-8.13 (m, 3H), ³¹P NMR (CDCl₃, 101.256 MHz) δ 18.09, ¹⁹F NMR (CDCl₃, 282.4 MHz) δ −66.03, MS (ESI, EI⁺) m/z = 255 (MH⁺). |
| 3e | 3-cyanophenyl-P(=O)(OEt)(OH) | Colorless oil, ¹H NMR (CDCl₃, 300 MHz) δ 1.33 (t, J = 7.05 Hz, 3H), 4.04 (quintuplet, J = 7.05 Hz, 2H), 7.27-8.09 (m, 5H), ³¹P NMR (CDCl₃, 101.256 MHz) δ 16.59, MS (ESI, EI⁺) m/z = 212 (MH⁺). |
| 3f | 3,5-dichlorophenyl-P(=O)(OEt)(OH) | Colorless oil, ¹H NMR (CDCl₃, 300 MHz) δ 1.33 (t, J = 7.05 Hz, 3H), 4.1 (quintuplet, J = 7.05 Hz, 2H), 7.51 (t, J = 1.8 Hz, 1H), 7.62 (d, J = 1.8 Hz, 1H), 7.67 (d, J = 1.8 Hz, 1H), 11.63 (brs, 1H), ³¹P NMR (CDCl₃, 121.49 MHz) δ 15.74, MS (ESI, EI⁺) m/z = 255 (MH⁺). |
| 3g | 3-ethylphenyl-P(=O)(OEt)(OH) | Colorless oil, ¹H NMR (CDCl₃, 300 MHz) δ 1.26 (t, J = 7.5 Hz, 3H), 1.33 (t, J = 7.2 Hz, 3H), 2.69 (q, J = 7.5 Hz, 2H), 4.1 (quintuplet, J = 7.2 Hz, 2H), 7.36-7.39 (m, 2H), 7.61-7.69 (m, 2H), 10.83 (brs, 1H), ³¹P NMR (CDCl₃, 121.49 MHz) δ 21.63, MS (ESI, EI⁺) m/z = 215 (MH⁺) |
| 3h | 3-isopropylphenyl-P(=O)(OEt)(OH) | Colorless oil, ¹H NMR (CDCl₃, 300 MHz) δ 1.25 (d, J = 6.9 Hz, 6H), 1.31 (t, J = 7.05 Hz, 3H), 2.88-2.98 (m, 1H), 4.03-4.13 (m, 2H), 7.35-7.41 (m, 2H), 7.60-7.69 (m, 2H), 11.26 (brs, 1H), ³¹P NMR (CDCl₃, 121.49 MHz) δ 21.85, MS (ESI, EI⁺) m/z = 229 (MH⁺) |
| 3i | 3-chloro-5-methylphenyl-P(=O)(OEt)(OH) | Colorless oil, ¹H NMR (CDCl₃, 300 MHz) δ 1.32 (d, J = 7.0 Hz, 6H), 2.35 (s, 3H), 4.04-4.14 (m, 2H), 7.32 (s, 1H), 7.45-7.59 (m, 2H), 8.28 (brs, 1H), ³¹P NMR (CDCl₃, 121.49 MHz) δ 19.16. |

TABLE 1-continued

| Compound | structure | Description |
|---|---|---|
| 3j | (Ph-substituted phenyl with P(=O)(OEt)(OH)) | Colorless oil, $^1$H NMR (CDCl$_3$, 300 MHz) δ 1.31 (d, J = 7.0 Hz, 6H), 2.35 (s, 3H), 4.05-4.17 (m, 2H), 7.32 (s, 1H), 7.36-7.83 (m, 8H), 8.03 (d, J = 14.3 Hz, 1H), 10.16 (brs, 1H), $^{31}$P NMR (CDCl$_3$, 121.49 MHz) δ 21.13, MS (ESI, EI$^+$) m/z 263 (MH$^+$). |
| 3k | (H$_3$CO-substituted phenyl with P(=O)(OEt)(OH)) | Colourless oil, $^1$H NMR (CDCl$_3$, 300 MHz) δ 1.32 (t, J = 7.0 Hz, 3H), 3.83 (s, 3H), 4.08 (quintuplet, J = 7.0 Hz, 2H), 7.05-7.09 (m, 1H), 7.3-7.44 (m, 3H), 10.25 (brs, 1H), $^{31}$P NMR (CDCl$_3$, 121.49 MHz) δ 20.36. |
| 3n | (3,5-bis(CF$_3$)phenyl with P(=O)(OEt)(OH)) | Light orange oil, $^1$H NMR (CDCl$_3$, 300 MHz) δ 1.36 (t, J = 7.2 Hz, 3H), 4.16 (quintuplet, J = 7.2 Hz, 2H), 8.06 (brs, 1H), 8.22 (brs, 1H), 8.27 (brs, 1H), 10.95 (brs, 1H), $^{31}$P NMR (CDCl$_3$, 121.49 MHz) δ 15.19, MS (ESI, EI$^+$) m/z = 322.99 (MH$^+$). |
| 3q | (3-F, 5-CH$_3$ phenyl with P(=O)(OEt)(OH)) | Light orange oil, $^1$H NMR (CDCl$_3$, 300 MHz) δ 1.34 (t, J = 7.05 Hz, 3H), 2.4 (s, 3H), 4.11 (quintuplet, J = 7.05 Hz, 2H), 7.04-7.08 (m, 1H), 7.27-7.35 (m, 1H), 7.4-7.43 (m, 1H), 11.37 (brs, 1H), $^{31}$P NMR (CDCl$_3$, 121.49 MHz) δ 19.37 (d, J = 9.6 Hz, 1P), MS (ESI, EI$^+$) m/z 219 (MH$^+$). |
| 3r | (naphthyl with P(=O)(OEt)(OH)) | Yellowish oil, $^1$H NMR (d$_6$-DMSO, 300 MHz) δ 1.18 (t, J = 7.1 Hz, 3H), 3.87-3.97 (m, 2H), 7.55-7.67 (m, 3H), 7.98-8.18 (m, 3H), 8.53 (d, J = 8.4 Hz, 1H), $^{31}$P NMR (d$_6$-DMSO, 300 MHz) δ 14.76, MS (ESI, EI$^+$) m/z = 237 (MH$^+$). |
| 3s | (3-F, 5-iPr phenyl with P(=O)(OH)(OEt)) | Yellowish oil, $^1$H NMR (CDCl$_3$, 300 MHz) δ 1.25 (d, J = 6.9 Hz, 6H), 1.31 (t, J = 6.9 Hz, 3H), 2.70-3.00 (m, 1H), 4.00-4.20 (m, 2H), 7.89 (d, J = 5.4 Hz, 1H), 7.25-7.36 (m, 1H), 7.47 (d, J = 13.5 Hz, 1H), 12.22 (brs, 1H) $^{31}$P NMR (CDCl$_3$, 121.49 MHz) δ 17.93, $^{19}$F NMR (CDCl$_3$, 282.40 MHz) δ −112.35 (m, 1F). |
| 3t | (3-iPr, 5-CN phenyl with P(=O)(OCH$_2$)(OH)) | Colorless oil, $^1$H NMR (CDCl$_3$, 300 MHz) δ 1.27 (d, J = 6.9 Hz, 6H), 1.33 (t, J = 6.9 Hz, 3H), 2.94-3.03 (m, 1H), 4.07-4.16 (m, 2H), 5.15 (brs, 1H), 7.66 (brs, 1H), 7.83-7.95 (m, 2H), $^{31}$P NMR (CDCl$_3$, 121.49 MHz) δ 17.61, MS (ESI, EI$^+$) m/z 254.3 (MH$^+$). |
| 3u | (3-F, 5-Cl phenyl with P(=O)(OEt)(OH)) | Colourless oil, $^1$H NMR (CDCl$_3$, 300 MHz) δ 1.33 (t, J = 7.05 Hz, 3H), 4.1 (quintuplet, J = 7.05 Hz, 2H), 7.24-7.28 (m, 1H), 7.35-7.44 (m, 1H), 7.55-7.60 (m, 1H), 12.16 (s, 1H), $^{31}$P NMR (CDCl$_3$, 121.49 MHz) δ 15.63 (d, J = 9.20 Hz, 1P). |

TABLE 1-continued

| Compound | structure | Description |
|---|---|---|
| 3v | 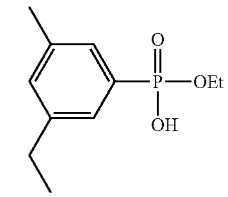 | Colorless oil, $^1$H NMR (d$_6$-DMSO, 300 MHz) δ 1.17 (t, J = 7.2 Hz, 3H), 1.17 (t, J = 7.5 Hz, 3H), 2.32 (s, 3H), 2.61 (q, J = 7.5 Hz, 2H), 3.81-3.91 (m, 2H), 7.21 (brs, 1H), 7.29 (brs, 1H), 7.34 brs, 1H), $^{31}$P NMR (d$_6$-DMSO, 121.49 MHz) δ 15.62, MS (ES$^+$) m/z = 229.3 (MH$^+$). |
| 3x | 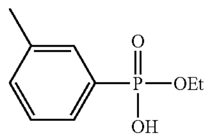 | Yellow oil, $^1$H NMR (d$_6$-DMSO, 300 MHz) δ 1,18 (t, J = 6.9 Hz, 3H), 2.36 (s, 3H), 3.87 (quintuplet, J = 7.2 Hz, 2H), 7.33-7.42 (m, 2H), 7.44-7.55 (m, 2H), $^{31}$P NMR (d$_6$-DMSO, 101.256 MHz) δ 16.41. |
| 3z | 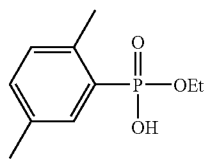 | Yellow pale oil, $^1$H NMR (d$_6$-DMSO, 300 MHz) δ 1,19 (t, J = 6.9 Hz, 3H), 2.30 (brs, 3H), 2.45 (brs, 3H), 3.87 (quintuplet, J = 7.5 Hz, 2H), 7.18-7.27 (m, 2H), 7.57 (d, J = 14.4 Hz, 1H), $^{31}$P NMR (d$_6$-DMSO, 101 MHz) δ 15.79. |
| 3aa | 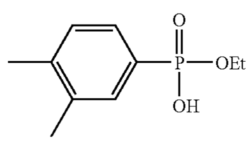 | Yellow pale oil, $^1$H NMR (d$_6$-DMSO, 300 MHz) δ 1,17 (t, J = 7.05 Hz, 3H), 2.27 (brs, 6H), 3.85 (quintuplet, J = 7.2 Hz, 2H), 7.23-7.27 (m, 1H), 7.37-7.47 (m, 2H), $^{31}$P NMR (d$_6$-DMSO, 101 MHz) δ 16.92, MS (ESI, EI$^+$) m/z = 215 (MH$^+$). |
| 3ad | 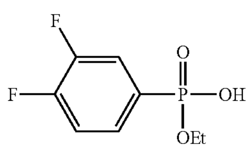 | Pale yellow oil, $^1$H NMR (d$_6$-DMSO, 300 MHz) δ 1.17 (t, J = 7.1 Hz, 6H), 3.84-3.94 (m, 2H), 7.51-7.69 (m, 3H), $^{19}$F NMR (d$_6$-DMSO, 300 MHz) δ -141.87 (m, 1F), -137.91 (m, 1F), $^{31}$P NMR (d$_6$-DMSO, 101.256 MHz) δ 12.80 (d, J = 6.5 Hz, 1P), MS (ESI, EI$^+$) m/z = 223 (MH$^+$). |
| 3ae | 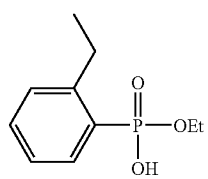 | Oil, $^1$H NMR (d$_6$-DMSO, 300 MHz) δ 1.18 (t, J = 7.5 Hz, 3H), 1.19 (t, J = 7.05 Hz, 3H), 2.91 (q, J = 7.5 Hz, 2H), 3.89 (quintuplet, J = 7.05 Hz, 2H), 7.24-7.36 (m, 2H), 7.46-7.52 (m, 1H), 7.74 (ddd, J = 1.2 and 7.5 and 13.8 Hz, 1H), $^{31}$P NMR (d$_6$-DMSO, 121.49 MHz) δ 15.66, MS (ESI, EI$^+$) m/z = 215 (MH$^+$). |
| 3af | 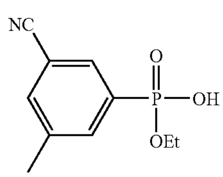 | Oil, $^1$H NMR (d$_6$-DMSO, 300 MHz) δ 1.18 (t, J = 6.9 Hz, 3H), 2.4 (s, 3H), 3.85-3.97 (m, 2H), 7.78-7.81 (m, 1H), 7.82-7.84 (m, 1H), 7.84-7.87 (m, 1H), $^{31}$P NMR (d$_6$-DMSO, 121.49 MHz) δ 11.67, MS (ES$^+$) m/z = 226.2 (MH$^+$). |
| 3ag | 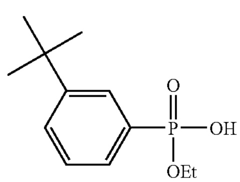 | Oil, $^1$H NMR (d$_6$-DMSO, 300 MHz) δ 1.17 (t, J = 7.1 Hz, 3H), 1.3 (s, 9H), 3.82-3.91 (m, 2H), 7.41-7.53 (m, 2H), 7.59-7.61 (m, 1H), 7.66-7.71 (m, 1H), MS (ES$^+$) m/z = 243 (MH$^+$). |
| 3ai | 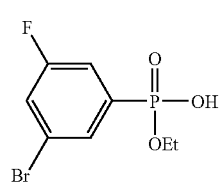 | Oil, $^1$H NMR (d$_6$-DMSO, 300 MHz) δ 1.19 (t, J = 6.9 Hz, 3H), 3.87-3.97 (m, 2H), 7.4-7.49 (m, 1H), 7.6-7.64 (m, 1H), 7.78-7.82 (m, 1H), $^{19}$F NMR (d$_6$-DMSO, 282.4 MHz) δ -109.3 (q, J = 8.2 Hz, 1F), MS (ES$^+$) m/z = 283/285 (MH$^+$). |

TABLE 1-continued

| Compound | structure | Description |
| --- | --- | --- |
| 3aj | (3-cyano-5-fluorophenyl)(ethoxy)phosphinic acid | Oil, ¹H NMR (d₆-DMSO, 300 MHz) δ 1.19 (t, J = 7.05 Hz, 3H), 3.87-3.97 (m, 2H), 7.55-7.65 (m, 1H), 7.85-7.91 (m, 1H), 8.03-8.09 (m, 1H), ³¹P NMR (d₆-DMSO, 121.49 MHz) δ 11.94 (d, J = 8.02 Hz, 1P), ¹⁹F NMR (d₆-DMSO, 282.4 MHz) −112.04 (m, 1F), MS (ES⁺) m/z 228.3 (MH⁺). |
| 3ak | (2-chlorophenyl)(ethoxy)phosphinic acid | Oil, ¹H NMR (d₆-DMSO, 300 MHz) δ 1.20 (t, J = 7.05 Hz, 3H), 3.87-3.97 (m, 2H), 7.4-7.47 (m, 1H), 7.51-7.59 (m, 2H), 7.83-7.91 (m, 1H), ³¹P NMR (d₆-DMSO, 121.49 MHz) δ 11.26, MS (ESI, EI⁺) m/z = 221.03 (MH⁺). |
| 3al | (2,5-difluorophenyl)(ethoxy)phosphinic acid | Oil, ¹H NMR (d₆-DMSO, 300 MHz) δ 1.19 (t, J = 7.2 Hz, 3H), 3.9-4 (m, 2H), 7.31-7.53 (m, 3H), ³¹P NMR (d₆-DMSO, 101.256 MHz) δ 8.05 (d, J = 5.5 Hz, 1P), ¹⁹F NMR (d₆-DMSO, 282.4 MHz) −110.71 (d, J = 19.4 Hz, 1F), −118.33 (dd, J = 5.9 and 19.2 Hz, 1F), MS (ES⁺) m/z = 223.03 (MH⁺). |

TABLE 2

| Compound | structure | Description |
| --- | --- | --- |
| 5a | ethyl 5-chloro-3-(ethoxy(phenyl)phosphoryl)-1-(phenylsulfonyl)-1H-indole-2-carboxylate | Colorless oil, ¹H NMR (d₆-DMSO, 300 MHz) δ 1.27 (t, J = 7.1 Hz, 3H), 1.36 (t, J = 7.1 Hz, 3H), 4.03 (m, 2H), 4.38 (q, J = 7.1 Hz, 2H), 7.51-7.83 (m, 11H), 8.05-8.11 (m, 3H), ³¹P NMR (d₆-DMSO, 101.256 MHz) δ 23.3, MS (ESI, EI⁺) m/z = 532 (MH⁺). |
| 5b | ethyl 3-(benzyloxy(phenyl)phosphoryl)-5-chloro-1-(phenylsulfonyl)-1H-indole-2-carboxylate | Thick yellow oil, ¹H NMR (CDCl₃, 300 MHz) δ 1.30 (t, J = 7.2 Hz, 3H), 4.22-4.34 (m, 2H), 5-5.12 (m, 2H), 7.26-7.33 (m, 6H), 7.42-7.54 (m, 5H), 7.60-7.66 (m, 1H), 7.77-7.78 (m, 1H), 7.85-7.92 (m, 3H), 8.07-8.10 (m, 2H), ³¹P NMR (CDCl₃, 101.256 MHz) δ 25.24, MS (ESI, EI⁺) m/z = 594 (MH⁺). |

TABLE 2-continued

| Compound | structure | Description |
|---|---|---|
| 5c | 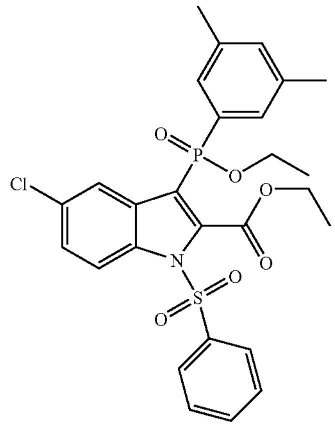 | Slight yellow solid, $^1$H NMR (d$_6$-DMSO, 300 MHz) δ 1.27 (t, J = 7.1 Hz, 3H), 1.36 (t, J = 7.1 Hz, 3H), 2.30 (s, 6H), 3.94-4.06 (m, 2H), 4.44 (q, J = 7.1 Hz, 2H), 7.25 (s, 1H), 7.39 (s, 1H), 7.42 (s, 1H), 7.53 (dd, J = 2.1 and 9.0 Hz, 1H), 7.65-7.71 (m, 2H), 7.77-7.82 (m, 2H), 8.05-8.11 (m, 3H), $^{31}$P NMR (d$_6$-DMSO, 101.256 MHz) δ 23.6, MS (ESI, EI$^+$) m/z = 560 (MH$^+$). |
| 5d | 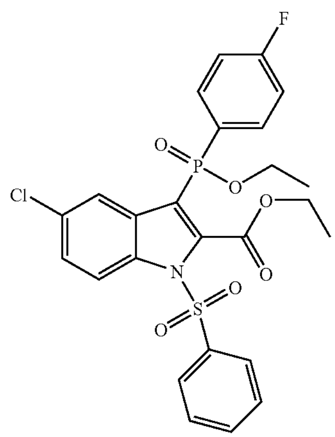 | Thick yellow oil, $^1$H NMR (CDCl$_3$, 300 MHz) δ 1,37 (t, J = 7.2 Hz, 3H), 1,44 (t, J = 7.2 Hz, 3H), 4.05-4.19 (m, 2H), 4.52 (q, J = 7.2 Hz, 2H), 7.11-7.17 (m, 2H), 7.32-7.36 (m, 1H), 7.48-7.54 (m, 2H), 7.60-7.63 (m, 1H), 7.84-7.93 (m, 4H), 8.07-8.09 (m, 2H), $^{31}$P NMR (CDCl$_3$, 101.256 MHz) δ 23.6, $^{19}$F NMR (CDCl$_3$, 282.4 MHz) δ −105.36 (m, 1F), MS (ESI, EI$^+$) m/z = 550 (MH$^+$). |
| 5e | 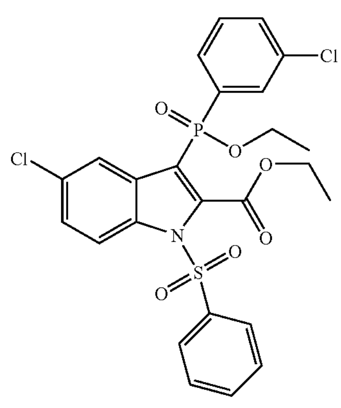 | Thick yellow oil, $^1$H NMR (CDCl$_3$, 300 MHz) δ 1.38 (t, J = 7.05 Hz, 3H), 1.46 (t, J = 7.2 Hz, 3H), 4.09-4.2 (m, 2H), 4.53 (q, J = 7.2 Hz, 2H), 7.35 (dd, J = 2.1 and 9 Hz, 1H), 7.37-7.43 (m, 1H), 7.48-7.54 (m, 3H), 7.6-7.95 (m, 5H), 8.07-8.1 (m, 2H), $^{31}$P NMR (CDCl$_3$, 101.256 MHz) δ 22.76, MS (ESI, EI$^+$) m/z = 566 (MH$^+$). |

TABLE 2-continued

| Compound | structure | Description |
|---|---|---|
| 5f | 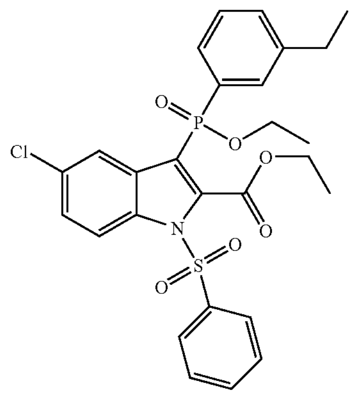 | Thick yellow oil, $^1$H NMR (CDCl$_3$, 300 MHz) δ 1.23 (t, J = 7.5 Hz, 3H), 1.37 (t, J = 7.05 Hz, 3H), 1.44 (t, J = 7.2 Hz, 3H), 2.68 (q, J = 7.5 Hz, 2H), 4.06-4.18 (m, 2H), 4.5 (q, J = 7.2 Hz, 2H), 7.3-7.39 (m, 3H), 7.47-7.52 (m, 2H), 7.59-7.76 (m, 3H), 7.87 (d, J = 1.8 Hz, 1H), 7.91 (dd, J = 1.5 and 9 Hz, 1H), 8.07-8.1 (m, 2H), $^{31}$P NMR (CDCl$_3$, 121.49 MHz) δ 21, MS (ESI, EI$^+$) m/z = 560 (MH$^+$). |
| 5g | 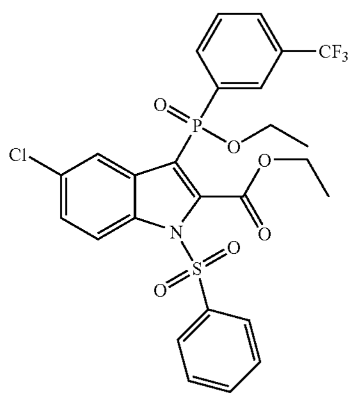 | Yellow solid, $^1$H NMR (CDCl$_3$, 400 MHz) δ 1.39 (t, J = 7 Hz, 3H), 1.44 (t, J = 7.2 Hz, 3H), 4.09-4.23 (m, 2H), 4.53 (qd, J = 2 and 7.2 Hz, 2H), 7.35 (dd, J = 2 and 9.2 Hz, 1H), 7.48-7.53 (m, 2H), 7.57-7.64 (m, 2H), 7.68-7.79 (m, 1H), 7.88 (d, J = 2 Hz, 1H), 7.94 (dd, J = 1.6 and 8.8 Hz, 1H), 8.04-8.1 (m, 3H), 8.16-8.2 (m, 1H), $^{31}$P NMR (CDCl$_3$, 101.256 MHz) δ 22.62, $^{19}$F NMR (CDCl$_3$, 235.36 MHz) δ −63.2, MS (ESI, EI$^+$) m/z = 600 (MH$^+$). |
| 5h | 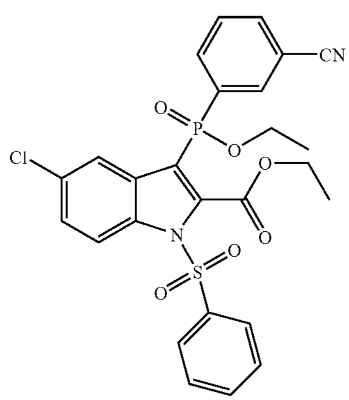 | Yellow solid, $^1$H NMR (CDCl$_3$, 300 MHz) δ 1.4 (t, J = 7.05 Hz, 3H), 1.46 (t, J = 7.2 Hz, 3H), 4.04-4.24 (m, 2H), 4.55 (q, J = 7.2 Hz, 2H), 7.37 (dd, J = 2.1 and 9 Hz, 1H), 7.51-7.67 (m, 4H), 7.80 (dd, J = 1.5 and J = 7.8 Hz, 1H), 7.84 (d, J = 2.1 Hz, 1H), 7.95 (dd, J = 1.5 and 8.7 Hz, 1H), 8.07-8.17 (m, 4H), $^{31}$P NMR (CDCl$_3$, 101.256 MHz) δ 21.64, MS (ESI, EI$^+$) m/z =557 (MH$^+$). |
| 5i | 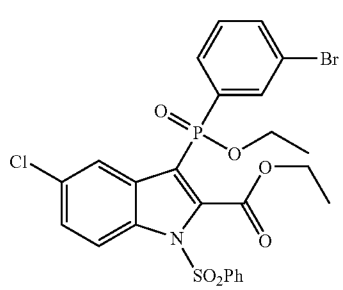 | White solid, $^1$H NMR (CDCl$_3$, 300 MHz) δ 1.38 (t, J = 7.05 Hz, 3H), 1.46 (t, J = 7.35 Hz, 3H), 4.10-4.19 (m, 2H), 4.53 (q, J = 7.2 Hz, 2H), 7.3-7.37 (m, 2H), 7.49-7.55 (m, 2H), 7.6-7.67 (m, 2H), 7.77-7.84 (m, 1H), 7.87 (d, J = 2.1 Hz, 1H), 7.93 (dd, J = 1.8 and 9 Hz, 1H), 8-8.06 (m, 1H), 8.07-8.11 (m, 2H), $^{31}$P NMR (CDCl$_3$, 121.49 MHz) δ 22.11, MS (ES$^+$) m/z = 609.73/611.77 (MH$^+$). |

TABLE 2-continued

| Compound | structure | Description |
|---|---|---|
| 5j | 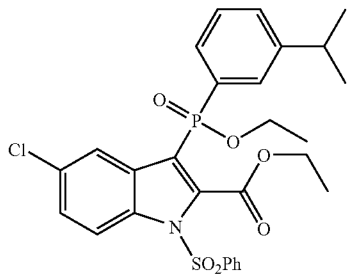 | Thick yellow oil, $^1$H NMR (d$_6$-DMSO, 300 MHz) δ 1.16 (d, J = 6.9 Hz, 3H), 1.17 (d, J = 6.9 Hz, 3H), 1.27 (t, J = 7.05 Hz, 3H), 1.38 (t, J = 7.2 Hz, 3H), 2.88-2.97 (m, 1H), 4.03 (q, J = 7.2 Hz, 2H), 4.45 (q, J = 7.05 Hz, 2H), 7.45-7.69 (m, 7H), 7.75-7.79 (m, 2H), 8.05-8.1 (m, 3H), MS (ES$^+$) m/z = 573.8 (MH$^+$). |
| 5k | 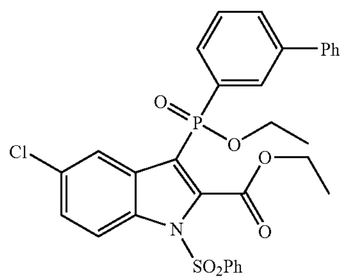 | Yellow solid; $^1$H NMR (d$_6$-DMSO, 300 MHz) δ 1.30 (t, J = 7.0 Hz, 3H), 1.35 (t, J = 7.0, Hz, 3H), 4.05-4.12 (m, 2H), 4.46 (q, J = 7.0 Hz, 2H), 5.56 (d, J = 12 Hz, 1H), 7.44-8.10 (m, 18H), $^{31}$P NMR (d$_6$-DMSO, 121.49 MHz) δ 22.07, MS (ES$^+$) m/z = 608 (MH$^+$). |
| 5l | 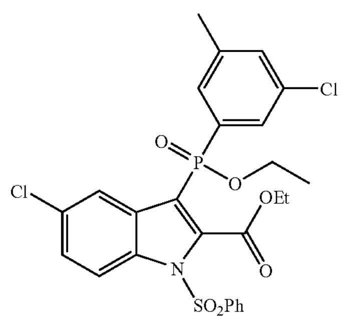 | Thick yellow oil, $^{31}$P NMR (d$_6$-DMSO, 121.49 MHz) δ 22.73, MS (ES$^+$) m/z = 580 (MH$^+$). |
| 5n | 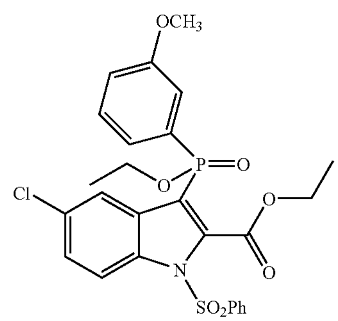 | White powder, $^1$H NMR (CDCl$_3$, 300 MHz) δ 1.37 (t, = 7.2 Hz, 3H), 1.45 (t, J = 7.2 Hz, 3H), 3.81 (s, 3H), 4.05-4.18 (m, 2H), 4.53 (q, J = 7.2 Hz, 2H), 7.07 (dt, J = 1.2 Hz and 8.1 Hz, 1H), 7.28-7.63 (m, 7H), 7.87 (d, J = 2.1, 1H), 7.90 (dd, J = 1.5 Hz and 9 Hz, 1H), 8.08 (dd, J = 1.5 Hz and 7.5 Hz, 2H), $^{31}$P NMR (CDCl$_3$, 121.49 MHz) δ 24.00 |
| 5p | 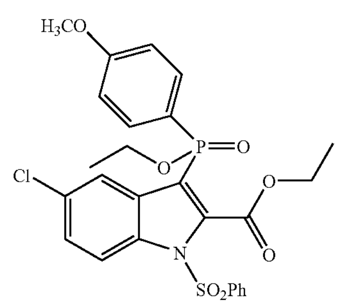 | Yellowish powder, $^1$H NMR (CDCl$_3$, 300 MHz) δ 1.38 (t, J = 7.2 Hz, 3H), 1.47 (t, J = 7.2 Hz, 3H), 3.85 (s, 3H), 4.13 (q, J = 7.2 Hz, 2H), 4.53 (q, J = 7.2 Hz, 2H), 6.97 (dd, J = 2.7 Hz and 8.7 Hz, 2H), 7.34 (dd, J = 2.1 Hz and 9.3 Hz, 1H), 7.49-7.55 (m, 2H), 7.6-7.66 (m, 1H), 7.8-7.94 (m, 4H), 8.08-8.11 (m, 2H), $^{31}$P NMR (CDCl$_3$, 121.49 MHz) δ 24.36, MS (ESI, EI$^+$) m/z = 562 (MH$^+$). |

TABLE 2-continued

| Compound | structure | Description |
|---|---|---|
| 5q | 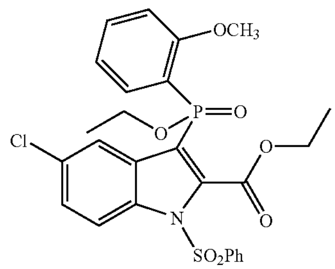 | Yellowish powder, $^1$H NMR (CDCl$_3$, 300 MHz) δ 1.36 (t, J = 7.2 Hz, H), 1.38 (t, J = 7.05 Hz, 3H), 3.55 (s, 3H), 4.05-4.23 (m, 2H), 4.42 (q, J = 7.2 Hz, 2H), 6.82-6.87 (m, 1H), 7.05-7.11 (m, 1H), 7.35 (dd, J = 2.1 Hz and 9 Hz, 1H), 7.89-7.53 (m, 3H), 7.6-7.66 (m, 1H), 7.9-7.98 (m, 2H), 8.03 (d, J = 2.1 Hz, 1H), 8.09-8.12 (m, 2H), $^{31}$P NMR (CDCl$_3$, 121.49 MHz) δ 21.9, MS (ESI, EI$^+$) m/z = 562 (MH$^+$). |
| 5r | 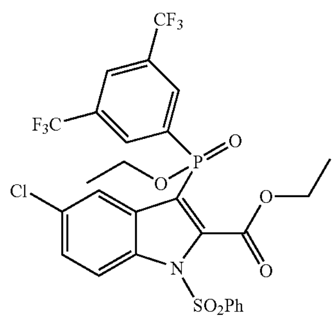 | Yellowish powder, $^{31}$P NMR (CDCl$_3$, 121.49 MHz) δ 20.6, $^{19}$F NMR (CDCl$_3$, 282.4 MHz) δ −63.3, MS (ESI, EI$^+$) m/z = 668 (MH$^+$). |
| 5s | 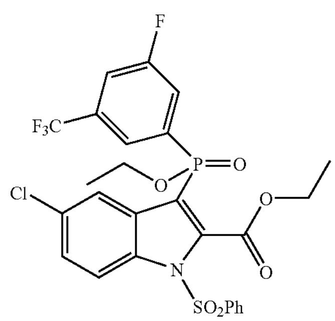 | Yellowish powder, $^{31}$P NMR (CDCl$_3$, 121.49 MHz) δ 20.86 (d, J = 7.8 Hz, 1P), $^{19}$F NMR (CDCl$_3$, 282.4 MHz) δ −63.2 (s, 3F), −108.7 (q, J = 7.3 Hz, 1F), MS (ESI, EI$^+$) m/z = 618 (MH$^+$). |
| 5u | 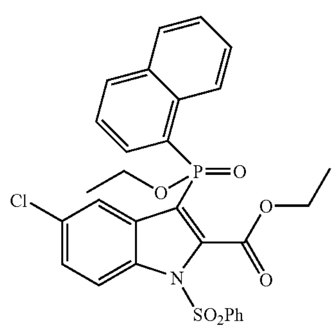 | Yellowish powder, $^1$H NMR (CDCl$_3$, 300 MHz) δ 1.36 (quintuplet, J = 7.2 Hz, 6H), 4.09-4.3 (m, 2H), 4.42 (q, J = 6.9 Hz, 2H), 7.31 (dd, J = 2.1 Hz and 9 Hz, 1H), 7.47-7.64 (m, 6H), 7.71 (d, J = 1.8 Hz, 1H), 7.87-7.95 (m, 2H), 8.04-8.09 (m, 3H). 8.16 (qd, J = 1.2 Hz and 7.2 Hz, 1H), 8.69-8.72 (m, 1H), $^{31}$P NMR (CDCl$_3$, 121.49 MHz) δ 24.31, MS (ESI, EI$^+$) m/z = 582 (MH$^+$). |
| 5v | 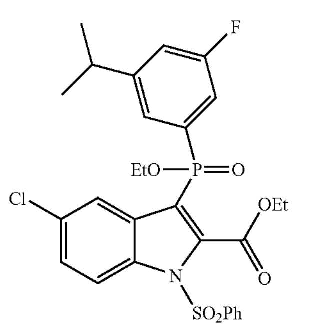 | Yellowish powder, $^1$H NMR (CDCl$_3$, 300 MHz) δ 1.23 (d, J = 7.2 Hz, 6H), 1.38 (t, J = 7.2 Hz, 3H), 1.46 (t, J = 7.2 Hz, 3H), 2.83-3.06 (m, 1H), 4.05-4.25 (m, 2H), 4.55 (q, J = 7.0 Hz, 2H), 7.05-7.10 (m, 1H), 7.33 (dd, J = 2.1 Hz and 9.0 Hz, 1H), 7.31-7.41 (m, 1H), 7.45-7.64 (m, 4H), 7.86 (d, J = 1.8 Hz, 1H), 7.94 (dd, J = 8.7 Hz and 1.8 Hz, 1H), 8.06-8.11 (m, 2H), $^{31}$P NMR (CDCl$_3$, 121.49 MHz) δ 22.83 (d, J = 7.65 Hz), MS (ES$^+$) m/z = 592 (MH$^+$). |

TABLE 2-continued

| Compound | structure | Description |
|---|---|---|
| 5w | 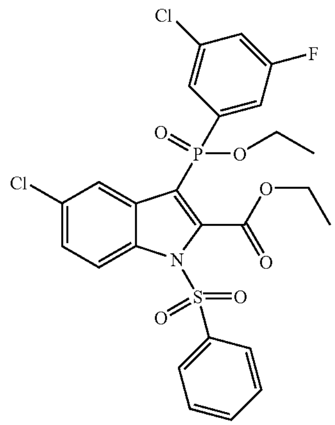 | Yellow resin, $^1$H NMR (CDCl$_3$, 300 MHz) δ 1.42 (t, J = 7.05 Hz, 3H), 1.49 (t, J = 7.2 Hz, 3H), 4.11-4.26 (m, 2H), 4.57 (q, J = 7.2 Hz, 2H), 7.23-7.27 (m, 1H), 7.38 (dd, J = 1.8 and 9 Hz, 1H), 7.5-7.57 (m, 3H), 7.62-7.72 (m, 2H), 7.87-7.88 (m, 1H), 7.94-7.98 (m, 1H), 8.09-8.12 (m, 2H), $^{31}$P NMR (CDCl$_3$, 121.49 MHz) δ 6.78, MS (ES$^+$) m/z = 584.26 (MH$^+$). |
| 5x | 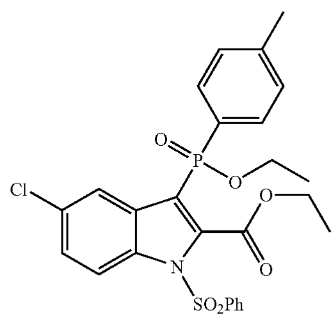 | Oil, $^1$H NMR (d$_6$-DMSO, 300 MHz) δ 1.27 (t, J = 6.9 Hz, 3H), 1.37 (t, J = 7.2 Hz, 3H), 2.34 (s, 3H), 3.97-4.02 (m, 2H), 4.44 (q, J = 7.2 Hz, 2H), 7.34-7.38 (m, 2H), 7.51-7.55 (dd, J = 2.1 and 9 Hz, 1H), 7.65-7.72 (m, 4H), 7.75-7.83 (m, 2H) $^{31}$P NMR (d$_6$-DMSO, 101.256 MHz) δ 23.57, MS (ESI, EI$^+$) m/z = 546 (MH$^+$). |
| 5aa | 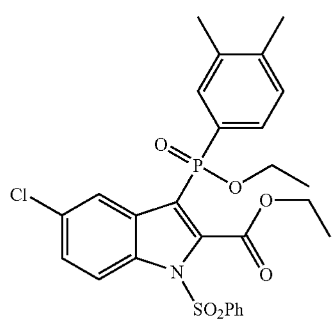 | Oil, $^1$H NMR (d$_6$-DMSO, 300 MHz) δ 1.27 (t, J = 7.05 Hz, 3H), 1.39 (t, J = 7.05 Hz, 3H), 2.25 (2s, 6H), 3.96-4.04 (m, 2H), 4.44 (q, J = 7.05 Hz, 2H), 7.3-7.34 (m, 1H), 7.48-7.58 (m, 3H), 7.66-7.72 (m, 2H), 7.77-7.83 (m, 2H), 8.09-8.11 (m, 3H), $^{31}$P NMR (d$_6$-DMSO, 101.256 MHz) δ 23.64, MS (ESI, EI$^+$) m/z = 560 (MH$^+$). |
| 5ad | 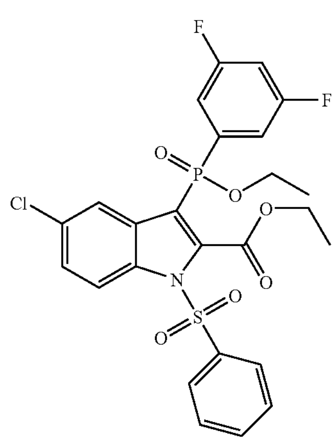 | Dark yellow oil, $^1$H NMR (d$_4$-DMSO, 300 MHz) δ 1.29 (t, J = 6.9 Hz, 3H), 1.37 (t, J = 7.2 Hz, 3H), 4.03-4.13 (m, 2H), 4.46 (q, J = 7.1 Hz, 2H), 7.44-7.63 (m, 4H), 7.65-7.71 (m, 2H), 7.78-7.83 (m, 1H), 7.88 (d, J = 2.4 Hz, 1H), 8.06-8.11 (m, 3H), $^{19}$F NMR (d$_6$-DMSO) δ −109.98 (m, 1F) + impureté, $^{31}$P NMR (d$_6$-DMSO, 101 MHz) δ 20.41 (t, J = 8.4 Hz, 1P), MS (ESI, EI$^+$) m/z = 569 (M + 2H$^+$). |

TABLE 2-continued

| Compound | structure | Description |
|---|---|---|
| 5ae | 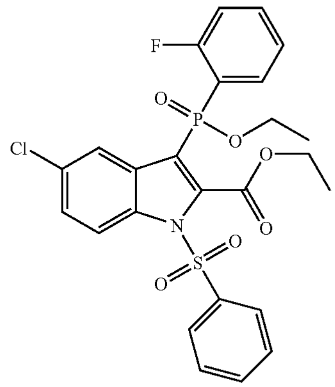 | Yellow oil; $^1$H NMR (d$_6$-DMSO, 300 MHz) δ 1.22-1.30 (m, 6H), 4.95-4.13 (m, 2H), 4.31 (d, J = 7.2 Hz, 2H), 7.25-7.45 (m, 3H), 7.55 (dd, J = 9.3 and 2.0 Hz, 1H), 7.66-7.85 (m, 6H), 8.06-8.10 (m, 2H), $^{31}$P NMR (d$_6$-DMSO, 101 MHz) δ 13.91, $^{19}$F NMR (d$_6$-DMSO) δ -107.59 (m, 1F), MS (ESI, (EI$^+$) m/z = 550 (MH$^+$). |
| 5ah | 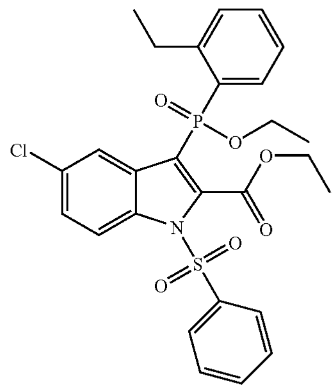 | Yellow powder, $^1$H NMR (d$_6$-DMSO, 300 MHz) δ 0.77 (t, J = 7.5 Hz, 3H), 1,23 (t, J = 6.9 Hz, 3H), 1.26 (t, J = 7.2 Hz, 3H), 2.76 (q, J = 7.5 Hz, 2H), 3.83-4.13 (m, 2H), 4.24-4.35 (m, 2H), 7.3-7.42 (m, 2H), 7.48-7.6 (m, 3H), 7.65-7.8 (m, 4H), 8.06-8.1 (m, 3H), $^{31}$P NMR (d$_6$-DMSO, 101 MHz) δ 22.65, MS (ESI, EI$^+$), m/z = 560 (M + H$^+$). |
| 5ai | 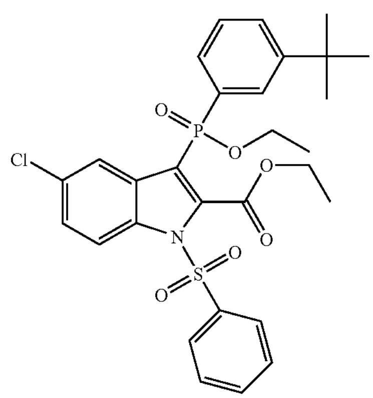 | Oil, $^1$H NMR (d$_6$-DMSO, 300 MHz) δ 1.25 (s, 9H), 1.25 (t, J = 7.2 Hz, 3H), 1.39 (t, J = 7.2 Hz, 3H), 3.99 (m, 2H), 4.46 (q, J = 7.2 Hz, 2H), 7.47-7.55 (m, 2H), 7.6-7.7 (m, 4H), 7.75-7.83 (m, 3H), 8.05-8.1 (m, 3H), $^{31}$P NMR (d$_6$-DMSO, 121.49 MHz) δ 22.6, MS (ES$^+$) m/z = 588.17 (MH$^+$). |
| 5aj | 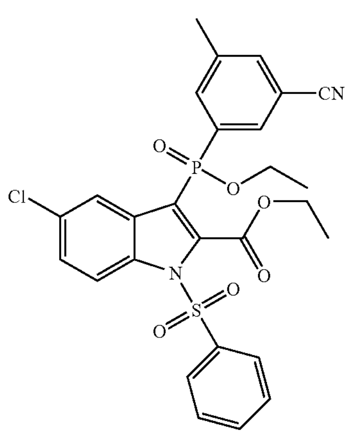 | Oil, $^1$H NMR (CDCl$_3$, 300 MHz) δ 1.4 (t, J = 7.05 Hz, 3H), 1.47 (t, J = 7.2 Hz, 3H), 2.44 (s, 3H), 4-4.25 (m, 2H), 4.55 (q, J = 7.2 Hz, 2H), 7.37 (dd, J = 2.1 and 9 Hz, 1H), 7.52-7.65 (m, 4H), 7.85-7.97 (m, 4H), 8.08-8.11 (m, 2H), $^{31}$P NMR (d$_6$-DMSO, 101.256 MHz) δ 21.58, MS (ES$^+$) m/z = 571.4 MH$^+$). |

TABLE 2-continued

| Compound | structure | Description |
| --- | --- | --- |
| 5ak | 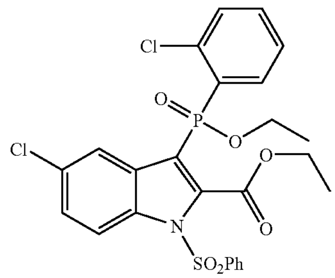 | Oil, ¹H NMR (d₆-DMSO, 300 MHz) δ 1.21 (t, J = 7.2 Hz, 3H), 1.26 (t, J = 6.9 Hz, 3H), 4.03 (q, J = 7.2 Hz, 2H), 4.18-4.26 (m, 2H), 7.52-7.63 (m, 3H), 7.66-7.71 (m, 4H), 7.78-7.83 (m, 1H), 7.92-8 (m, 1H), 8.05-8.09 (m, 3H), ³¹P NMR (d₆-DMSO, 121.49 MHz) δ 18.06, MS (ES⁺) m/z = 565.93 (MH⁺). |
| 5al | 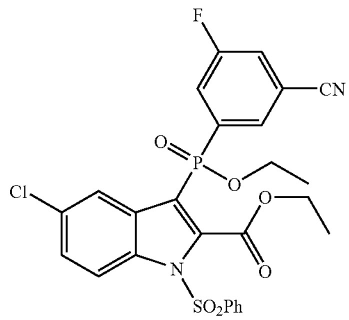 | Oil, ¹H NMR (d₆-DMSO, 300 MHz) δ 1.3 (t, J = 7.05 Hz, 3H), 1.37 (t, J = 7.05 Hz, 3H), 4-4.16 (m, 2H), 4.46 (q, J = 7.05 Hz, 2H), 7.56 (dd, J = 2.1 and 9 Hz, 1H), 7.66-7.71 (m, 2H), 7.79-7.84 (m, 1H), 7.91-7.99 (m, 2H), 8.08-8.18 (m, 5H), ¹⁹F NMR (d₆-DMSO, 282.40 MHz) −112.68 (q, J = 8.2 Hz, 1F), MS (ES⁺) m/z 575 (MH⁺). |
| 6a | 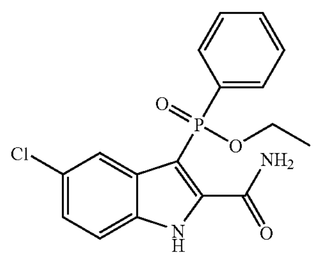 | White solid, ¹H NMR (d₆-DMSO, 300 MHz) δ 1.34 (t, J = 7.1 Hz, 3H), 4.05 (m, 1H), 4.20 (m, 1H), 7.32 (dd, J = 2.1 and 8.7 Hz, 1H), 7.49-7.61 (m, 5H), 7.68-7.75 (m, 2H), 8.02 (brs, 1H), 10.27 (brs, 1H), 12.77 (brs, 1H), ³¹P NMR (d₆-DMSO, 101.256 MHz) δ 31.1, MS (ESI, EI⁺) m/z = 363. (MH⁺). |
| 6b | 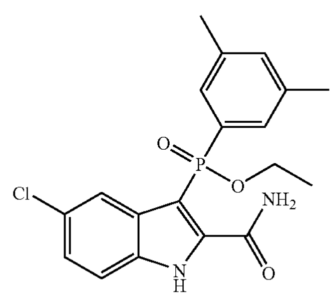 | White solid; ¹H NMR (d₆-DMSO, 300 MHz) δ 1.32 (t, J = 7.0 Hz, 3H), 2.26 (s, 6H), 3.90-4.03 (m, 1H), 4.09-4.22 (m, 1H), 7.21 (s, 1H), 7.29-7.33 (m, 3H), 7.57 (dd, J = 1.8 and 9.0 Hz, 1H), 7.60 (d, J = 1.8 Hz, 1H), 7.99 (brs, 1H), 10.3 (brs, 1H), 12.7 (brs, 1H), ³¹P NMR (d₆-DMSO, 101.256 MHz) δ 31.3, MS (ESI, EI⁺), m/z = 391 (MH⁺). |
| 6c | 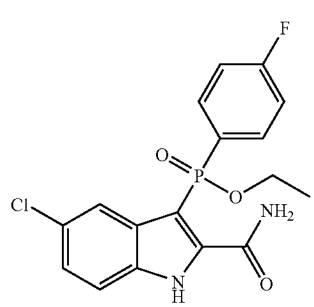 | White Solid, ¹H NMR (d₆-DMSO, 300 MHz) δ 1.34 (t, J = 6.9 Hz, 3H), 4-4.04 (m, 1H), 4.18-4.21 (m, 1H), 7.31-7.4 (m, 3H), 7.57-7.62 (m, 2H), 7.74-7.83 (m, 2H), 8.02 (brs, 1H), 10.18 (brs, 1H), 12.79 (brs, 1H), ³¹P NMR (d₆-DMSO, 121.49 MHz) δ 29.29, ¹⁹F NMR (d₆-DMSO, 282.4 MHz) δ −106.3, MS (ESI, EI⁺) m/z = 381 (MH⁺). |

TABLE 2-continued

| Compound | structure | Description |
|---|---|---|
| 6d | 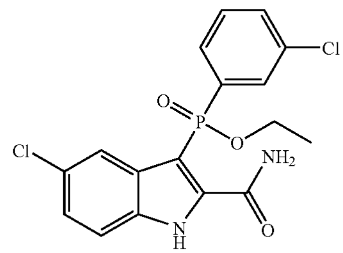 | White solid, ¹H NMR (d₆-DMSO, 300 MHz) δ 1.35 (t, J = 7.05 Hz, 3H), 4-4.09 (m, 1H), 4.17-4.25 (m, 1H), 7.3-7.35 (m, 1H), 7.55-7.74 (m, 6H), 8.05 (brs, 1H), 10.07 (brs, 1H), 12.84 (brs, 1H), ³¹P NMR (d₆-DMSO, 121.49 MHz) δ 28.24, MS (ESI, EI⁺) m/z = 397 (MH⁺). |
| 6e | 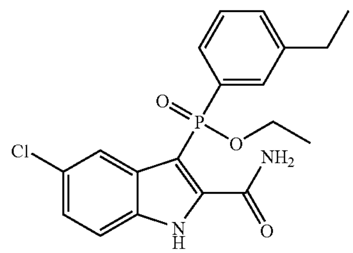 | White solid, ¹H NMR (d₆-DMSO, 300 MHz) δ 1.13 (t, J = 7.5 Hz, 3H), 1.33 (t, J = 6.9 Hz, 3H), 2.62 (q, J = 7.5 Hz, 2H), 3.95-4.06 (m, 1H), 4.14-4.22 (m, 1H), 7.3 (dd, J = 1.65 and 8.85 Hz, 1H), 7.43-7.5 (m, 3H), 7.56-7.61 (m, 3H), 8 (brs, 1H), 10.31 (brs, 1H), 12.74 (brs, 1H), MS (ESI, EI⁺) m/z = 391 (MH⁺). |
| 6f | 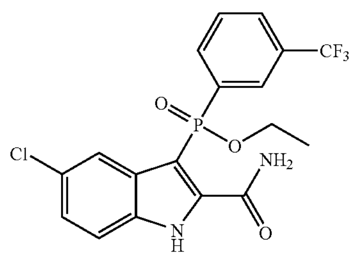 | White solid, ³¹P NMR (CDCl₃, 101.256 MHz) δ 29.02, ¹⁹F NMR (CDCl₃, 235.36 MHz) δ −61.07, MS (ESI, EI⁺) m/z = 431 (MH⁺). |
| 6g | 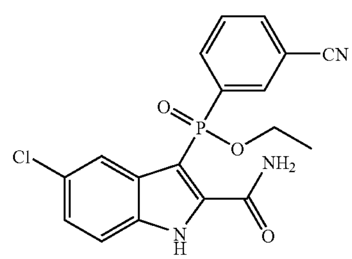 | White solid, ¹H NMR (d₆-DMSO, 400 MHz) δ 1.36 (t, J = 7.05 Hz, 3H), 4-4.12 (m, 1H), 4.17-4.27 (m, 1H), 7.33 (dd, J = 2 and 8.76 Hz, 1H), 7.59 (dd, J = 1.56 and 8.78 Hz, 1H), 7.66 (d, J = 1.99 Hz, 1H), 7.73 (td, J = 3.3 and 7.78 Hz, 1H), 7.97-8.08 (m, 3H), 8.17-8.21 (m, 1H), 9.98 (brs, 1H), 12.83 (brs, 1H), ³¹P NMR (d₆-DMSO, 101.256 MHz) δ 28.62, MS (ESI, EI⁺) m/z = 388 (MH⁺). |
| 6i | 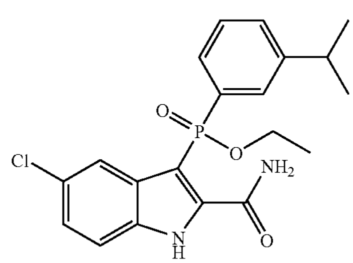 | White solid, ¹H NMR (d₆-DMSO, 300 MHz) δ 1.16 (d, J = 6.9 Hz, 3H), 1.17 (d, J = 6.9 Hz, 3H), 1.34 (t, J = 7.05 Hz, 3H), 2.88-2.97 (m, 1H), 3.97-4.06 (m, 1H), 4.15-4.23 (m, 1H), 7.31 (dd, J = 1.8 and 8.7 Hz, 1H), 7.42-7.66 (m, 6H), 8.01 (brs, 1H), 10.31 (brs, 1H), 12.74 (brs, 1H), ³¹P NMR (d₆-DMSO, 121.49 MHz) δ 30.22, MS (ES⁺) m/z = 404.8 (MH⁺). |
| 6j | 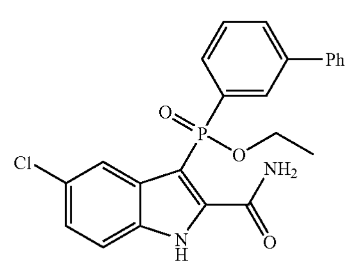 | White solid; ¹H NMR (d₆-DMSO, 300 MHz) δ 1.37 (t, J = 7.0 Hz, 3H), 3.99-4.09 (m, 2H), 4.25 (q, J = 7.0 Hz, 2H), 5.56 (m, J = 12 Hz, 1H), 7.35-8.04 (m, 14H), 10.20 (brs, 1H), 12.78 (brs, 1H), ³¹P NMR (d₆-DMSO, 121.49 MHz) δ 22.07, MS (ES⁺) m/z = 439 (MH⁺). |

TABLE 2-continued

| Compound | structure | Description |
|---|---|---|
| 6k | (structure) | Yellow solid; ¹H NMR (d₆-DMSO, 300 MHz) δ 1.35 (t, J = 7.0 Hz, 3H), 4.01-4.12 (m, 2H), 4.17-4.25 (m, 2H), 7.35 (dd, J = 8.8 and 1.8 Hz), 7.50-7.71 (m, 4H), 7.83-7.87 (m, 1H), 8.04 (brs, 1H), 9.87 (brs, 1H), 12.86 (brs, 1H), ³¹P NMR (d₆-DMSO, 121.49 MHz) δ 26.47 (d, J = 7.4 Hz), ¹⁹F NMR (d₆-DMSO, 282.4 MHz) δ -111.96 (q, J = 7.9 Hz, MS (ES⁺) m/z = 459/460 (MH⁺). |
| 6l | (structure) | White solid; ³¹P NMR (d₆-DMSO, 121.49 MHz) δ 28.35, MS (ES⁺) m/z = 411 (MH⁺). |
| 6m | (structure) | White powder, ¹H NMR (d₆-DMS0, 300 MHz) δ 1.39 (t, J = 7.04 Hz, 3H), 3.77 (s, 3H), 4.25-3.95 (two m, 2H), 7.29-7.14 (m, 4H), 7.33 (dd, J = 8.8 and 1.98 Hz, 1H), 7.49-7.42 (m, 1H), 7.59 (dd, J = 8.8 and J < 1.5 Hz, 1H), 7.66 (d, J = 1.93 Hz, 1H), 8.00 (brs, 1H), 10.20 (brs, 1H), 12.75 (brs, 1H), ³¹P NMR (d₆-DMSO, 121.49 MHz) δ 30.85, MS (ESI, EI⁺) m/z = 393 (MH⁺), 785 (2M + H⁺). |
| 6q | (structure) | White powder, ¹H NMR (d₆-DMSO, 300 MHz) δ 1.35 (t, J = 6.9 Hz, 3H), 4.05-4.14 (m, 1H), 4.18-4.26 (m, 1H), 7.33 (dd, J = 1.8 Hz and 8.7 Hz, 1H), 7.59 (dd, J = 1.8 Hz and 8.7 Hz, 1H), 7.74 (d, J = 1.8 Hz, 1H), 7.83-7.9 (m, 2H), 7.97-8.03 (m, 2H), 9.74 (brs, 1H), 12.87 (brs, 1H), ³¹P NMR (d₆-DMSO, 300 MHz) δ 27.25 (d, J = 6.57 Hz, 1P), MS (ESI, EI⁺) m/z = 449 (MH⁺) |
| 6r | (structure) | White powder, ¹H NMR (d₆-DMSO, 300 MHz) δ 1.35 (t, J = 7.2 Hz, 3H), 4.08-4.29 (m, 2H), 7.35 (dd, J = 2.1 Hz and 8.7 Hz, 1H), 7.6 (dd, J = 1.5 Hz and 8.7 Hz, 1H), 7.8 (d, J = 1.8 Hz, 1H), 8.08 (brs, 1H), 8.31 (brs, 1H), 8.36 (brs, 1H), 8.41 (brs, 1H), 9.6 (brs, 1H), 12.88 (brs, 1H), ³¹P NMR (d₆-DMSO, 121.48 MHz) δ 26.63, MS (ESI, EI⁺) m/z = 499 (MH⁺). |

TABLE 2-continued

| Compound | structure | Description |
|---|---|---|
| 6t | 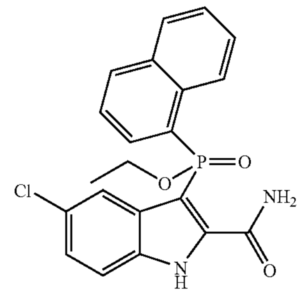 | White solid, ¹H NMR (d₆-DMSO, 300 MHz) δ 1.35 (t, J = 6.9 Hz, 3H), 3.95-4.08 (m, 1H), 4.26-4.37 (m, 1H), 7.27 (dd, J = 1.8 Hz and 8.7 Hz, 1H), 7.38 (d, J = 1.8 Hz, 1H), 7.56-7.65 (m, 4H), 7.86-7.94 (m, 1H), 8.02-8.06 (m, 1H), 8.12 (brs, 1H), 8.19 (d, J = 8.1 Hz, 1H), 8.54-8.57 (m, 1H), 10.45 (brs, 1H), 12.83 (brs, 1H), MS (ESI, EI⁺) m/z = 413 (MH⁺). |
| 6u | 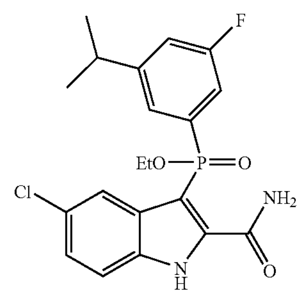 | Yellowish powder, ³¹P NMR (CDCl₃, 121.49 MHz) δ 29.27 (d, J = 8.0 Hz, 1P), MS (ES⁺) m/z = 423 (MH⁺). |
| 6v | 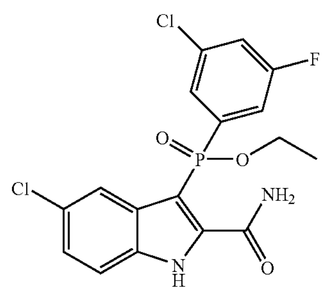 | Colourless oil, ¹H NMR (CDCl₃, 300 MHz) δ 1.48 (t, J = 7.05 Hz, 3H), 4.05-4.18 (m, 1H), 4.28-4.41 (m, 1H), 6.18 (brs, 1H), 7.22-7.26 (m, 1H), 7.31-7.4 (m, 2H), 7.53-7.55 (m, 1H), 7.57-7.58 (m, 1H), 7.67-7.68 (m, 1H), 10.90 (brs, 1H), 11.13 (brs, 1H), ³¹P NMR (CDCl₃, 121.49 MHz) δ 27.7 (d, J = 7.8 Hz, 1P), MS (ES⁺) m/z = 415.28 (MH⁺). |
| 6w | 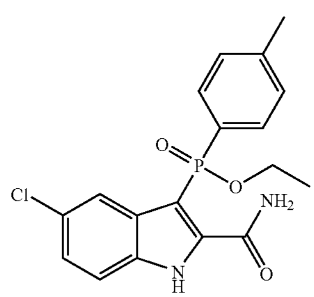 | Off white powder, ¹H NMR (d₆-DMSO, 400 MHz) δ 1.31 (t, J = 7 Hz, 3H), 2.33 (s, 3H), 3.94-4.04 (m, 1H), 4.11-4.22 (m, 1H), 7.30-7.34 (m, 3H), 7.57-7.62 (m, 4H), 7.98 (brs, 1H), 10.3 (brs, 1H), 12.72 (brs, 1H), ³¹P NMR (d₆-DMSO, 101.256 MHz) δ 31.46, MS (ESI, EI⁺) m/z = 377 (MH⁺). |
| 6z | 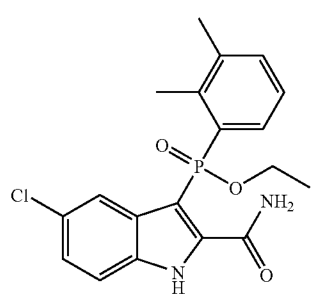 | Yellow powder, ¹H NMR (d₆-DMSO, 300 MHz) δ 1.29 (t, J = 7.05 Hz, 3H), 2.22 (s, 3H), 2.37 (s, 3H), 3.81-3.94 (m, 1H), 4.11-4.24 (m, 1H), 7.21-7.26 (m, 1H), 7.27 (dd, J = 2.1 and 8.7 Hz, 1H), 7.32 (d, J = 1.8 Hz, 1H), 7.4 (d, J = 7.5 Hz, 1H), 7.48-7.6 (m, 2H), 8.01 (brs, 1H), 10.42 (brs, 1H), 12.75 (brs, 1H), ³¹P NMR (d₆-DMSO, 101.256 MHz) δ 31.55, MS (ESI, EI⁺) m/z = 391 (MH⁺). |

TABLE 2-continued

| Compound | structure | Description |
|---|---|---|
| 6ab | 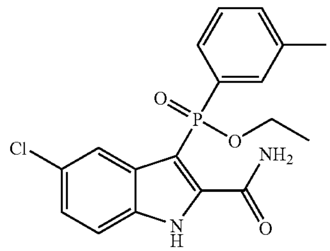 | Off white powder; $^1$H NMR (d$_6$-DMSO, 300 MHz) δ 1.33 (t, J = 6.9 Hz, 3H), 2.32 (s, 3H), 3.95-4.04 (m, 1H), 4.12-4.24 (m, 1H), 7.31 (dd, J = 1.5 and 8.7 Hz, 1H), 7.41-7.61 (m, 6H), 8.00 (brs, 1H), 10.28 (brs, 1H), 12.74 (brs, 1H), $^{31}$P NMR (d$_6$-DMSO, 101.256 MHz) δ 31.28, MS (ESI, EI$^+$) m/z = 377 (MH$^+$). |
| 6ac | 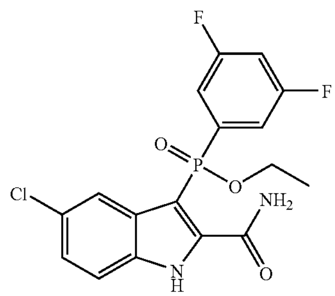 | Pale yellow powder, $^1$H NMR (d$_6$-DMSO, 300 MHz) δ 1.35 (t, J = 6.9 Hz, 3H), 3.99-4.13 (m, 1H), 4.17-4.28 (m, 1H), 7.32-7.43 (m, 3H), 7.50-7.61 (m, 2H), 7.68 (4, J = 1.8 Hz, 1H), 8.04 (brs, 1H) 9.91 (brs, 1H), 12.9 (brs, 1H), $^{31}$P NMR (d$_6$-DMSO, 101 MHz) δ 28.0 (t, J = 8.1 Hz, 1P), $^{19}$F NMR (d$_6$-DMSO) δ −106.92 (m, 2F), MS (ESI, EI$^+$) m/z = 399 (MH$^+$). |
| 6ad | 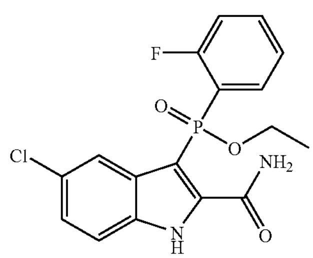 | Pale yellow powder, $^1$H NMR (d$_6$-DMSO, 300 MHz) δ 1.35 (t, J = 6.9 Hz, 3H), 3.97-4.11 (m, 1H), 4.16-4.29 (m, 1H), 7.22-7.42 (m, 3H), 7.56-7.59 (m, 2H), 7.61-7.75 (m, 1H), 7.77-7.88 (m, 1H), 8.01 (brs, 1H), 10.08 (brs, 1H), 12.78 (brs, 1H), $^{31}$P NMR (d$_6$-DMSO, 101 MHz) δ 25.2 (d, J = 11.3 Hz, 1P), $^{19}$F NMR (d$_6$-DMSO) δ −104.85 (m, 1F), MS (ESI, EI$^+$) m/z = 381 (MH$^+$). |
| 6ah | 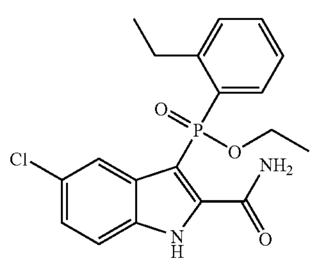 | Yellow powder, $^1$H NMR (d$_6$-DMSO, 300 MHz) δ 0.94 (t, J = 7.5 Hz, 3H), 1.3 (t, J = 7.05 Hz, 3H), 2.73-2.98 (m, 2H), 3.83-3.96 (m, 1H), 4.1-4.25 (m, 1H), 7.28 (dd, J = 2.1 and 8.7 Hz, 1H), 7.32-7.38 (m, 3H), 7.5-7.6 (m, 2H), 7.66-7.73 (m, 1H), 8.02 (brs, 1H), 10.42 (brs, 1H), 12.76 (brs, 1H), $^{31}$P NMR (d$_6$-DMSO, 121.69 MHz) δ 29.63, MS (ESI, EI$^+$) m/z = 391 (MH$^+$). |
| 6ai | 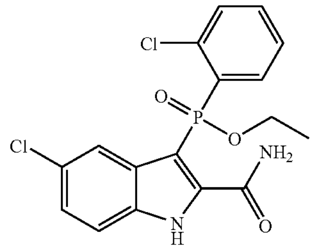 | Off white powder, $^1$H NMR (d$_6$-DMSO, 300 MHz) δ 1.31 (t, J = 7.05 Hz, 3H), 3.92-4.05 (m, 1H), 4.15-4.28 (m, 1H), 7.25 (dd, J = 1.95 and 8.85 Hz, 1H), 7.35 (d, J = 2.1 Hz, 1H), 7.47-7.61 (m, 4H), 8-8.1 (m, 2H), 10.17 (brs, 1H), 12.71 (brs, 1H), $^{31}$P NMR (d$_6$-DMSO, 101 MHz) δ 25.31, MS (ESI, EI$^+$) m/z = 397 (MH$^+$). |

TABLE 2-continued

| Compound | structure | Description |
|---|---|---|
| 6aj | 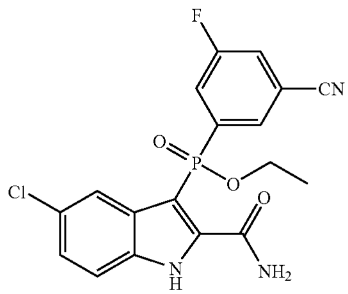 | Orange oil, $^1$H NMR (CDCl$_3$, 300 MHz) δ 1.48 (t, J = 7.05 Hz, 3H), 4.05-4.23 (m, 1H), 4.29-4.4 (m, 1H), 6.33 (brs, 1H), 7.33 (dd, J = 1.8 and 8.7 Hz, 1H), 7.4-7.52 (m, 1H), 7.57-7.62 (m, 2H), 7.64-7.72 (m, 1H), 7.81-7.85 (m, 1H), 10.81 (brs, 1H), 11.42 (brs, 1H), $^{31}$P NMR (CDCl$_3$, 121.49 MHz) δ 26.56 (d, J = 3.1 Hz, 1P), $^{19}$F NMR (CDCl$_3$, 282.40 MHz) −107 (q, J = 7.34 Hz, 1F), MS (ES$^+$) m/z = 406.3 (MH$^+$). |
| 6ak | 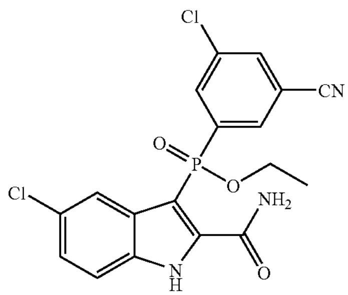 | White solid, $^1$H NMR (d$_6$-DMSO, 300 MHz) δ 1.35 (t, J = 7.0 Hz, 3H), 4.02-4.25 (m, 2H), 7.34 (d, J = 8.5 Hz, 2H), 7.59 (d, J = 8.5 Hz, 1H), 7.74 (d, J = 8.5 Hz, 1H), 8.04 (m, 2H), 8.16 (m, 1H), 8.29 (brs, 1H), 9.70 (brs, 1H), 14.73 (brs, 1H), $^{31}$P NMR (d$_6$-DMSO, 121.49 MHz) δ 26.87, MS (ES$^+$) m/z = 575 (MH$^+$), MS (ES$^+$) m/z = 422 (MH$^+$). |
| 7a | 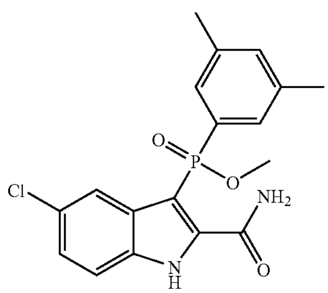 | Slight yellow solid, $^1$H NMR (d$_6$-DMSO, 300 MHz) δ 2.27 (s, 6H), 3.73 (d, J = 11.7 Hz, 3H), 7.23 (brs, 1H), 7.29-7.33 (m, 3H), 7.56-7.59 (m, 2H), 8 (brs, 1H), 10.27 (brs, 1H), 12.75 (brs, 1H, $^{31}$P NMR (d$_6$-DMSO, 101.256 MHz) δ 33.27, MS (ESI, EI$^+$), m/z = 377 (MH$^+$) |
| 7b | 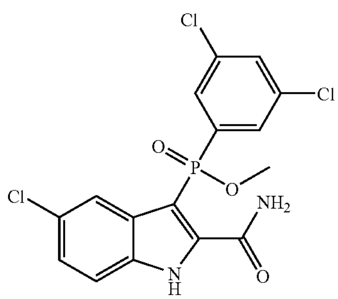 | White solid, $^1$H NMR (d$_6$-DMSO, 300 MHz) δ 3.79 (d, J = 11.7 Hz, 3H), 7.35 (dd, J = 1.8 and 8.7 Hz, 1H), 7.6 (dd, J = 1.8, and 8.7 Hz, 1H), 7.67 (d, J = 1.8 Hz, 1H), 7.7 (t, J = 1.8 Hz, 2H), 7.89 (t, J = 1.8 Hz, 1H), 8.06 (brs, 1H), 9.78 (brs, 1H), 12.89 (brs, 1H), $^{31}$P NMR (d$_6$-DMSO, 101.256 MHz) δ 29.44, MS (ESI, EI$^+$) m/z = 417 (MH$^+$). |
| 7c | 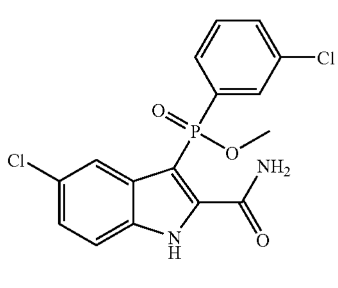 | White solid, $^1$H NMR (d$_6$-DMSO, 300 MHz) δ 3.77 (d, J = 11.7 Hz, 3H), 7.33 (dd, J = 1.8 and 8.7 Hz, 1H), 7.54-7.74 (m, 6H), 8.05 (brs, 1H), 10.01 (brs, 1H), 12.84 (brs, 1H), $^{31}$P NMR (d$_6$-DMSO, 121.49 MHz) δ 30.23, MS (ESI, EI$^+$) m/z = 383 (MH$^+$). |

TABLE 2-continued

| Compound | structure | Description |
|---|---|---|
| 7d | (5-chloro-3-[methoxy(3-ethylphenyl)phosphoryl]-1H-indole-2-carboxamide) | White solid, $^1$H NMR (d$_6$-DMSO, 300 MHz) δ 1.14 (t, J = 7.5 Hz, 3H), 2.63 (q, J = 7.5 Hz, 2H), 3.75 (d, J = 11.4 Hz, 3H), 7.32 (dd, J = 1.95 and 8.85 Hz, 1H), 7.41-7.52 (m, 3H), 7.57-7.63 (m, 3H), 8.02 (brs, 1H), 10.27 (brs, 1H), 12.78 (brs, 1H), $^{31}$P NMR (CDCl$_3$, 121.49 MHz) δ 32.2; MS (ESI, EI$^+$) m/z = 377 (MH$^+$). |
| 7e | (5-chloro-3-[methoxy(3-trifluoromethylphenyl)phosphoryl]-1H-indole-2-carboxamide) | White solid, $^1$H NMR (d$_4$-DMSO, 300 MHz) δ 3.8 (d, J = 11.7 Hz, 3H), 7.34 (dd, J = 1.8 and 8.7 Hz, 1H), 7.6 (dd, J = 1.5 and 8.7 Hz, 1H), 7.64 (d, J = 1.8 Hz, 1H), 7.76 (td, J = 3.3 and 7.8 Hz, 1H), 7.94-8.07 (m, 4H), 9.97 (brs, 1H), 12.7 (brs, 1H), $^{31}$P NMR (d$_6$-DMSO, 121.49 MHz) δ 29.98, $^{19}$F NMR (CDCl$_3$, 282.4 MHz) δ 118.06 (s, 3F), MS (ESI, EI$^+$) m/z = 417 (MH$^+$). |
| 7f | (5-chloro-3-[methoxy(3-cyanophenyl)phosphoryl]-1H-indole-2-carboxamide) | White solid, $^1$H NMR (d$_6$-DMSO, 300 MHz) δ 3.79 (d, J = 11.7 Hz, 3H), 7.33 (dd, J = 1.95 and 8.7 Hz, 1H), 7.59 (dd, J = 1.8 and 8.7 Hz, 1H), 7.65 (d, J = 1.8 Hz, 1H), 7.69-7.75 (m, 1H), 7.96-8.08 (m, 3H), 8.17-8.21 (m, 1H), 9.9 (brs, 1H), 12.88 (brs, 1H), $^{31}$P NMR (d$_6$-DMSO, 121.49 MHz) δ 29.65, MS (ES$^+$) m/z = 373.86 (MH$^+$). |
| 7g | (5-chloro-3-[methoxy(3-isopropylphenyl)phosphoryl]-1H-indole-2-carboxamide) | White solid, $^1$H NMR (d$_6$-DMSO, 300 MHz) δ 1.16 (d, J = 6.9 Hz, 3H), 1.17 (d, J = 6.9 Hz, 3H), 2.88-2.98 (m, 1H), 3.76 (d, J = 11.4 Hz, 3H), 7.32 (dd, J = 1.95 and 8.85 Hz, 1H), 7.41-7.68 (m, 6H), 8.03 (brs, 1H), 10.28 (brs, 1H), 12.77 (brs, 1H), $^{31}$P NMR (d$_6$-DMSO, 121.49 MHz) δ 32.16, MS (ES$^+$) m/z = 390.9 (MH$^+$). |
| 7h | (5-chloro-3-[methoxy(3-fluoromethylphenyl)phosphoryl]-1H-indole-2-carboxamide) | White solid, $^1$H NMR (d$_6$-DMSO, 300 MHz) δ 3.77 (d, J = 11.7 Hz, 3H), 5.47 (d, J = 47.4 Hz, 2H), 7.33 (dd, J = 2.1 and 8.7 Hz, 1H), 7.55-7.81 (m, 6H), 8.04 (brs, 1H), 10.19 (brs, 1H), 12.78 (brs, 1H), $^{31}$P NMR (d$_6$-DMSO, 121.49 MHz) δ 31.62, $^{19}$F NMR (d$_6$-DMSO, 282.40 MHz) δ −207.99 (t, J = 47.4 Hz, 1F), MS (ES$^+$) m/z = 380.83 (MH$^+$). |
| 7i | (5-chloro-3-[methoxy(3-phenylphenyl)phosphoryl]-1H-indole-2-carboxamide) | White solid; $^1$H NMR (d$_6$-DMSO, 300 MHz) δ 3.81 (d, J = 11.7 Hz, 3H), 7.33 (dd, J = 8.7 and 2.1 Hz, 1H), 7.41-7.72 (m, 9H), 7.87-8.01 (m, 2H), 8.05 (brs, 1H), 10.21 (brs, 1H), 12.79 (brs, 1H), $^{31}$P NMR (d$_6$-DMSO, 121.49 MHz) δ 31.74, MS (ES$^+$), m/z = 425 (MH$^+$). |

TABLE 2-continued

| Compound | structure | Description |
| --- | --- | --- |
| 7j | 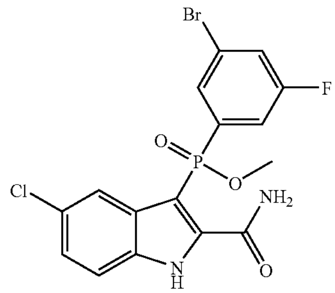 | White solid; $^1$H NMR (d$_6$-DMSO, 300 MHz) δ 3.79 (d, J = 11.7 Hz, 3H), 7.35 (dd, J = 8.7 and 2.1 Hz, 1H), 7.51-7.72 (m, 9H), 7.83-7.87 (m, 2H), 8.06 (brs, 1H), 9.83 (brs, 1H), 12.88 (brs, 1H), $^{31}$P NMR (d$_6$-DMSO, 121.49 MHz) δ 28.46 (d, J = 7.2 Hz), $^{19}$F NMR (d$_6$-DMSO, 282.4 MHz) δ −110.60 (m), MS (ES$^+$) m/z = 445/447 (MH$^+$). |
| 7k | 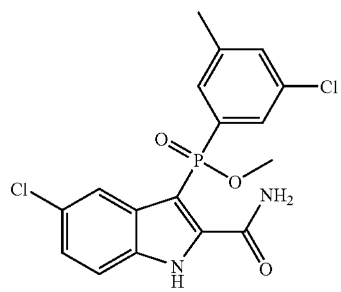 | White solid; $^1$H NMR (d$_6$-DMSO, 300 MHz) δ 2.32 (s, 3H), 3.77 (d, J = 11.4 Hz, 3H), 7.34 (dd, J = 9.0 and 2.1 Hz, 1H), 7.47-7.59 (m, 5H), 8.04 (brs, 1H), 10.04 (brs, 1H), 12.88 (brs, 1H), $^{31}$P NMR (d$_6$-DMSO, 121.49 MHz) δ 30.31, MS (ES$^+$) m/z = 397 (MH$^+$). |
| 7l | 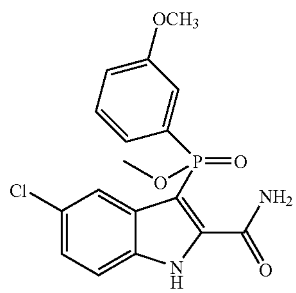 | White powder, $^1$H NMR (CDCl$_3$, 300 MHz) δ 3.81 (s, 3H), 3.87 (d, J = 11.4 Hz, 3H), 6.02 (brs, 1H), 7.06-7.08 (m, 1H), 7.28-7.37 (m, 4H), 7.49-7.52 (m, 1H), 7.73 (brs, 1H), 10.67 (brs, 1H), 11.01 (brs, 1H);, $^{31}$P NMR (CDCl$_3$, 121.49 MHz) δ 32.67, MS (ESI, EI$^+$) m/z = 379 (MH$^+$). |
| 7q | 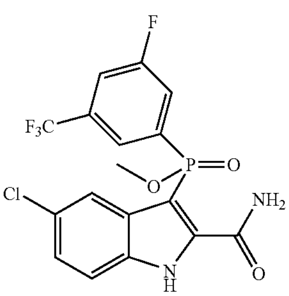 | White powder, $^1$H NMR (CDCl$_3$, 300 MHz) δ 3.92 (d, J = 11.7 Hz, 3H), 6.12 (brs, 1H), 7.36 (dd, J = 1.8 Hz and 8.7 Hz, 1H), 7.48-7.51 (m, 1H), 7.55-7.65 (m, 3H), 7.9 (d, J = 12.9 Hz, 1H), 10.81 (brs, 1H), 10.97 (brs, 1H), $^{31}$P NMR (CDCl$_3$, 121.49 MHz) δ 29.27 (d, J = 6.8 Hz, 1P), $^{19}$F NMR (CDCl$_3$, 282.40 MHz) δ −62.89 (s, 3F), −107.86 (q, J = 7.6 Hz, 1F), MS (ESI, EI$^+$) m/z = 435 (MH$^+$). |
| 7s | 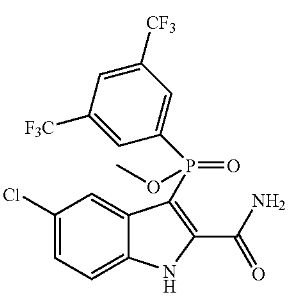 | White powder, $^1$H NMR (CDCl$_3$, 300 MHz) δ 3.94 (d, J = 11.7 Hz, 3H), 6.12 (brs, 1H), 7.37 (dd, J = 2.1 Hz and 9 Hz, 1H), 7.57 (dd, J = 1.8 Hz and 8.7 Hz, 1H), 7.63-7.637 (m, 1H), 8.04 (brs, 1H), 8.21 (brs, 1H), 8.26 (brs, 1H), 10.81 (brs, 1H), 10.94 (brs, 1H), $^{19}$F NMR (CDCl$_3$, 282.40 MHz) δ −62.96, MS (ESI, EI$^+$) m/z = 485 (MH$^+$). |

TABLE 2-continued

| Compound | structure | Description |
|---|---|---|
| 7t | 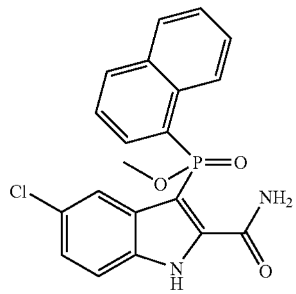 | White powder, ¹H NMR (CDCl₃, 300 MHz) δ 3.92 (d, J = 11.7 Hz, 3H), 6.04 (brs, 1H), 7.3 (dd, J = 2.1 Hz and 9 Hz, 1H), 7.42-7.65 (m, 5H), 7.77 (qd, J = 1.2 Hz and 7.2 Hz, 1H), 7.9-7.93 (m, 1H), 8.03-8.06 (m, 1H), 8.68 (d, J = 8.4 Hz, 1H), 10.58 (brs, 1H), 11.19 (brs, 1H), ³¹P NMR (CDCl₃, 121.49 MHz) δ 34.98, MS (ESI, EI⁺) m/z = 399 (MH⁺). |
| 7u | 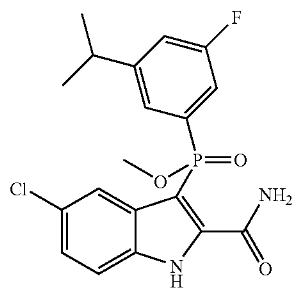 | Off-white powder, ¹H NMR (CDCl₃, 300 MHz) δ 1.24 (d, J = 6.9 Hz, 3H), 1.23 (d, J = 6.9 Hz, 3H), 2.96 (hept., J = 6.9 Hz, 1H), 3.83 (d, J = 11.7 Hz., 3H), 5.99 (brs, 1H), 7.07-7.13 (m, 1H), 7.20-7.29 (m, 1H), 7.34 (dd, J = 2.1 Hz and 9 Hz, 1H), 7.49-7.53 (m, 2H), 7.68 (d, J = 2.1 Hz, 1H), 7.95 (dd, J = 9.6 Hz and 1.8 Hz, 1H), 8.08-8.14 (m, 2H), 10.54 (brs, 1H), 10.95 (brs, 1H), ³¹P NMR (CDCl₃, 121.49 MHz) δ 31.35 (d, J = 8.4 Hz, 1P), MS (ES⁺) m/z = 409 (MH⁺). |
| 7v | 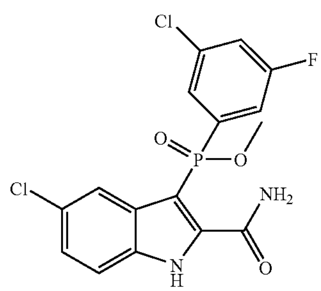 | Off-white solid, ¹H NMR (CDCl₃, 300 MHz) δ 3.9 (d, J = 11.7 Hz, 3H), 6.09 (brs, 1H), 7.24-7.28 (m, 1H), 7.32-7.40 (m, 2H), 7.53-7.59 (m, 2H), 7.65-7.66 (m, 1H), 10.81 (brs, 1H), 10.87 (brs, 1H), ³¹P NMR (CDCl₃, 121.49 MHz) δ 29.77 (d, J = 7.78 Hz, 1P), ¹⁹F NMR (CDCl₃, 282.40 MHz) δ -111.22 (m, 1F), MS (ES⁺) m/z = 401.29 (MH⁺). |
| 7w | 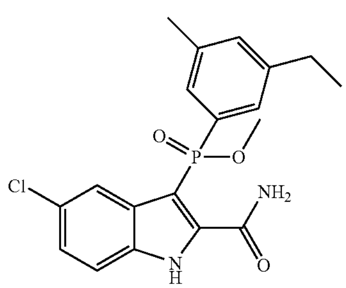 | White solid, ¹H NMR (d₆-DMSO, 300 MHz) δ 1.12 (t, J = 7.5 Hz, 3H), 2.28 (s, 3H), 2.58 (q, J = 7.5 Hz, 2H), 3.74 (d, J = 11.4 Hz, 3H), 7.26 (brs, 1H), 7.31 (dd, J = 1.8 and 8.7 Hz, 1H), 7.34-7.40 (m, 2H), 7.56-7.60 (m, 2H), 8 (brs, 1H), 10.29 (brs, 1H), 12.75 (brs, 1H), ³¹P NMR (d₆-DMSO, 121.49 MHz) δ 32.21, MS (ES⁺) m/z = 391.3 (MH⁺). |
| 7x | 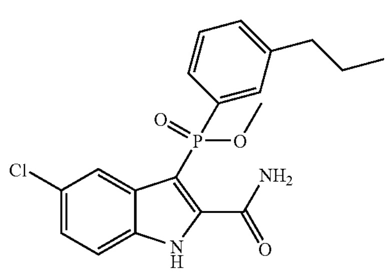 | White solid, ¹H NMR (d₆-DMSO, 300 MHz) δ 0.83 (t, J = 7.2 Hz, 3H), 1.54 (sextuplet, J = 7.2 Hz, 2H), 2.58 (t, J = 7.2 Hz, 2H), 3.75 (d, J = 11.4 Hz, 3H), 7.31 (dd, J = 2.1 and 8.7 Hz, 1H), 7.4-7.51 (m, 3H), 7.55-7.60 (m, 3H), δ (brs, 1H), 10.25 (brs, 1H), 12.75 (brs, 1H), ³¹P NMR (d₆-DMSO, 121.49 MHz) δ 32.17, MS (ES⁺) m/z = 391.26 (MH⁺). |

TABLE 2-continued

| Compound | structure | Description |
|---|---|---|
| 7y | 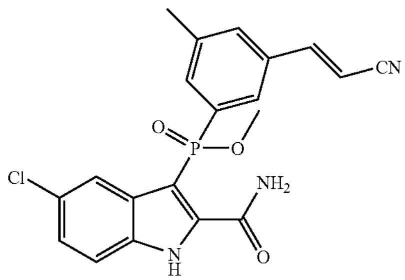 | White solid, $^1$H NMR (CDCl$_3$, 300 MHz) δ 2.40 (s, 3H), 3.88 (d, J = 11.7 Hz, 3H), 5.89 (d, J = 16.5 Hz, 1H), 5.97 (brs, 1H), 7.33-7.67 (m, 7H), 10.46 (s, 1H), 10.89 (brs, 1H), $^{31}$P NMR (CDCl$_3$, 121.49 MHz) δ 31.54, MS (ES$^+$) m/z = 414 (MH$^+$). |
| 7z | 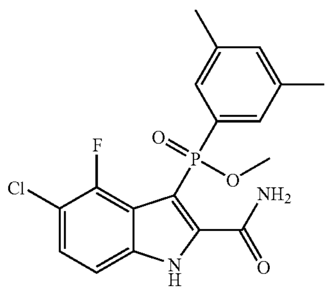 | Off-white solid, $^1$H NMR (d$_6$-DMSO, 300 MHz) δ 2.26 (s, 6H), 3.69 (m, J = 11.4 Hz, 3H), 7.20 (brs, 1H). 7.25 (brs, 1H), 7.29 (brs, 1H), 7.38 (dd, J = 6.3 and 8.4 Hz, 1H), 7.44 (dd, J = 1.5 and 8.7 Hz, 1H) 8.02 (brs, 1H), 10.77 (brs, 1H), 12.96 (brs, 1H), $^{31}$P NMR (d$_6$-DMSO, 121.49 MHz) δ 31.74, MS (ES$^+$) m/z = 394.9 (MH$^+$). |
| 7aa | 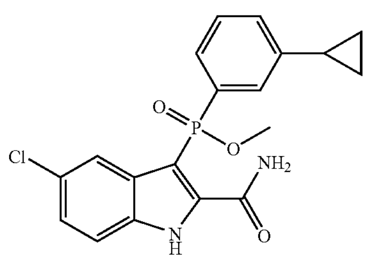 | Off-white solid, $^1$H NMR ((CDCl$_3$, 300 MHz) δ 0.69-0.71 (m, 2H), 0.98-1,02 (m, 2H), 1.85-1.95 (m, 1H), 3.86 (d, J = 11.7 Hz, 3H), 5.98 (brs, 1H), 7.2-7.22 (m, 1H), 7.28-7.35 (m, 3H), 7.47-7.58 (m, 3H), 7.71-7.72 (m, 1H), 10.50 (brs, 1H), 11.04 (brs, 1H), $^{31}$P NMR (CDCl$_3$, 121.49 MHz) δ 33.04, MS (ES$^+$) m/z = 389.08 (MH$^+$). |
| 7ab | 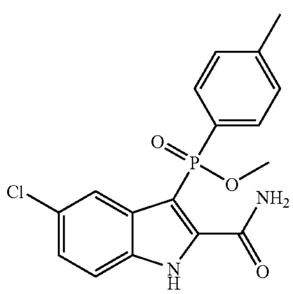 | Yellow powder, $^1$H NMR (d$_6$-DMSO, 300 MHz) δ 2.33 (s, 3H), 3.74 (d, J = 11.7 Hz, 3H), 7.31-7.33 (m, 3H), 7.57-7.60 (m, 4H), 8 (brs, 1H), 10.26 (brs, 1H), 12.76 (brs, 1H), $^{31}$P NMR (d$_6$-DMSO, 121.49 MHz) δ 32.48, MS (ESI, EI$^+$) m/z = 363 (MH$^+$). |
| 7ae | 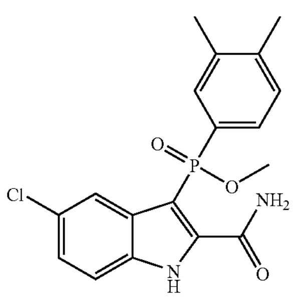 | Yellow pale powder, $^1$H NMR (d$_6$-DMSO, 300 MHz) δ 2.23 (s, 6H), 3.73 (d, J = 11.4 Hz, 3H), 7.25-7.33 (m, 2H), 7.36-7.43 (m, 1H=), 7.49 (m, J = 12.9 Hz, 1H), 7.56-7.60 (m, 2H), 7.99 (brs, 1H), 10.28 (brs, 1H), 12.74 (brs, 1H), $^{31}$P NMR (d$_6$-DMSO, 101.256 MHz) δ 33.45, MS (ESI, EI$^+$) m/z = 377 (MH$^+$). |

TABLE 2-continued

| Compound | structure | Description |
|---|---|---|
| 7ah | 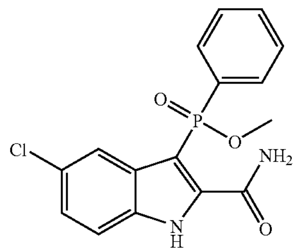 | Pale yellow powder, $^1$H NMR (CDCl$_3$, 300 MHz) δ 3.85 (d, J = 11.4 Hz, 3H), 6.08 (brs, 1H), 7.30 (dd, J = 2.0 and 9.0 Hz, 1H), 7.36-7.56 (m, 4H), 7.68 (m, J = 1.8 Hz, 1H), 7.73-7.81 (m, 2H), 10.78 (brs, 1H), 10.03 (brs, 1H), $^{31}$P NMR (CDCl$_3$, 101 MHz) δ 33.3, MS (ESI, EI$^+$) m/z = 349 (MH$^+$). |
| 7ai | 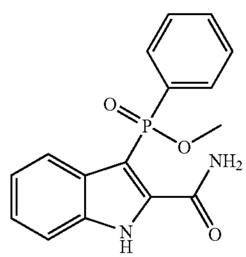 | Pale orange powder, $^1$H NMR (CDCl$_3$, 300 MHz) δ 3.84 (d, J = 11.4 Hz, 3H), 5.97 (brs, 1H), 7.18-7.23 (m, 1H), 7.32-7.56 (m, 5H), 7.69-7.83 (m, 3H), 10.44 (brs, 1H), 11.04 (brs, 1H), $^{31}$P NMR (CDCl$_3$, 101 MHz) δ 33.8, MS (ESI, EI$^+$) m/z = 315 (MH$^+$). |
| 7aj | 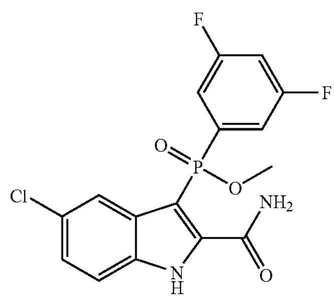 | Orange powder, $^1$H NMR (d$_6$-DMSO, 300 MHz) δ 3.79 (d, J = 11.4 Hz, 3H), 7.32-7.44 (m, 3H), 7.51-7.61 (m, 2H), 7.67 (d, J = 1.8 Hz, 1H), 8.05 (brs, 1H), 9.86 (brs, 1H), 12.86 (brs, 1H), $^{31}$P NMR (d$_6$-DMSO, 101 MHz) δ 29.99 (t, J = 8.3 Hz, 1P), $^{19}$F NMR (d$_6$-DMSO, 300 MHz) δ −106.93 (m, 2F), MS (ESI, EI$^+$) m/z = 385 (MH$^+$). |
| 7ak | 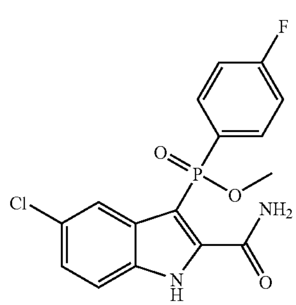 | Pale yellow powder, $^1$H NMR (d$_6$-DMSO, 300 MHz) δ 3.75 (d, J = 11.4 Hz, 3H), 7.31-7.38 (m, 3H), 7.54-7.62 (m, 2H), 7.71-7.83 (m, 2H), 8.01 (brs, 1H), 10.10 (brs, 1H), 12.76 (brs, 1H), $^{31}$P NMR (d$_6$-DMSO, 101 MHz) δ 32.30, $^{19}$F NMR (d$_6$-DMSO) δ −106.35 (m, 1F), MS (ESI, EI$^+$), m/z = 367 (MH$^+$). |
| 7an | 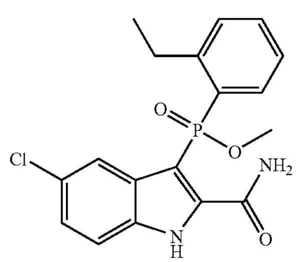 | Off white powder, $^1$H NMR (d$_6$-DMSO, 300 MHz) δ 0.92 (t, J = 7.5 Hz, 3H), 2.78-2.92 (m, 2H), 3.7 (d, J = 11.7 Hz, 3H), 7.25-7.38 (m, 4H), 7.52-7.59 (m, 2H), 7.67-7.75 (m, 1H), 8.02 (brs, 1H), 10.36 (brs, 1H), 12.78 (brs, 1H), $^{31}$P NMR (d$_6$-DMSO, 101 MHz) δ 32.41, MS (ESI, EI$^+$) m/z = 377 (MH$^+$). |

TABLE 2-continued

| Compound | structure | Description |
| --- | --- | --- |
| 7ao | 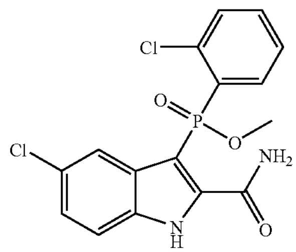 | White powder, ¹H NMR (d₆-DMSO, 300 MHz) δ 3.75 (d, J = 11.7 Hz, 3H), 7.27 (dd, J = 2.1 and 8.7 Hz, 1H), 7.34 (d, J = 1.5 Hz, 1H), 7.49-7.65 (m, 4H), 8.04-8.11 (m, 2H), 10.15 (brs, 1H), 12.8 (brs, 1H), ³¹P NMR (d₆-DMSO, 101 MHz) δ 27.33, MS (ESI, EI⁺) m/z = 383 (MH⁺). |
| 7ap | 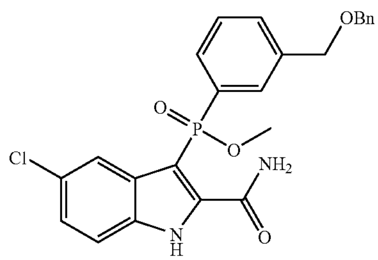 | White powder, ¹H NMR (d₆-DMSO, 300 MHz) δ 3.75 (d, J = 11.7 Hz, 3H), 4.47 (s, 2H), 4.54 (s, 2H), 7.23-7.37 (m, 6H), 7.5-7.73 (m, 6H), 8.01 (brs, 1H), 10.21 (brs, 1H), 12.8 (brs, 1H), ³¹P NMR (d₆-DMSO, 121.49 MHz) δ 32.13, MS (ES⁺) m/z = 468.86 (MH⁺). |
| 7aq | 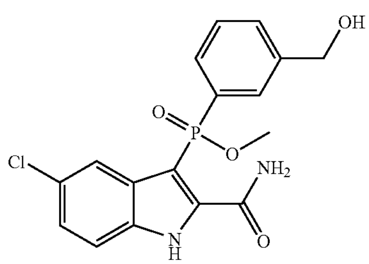 | Pale yellow powder, ¹H NMR (CDCl₃, 300 MHz) δ 3.88 (d, J = 11.7 Hz, 3H), 4.73 (s, 2H), 5.98 (brs, 1H), 7.3-7.35 (m, 1H), 7.42-7.49 (m, 2H), 7.56-7.59 (m, 1H), 7.66-7.73 (m, 2H), 7.8-7.85 (m, 1H), 10.34 (brs, 1H), 10.99 (brs, 1H), ³¹P NMR (CDCl₃, 101.256 MHz) δ 32.85, MS (ES⁺) m/z = 378.86 (MH⁺). |
| 7ar | 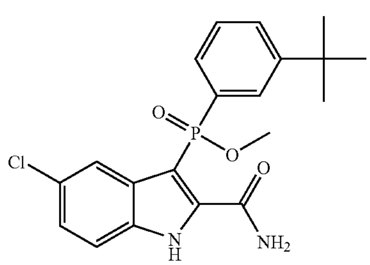 | White powder, ¹H NMR (d₆-DMSO, 300 MHz) δ 1.24 (s, 9H), 3.76 (m, J = 11.4 Hz, 3H), 7.3-7.34 (m, 1H), 7.4-7.65 (m, 5H), 7.76-7.81 (m, 1H), 8.02 (brs, 1H), 10.27 (brs, 1H), 12.75 (brs, 1H), ³¹P NMR (d₆-DMSO, 121.49 MHz) δ 32.29, MS (ES⁺) m/z = 405.11 (MH⁺). |
| 7as | 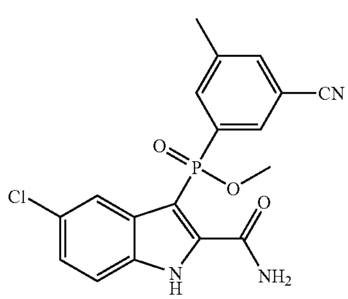 | White powder, ¹H NMR (CDCl₃, 300 MHz) δ 2.4 (s, 3H), 3.9 (d, J = 11.7 Hz, 3H), 6.1 (brs, 1H), 7.34 (dd, J = 1.8 and 8.7 Hz, 1H), 7.53-7.6 (m, 3H), 7.76-7.85 (m, 2H), 10.84 (brs, 1H), 10.92 (brs, 1H), ³¹P NMR (CDCl₃, 101.256 MHz) δ 7.27, MS (ES⁺) m/z = 388.3 (MH⁺). |

TABLE 2-continued

| Compound | structure | Description |
|---|---|---|
| 7au | 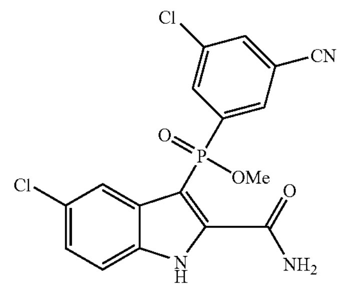 | White powder, $^1$H NMR (d$_6$-DMSO, 300 MHz) δ 3.78 (d, J = 11.4 Hz, 3H), 6.60 (m, J = 8.4 Hz, 1H), 7.34 (d, J = 1.8 Hz, 1H), 7.74 (dd, J = 1.7 and 8.4 Hz, 1H), 8.03-8.18 (m, 3H), 8.29 (brs, 1H), 9.67 (brs, 1H), 12.89 (brs, 1H), $^{31}$P NMR (d$_6$-DMSO, 121.49 MHz) δ 27.88, MS (ES$^+$) m/z = 406 (MH$^+$). |
| 7av | 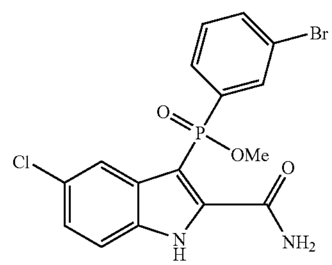 | White powder, $^1$H NMR (d$_6$-DMSO, 300 MHz) δ 3.78 (d, J = 11.4 Hz, 3H), 7.34 (dd, J = 1.8 and 8.4 Hz, 1H), 7.42-7.56 (m, 1H), 7.58-7.73 (m, 3H), 7.80-7.89 (m, 2H), 8.05 (brs, 1H), 10.01 (brs, 1H), 12.86 (brs, 1H), $^{31}$P NMR (d$_6$-DMSO, 121.49 MHz) δ 30.0, MS (ES) m/z = 427/429 (MH$^+$). |
| 7aw | 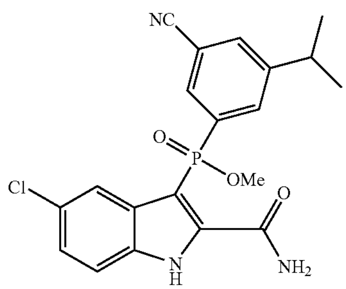 | |
| 7ax | 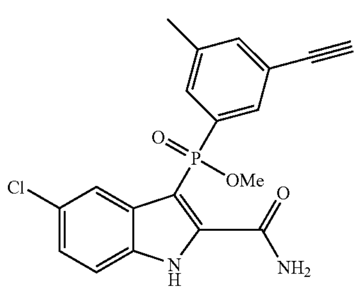 | |
| 7ay | 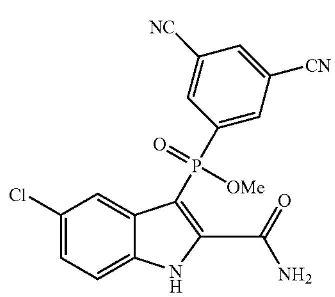 | |

TABLE 2-continued

| Compound | structure | Description |
| --- | --- | --- |
| 7az | 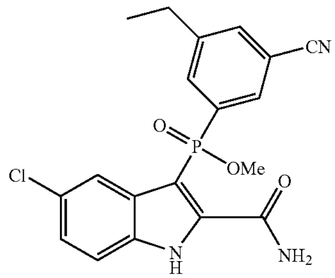 | |
| 7aaa | 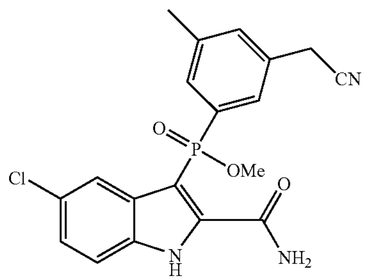 | |
| 7aab | 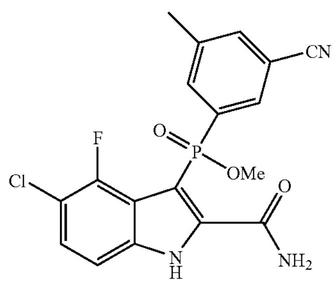 | |
| 7aac | 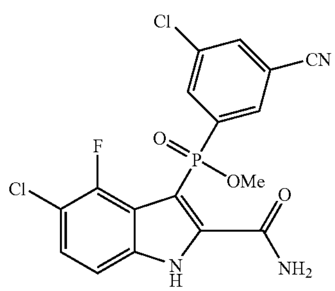 | |
| 7aad | 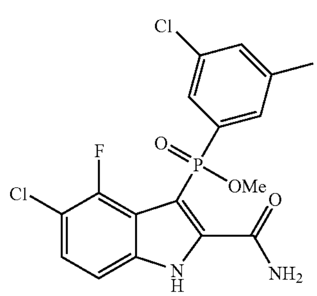 | |

TABLE 2-continued

| Compound | structure | Description |
|---|---|---|
| 7aae | 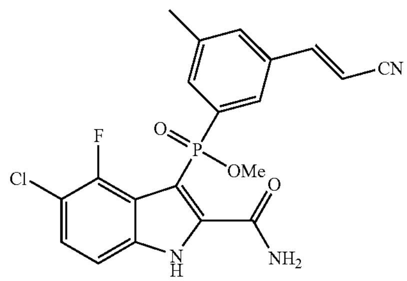 | |
| 7aaf | 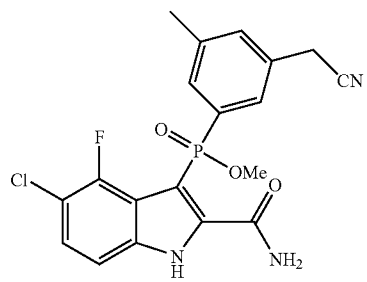 | |
| 8a | 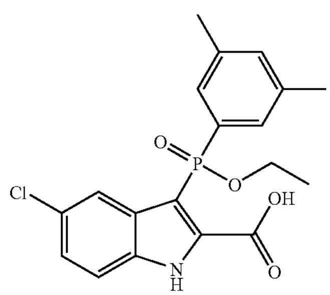 | Off white solid; $^1$H NMR (CDCl$_3$, 250 MHz) δ 1.43 (t, J = 7.0 Hz, 3H), 2.33 (s, 6H), 4.03-4.10 (m, 1H), 4.28-4.35 (m, 1H), 7.20 (s, 1H), 7.35 (dd, J = 2.0 and 8.7 Hz, 1H), 7.41 (s, 1H), 7.46 (s, 1H), 7.56-7.60 (m, 1H), 10.7 (brs, 1H), $^{31}$P NMR (CDCl$_3$, 101.256 MHz) δ 33.9, MS (ESI, EI$^+$) m/z = 392 (MH$^+$). |
| 9a | 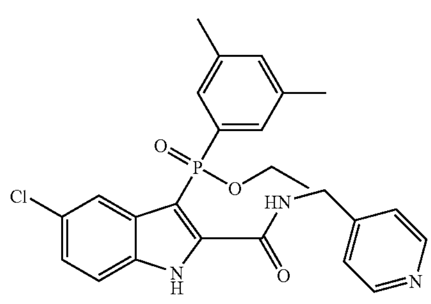 | Pale yellow solid, $^1$H NMR (CDCl$_3$, 300 MHz) δ 1.45 (t, J = 7.2 Hz, 3H), 2.29 (s, 6H), 4-4.13 (m, 1H), 4.22-4.33 (m, 1H), 4.65 (dd, J = 5.6 and 16.1 Hz, 1H), 4.80 (dd, J = 6.1 and 16.1 Hz, 1H), 7.15 (brs, 1H), 7.24-7.34 (m, 6H), 7.75 (d, J = 2.1 Hz, 1H), 8.54-8.56 (m, 2H), 10.60 (brs, 1H), 11.81 (t, J = 5.7 Hz, 1H), $^{31}$P NMR (CDCl, 101.256 MHz) δ 32.8, MS (ESI, EI$^+$) m/z = 482 (MH$^+$). |
| 11a | 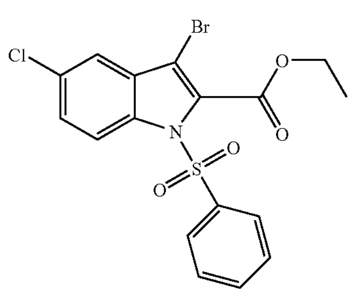 | Off white solid, $^1$H NMR (d$_6$-DMSO) δ 1.37 (t, J = 7.2 Hz, 3H), 4.48 (q, J = 7.2 Hz, 2H), 7.59-7.68 (m, 4H), 7.77 (m, 1H), 7.96-8.09 (m, 3H), MS (ESI, EI$^+$) m/z = 442-444 (MH$^+$). |

TABLE 2-continued

| Compound | structure | Description |
| --- | --- | --- |
| 11b | 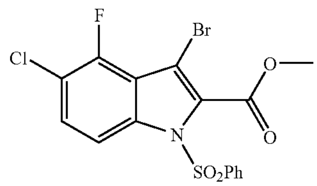 | Off-white solid, ¹H NMR (d₆-DMSO, 300 MHz) δ 4 (s, 3H), 7.66-7.72 (m, 3H), 7.78-7.83 (m, 1H), 7.93 (d, J = 9 Hz, 1H), 7.99-8.02 (m, 2H), MS (ES⁺) m/z = 468.18/470.15 (MH⁺). |
| 11c | 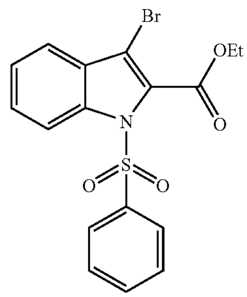 | Yellow powder, ¹H NMR (CDCl₃, 300 MHz) δ 1.46 (t, J = 7.2 Hz, 3H), 4.53 (q, J = 7.1 Hz, 2H), 7.31-7.36 (m, 1H), 7.42-7.59 (m, 5H), 7.95-8.04 (m, 3H), MS (ESI, EI⁺) m/z = 408 (MH⁺). |
| 14a | 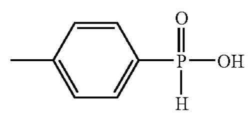 | Colorless oil, ¹H NMR (d₆-DMSO, 300 MHz) δ 2.37 (s, 3H), 7.45 (d, J = 544 Hz, 1H), 7.35 (dd, J = 2.85 and 7.95 Hz, 2H), 7.57 (d, J = 13.2 Hz, 1H), 7.6 (d, J = 13.5 Hz, 1H), ³¹P NMR (CDCl₃, 101.256 MHz) δ 23.8. |
| 16a | 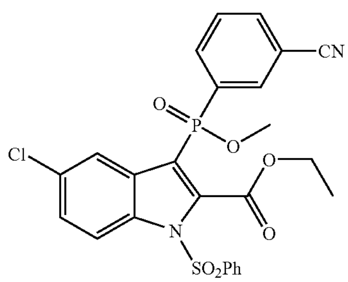 | Yellow solid, ¹H NMR (d₆-DMSO, 300 MHz) δ 1.37 (t, J = 7.2 Hz, 3H), 3.75 (d, J = 11.7 Hz, 3H), 4.46 (q, J = 7.2 Hz, 2H), 7.54-7.58 (m, 1H), 7.67-7.9 (m, 5H), 8.07-8.24 (m, 6H), ³¹P NMR (d₆-DMSO, 101.256 MHz) δ 22.98, MS (ES⁺) m/z = 542.7 (MH⁺). |
| 16b | 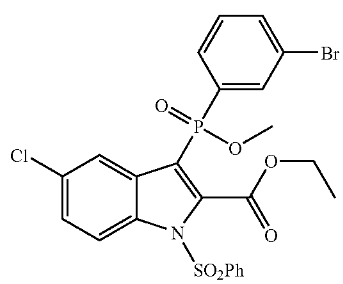 | Thick yellow oil; ¹H NMR (CDCl₃, 300 MHz) δ 1.46 (t, J = 7.05 Hz, 3H), 3.8 (d, J = 11.7 Hz, 3H), 4.54 (q, J = 7.05 Hz, 2H), 7.32-7.38 (m, 2H), 7.5-8.1 (m, 10H), ³¹P NMR (CDCl₃, 101.256 MHz) δ 24.54, MS (ES⁺) m/z = 595.74/597.72 (MH⁺). |
| 16c | 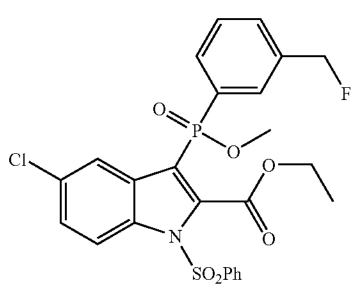 | Thick yellow oil, ¹H NMR (d₆-DMSO, 300 MHz) δ 1.36 (t, J = 7.2 Hz, 3H), 3.7 (d, J = 11.7 Hz, 3H), 4.44 (q, J = 7.2 Hz, 2H), 5.49 (d, J = 47.4 Hz, 2H), 7.54 (dd, J = 2.1 and 9 Hz, 1H), 7.6-7.88 (m, 8H), 8.05-8.11 (m, 3H), ³¹P NMR (d₆-DMSO, 121.49 MHz) δ 23.82, MS (ES⁺) m/z = 550 (MH⁺). |

TABLE 2-continued

| Compound | structure | Description |
|---|---|---|
| 16d | 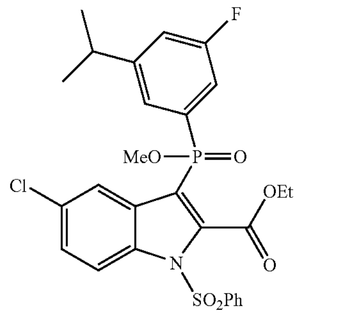 | Yellowish powder, $^1$H NMR (CDCl$_3$, 300 MHz) δ 1.26 (d, J = 6.9 Hz, 6H), 1.28 (t, J = 6.9 Hz, 3H), 1.48 (t, J = 6.9 Hz, 3H), 2.96 (quint., J = 6.9 Hz, 1H), 3.83 (d, J = 11.4 Hz,, 3H), 4.56 (q, J = 6.9 Hz, 2H), 7.07-7.13 (m, 1H), 7.37 (dd, J = 2.1 Hz and 9.0 Hz, 1H), 7.31-7.40 (m, 1H), 7.49-7.68 (m, 4H), 7.85 (d, J = 1.8 Hz, 1H), 7.95 (dd, J = 9.6 Hz and 1.8 Hz, 1H), 8.08-8.14 (m, 2H), MS (ES$^+$) m/z = 578 (MH$^+$). |
| 16e | 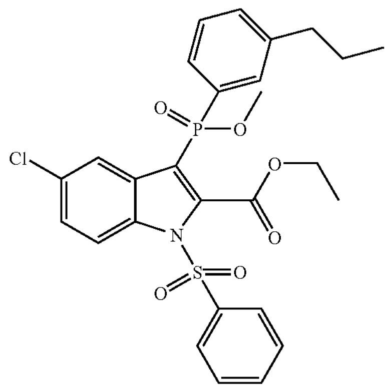 | Yellow resin, $^1$H NMR (d$_6$-DMSO, 300 MHz) δ 0.83 (t, J = 7.5 Hz, 3H), 1.38 (t, J = 7.2 Hz, 3H), 1.55 (sextuplet, J = 7.5 Hz, 2H), 2.59 (t, J = 7.5 Hz, 2H), 3.69 (d, J = 11.7 Hz, 3H), 4.45 (q, J = 7.2 Hz, 2H), 7.44-7.8 (m, 9H), 8.05-8.12 (m, 3H), $^{31}$P NMR (d$_6$-DMSO, 121.49 MHz) δ 24.36, MS (ES$^+$) m/z = 560.38 (MH$^+$). |
| 16f | 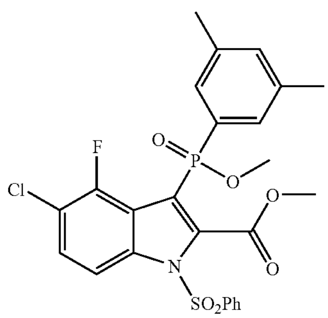 | Thick yellow oil, $^1$H NMR (d$_6$-DMSO, 300 MHz) δ 2.29 (s, 6H), 3.64 (d, J = 11.7 Hz, 3H), 4.04 (s, 3H), 7.25-7.34 (m, 3H), 7.6-7.75 (m, 3H), 7.81-7.84 (m, 1H), 7.9-7.94 (m, 1H), 8.12-8.16 (m, 2H), MS (ES$^+$) m/z = 550 (MH$^+$). |
| 16g | 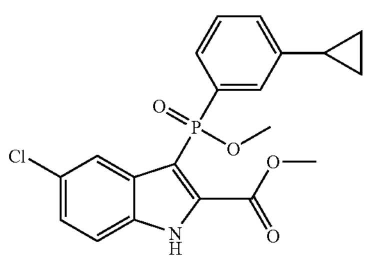 | Off-white solid, $^1$H NMR (CDCl$_3$, 300 MHz) δ 0.66-0.71 (m, 2H), 0.91-0.99 (m, 2H), 1.81-1.94 (m, 1H), 3.69 (s, 3H), 3.79 (d, J = 11.4 Hz, 3H), 7.13-7.17 (m, 1H), 7.28-7.4 (m, 3H), 7.51-7.64 (m, 2H), 8.39-8.4 (m, 1H), 9.96 (brs, 1H), $^{31}$P NMR (CDCl$_3$, 121.49 MHz) δ 31.29. |
| 16h | 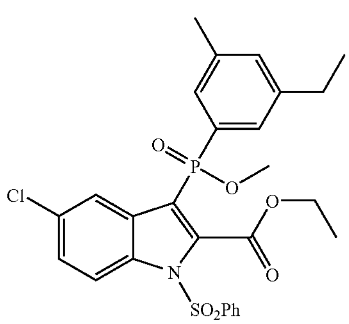 | Thick yellow oil, $^1$H NMR (d$_6$-DMSO, 300 MHz) δ 1.15 (t, J = 7.5 Hz, 3H), 1.39 (t, J = 7.2 Hz, 3H) 2.32 (s, 3H), 3.69 (d, J = 11.7 Hz, 3H), 4.46 (q, J = 7.5 Hz, 2H), 7.29 (brs, 1H), 7.4-7.46 (m, 2H), 7.53-7.56 (m, 1H), 7.63-7.81 (m, 4H), 8.03-8.12 (m, 3H), $^{31}$P NMR (d$_6$-DMSO, 121.49 MHz) δ 24.57, MS (ES$^+$) m/z = 560.5 (MH$^+$). |

TABLE 2-continued

| Compound | structure | Description |
|---|---|---|
| 16i | 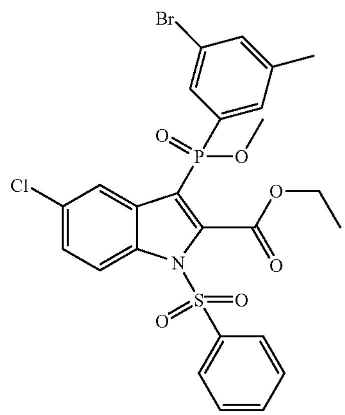 | Yellow resin, $^1$H NMR (d$_6$-DMSO, 300 MHz) δ 1.39 (t, J = 7.2 Hz, 3H), 2.35 (s, 3H), 1.38 (t, J = 7.2 Hz, 3H), 3.71 (d, J = 11.5 Hz, 3H), 4.46 (q, J = 7.2 Hz, 2H), 7.53-7.85 (m, 8H), 8.05-8.12 (m, 3H), $^{31}$P NMR (d$_6$-DMSO, 121.49 MHz) δ 22.40, MS (ES$^+$) m/z 610/612 (MH$^+$). |
| 16j | 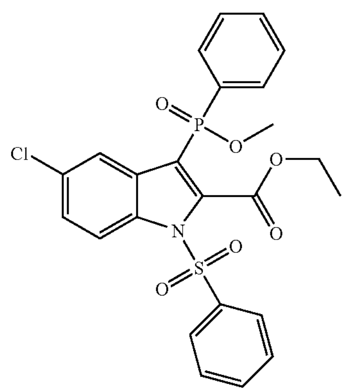 | Colorless oil, $^1$H NMR (CDCl$_3$, 300 MHz) δ 1.45 (t, J = 7.2 Hz, 3H), 3.80 (d, J = 11.4 Hz, 3H), 4.54 (q, J = 7.2 Hz, 2H), 7.36 (dd, J = 2.1 and 9.0 Hz, 1H), 7.47-7.67 (m, 6H), 7.84-7.96 (m, 4H), 8.09-8.12 (m, 2H), $^{31}$P NMR (CDCl$_3$, 101 MHz) δ 26.7, MS (ESI, EI$^+$) m/z = 518 (MH$^+$). |
| 16k | 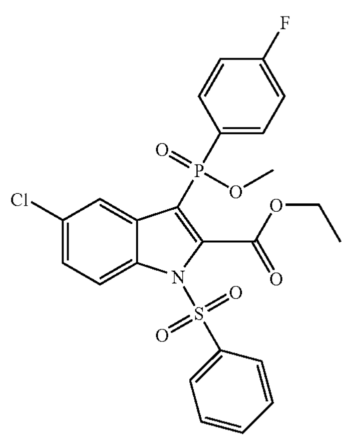 | Pale yellow oil, $^1$H NMR (d$_6$-DMSO, 300 MHz) δ 1.36 (t, J = 7.5 Hz, 3H), 3.69 (d, J = 11.7 Hz, 3H), 4.45 (q, J = 7.1 Hz, 2H), 7.41 (td, J = 8.9 and 2.5 Hz, 2H), 7.54 (dd, J = 9.0 and 2.1 Hz, 1H), 7.66-7.71 (m, 2H), 7.78-7.90 (m, 4H), 8.05-8.11 (m, 3H), $^{19}$F NMR (d$_6$-DMSO) δ −105.46 (m, 1F), $^{31}$P NMR (d$_6$-DMSO, 101 MHz) δ 24.32, MS (ESI, EI$^+$) m/z = 558 (M + Na$^+$). |

TABLE 2-continued

| Compound | structure | Description |
| --- | --- | --- |
| 16m | 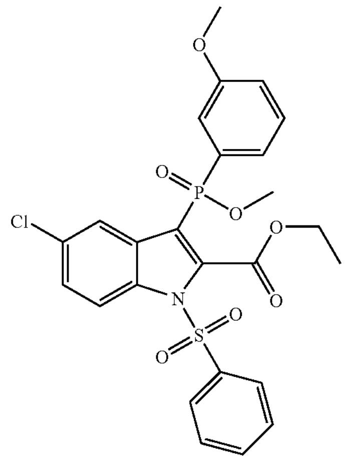 | Oil, ¹H NMR (d₆-DMSO, 300 MHz) δ 1.38 (t, J = 7.05 Hz, 3H), 3.7 (d, J = 11.7 Hz, 3H), 3.78 (s, 3H), 4.46 (q, J = 7.05 Hz, 2H), 7.19-7.4 (m, 3H), 7.47-7.56 (m, 2H), 7.66-7.71 (m, 2H), 7.79-7.81 (m, 2H), 8.06-8.12 (m, 3H), ³¹P NMR (d₆-DMSO, 101.256 MHz) δ 24.91. |
| 16n | 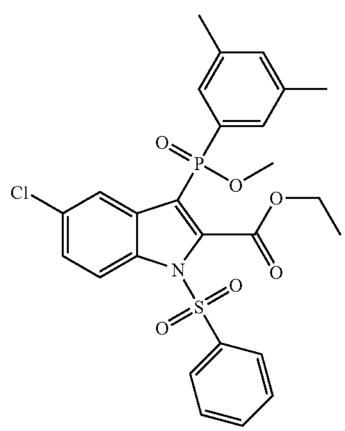 | Oil, ¹H NMR (d₆-DMSO, 300 MHz) δ 1.37 (t, J = 7.1 Hz, 3H), 2.29 (s, 6H), 3.66 (d, J = 11.4 Hz, 3H), 4.44 (q, J = 7.1 Hz, 2H), 7.25 (s, 1H), 7.37 (s, 1H), 7.42 (s, 1H), 7.53 (dd, J = 2.1 and 9.0 Hz, 1H), 7.65-7.71 (m, 2H), 7.78-7.83 (m, 2H), 8.05-8.11 (m, 3H), MS (ESI, EI⁺) m/z = 546 (MH⁺). |
| 16p | 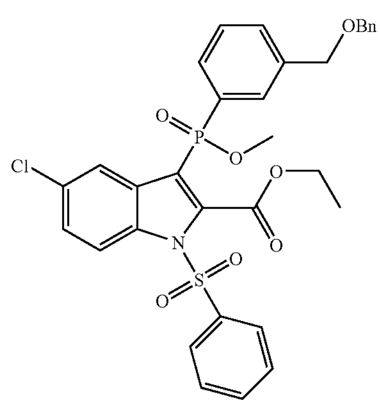 | Brown oil, ¹H NMR (d₆-DMSO, 300 MHz) δ 1.33 (t, J = 7.05 Hz, 3H), 3.69 (d, J = 11.4 Hz, 3H), 4.42 (q, J = 7.05 Hz, 2H), 4.52 (s, 2H), 4.57 (s, 2H), 7.28-7.37 (m, 6H), 7.52-7.78 (m, 9H), 8.05-8.1 (m, 2H), ³¹P NMR (d₆-DMSO, 101.256 MHz) δ 24.18, MS (ES⁺) m/z = 638 (MH⁺). |

TABLE 2-continued

| Compound | structure | Description |
|---|---|---|
| 16q | 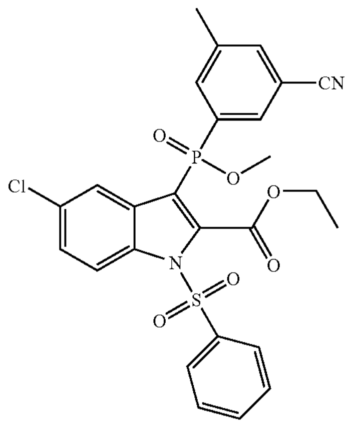 | Yellow oil, $^1$H NMR (d$_6$-DMSO, 300 MHz) δ 1.37 (t, J = 7.2 Hz, 3H), 2.4 (s, 3H), 3.73 (d, J = 11.4 Hz, 3H), 4.45 (q, J = 7.2 Hz, 2H), 7.55 (dd, J = 1.8 and 8.7 Hz, 1H), 7.66-7.71 (m, 2H), 7.78-7.82 (m, 1H), 7.89-7.9 (m, 2H), 7.94-8.12 (m, 5H), $^{31}$P NMR (d$_6$-DMSO, 121.49 MHz) δ 22.16, MS (ES$^+$) m/z = 557.4 (MH$^+$). |
| 17a | 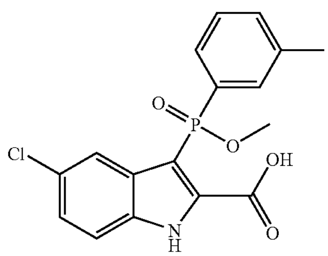 | White solid, $^1$H NMR (d$_6$-DMSO, 300 MHz) δ 2.33 (s, 3H), 3.73 (d, J = 11.7 Hz, 3H), 7.36-7.43 (m, 3H), 7.57-7.66 (m, 3H), 7.81-7.82 (m, 1H), 13.01 (brs, 1H), $^{31}$P NMR (d$_6$-DMSO, 121.49 MHz) δ 32.55, MS (ES$^+$) m/z = 362 (M − H$^+$). |
| 17b | 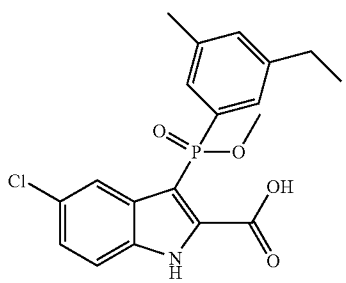 | Off-white solid, $^1$H NMR (d$_6$-DMSO, 300 MHz) δ 1.15 (t, J = 7.5 Hz, 3H), 2.3 (s, 3H), 2.61 (q, J = 7.5 Hz, 2H), 3.73 (d, J = 11.7 Hz, 3H), 7.28 (brs, 1H), 7.36-7.40 (m, 1H), 7.39-7.5 (m, 2H), 7.57-7.61 (m, 1H), 7.78 (brs, 1H), 13.01 (brs, 1H), 14.82 (brs, s, 1H), $^{31}$P NMR (d$_6$-DMSO, 121.49 MHz) δ 32.89, MS (ES$^+$) m/z = 392 (MH$^+$). |
| 17c | 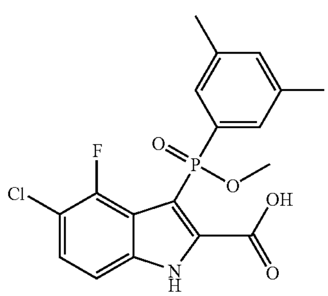 | Off-white solid, $^1$H NMR (d$_6$-DMSO, 300 MHz) δ 2.29 (s, 6H), 3.78 (d, J = 11.7 Hz, 3H), 7.28 (brs, 1H), 7.37 (brs, 1H), 7.42 (brs, 1H), 7.46-7.48 (m, 2H), 13.35 (s, 1H), $^{31}$P NMR (d$_6$-DMSO, 121.49 MHz) δ 35.15, $^{19}$F NMR (d$_6$-DMSO, 282.40 MHz) δ-115.84 (s, 1F) + MS (ES$^+$) m/z = 395.9 (MH$^+$). |
| 17d | 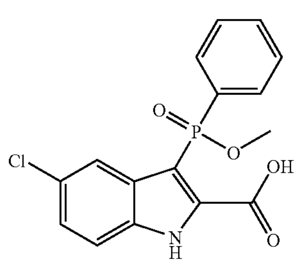 | Yellow powder, $^1$H NMR (CDCl$_3$, 300 MHz) δ 3.88 (d, J = 12.0 Hz, 3H), 7.37 (dd, J = 2.0 and 9.0 Hz, 1H), 7.47-7.63 (m, 5H), 7.81-7.89 (m, 2H), 10.33 (brs, 1H), MS (ESI, EI$^+$) m/z = 350 (MH$^+$). |

TABLE 2-continued

| Compound | structure | Description |
| --- | --- | --- |
| 17e | 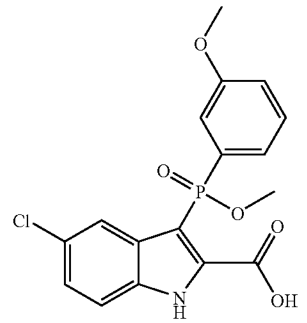 | Oil, $^1$H NMR (d$_6$-DMSO, 300 MHz) δ 3.71 (d, J = 11.7 Hz, 3H), 3.76 (s, 3H), 7.13-7.16 (m, 1H), 7.29-7.45 (m, 4H), 7.56 (dd, J = 1.8 and 9.0 Hz, 1H), 7.91 (d, J = 1.8 Hz, 1H), 12.86 (brs, 1H), 14.51 (brs, 1H), $^{31}$P NMR (d$_6$-DMSO, 121.49 MHz) δ 31.68, MS (ESI, EI$^+$) m/z = 380 (MH$^+$). |
| 17f | 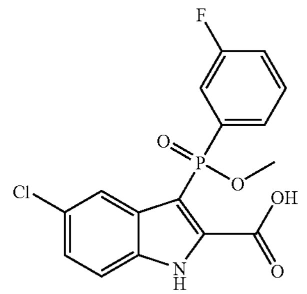 | Pale brown oil, $^1$H NMR (d$_6$-DMSO, 300 MHz) δ 3.72 (d, J = 11.7 Hz, 3H), 7.25-7.64 (m, 6H), 8.06 (d, J = 2.1 Hz, 1H), 12.99 (brs, 1H), $^{31}$P NMR (d$_6$-DMSO, 121.49 MHz) δ 29.23 (d, J = 7.3 Hz, 1P), $^{19}$F NMR (d$_6$-DMSO, 300 MHz) δ -112.01 (m, 1F), MS (ESI, EI$^+$) m/z = 368 (MH$^+$). |
| 17g | 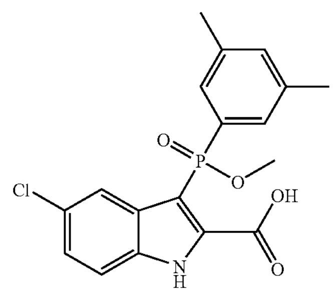 | Oil, $^1$H NMR (d$_6$-DMSO, 300 MHz) δ 2.28 (s, 6H), 3.71 (d, J = 11.7 Hz, 3H), 7.2-7.24 (m, 1H), 7.36-7.45 (m, 3H), 7.57-7.6 (m, 1H), 7.78-7.79 (m, 1H), 13.05 (brs, 1H); 14.8 (brs, 1H), $^{31}$P NMR (d$_6$-DMSO, 121.49 MHz) δ 32.87, MS (ES$^+$) m/z = 378 (MH$^+$). |
| 17h | 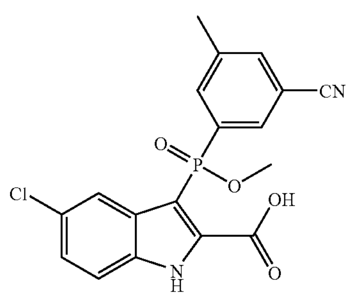 | Off-white solid, MS (ES$^+$) m/z = 389 (MH$^+$). |
| 18a | 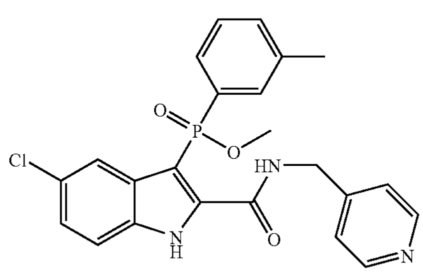 | Pink solid, $^1$H NMR (d$_6$-DMSO, 300 MHz) δ 2.3 (s, 3H), 3.76 (d, J = 11.7 Hz, 3H), 4.57-4.75 (m, 2H), 7.31-7.61 (m, 9H), 8.52-8.54 (m, 2H), 11.37 (t, J = 5.7 Hz, 1H), 12.87 (brs. 1H), $^{31}$P NMR (d$_6$-DMSO, 121.49 MHz) δ 32.81, MS (ES$^+$) m/z = 453.9 (MH$^+$). |

TABLE 2-continued

| Compound | structure | Description |
|---|---|---|
| 18b | 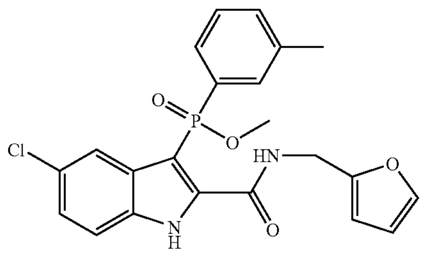 | White solid, $^1$H NMR (d$_6$-DMSO, 300 MHz) δ 2.3 (s, 3H), 3.74 (d, J = 11.4 Hz, 3H), 4.56-4.65 (m, 2H), 6.38-6.45 (m, 2H), 7.31-7.65 (m, 8H), 11.23-11.27 (m, 1H), 12.84 (brs, 1H), $^{31}$P NMR (d$_6$-DMSO, 121.49 MHz) δ 32.72, MS (ES$^+$) m/z = 442.9 (MH$^+$). |
| 18c | 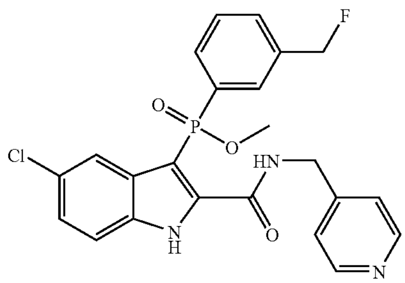 | White solid, $^1$H NMR (d$_6$-DMSO, 300 MHz) δ 3.78 (d, J = 11.7 Hz, 3H), 4.58-4.74 (m, 2H), 5.46 (d, J = 47.4 Hz, 2H), 7.32-7.38 (m, 3H), 7.55-7.82 (m, 6H), 8.51-8.53 (m, 2H), 11.3 (t, J = 5.7 Hz, 1H), 12.92 (d, J = 2.1 Hz, 1H), $^{19}$F NMR (d$_6$-DMSO, 282.40 MHz) δ −211.09 (t, J = 47.4 Hz, 1F), MS (ES$^+$) m/z = 472 (MH$^+$). |
| 18d | 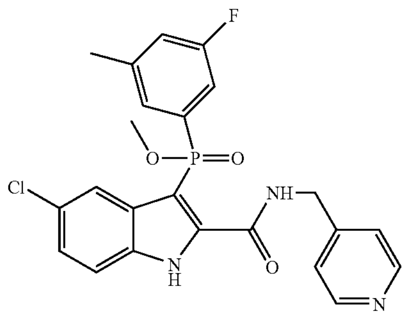 | Off-white powder, $^1$H NMR (CDCl$_3$, 300 MHz) δ 2.35 (s, 3H, 3.88 (d, J = 11.7 Hz, 3H), 4.77 (qd, J = 6 Hz and 15.9 Hz, 2H), 7.04-7.35 (m, 7H), 7.68 (brs, 1H), 8.59-9.61 (m, 2H), 11.22 (brs, 1H), 11.71 (t, J = 5.7 Hz, 1H), $^{31}$P NMR (CDCl$_3$, 121.49 MHz) δ 32.55 (d, J = 8.2 Hz, 1P), $^{19}$F NMR (CDCl$_3$, 282.40 MHz) δ −111.55 (q, J = 8.2 Hz, 1F), MS (ES$^+$) m/z = 471.92 (MH$^+$). |
| 18e | 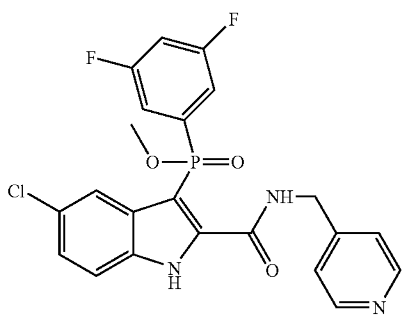 | Pale yellow powder, $^1$H NMR (CDCl$_3$, 300 MHz) δ 3.88 (d, J = 11.7 Hz, 3H), 4.7-4.77 (m, 2H), 6.97 (tt, J = 2.4 Hz and 8.7 Hz, 1H), 7.2-7.33 (m, 6H), 7.64 (brs, 1H), 8.52-8.6 (m, 2H), 11.55-11.58 (m, 2H), $^{31}$P NMR (CDCl$_3$, 121.49 MHz) δ 31.11 (t, J = 8.5 Hz, 1P), $^{19}$F NMR (CDCl$_3$, 282.40 MHz) δ −106.21 (m, 2F), MS (ES$^+$) m/z = 476.17 (MH$^+$). |
| 18f | 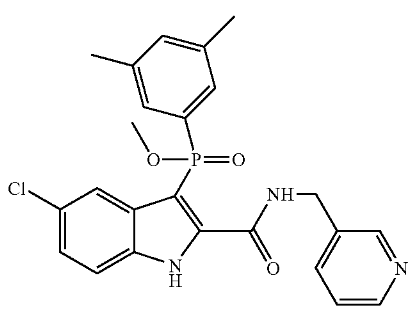 | White powder, $^1$H NMR (CDCl$_3$, 300 MHz) δ 2.28 (s, 6H), 3.82 (d, J = 11.7 Hz, 3H), 4.69 (dd, J = 6 Hz and 15 Hz, 1H), 4.78 (dd, J = 6 Hz and 15 Hz, 1H), 7.13 (brs, 1H), 7.24-7.28 (m, 5H), 7.29-7.31 (m, 1H), 7.38-7.39 (m, 1H), 7.68-7.69 (m, 1H), 7.76-7.8 (m, 1H), 8.56 (dd, J = 1.5 Hz and 4.5 Hz, 1H), 8.7 (d, J = 2.1 Hz, 1H), $^{31}$P NMR (CDCl$_3$, 121.49 MHz) δ 34.18, MS (ES$^+$) m/z = 468.33 (MH$^+$). |

TABLE 2-continued

| Compound | structure | Description |
|---|---|---|
| 18g | 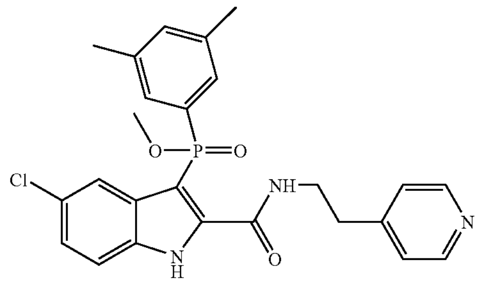 | White powder, $^1$H NMR (CDCl$_3$, 300 MHz) δ 2.3 (s, 6H), 3.03 (t, J = 7.2 Hz, 2H), 3.76-3.88 (m, 2H), 3.79 (d, J = 11.7 Hz, 3H), 7.16-7.3 (m, 6H), 7.47-7.5 (m, 1H), 7.62-7.63 (m, 1H), 8.43-8.45 (m, 2H), 10.83 (brs, 1H), 11.36-11.38 (m, 1H), $^{31}$P NMR (CDCl$_3$, 121.49 MHz) δ 34.38, MS (ES$^+$) m/z = 482.38 (MH$^+$). |
| 18h | 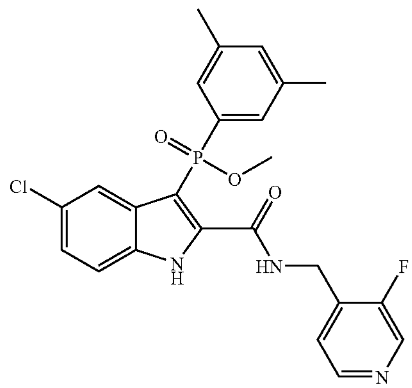 | White solid, $^1$H NMR (d$_6$-DMSO, 300 MHz) δ 2.26 (s, 6H), 3.75 (d, J = 11.4 Hz, 3H), 4.66 (dd, J = 5.4 and 15.9 Hz, 1H), 4.78 (dd, J = 5.7 and 15.9 Hz, 1H), 7.24 (brs, 1H), 7.3-7.35 (m, 3H), 7.45-7.49 (m, 1H), 7.6 (dd, J = 1.8 and 9 Hz, 1H), 7.62 (d, J = 1.8 Hz, 1H), 8.4 (dd, J = 1.2 and 4.8 Hz, 1H), 8.58 (d, J = 1.5 Hz, 1H), 11.41 (t, J = 5.4 Hz, 1H), 12.86 (brs, 1H), $^{31}$P NMR (d$_6$-DMSO, 121.49 MHz) δ 32.81, $^{19}$F NMR (d$_6$-DMSO, 282.40 MHz) δ −132.93 (d, J = 5.9 Hz, 1F), MS (ES$^+$) m/z = 486.3 (MH$^+$). |
| 18i | 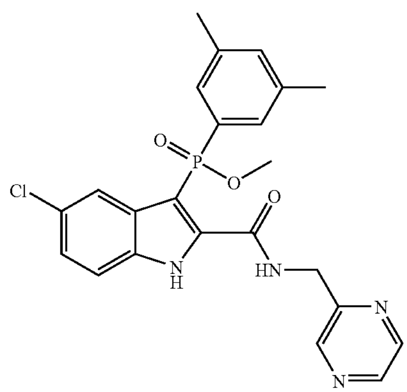 | White solid,, $^1$H NMR (d$_6$-DMSO, 300 MHz) δ 2.26 (s, 6H), 3.75 (d, J = 11.4 Hz, 3H), 4.7 (dd, J = 5.1 and 15.9 Hz, 1H), 4.84 (dd, J = 6 and 15.9 Hz, 1H), 7.22 (brs, 1H), 7.33 (dd, J = 2.1 and 8.7 Hz, 1H), 7.32-7.36 (m, 2H), 7.59 (dd, J = 1.8 and 8.7 Hz, 1H), 7.63 (d, J = 1.5 Hz, 1H), 8.6 (dd, J = 2.55 and 14.4 Hz, 1H), 8.62 (d, J = 2.4 Hz, 1H), 8.72 (d, J = 1.5 Hz, 1H), 11.46 (t, J = 5.7 Hz, 1H), 12.87 (brs, 1H), $^{31}$P NMR (d$_6$-DMSO, 121.49 MHz) δ 32.69, MS (ES$^+$) m/z = 469.4 (MH$^+$). |
| 18k | 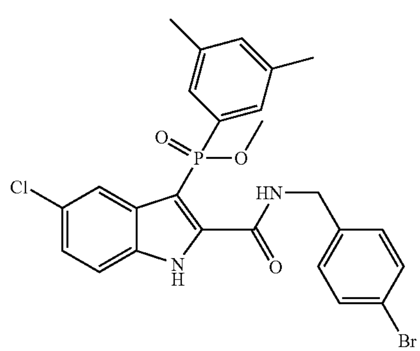 | White solid, $^1$H NMR (d$_6$-DMSO, 300 MHz) δ 2.24 (s, 6H), 3.74 (d, J = 11.7 Hz, 3H), 4.51 (dd, J = 5.25 and 15 Hz, 1H), 4.67 (dd, J = 6.0 and 15 Hz, 1H), 7.22-7.38 (m, 6H), 7.53-7.64 (m, 4H), 11.34 (t, J = 5.7 Hz, 1H), 12.66 (brs, 1H), $^{31}$P NMR (d$_6$-DMSO, 121.49 MHz) δ 32.79, MS (ES$^+$) m/z = 545.33/547.31 (MH$^+$). |

TABLE 2-continued

| Compound | structure | Description |
|---|---|---|
| 18l | 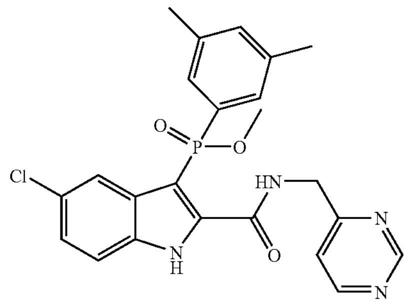 | Off-white solid, $^1$H NMR (d$_6$-DMSO, 300 MHz) δ 2.28 (s, 6H), 3.77 (d, J = 11.4 Hz, 3H), 4.64-4.82 (m, 2H), 7.24 (brs, 1H), 7.34 (dd, J = 1.8 and 8.7 Hz, 1H), 7.36 (brs, 1H), 7.4 (brs, 1H), 7.52 (dd, J = 1.5 and 5.4 Hz, 1H), 7.58-7.63 (m, 2H), 8.76 (d, J = 5.1 Hz, 1H), 9.14 (d, J = 1.5 Hz, 1H), 11.48 (t, J = 6.0 Hz, 1H), 12.85 (brs, 1H), $^{31}$P NMR d$_6$-DMSO, 121.49 MHz) δ 32.68, MS (ES$^+$) m/z = 469.4 (MH$^+$). |
| 18m | 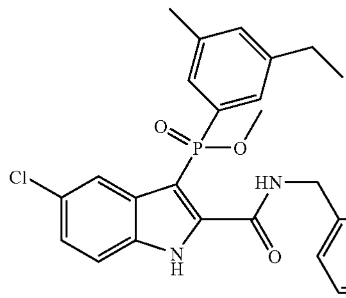 | Off-white solid, $^1$H NMR (CDCl$_3$, 300 MHz) δ 1.19 (t, J = 7.6 Hz, 3H), 2.60 (q, J = 7.6 Hz, 2H), 2.31 (s, 3H), 3.84 (d, J = 11.7 Hz, 3H), 4.76 (m, 2H), 7.18-7.43 (m, 6H), 7.70 (m, 1H), 7.81 (m, 1H), 8.57 (d, J = 4.8 Hz, 1H), 8.72 (s, 1H), 10.62 (brs, 1H), 11.78 (t, J = 7.6 Hz, 1H), $^{31}$P NMR (CDCl$_3$, 121.49 MHz) δ 34.08. |
| 18n | 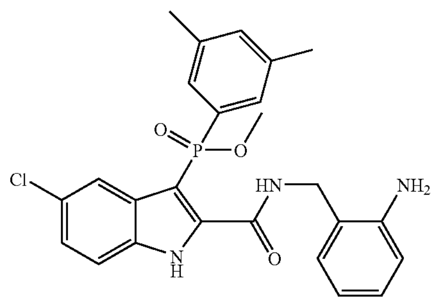 | Off-white solid, $^1$H NMR (d$_6$-DMSO, 300 MHz) δ 2.24 (s, 6H), 3.74 (d, J = 11.5 Hz, 3H), 4.39 (dd, J = 5.7 and 15.6 Hz, 1H), 4.53 (dd, J = 5.7 and 15.6 Hz, 1H), 5.62 (brs, 2H), 6.52 (t, J = 7.2 Hz, 1H), 6.63-6.70 (m, 1H), 6.97-7.35 (m, 6H), 7.58-7.65 (m, 2H), 11.34 (t, J = 5.7 Hz, 1H), 12.66 (brs, 1H), $^{31}$P NMR (d$_6$-DMSO, 121.49 MHz) δ 8.51, MS (ES$^+$) m/z = 482 (MH$^+$). |
| 18p | 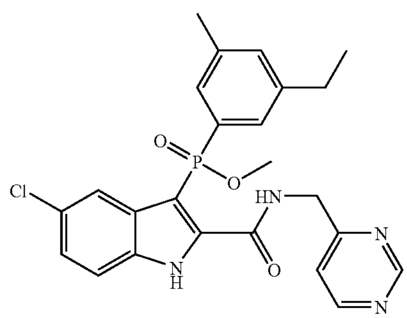 | Off-white powder, $^1$H NMR (d$_6$-DMSO, 300 MHz) δ 1.12 (t, J = 7.5 Hz, 3H), 2.28 (s, 3H), 2.58 (q, J = 7.5 Hz, 2H), 3.77 (d, J = 11.7 Hz, 3H), 4.68 (dd, J = 5.4 and 17.1 Hz, 1H), 4.78 (dd, J = 5.7 and 16.8 Hz, 1H), 7.27 (brs, 1H), 7.33 (dd, J = 2.1 and 8.7 Hz, 1H), 7.36-7.46 (m, 2H), 7.52 (dd, J = 1.2 and 5.1 Hz, 1H), 7.60 (dd, J = 1.8 and 8.7 Hz, 1H), 7.63 (d, J = 1.5 Hz, 1H), 8.76 (d, J = 5.4 Hz, 1H), 9.14 (d, J = 1.2 Hz, 1H), 11.47 (t, J = 5.4 Hz, 1H), 12.82 (brs, 1H), $^{31}$P NMR (d$_6$-DMSO, 121.49 MHz) δ 32.62, MS (ES$^+$) m/z = 483 (MH$^+$). |
| 18q | 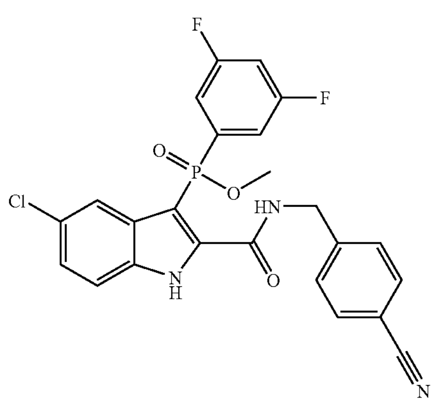 | Off-white solid, $^1$H NMR (d$_6$-DMSO, 300 MHz) δ 3.78 (d, J = 11.7 Hz, 3H), 4.61-4.78 (m, 2H), 7.35 (dd, J = 2.1 and 8.7 Hz, 2H), 7.38-7.41 (m, 1H), 7.5-7.55 (m, 1H), 7.57-7.6 (m, 3H), 7.73 (d, J = 2.1 Hz, 1H), 7.82-7.85 (m, 2H), 10.87-10.91 (m, 1H), 12.96 (brs, 1H), MS (ES$^+$) m/z = 498.35 (MH$^+$). |

TABLE 2-continued

| Compound | structure | Description |
| --- | --- | --- |
| 18r | 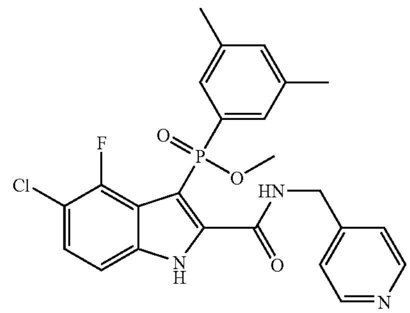 | Off-white solid, $^1$H NMR (d$_6$-DMSO, 300 MHz) δ 2.27 (s, 6H), 3.72 (d, J = 11.7 Hz, 3H), 4.65-4.68 (m, 2H), 7.22 (brs, 1H), 7.29 (brs, 1H), 7.33 (brs, 1H), 7.38-7.48 (m, 4H), 8.53-8.55 (m, 2H), 11.86 (t, J = 5.4 Hz, 1H), 13.08 (brs, 1H), $^{31}$P NMR (d$_6$-DMSO, 121.49 MHz) δ 32.16, MS (ES$^+$) m/z = 485.9 (MH$^+$). |
| 18s | 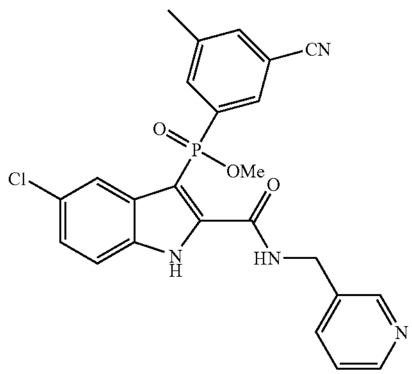 | |
| 18t | 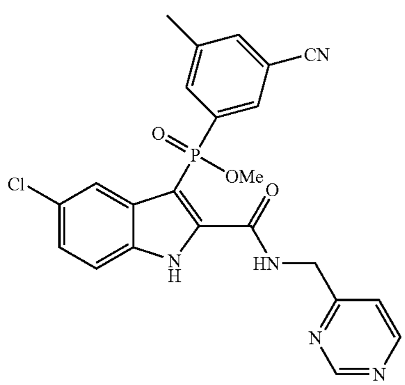 | |
| 18u | 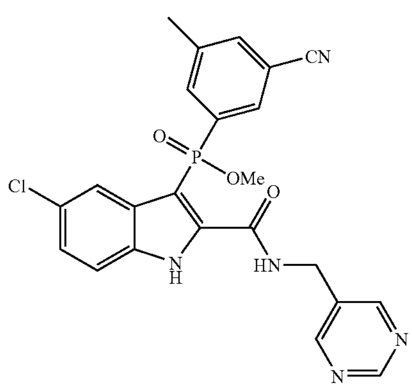 | |

TABLE 2-continued

| Compound | structure | Description |
| --- | --- | --- |
| 18v | 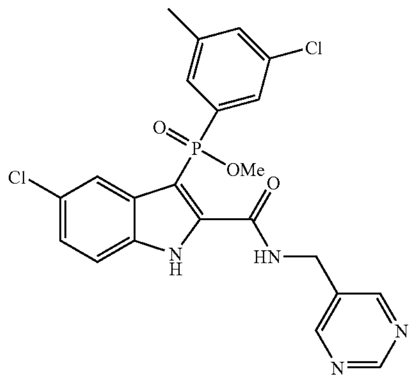 | |
| 18w | 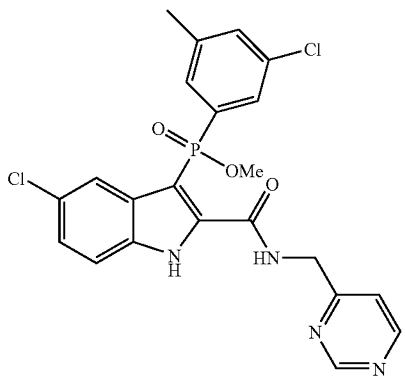 | |
| 18x | 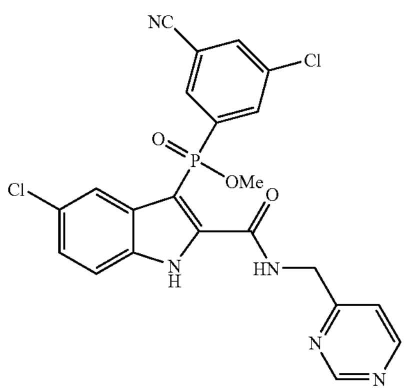 | |
| 18y | 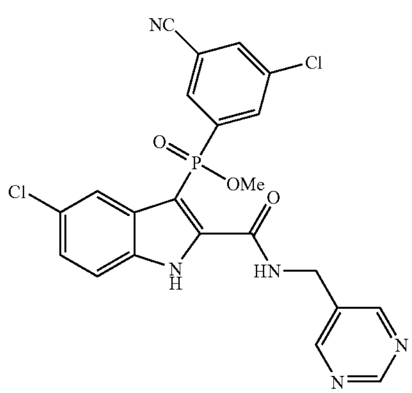 | |

TABLE 2-continued

| Compound | structure | Description |
|---|---|---|
| 18z | 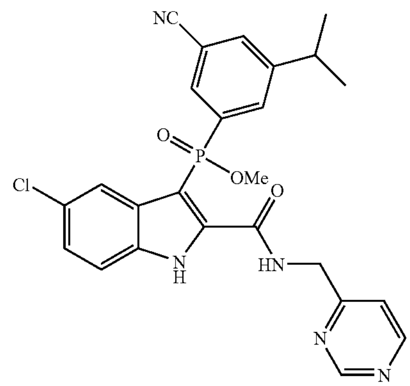 | |
| 18aa | 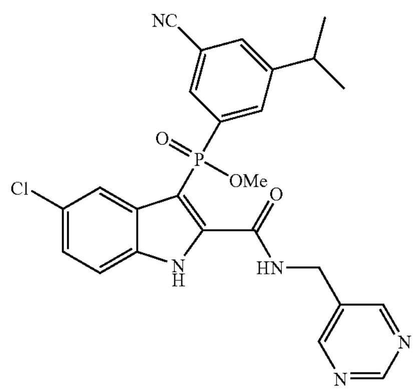 | |
| 18ab | 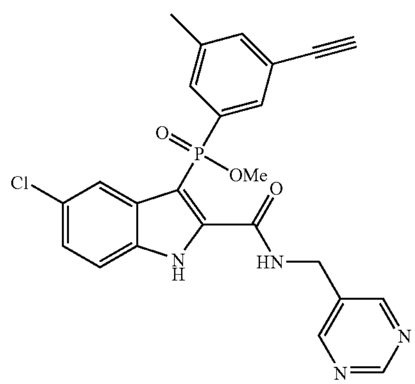 | |
| 18ac | 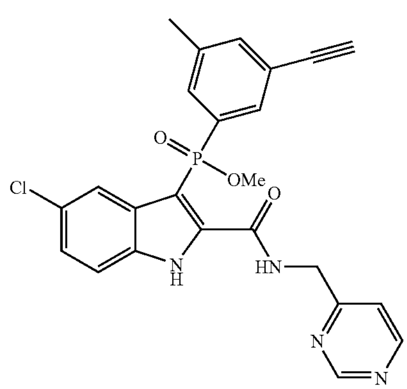 | |

TABLE 2-continued

| Compound | structure | Description |
| --- | --- | --- |
| 18ad | 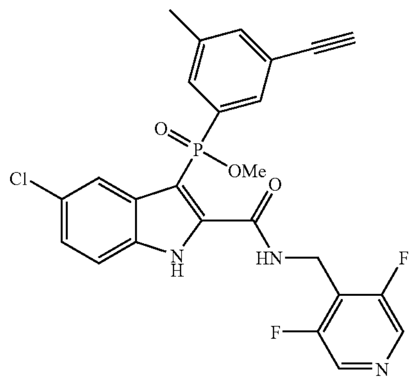 | |
| 18ae | 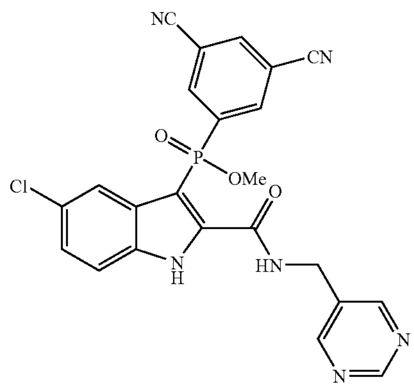 | |
| 18af | 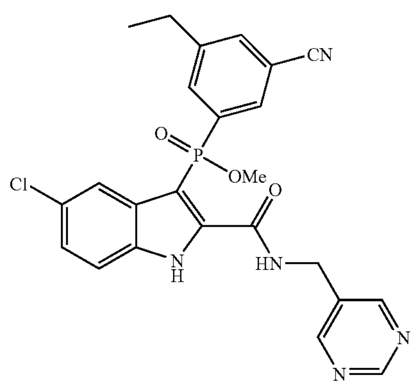 | |
| 18ag | 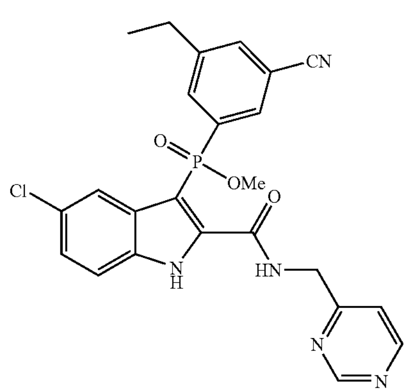 | |

TABLE 2-continued

| Compound | structure | Description |
| --- | --- | --- |
| 18ah | 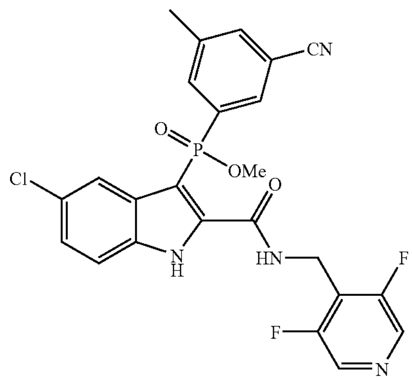 | |
| 18ai | 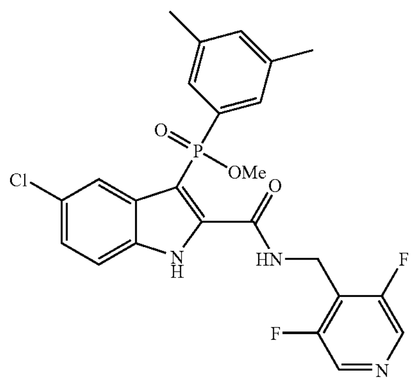 | |
| 18aj | 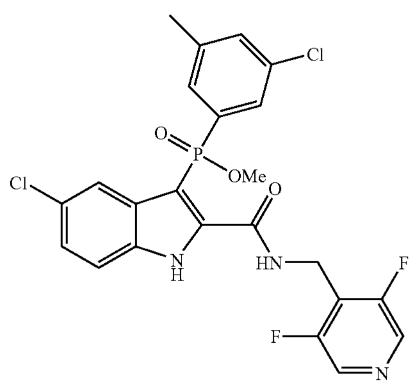 | |
| 18ak | 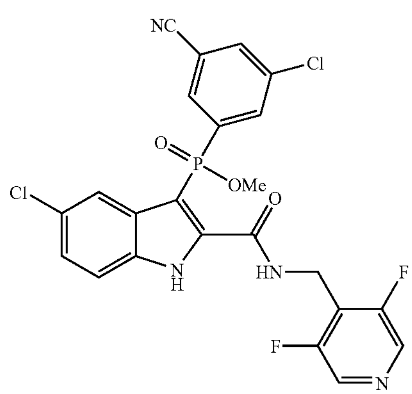 | |

TABLE 2-continued
| Compound | structure | Description |
|---|---|---|
| 18al | 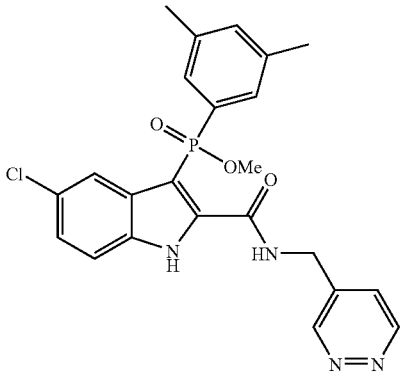 | |
| 18am | 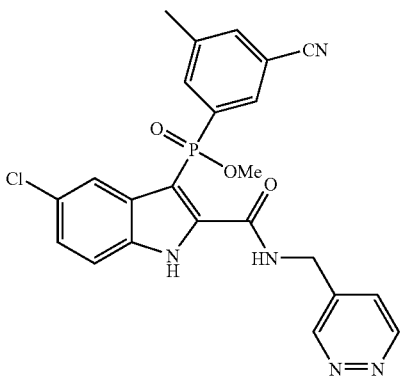 | |
| 18an | 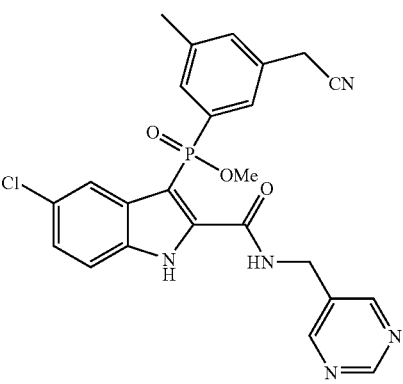 | |
| 18ao | 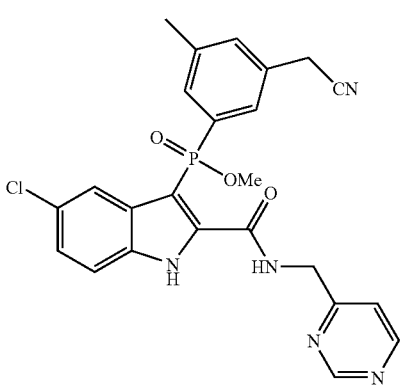 | |

TABLE 2-continued

| Compound | structure | Description |
| --- | --- | --- |
| 18ap | 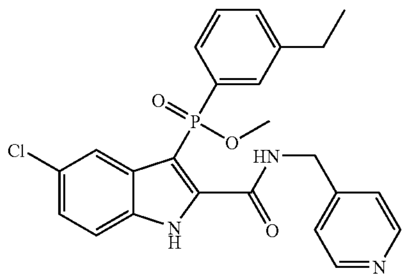 | Yellow pale powder, $^1$H NMR (d$_6$-DMSO, 300 MHz) δ 1.12 (t, J = 7.5 Hz, 3H), 2.61 (q, J = 7.5 Hz, 2H), 3.77 (d, J = 11.7 Hz, 3H), 4.61 (dd, J = 5.4 and 15.9 Hz, 1H), 4.72 (dd, J = 6.0 and 15.9 Hz, 1H), 7.31-7.61 (m, 9H), 8.51-8.53 (m, 2H), 11.4 (t, J = 5.4 Hz, 1H), 12.87 (brs, 1H), $^{31}$P NMR (d$_6$-DMSO, 121.49 MHz) δ 32.74, MS (ES$^+$) m/z = 467.89 (MH$^+$). |
| 18aq | 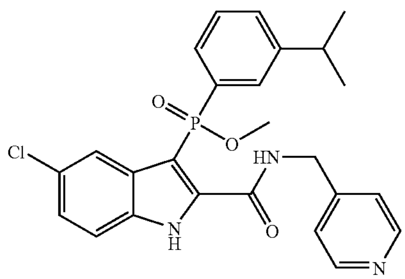 | Yellow pale powder, $^1$H NMR (d$_6$-DMSO, 300 MHz) δ 1.15 (d, J = 6.9 Hz, 6H), 2.9 (quintuplet, J = 6.9 Hz, 1H), 3.77 (d, J = 11.4 Hz, 3H), 4.61 (dd, J = 5.4 and 16.5 Hz, 1H), 4.72 (dd, J = 6 and 16.2 Hz, 1H), 7.33 (dd, J = 2.1 and 8.7 Hz, 1H), 7.37-7.39 (m, 2H), 7.41-7.54 (m, 3H), 7.58-7.66 (m, 3H), 8.52-8.54 (m, 2H), 11.42 (t, J = 5.7 Hz, 1H), 12.87 (brs, 1H), $^{31}$P NMR (d$_6$-DMSO, 121.49 MHz) δ 33.64, MS (ES$^+$) m/z = 481.94 (MH$^+$). |
| 18ar | 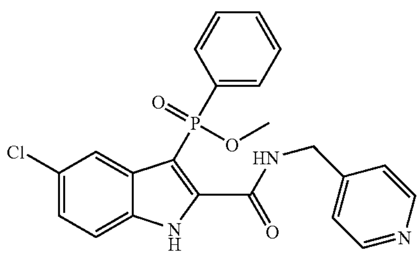 | Pale yellow solid, $^1$H NMR (CDCl$_3$, 400 MHz) δ 3.86 (d, J = 11.8, 3H), 4.67 (dd, J = 5.7 and 15.9 Hz, 1H), 4.79 (dd, J = 6.0 and 15.9 Hz, 1H), 7.25-7.28 (dd, J = 1.9 and 8.4 Hz, 1H), 7.30-7.34 (m, 3H), 7.41-7.45 (m, 2H), 7.52-7.56 (m, 1H), 7.69-7.75 (m, 3H), 8.55-8.57 (m, 2H), 10.76 (s, 1H), 11.72 (t, J = 5.8 Hz, 1H), $^{31}$P NMR (CDCl$_3$, 101 MHz) δ 34.2, MS (ESI, EI$^+$) m/z = 440 (MH$^+$). |
| 18as | 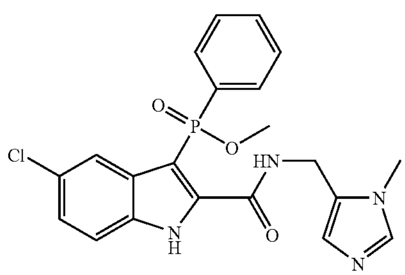 | White powder, $^1$H NMR (d$_6$-DMSO, 300 MHz) δ 3.62 (s, 3H), 3.74 (d, J = 11.7 Hz, 3H), 4.53-4.67 (m, 2H), 6.9 (brs, 1H), 7.32 (dd, J = 1.8 and 8.7 Hz, 1H), 7.46-7.65 (m, 8H), 11.09 (t, J = 5.1 Hz, 1H), 12.85 (brs, 1H), $^{31}$P NMR (d$_6$-DMSO, 101.256 MHz) δ 33.71, MS (ESI, EI$^+$) m/z = 443 (MH$^+$). |
| 18at | 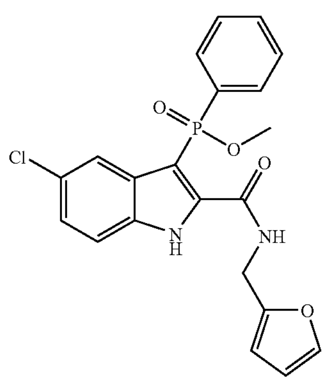 | Off white powder, $^1$H NMR (d$_6$-DMSO, 300 MHz) δ 3.76 (d, J = 11.4 Hz, 3H), 4.56 (dd, J = 4.8 and 15.6 Hz, 1H), 4.66 (dd, J = 5.7 and 15.6 Hz, 1H), 6.38-6.45 (m, 2H), 7.33 (dd, J = 2.1 and 8.7 Hz, 1H), 7.48-7.7 (m, 8H), 11.21 (t, J = 5.25 Hz, 1H), 12.86 (brs, 1H), $^{31}$P NMR (d$_6$-DMSO, 101.256 MHz) δ 33.59, MS (ESI, EI$^+$) m/z = 429 (MH$^+$). |

TABLE 2-continued

| Compound | structure | Description |
|---|---|---|
| 18au | 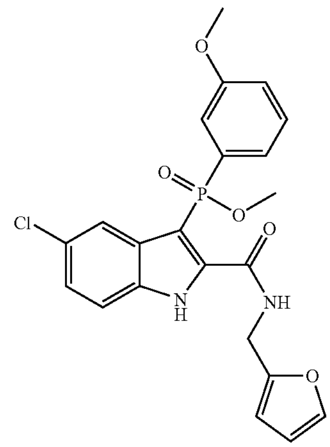 | Yellow powder, ¹H NMR (CDCl₃, 300 MHz) δ 3.76 (s, 3H), 3.84 (d, J = 11.4 Hz, 3H), 4.7 (dd, J = 5.1 and 15.6 Hz, 1H), 4.83 (dd, J = 5.5 and 15.75 Hz, 1H), 6.33-6.36 (m, 2H), 7-7.04 (m, 1H), 7.23-7.32 (m, 4H), 7.38-7.4 (m, 1H), 7.48 (dd, J = 1.5 and 8.7 Hz, 1H), 7.7 (d, J = 2.1 Hz, 1H), 11.61-11.64 (m, 2H), ³¹P NMR (CDCl₃, 121.49 MHz) δ 33.64, MS (ESI, EI⁺) m/z = m/z = 459 (MH⁺). |
| 18av | 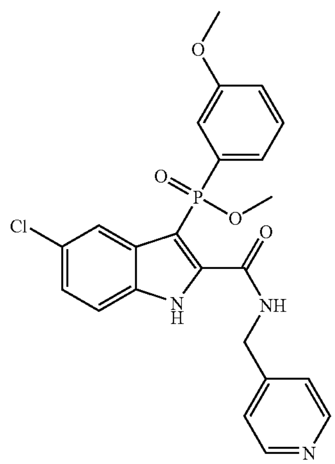 | Pale yellow powder, ¹H NMR (CDCl₃, 300 MHz) δ 3.76 (s, 3H), 3.86 (d, J = 11.7 Hz, 3H), 4.69 (dd, J = 5.7 and 15.9 Hz, 1H), 4.83 (dd, J = 5.7 and 15.9 Hz, 1H), 7.03-7.07 (m, 1H), 7.2-7.37 (m, 7H), 7.71 (brs, 1H), 8.55-8.58 (m, 2H), 11.48 (brs, 1H), 11.8 (t, J = 5.7 Hz, 1H), ³¹P NMR (CDCl₃, 121.49 MHz) δ 33.93, MS (ESI, EI⁺) m/z = 470 (MH⁺). |
| 18aw | 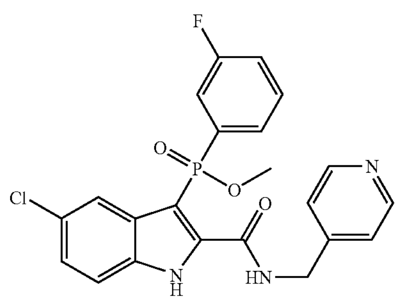 | Pale yellow solid, ¹H NMR (d₆-DMSO, 300 MHz) δ 3.78 (d, J = 11.7 Hz, 3H), 4.65 (m, 2H), 7.33-7.65 (m, 9H), 8.52 (d, J = 6 Hz, 2H), 11.13 (t, J = 5.5 Hz, 1H), 12.94 (brs, 1H), ³¹P NMR (d₆-DMSO, 121.49 MHz) δ 30.76 (d, J =7.4 Hz, 1P), ¹⁹F NMR (d₆-DMSO, 300 MHz) δ −111.0 (m, 1F), MS (ESI, EI⁺) m/z = 458 (MH⁺). |
| 18ax | 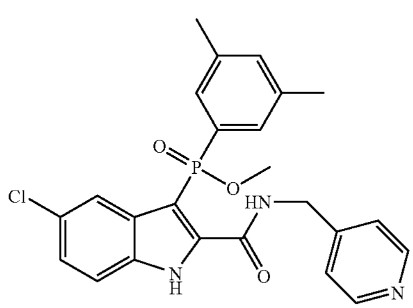 | Yellow powder, ¹H NMR (d₆-DMSO, 300 MHz) δ 2.25 (s, 6H), 3.75 (d, J = 11.4 Hz, 3H), 4.6 (dd, J = 5.4 and 16.2 Hz, 1H), 4.72 (dd, J = 5.7 and 16.2 Hz, 1H), 7.24-7.39 (m, 6H), 7.59-7.63 (m, 2H), 8.52-8.54 (m, 2H), 11.41 (t, J = 5.7 Hz, 1H), 12.86 (brs, 1H), ³¹P NMR (d₆-DMSO, 121.49 MHz) δ 32.88, MS (ES⁺) m/z = 467.9 (MH⁺). |

TABLE 2-continued

| Compound | structure | Description |
|---|---|---|
| 18ay | 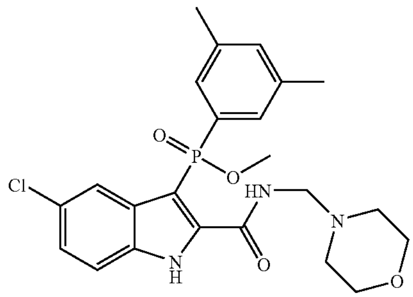 | White powder, $^1$H NMR (CDCl$_3$, 300 MHz) δ 2.3 (s, 6H), 2.7-2.75 (m, 4H), 3.73-3.77 (m, 4H), 3.86 (d, J = 11.7 Hz, 3H), 4.43 (dd, J = 5.7 and 12.9 Hz, 1H), 4.52 (dd, J = 6 and 12.9 Hz, 1H), 7.17 (brs, 1H), 7.32 (dd, J = 2.1 and 8.7 Hz, 1H), 7.36 (brs, 1H), 7.41 (brs, 1H), 7.49 (dd, J = 2.1 and 8.7 Hz, 1H), 7.71-7.72 (m, 1H), 10.5 (brs, 1H), 11.46 (t, J = 5.7 Hz, 1H), $^{31}$P NMR (CDCl$_3$, 101.256 MHz) δ 34.52, MS (ES$^+$) m/z = 475.87 (MH$^+$). |
| 18az | 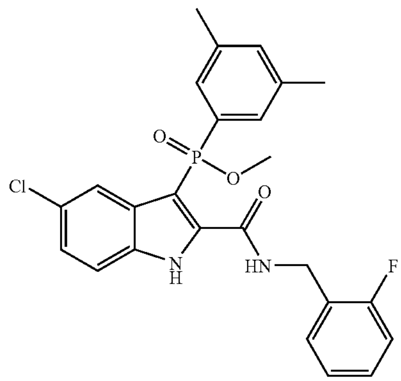 | Pale yellow powder, $^1$H NMR (d$_6$-DMSO, 300 MHz) δ 2.24 (s, 6H), 3.73 (d, J = 11.7 Hz, 3H), 4.56 (dd, J = 5.4 and 15.3 Hz, 1H), 4.73 (dd, J = 5.4 and 15.3 Hz, 1H), 7.15-7.4 (m, 7H), 7.47 (td, J = 1.8 and 7.5 Hz, 1H), 7.59 (dd, J = 1.8 and 8.1 Hz, 1H), 7.63 (d, J = 2.1 Hz, 1H), 11.32 (t, J = 5.4 Hz, 11.1), 12.83 (brs, 1H), $^{31}$P NMR (d$_6$-DMSO, 121.49 MHz) δ 32.76, $^{19}$F NMR (d$_6$-DMSO, 282.40 MHz) δ −118.4 (m, 1F), MS (ES$^+$) m/z = 485 (MH$^+$). |
| 18aaa | 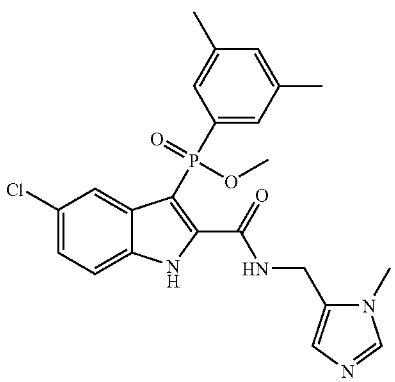 | White powder, $^1$H NMR (d$_6$-DMSO, 300 MHz) δ 2.25 (s, 6H), 3.66 (s, 3H), 3.72 (d, J = 11.7 Hz, 3H), 4.52-4.7 (m, 2H), 6.9 (brs, 1H), 7.22 (brs, 2H), 7.26 (brs, 1H), 7.33 (dd, J = 2.1 and 9.3 Hz, 1H), 7.59-7.61 (m, 3H), 11.17 (t, J = 5.1 Hz, 1H), 12.83 (brs, 1H), $^{31}$P NMR (d$_6$-DMSO, 121.49 MHz) δ 32.93, MS (ES$^+$) m/z = 471.36 (MH$^+$). |
| 18aab | 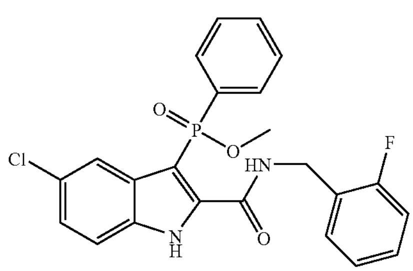 | Off-white powder, $^1$H NMR (d$_6$-DMSO, 300 MHz) δ 3.75 (d, J = 11.7 Hz, 3H), 4.58 (dd, J = 5.1 and 15.3 Hz, 1H), 4.7 (dd, J = 5.7 and 15.3 Hz, 1H), 7.17-7.28 (m, 2H), 7.32-7.52 (m, 5H), 7.57-7.7 (m, 5H), 11.24 (t, J = 5.4 Hz, 1H), 12.87 (brs, 1H), $^{31}$P NMR (d$_6$-DMSO, 121.49 MHz) δ 32.64, $^{19}$F NMR (d$_6$-DMSO, 282.40 MHz) δ −118.41 (m, 1F), MS (ES$^+$) m/z = 456.8 (MH$^+$). |
| 18aac | 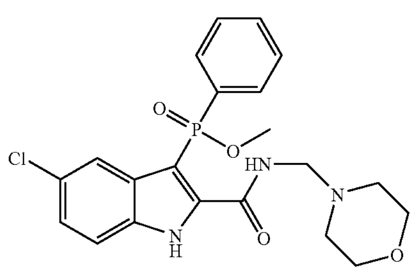 | Off white powder, $^1$H NMR (CDCl$_3$, 300 MHz) δ 2.67-2.72 (m, 4H), 3.71-3.75 (m, 4H), 3.86 (d, J = 11.7 Hz, 3H), 4.39-4.5 (m, 2H), 7.3 (dd, J = 1.8 and 8.7 Hz, 1H), 7.41-7.54 (m, 4H), 7.66-7.67 (m, 1H), 7.73-7.81 (m, 2H), 10.49 (brs, 1H), 11.42 (t, J = 5.7 Hz, 1H), $^{31}$P NMR (CDCl$_3$, 121.49 MHz) δ 33.56, MS (ES$^+$) m/z = 447.92 (MH$^+$). |

TABLE 2-continued

| Compound | structure | Description |
| --- | --- | --- |
| 18aad | 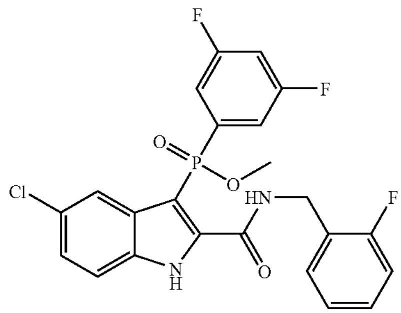 | Pale yellow powder, $^1$H NMR (d$_6$-DMSO, 300 MHz) δ 3.78 (d, J = 11.7 Hz, 3H), 4.54-4.74 (m, 2H), 7.16-7.28 (m, 2H), 7.28-7.65 (m, 7H), 7.74-7.75 (m, 1H), 10.84 (brs, 1H), 12.95 (brs, 1H), $^{31}$P NMR (d$_6$-DMSO, 121.49 MHz) δ 29.36, $^{19}$F NMR (d$_6$-DMSO, 282.40 MHz) δ −138 (m, 1F), −126.5 (m, 2F), MS (ES$^+$) m/z = 493 (MH$^+$). |
| 18aae | 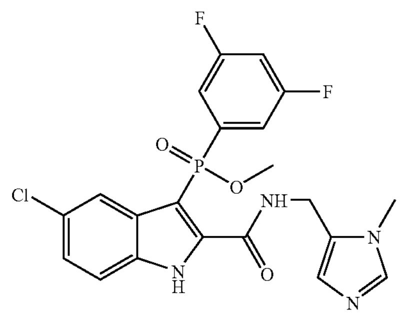 | White powder, $^1$H NMR (d$_6$-DMSO, 300 MHz) δ 3.64 (s, 3H), 3.77 (d, J = 11.4 Hz, 3H), 4.54-4.67 (m, 2H), 6.91 (brs, 1H), 7.33-7.39 (m, 3H), 7.5-7.62 (m, 3H), 7.67-7.68 (m, 1H), 10.68-10.72 (m, 1H), 12.95 (brs, 1H), $^{31}$P NMR (d$_6$-DMSO, 121.49 MHz) δ 30.92 (t, J = 8.5 Hz, 1P), $^{19}$F NMR (d$_6$-DMSO, 282.40 MHz) δ −106.77 (m, 2F), MS (ES$^+$) m/z = 479 (MH$^+$). |
| 18aaf | 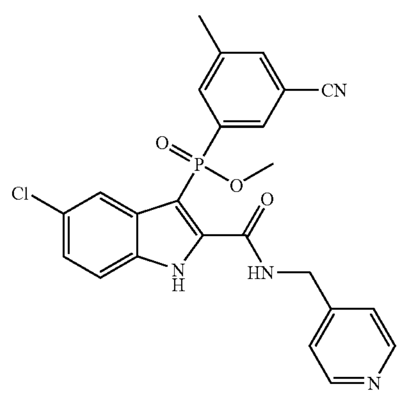 | Pale yellow powder, $^1$H NMR (CDCl$_3$, 300 MHz) δ 2.39 (s, 3H), 3.88 (d, J = 11.7 Hz, 3H), 4.76 (d, J = 5.4 Hz, 2H), 7.25-7.33 (m, 4H), 7.57-7.61 (m, 2H), 7.71-7.8 (m, 2H), 8.58-8.6 (m, 2H), 11.27 (brs, 1H), 11.59 (t, J = 5.4 Hz, 1H), $^{31}$P NMR (CDCl$_3$, 121.49 MHz) δ 31.35, MS (ES$^+$) m/z = 479.35 (MH$^+$). |
| 18aag | 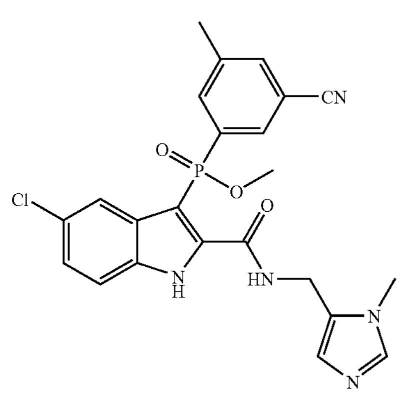 | Pale yellow powder, $^1$H NMR (CDCl$_3$, 300 MHz) δ 2.39 (s, 3H), 3.72 (s, 3H), 3.84 (d, J = 11.4 Hz, 3H), 4.71 (d, J = 5.4 Hz, 2H), 7.12 (s, 1H), 7.32 (dd, J = 1.5 and 8.7 Hz, 1H), 7.47-7.59 (m, 4H), 7.66-7.74 (m, 2H), 11.21 (brs, 1H), 11.38 (t, J = 5.4 Hz, 1H), $^{31}$P NMR (CDCl$_3$, 121.49 MHz) δ 31.21, MS (ES$^+$) m/z = 482.38 (MH$^+$). |

TABLE 2-continued

| Compound | structure | Description |
|---|---|---|
| 18aaj | 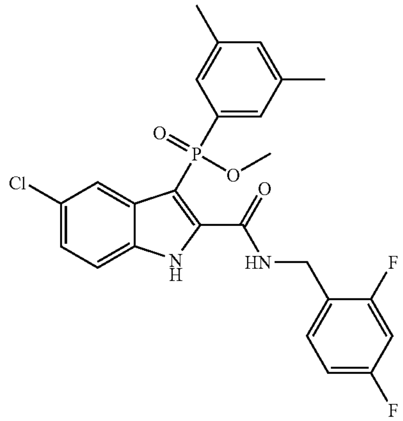 | Off-white solid, $^1$H NMR (d$_6$-DMSO, 300 MHz) δ 2.24 (s, 6H), 3.72 (d, J = 11.7 Hz, 3H), 4.53 (dd, J = 5.1 and 15.3 Hz, 1H), 4.68 (dd, J = 5.4 and 15 Hz, 1H), 7.06-7.12 (m, 1H), 7.21-7.34 (m, 5H), 7.48-7.53 (m, 1H), 7.58 (dd, J = 1.8 and 8.7 Hz, 1H), 7.63 (d, J = 1.8 Hz, 1H), 11.29 (t, J = 5.1 Hz, 1H), 12.82 (brs, 1H), $^{31}$P NMR (d$_6$-DMSO, 121.49 MHz) δ 32.79, MS (ES$^+$) m/z = 503 (MH$^+$). |
| 18aak | 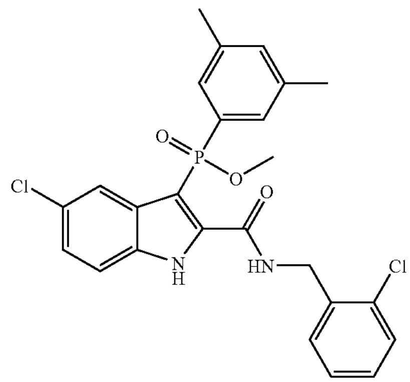 | Off-white solid, $^1$H NMR (d$_6$-DMSO, 300 MHz) δ 2.26 (s, 6H), 3.74 (d, J = 11.4 Hz, 3H), 4.60 (dd, J = 5.4 and 15.3 Hz, 1H), 4.77 (dd, J = 5.4 and 15.3 Hz, 1H), 7.22 (brs, 1H), 7.29 (brs, 1H), 7.31-7.38 (m, 4H), 7.49-7.52 (m, 2H), 7.6 (dd, J = 1.5 and 9 Hz, 1H), 7.64 (d, J = 1.8 Hz, 1H), 11.35 (t, J = 5.4 Hz, 1H), 12.84 (brs, 1H), $^{31}$P NMR (d$_6$-DMSO, 121.49 MHz) δ 32.72, MS (ES$^+$) m/z = 501 (MH$^+$) |
| 18aal | 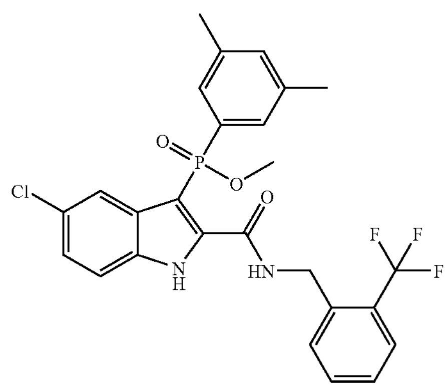 | Light yellow solid, $^1$H NMR (d$_6$-DMSO, 300 MHz) δ 2.24 (s, 6H), 3.73 (d, J = 11.7 Hz, 3H), 4.71 (dd, J = 4.8 and 15.3 Hz, 1H), 4.85 (dd, J = 4.8 and 15.3 Hz, 1H), 7.22-7.31 (m, 3H), 7.32 (dd, J = 2.1 and 8.7 Hz, 1H), 7.5-7.56 (m, 1H), 7.6 (dd, J = 1.8 and 9 Hz, 1H), 7.64 (dd, J = 1.8 and 10.5 Hz, 1H), 7.67 (d, J = 1.2 Hz, 1H), 7.76-7.79 (m, 1H), 11.38 (t, J = 5.4 Hz, 1H), 12.86 (brs, 1H), $^{31}$P NMR (d$_6$-DMSO, 121.49 MHz) δ 32.74, MS (ES$^+$) m/z = 535 (MH$^+$) |
| 18aam | 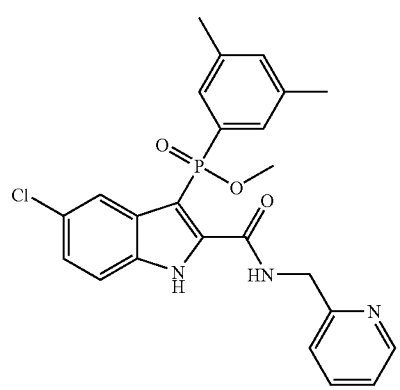 | White powder, $^1$H NMR (d$_6$-DMSO, 300 MHz) δ 2.26 (s, 6H), 3.75 (d, J = 11.7 Hz, 3H), 4.64 (dd, J = 5.4 and 15.9 Hz, 1H), 4.78 (dd, J = 6 and 15.9 Hz, 1H), 7.23 (brs, 1H), 7.29-7.42 (m, 5H), 7.6 (dd, J = 1.5 and 8.7 Hz, 1H), 7.65 (d, J = 1.8 Hz, 1H), 7.78 (td, J = 1.8 and 7.5 Hz, 1H), 8.54-8.57 (m, 1H), 11.39 (t, J = 5.7 Hz, 1H), 12.82 (brs, 1H), $^{31}$P NMR (d$_6$-DMSO, 121.49 MHz) δ 32.70, MS (ES$^+$) m/z = 468 (MH$^+$) |

TABLE 2-continued

| Compound | structure | Description |
| --- | --- | --- |
| 18aan | 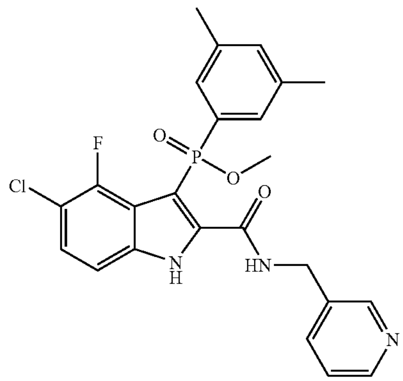 | White powder, $^1$H NMR (d$_6$-DMSO, 300 MHz) δ 2.26 (s, 6H), 3.69 (d, J = 11.7 Hz, 3H), 4.65 (ddd, J = 5.7 and 15.3 and 21.6 Hz, 2H), 7.21 (brs, 1H), 7.25 (brs, 1H), 7.3 (brs, 1H), 7.37-7.45 (m, 2H), 7.46 (dd, J = 1.5 and 8.7 Hz, 1H), 7.82 (td, J = 1.8 and 7.8 Hz, 1H), 8.49 (dd, J = 1.95 and 4.65 Hz, 1H), 8.64 (d, J = 1.8 Hz, 1H), 11.81 (t, J = 5.7 Hz, 1H), 13.06 (brs, 1H), $^{31}$P NMR (d$_6$-DMSO, 121.49 MHz) δ 32.10, MS (ES$^+$) m/z = 486 (MH$^+$) |
| 18aao | 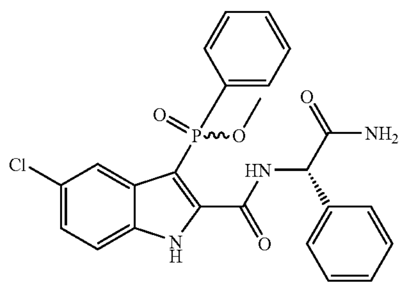 | Light yellow solid, $^1$H NMR (d$_6$-DMSO, 300 MHz) δ 3.75 (d, J = 11.4 Hz, 3H), 5.67 (d, J = 7.5 Hz, 1H), 7.2 (brs, 1H), 7.85 (dd, J = 1.8 and 8.7 Hz, 1H), 7.85-7.95 (m, 3H), 8.02-8.16 (m, 6H), 8.22 (d, J = 1.8 Hz, 1H), 8.28 (brs, 1H), 8.46-8.53 (m, 2H), 11.47 (d, J = 7.5 Hz, 1H), 12.76 (brs, 1H), $^{31}$P NMR (d$_6$-DMSO, 121.49 MHz) δ 31.79, MS (ES$^+$) m/z = 482 (MH$^+$) |
| 18aap | 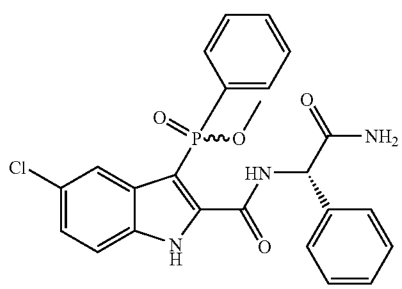 | Off-white solid, $^1$H NMR (d$_6$-DMSO, 300 MHz) δ 3.80 (d, J = 11.4 Hz, 3H), 5.63 (d, J = 7.5 Hz, 1H), 7.2 (brs, 1H), 7.33 (dd, J = 2.1 and 8.7 Hz, 1H), 7.33-7.45 (m, 5H), 7.52-7.61 (m, 6H), 7.69 (d, J = 2.1 Hz, 1H), 7.77 (brs, 1H), 11.32 (d, J = 7.5 Hz, 1H), 12.8 (brs, 1H), $^{31}$P NMR (d$_6$-DMSO, 121.49 MHz) δ 32.12. |
| 18aaq | 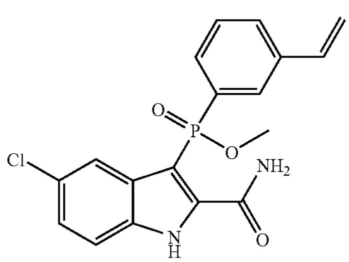 | White solid, $^1$H NMR (d$_6$-DMSO, 300 MHz) δ 3.77 (d, J = 11.4 Hz, 3H), 5.34 (d, J = 11.1 Hz, 1H), 5.86 (d, J = 17.7 Hz, 1H), 6.79 (dd, J = 11.1 and 17.7 Hz, 1H), 7.32 (dd, J = 2.1 and 8.7 Hz, 1H), 7.48-7.61 (m, 4H), 7.73 (dd, J = 1.5 and 7.8 Hz, 1H), 7.78-7.83 (m, 1H), 8.03 (brs, 1H), 10.2 (brs, 1H), 12.8 (brs, 1H), $^{31}$P NMR (d$_6$-DMSO, 121.49 MHz) δ 31.86, MS (ES$^+$) m/z = 374.83 (MH$^+$) |
| 18aar | 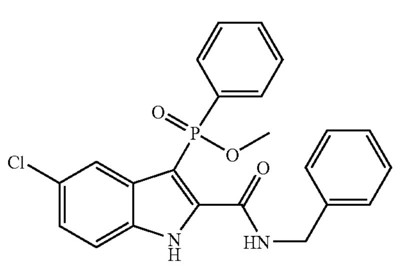 | Sticky off-white solid, $^1$H NMR (CDCl$_3$, 300 MHz) δ 3.84 (d, J = 11.4 Hz, 3H), 4.70 (dd, J = 5.4 and 15 Hz, 1H), 4.85 (dd, J = 6 and 15 Hz, 1H), 7.16 (dd, J = 1.8 and 8.7 Hz, 1H), 7.22-7.51 (m, 9H), 7.65-7.73 (m, 3H), 11.63 (brs, 1H), 11.68 (t, J = 5.4 Hz, 1H), $^{31}$P NMR (CDCl$_3$, 121.49 MHz) δ 33.98, MS (ES$^+$) m/z = 438.87 (MH$^+$) |

TABLE 2-continued

| Compound | structure | Description |
|---|---|---|
| 18aas | 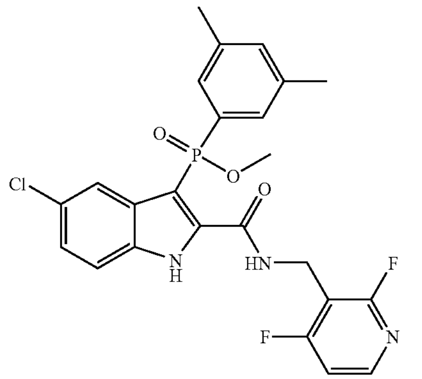 | |
| 18aat | 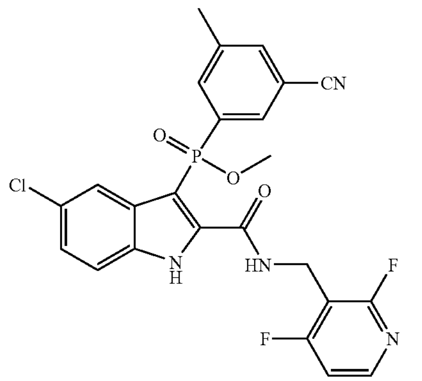 | |
| 19a | 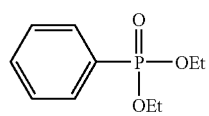 | Colorless oil, ¹H NMR (CDCl₃, 300 MHz) δ 3.76 (d, J = 11.1 Hz, 3H), 7.44-7.58 (m, 3H), 7.76-7.84 (m, 2H), ³¹P NMR (CDCl₃, 101.256 MHz) δ 22.2. |
| 19b | 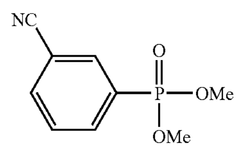 | Colorless oil, ¹H NMR (CDCl₃, 300 MHz) δ 3.81 (d, J = 11.1 Hz, 6H), 7.59-7.66 (m, 1H), 7.84-7.87 (m, 1H), 8-8.1 (m, 2H), ³¹P NMR (CDCl₃, 121.49 MHz) δ 17.94, MS (ES⁺) m/z = 212 (MH). |
| 19c | 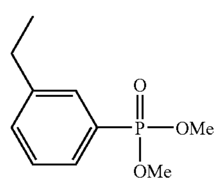 | Colorless oil, ¹H NMR (CDCl₃, 300 MHz) δ 1.27 (t, J = 7.5 Hz, 3H), 2.72 (q, J = 7.5 Hz, 2H), 3.78 (d, J = 11.1 Hz, 6H), 7.4-7.43 (m, 2H), 7.59-7.69 (m, 2H), MS (ES⁺) m/z = 215 (MH). |
| 19d | 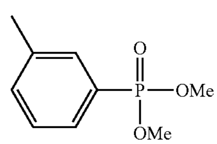 | Oil, ¹H NMR (CDCl₃, 300 MHz) δ 3.77 (d, J = 11.1 Hz, 6H), .7.28-7.39 (m, 2H), 7.57-7.66 (m, 2H), MS (ES⁺) m/z = 201 (MH). |
| 19e | 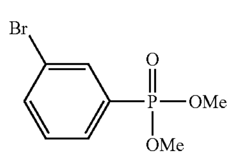 | Colorless oil, ¹H NMR (CDCl₃, 300 MHz) δ 3.78 (d, J = 11.4 Hz, 6H), 7.33-7.4 (m, 1H), 7.69-7.77 (m, 2H, 7.91-7.96 (m, 1H), ³¹P NMR (CDCl₃, 121.49 MHz) δ 19.2, MS (ES⁺) m/z = 265/267 (MH). |

TABLE 2-continued

| Compound | structure | Description |
|---|---|---|
| 19f | [structure: 3-(fluoromethyl)phenyl dimethyl phosphonate] | Colorless oil, $^1$H NMR (CDCl$_3$, 300 MHz) δ 3.79 (d, J = 11.1 Hz, 6H), 5.44 (d, J = 47.4 Hz, 2H), 7.5-7.63 (m, 2H), 7.78-7.85 (m, 2H), $^{31}$P NMR (CDCl$_3$, 121.49 MHz) δ 22, $^{19}$F NMR (CDCl$_3$, 282.40 MHz) δ −209.94 (t, J = 47.4 Hz, 1F), MS (ES$^+$) m/z = 219 (MH). |
| 19g | [structure: 3-fluoro-5-methylphenyl dimethyl phosphonate] | Yellowish oil, $^1$H NMR (CDCl$_3$, 300 MHz) δ 2.41 (s, 3H), 3.77 (d, J = 11.1 Hz, 6H), 7.06-7.1 (m, 1H), 7.24-7.32 (m, 1H), 7.4-7.44 (m, 1H), $^{31}$P NMR (CDCl$_3$, 121.49 MHz) δ 20.13 (d, J = 9.7 Hz, 1P), $^{19}$F NMR (CDCl$_3$, 282.40 MHz) δ −112.5 (m, 1F). |
| 19h | [structure: 3-propylphenyl dimethyl phosphonate] | Colourles oil, $^1$H NMR (d$_6$-DMSO, 300 MHz) δ 0.89 (t, J = 7.5 Hz, 3H), 1.6 (sextuplet, J = 7.5 Hz, 2H), 2.63 (t, J = 7.5 Hz, 2H), 3.65 (d, J = 11.4 Hz, 3H), 3.654 (d, J = 11.1 Hz, 3H), 7.47-7.50 (m, 3H), 7.54-7.55 (m, 1H), $^{31}$P NMR (d$_6$-DMSO, 121.49 MHz) δ 21.04, MS (ES$^+$) m/z = 229.3 (MH$^+$). |
| 19i | [structure: 3-ethyl-5-methylphenyl dimethyl phosphonate] | Colorless oil, $^1$H NMR (d$_6$-DMSO, 300 MHz) δ 1.18 (t, J = 7.5 Hz, 3H), 2.35 (s, 3H), 2.63 (q, J = 7.5 Hz, 2H), 3.64 (d, J = 11.1 Hz, 3H), 3.65 (d, J = 11.1 Hz, 3H), 7.31 (brs, 2H), 7.45-7.48 (m, 1H), $^{31}$P NMR (d$_6$-DMSO, 121.49 MHz) δ 21.40, MS (ES$^+$) m/z = 229.3 (MH$^+$). |
| 19j | [structure: 3-cyclopropylphenyl dimethyl phosphonate] | Colorless oil, $^1$H NMR (d$_6$-DMSO, 300 MHz) δ 0.68-0.74 (m, 2H), 0.97-1.03 (m, 2H), 2-2.07 (m, 1H), 3.65 (d, J = 11.1 Hz, 3H), 7.29-7.33 (m, 1H), 7.4-7.49 (m, 3H), $^{31}$P NMR (d$_6$-DMSO, 121.49 MHz) δ 21.05, MS (ES$^+$) m/z = 227 (MH$^+$). |
| 19k | [structure: 3-bromo-5-methylphenyl dimethyl phosphonate] | Colorless oil, $^1$H NMR (d$_6$-DMSO, 300 MHz) δ 2.37 (s, 3H), 3.67 (d, J = 11.1 Hz, 3H), 7.51-7.72 (m, 3H), $^{31}$P NMR (d$_6$-DMSO, 121.49 MHz) δ 18.44, MS (ES$^+$) m/z = 279/281 (MH$^+$). |
| 19l | [structure: 3-isopropylphenyl dimethyl phosphonate] | Yellow oil, $^1$H NMR (CDCl$_3$, 300 MHz) δ 1.27 (d, J = 6.9 Hz, 6H), 2.95 (quintuplet, J = 6.9 Hz, 1H), 3.77 (d, J = 11.1 Hz, 6H), 7.39-7.46 (m, 2H), 7.56-7.7 (m, 2H), $^{31}$P NMR (CDCl$_3$, 121.49 MHz) δ 22.41. |
| 19m | [structure: 3,5-difluorophenyl dimethyl phosphonate] | Colorless oil, $^1$H NMR (CDCl$_3$, 300 MHz) δ 3.8 (d, J = 11.1 Hz, 6H), 6.98-7.05 (m, 1H), 7.27-7.36 (m, 2H), $^{31}$P NMR (CDCl$_3$, 121.49 MHz) δ 17.87 (t, J = 9.96 Hz, 1P), $^{19}$F NMR (CDCl$_3$, 282.40 MHz) δ −107.27 (m, 2F). |

TABLE 2-continued

| Compound | structure | Description |
|---|---|---|
| 19n | 3-methoxyphenyl-P(=O)(OMe)₂ | Yellow oil, ¹H NMR (d₆-DMSO, 300 MHz) δ 3.65 (d, J = 11.1 Hz, 6H), 3.8 (s, 3H), 7.14-7.31 (m, 3H), 7.45-7.52 (m, 1H), ³¹P NMR (d₆-DMSO, 121.49 MHz) δ 20.45, MS (ESI, EI⁺) m/z = 217.2 (MH⁺) |
| 19p | 3,5-dimethylphenyl-P(=O)(OMe)₂ | Oil, ¹H NMR (d₆-DMSO, 300 MHz) δ 2.33 (s, 6H), 3.63 (d, J = 11.1 Hz, 6H), 7.28-7.29 (m, 2H), 7.32-7.34 (m, 1H), ³¹P NMR (d₆-DMSO, 121.49 MHz) δ 21.34, MS (ESI, EI⁺) m/z = 215 (MH⁺) |
| 19q | 3-fluorophenyl-P(=O)(OMe)₂ | Oil, ¹H NMR (CDCl₃, 300 MHz) δ 3.79 (d, J = 11.1 Hz, 6H), 7.25-7.3 (m, 1H), 7.43-7.64 (m, 3H), ³¹P NMR (CDCl₃, 101.256 MHz) δ 20 (d, J = 8.66 Hz, 1P), ¹⁹F NMR (CDCl₃, 282.4 MHz) δ −130.9 (m, 1F), MS (ESI, EI⁺) m/z = 205 (MH⁺). |
| 19r | 3-(benzyloxymethyl)phenyl-P(=O)(OMe)₂ | Oil, ¹H NMR (d₆-DMSO, 300 MHz) δ 3.65 (d, J = 11.1 Hz, 6H), 4.56 (s, 2H), 4.61 (s, 2H), 7.28-7.41 (m, 4H), 7.51-7.71 (m, 5H), ³¹P NMR (d₆-DMSO, 121.49 MHz) δ 20.68; MS (ES⁺) m/z = 307 (MH⁺) |
| 20a | phenyl-P(=O)(OEt)(OH) | Colorless oil; ¹H NMR (CDCl₃, 300 MHz) δ 3.71 and 3.74 (2s, 3H), 7.41-7.54 (m, 3H), 7.77-7.84 (m, 2H), 10.70 (brs, 1H); ³¹P NMR (CDCl₃, 101 MHz) δ 22.3. |
| 20b | 3-cyanophenyl-P(=O)(OMe)(OH) | Colorless oil, ¹H NMR (CDCl₃, 300 MHz) δ 3.76 (d, J = 11.4 Hz, 3H), .7.57-7.64 (m, 1H), 7.82-7.85 (m, 1H), 7.99-8.1 (m, 2H), 8.9 (brs, 1H), ³¹P NMR (CDCl₃, 121.49 MHz) δ 18.13, MS (ES⁺) m/z = 197.9 (MH). |
| 20c | 3-methylphenyl-P(=O)(OMe)(OH) | Colorless oil; ¹H NMR (CDCl₃, 300 MHz) δ 2.37 (s, 3H), 3.71 (d, J = 11.4 Hz, 3H), 7.32-7.35 (m, 2H), 7.58-7.64 (m, 2H), 10.73 (brs, 1H), ³MS (ES⁺) m/z = 187 (MH). |
| 20d | 3-bromophenyl-P(=O)(OMe)(OH) | Colorless oil, ¹H NMR (CDCl₃, 300 MHz) δ 3.71 (d, J = 11.1 Hz, 3H), 7.26-7.32 (m, 1H), 7.65-7.95 (m, 4H), ³¹P NMR (CDCl₃, 121.49 MHz) δ 19.07, MS (ES⁺) m/z = 251/253 (MH⁺). |
| 20e | 3-(fluoromethyl)phenyl-P(=O)(OMe)(OH) | Colorless oil, ¹H NMR (CDCl₃, 300 MHz) δ 3.75 (d, J = 11.4 Hz, 3H), 5.42 (d, J = 47.4 Hz, 2H), 7.4-7.6 (m, 3H), 7.8-7.85 (m, 2H), ³¹P NMR (CDCl₃, 121.49 MHz) δ 21.42, ¹⁹F NMR (CDCl₃, 282.40 MHz) δ −209.80 (t, J = 47.4 Hz, 1F), MS (ES⁺) m/z = 205 (MH). |

TABLE 2-continued

| Compound | structure | Description |
| --- | --- | --- |
| 20f | 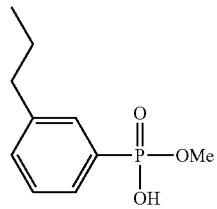 | Colorless oil, $^1$H NMR (CDCl$_3$, 300 MHz) δ 0.93 (t, J = 7.5 Hz, 3H), 1.64 (sextuplet, J = 7.5 Hz, 2H), 2.6 (t, J = 7.5 Hz, 2H), 3.71 (d, J = 11.4 Hz, 3H), 7.34-7.37 (m, 2H), 7.59-7.66 (m, 2H), 9.78 (brs, 1H), $^{31}$P NMR (CDCl$_3$, 121.49 MHz) δ 22.76, MS (ES$^+$) m/z = 215.2 (MH$^+$). |
| 20g | 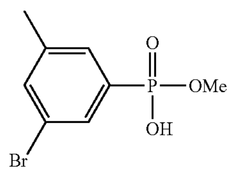 | Colorless oil, $^1$H NMR (d$_6$-DMSO, 300 MHz) δ 2.36 (s, 3H), 3.53 (d, J = 10.0 Hz, 3H), 7.47-7.64 (m, 3H), $^{31}$P NMR (d$_6$-DMSO, 121.49 MHz) δ 14.79, MS (ES$^+$) m/z = 263/265 (MH$^+$). |
| 20h | 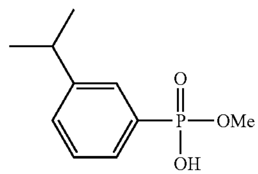 | Yellow pale oil, $^1$H NMR (CDCl$_3$, 300 MHz) δ 1.25 (d, J = 6.9 Hz, 6H), 2.89-2.98 (m, 1H), 3.72 (d, J = 11.4 Hz, 3H), 6.59 (brs, 1H), 7.34-7.43 (m, 2H), 7.59-7.69 (m, 2H), $^{31}$P NMR (CDCl$_3$, 121.49 MHz) δ 23.21. |
| 20i | 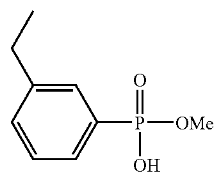 | Yellow pale oil, $^1$H NMR (CDCl$_3$, 300 MHz) δ 1.24 (t, J = 7.5 Hz, 3H), 2.67 (q, J = 7.5 Hz, 2H), 3.72 (d, J = 11.4 Hz, 3H), 7.35-7.39 (m, 2H), 7.59-7.67 (m, 3H), $^{31}$P NMR (CDCl$_3$, 121.49 MHz) δ 23.07, MS (ES$^+$) m/z = 201 (MH$^+$). |
| 20j | 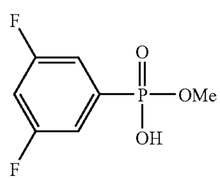 | Yellow oil, $^1$H NMR (CDCl$_3$, 300 MHz) δ 3.66 (d, J = 11.4 Hz, 3H), 6.92-6.98 (m, 1H), 7.24-7.31 (m, 2H), 7.64 (brs, 1H), $^{31}$P NMR (CDCl$_3$, 121.49 MHz) δ 16.92. |
| 20k | 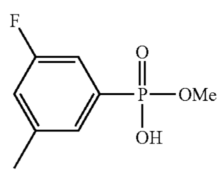 | Oil, $^1$H NMR (CDCl$_3$, 300 MHz) δ 2.37 (s, 3H), 3.71 (d, J = 11.4 Hz, 3H), 7.02-7.05 (m, 1H), 7.24-7.32 (m, 1H), 7.36-7.41 (m, 1H), $^{31}$P NMR (CDCl$_3$, 121.49 MHz) δ 19.66 (d, J = 9.6 Hz, 1P), $^{19}$F NMR (CDCl$_3$, 282.40 MHz) δ −112.7 (q, J = 9.32 Hz, 1F). |
| 20l | 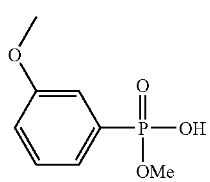 | Yellow oil, $^1$H NMR (d$_6$-DMSO, 300 MHz) δ 3.51 (d, J = 11.1 Hz, 3H), 3.79 (s, 3H), 7.12-7.28 (m, 3H), 7.39-7.46 (m, 1H), $^{31}$P NMR (d$_6$-DMSO, 101.256 MHz) δ 17.03, MS (ESI, EI$^+$), m/z = 203.2 (MH$^+$). |
| 20m | 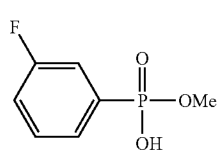 | Pale pink oil, $^1$H NMR (d$_6$-DMSO, 300 MHz) δ 3.53 (d, J = 11.1 Hz, 3H), 7.37-7.62 (m, 4H), $^{31}$P NMR (d$_6$-DMSO, 101.256 MHz) δ 15.11 (d, J = 8.77 Hz, 1P), $^{19}$F NMR (d$_6$-DMSO, 235.36 MHz) δ −111.8 (m, 1F), MS (ESI, EI$^+$) m/z = 191 (MH$^+$). |

TABLE 2-continued

| Compound | structure | Description |
|---|---|---|
| 20n | 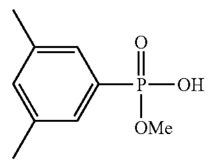 | Oil, ¹H NMR (d₆-DMSO, 300 MHz) δ 2.31 (s, 6H), 3.50 (d, J = 11.1 Hz, 3H), 7.20 (s, 1H), 7.26 (s, 1H), 7.31 (s, 1H), 12.03 (brs, 1H), MS (ESI, EI⁺) m/z = 201 (MH⁺) |
| 20p | 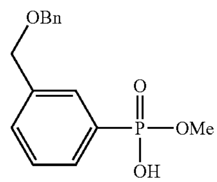 | Oil, ¹H NMR (d₆-DMSO, 300 MHz) δ 3.51 (d, J = 11.4 Hz, 3H), 4.56 (s, 2H), 4.59 (s, 2H), 7.3-7.71 (m, 9H), ³¹P NMR (d₆-DMSO, 121.49 MHz) δ 16.22, MS (ES⁺) m/z = 293 (MH⁺). |
| 22a | 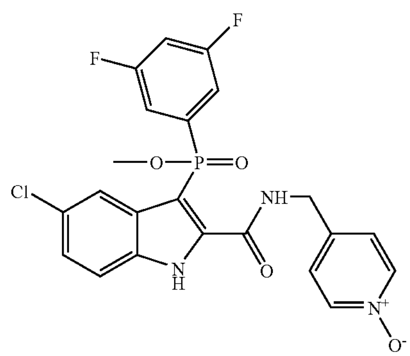 | White powder, ¹H NMR (CDCl₃, 300 MHz) δ 3.87 (d, J = 11.7 Hz, 3H), 4.55-4.74 (m, 2H), 6.97 (tt, J = 2.4 Hz and 8.7 Hz, 1H), 7.18-7.26 (m, 2H), 7.28-7.3 (m, 1H), 7.32-7.35 (m, 2H), 7.57 (dd, J = 1.8 Hz and 8.7 Hz, 1H), 7.61 (d, J = 2.1 Hz, 1H), 8.33 (d, J = 6.9 Hz, 2H), 11.51 (t, J = 5.7 Hz, 1H), 12.15 (brs, 1H), ³¹P NMR (CDCl₃, 121.49 MHz) δ 31.42 (t, J = 8.5 Hz, 1P), ³¹P NMR (CDCl₃, 282.40 MHz) δ POSITIF, MS (ES⁺) m/z = 492.28 (MH⁺). |
| 22b | 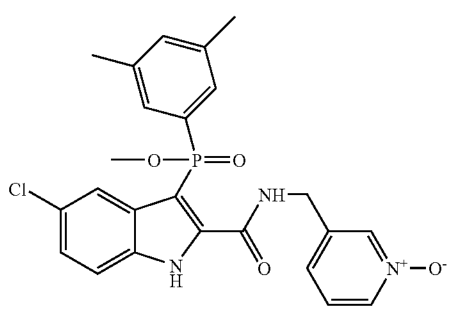 | Light orange powder, ¹H NMR (CDCl₃, 300 MHz) δ 2.31 (s, 6H), 3.83 (d, J = 11.7 Hz, 3H), 4.6-4.77 (m, 2H), 7.16-7.37 (m, 6H), 7.46-7.49 (m, 1H), 7.66-7.67 (m, 1H), 8.16-8.18 (m, 1H), 8.48 (brs, 1H), 11.31 (brs, 1H), ³¹P NMR (CDCl₃, 121.49 MHz) δ 34.5, MS (ES⁺) m/z = 484.43 (MH⁺). |
| 22c | 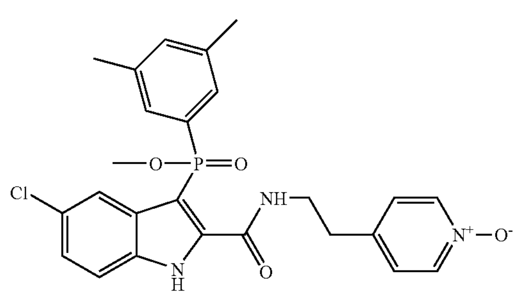 | White powder, ¹H NMR (CDCl₃, 300 MHz) δ 2.33 (s, 6H), 3.02 (t, J = 7.2 Hz, 2H), 3.77-3.82 (m, 2H), 3.81 (d, J = 11.7 Hz, 3H), 7.19-7.21 (m, 3H), 7.26-7.33 (m, 3H), 7.47-7.51 (m, 1H), 7.63-7.64 (m, 1H), 8.04-8.07 (m, 2H), 10.59 (brs, 1H), 11.32-11.35 (m, 1H), ³¹P NMR (CDCl₃, 121.49 MHz) δ 34.58, MS (ES⁺) m/z = 498.42 (MH⁺). |

TABLE 2-continued

| Compound | structure | Description |
|---|---|---|
| 22d | 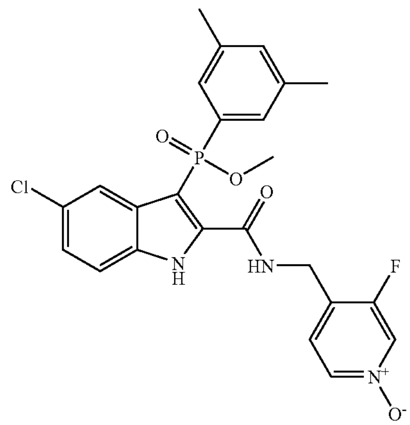 | White solid, $^1$H NMR (d$_6$,-DMS0, 300 MHz) δ 2.26 (s, 6H), 3.74 (d, J = 11.7 Hz, 3H), 4.57 (dd, J = 5.1 and 15.6 Hz, 1H), 4.67 (dd, J = 5.7 and 15.6 Hz, 1H), 7.22-7.34 (m, 4H), 7.44-7.49 (m, 1H), 7.57-7.60 (m, 2H), 8.11-8.14 (m, 1H), 8.55-8.57 (m, 1H), 11.37 (t, J = 5.4 Hz, 1H), 12.86 (brs, 1H), $^{31}$P NMR (d$_6$-DMSO, 121.49 MHz) δ 32.78, $^{19}$F NMR (d$_6$-DMSO, 282.40 MHz) δ −126.51 (m, 1F), MS (ES$^+$) m/z = 502.4 (MH$^+$). |
| 22e | 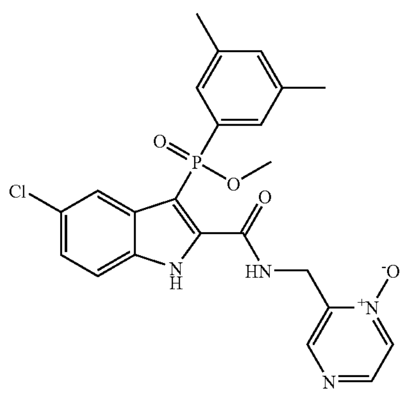 | White solid, $^1$H NMR (CDCl$_3$, 300 MHz) δ 2.34 (s, 6H), 3.86 (d, J = 11.4 Hz, 3H), 4.82-4.85 (m, 2H), 7.18 (brs, 1H), 7.33 (dd, J = 1.95 and 8.85 Hz, 1H), 7.36 (brs, 1H), 7.41 (brs, 1H), 7.47 (dd, J = 1.8 and 8.85 Hz, 1H), 7.7 (d, J = 1.8 Hz, 1H), 8-8.01 (m, 1H), 8.23 (brs, 1H), 8.41-8.42 (m, 1H), 10.45 (brs, 1H), 11.89-11.93 (m, 1H), $^{31}$P NMR (CDCl$_3$, 121.49 MHz) δ 34.03, MS (ES$^+$) m/z = 485.4 (MH$^+$). |
| 22f | 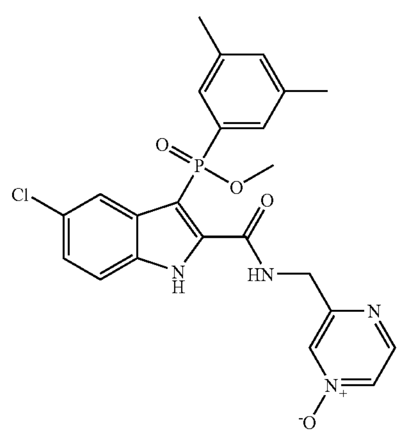 | White solid, $^1$H NMR (CDCl$_3$, 300 MHz) δ 2.33 (s, 6H), 3.87 (d, J = 11.4 Hz, 3H), 4.92 (d, J = 5.4 Hz, 1H), 7.18 (brs, 1H), 7.32 (dd, J = 1.8 and 9 Hz, 1H), 7.38 (brs, 1H), 7.43 (brs, 1H), 7.45 (dd, J = 2.1 and 8.4 Hz, 1H), 7.74 (d, J = 1.8 Hz, 1H), 8.17 (d, J = 3.9 Hz, 1H), 8.4 (d, J = 3.9 Hz, 1H), 8.62 (brs, 1H), 10.39 (brs, 1H), 11.85 (t, J = 5.7 Hz, 1H), MS (ES$^+$) m/z = 485.4 (MH$^+$). |

TABLE 2-continued

| Compound | structure | Description |
| --- | --- | --- |
| 22g | 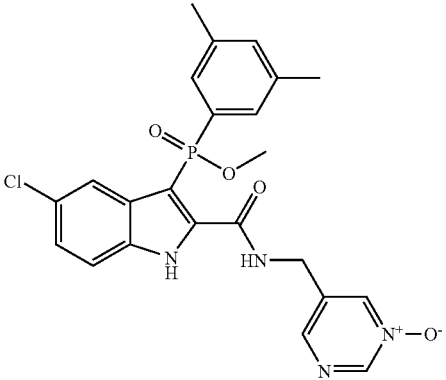 | White solid, $^1$H NMR (d$_6$-DMSO, 300 MHz) δ 2.26 (s, 6H), 3.74 (d, J = 11.4 Hz, 3H), 4.59 (dd, J = 5.1 and 15.9 Hz, 1H), 4.69 (dd, J = 5.40 and 15.9 Hz, 1H), 7.22 (brs, 1H), 7.31-7.34 (m, 3H), 7.59 (dd, J = 1.8 and 9 Hz, 2H), 8.34 (d, J = 1.8 Hz, 1H), 8.64 (t, J = 1.8 Hz, 1H), 9.01 (d, J = 2.1 Hz, 1H), 11.34 (t, J = 5.7 Hz, 1H), 12.87 (brs, 1H), $^{31}$P NMR (d$_6$-DMSO, 121.49 MHz) δ 32.70, MS (ES$^+$) m/z = 485.3 (MH$^+$). |
| 22h | 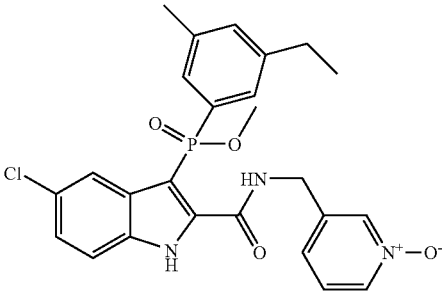 | White solid, $^1$H NMR (CDCl$_3$, 300 MHz) δ 1.20 (t, J = 7.5 Hz, 3H), 2.33 (s, 3H), 2.62 (q, J = 7.5 Hz, 2H), 3.84 (d, J = 11.7 Hz, 3H), 4.65 (dd, J = 5.7 and 15.5 Hz, 1H), 4.73 (dd, J = 5.7 and 15.6 Hz, 1H), 7.19-7.49 (m, 6H), 7.68 (m, 1H), 7.81 (m, 1H), 8.15 (d, J = 6.6 Hz, 1H), 8.42 (s, 1H), 10.70 (brs, 1H), 11.86 (t, J = 5.7 Hz, 1H), $^{31}$P NMR (CDCl$_3$, 121.49 MHz) δ 34.10, MS (ES$^+$) m/z = 498 (MH$^+$). |
| 22i | 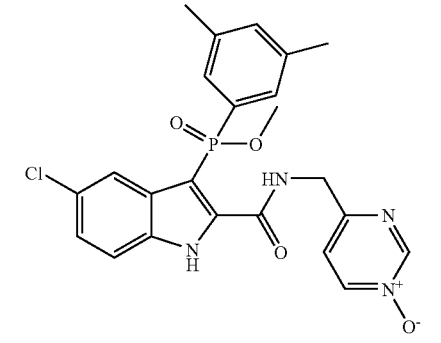 | Off-white solid, $^1$H NMR (d$_6$-DMSO, 300 MHz) δ 2.27 (s, 6H), 3.76 (d, J = 11.7 Hz, 3H), 4.59-4.74 (m, 2H), 7.24 (brs, 1H), 7.34 (dd, J = 2.1 and 8.7 Hz, 1H), 7.33 (brs, 1H), 7.37 (brs, 1H), 7.53-7.55 (m, 1H), 7.58-7.62 (m, 2H), 8.56 (dd, J = 2.1 and 6.9 Hz, 1H), 9.03-9.04 (m, 1H), 11.45 (t, J = 5.4 Hz, 1H), 12.86 (brs, 1H), $^{31}$P NMR (d$_6$-DMSO, 121.49 MHz) δ 32.67, MS (ES$^+$) m/z = 485.35 (MH$^+$). |
| 22j | 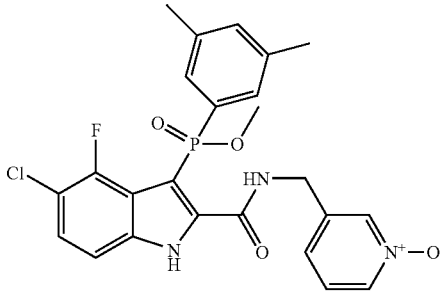 | Off-white solid, $^1$H NMR (d$_6$-DMSO, 300 MHz) δ 2.27 (s, 6H), 3.70 (d, J = 11.7 Hz, 3H), 4.59-4.60 (m, 2H), 7.22 (brs, 1H), 7.28 (brs, 1H), 7.33 (brs, 1H), 7.35-7.47 (m, 4H), 8.14 (d, J = 5.1 Hz, 1H), 8.29 (brs, 1H), 11.73 (t, J = 5.1 Hz, 1H), 13.07 (brs, 1H), $^{31}$P NMR (d$_6$-DMSO, 121.49 MHz) δ 32.03, MS (ES$^+$) m/z = 502.45 (MH$^+$). |

TABLE 2-continued

| Compound | structure | Description |
|---|---|---|
| 22k | 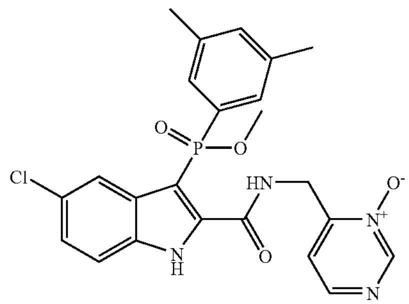 | Off-white solid, $^1$H NMR (CDCl$_3$, 300 MHz) δ 2.19 (s, 6H), 3.88 (d, J = 11.4 Hz, 3H), 4.96 (m, 2H), 7.24 (brs, 1H), 7.20-749 (m, 6H), 7.75 (m, 1H), 8.15 (d, J = 5.1 Hz, 1H), 9.40 (s, $^1$H), 10.23 (brs, 1H), 11.79 (brs, 1H), $^{31}$P NMR (CDCl$_3$, 121.49 MHz) δ 34.2, MS (ES$^+$) m/z = 485.35 (MH$^+$). |
| 22l | 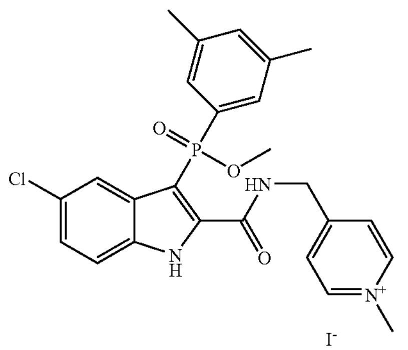 | Off-white solid, $^1$H NMR (d$_6$-DMSO, 300 MHz) δ 2.29 (s, 6H), 3.64 (d, J = 12 Hz, 3H), 4.32 (s, 3H), 4.95 (d, J = 5.4 Hz, 2H), 7.26 (brs, 1H), 7.35 (dd, J = 2.1 and 9 Hz, 1H), 7.38 (brs, 1H), 7.42 (brs, 1H), 7.57 (d, J = 1.8 Hz, 1H), 7.62 (dd, J = 1.8 and 9 Hz, 1H), 8.08 (d, J = 6.6 Hz, 2H), 8.93 (d, J = 6.6 Hz, 2H), 11.6 (t, J = 5.4 Hz, 1H), 12.88 (d, J = 3.6 Hz, 1H), $^{31}$P NMR (d$_6$-DMSO, 121.49 MHz) δ 32.64, MS (ES$^+$) m/z = 482.43 (M$^+$). |
| 22m | 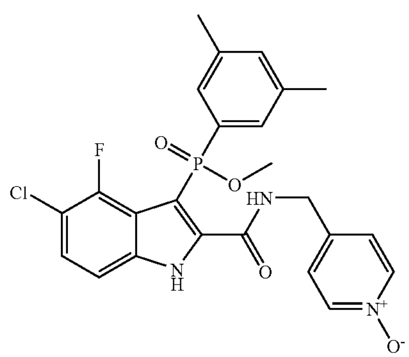 | Off-white solid, $^1$H NMR (CDCl$_3$, 300 MHz) δ 2.32 (s, 6H), 3.84 (d, J = 12 Hz, 3H), 4.68 (t, J = 5.1 Hz, 2H), 7.17 (brs, 1H), 7.28-7.38 (m, 6H), 8.26-8.28 (m, 2H), 11.39 (brs, 1H), 12.44 (t, J = 5.1 Hz, 1H), $^{31}$P NMR (CDCl$_3$, 121.49 MHz) δ 33.73, MS (ES$^+$) m/z = 502 (MH$^+$). |
| 22n | 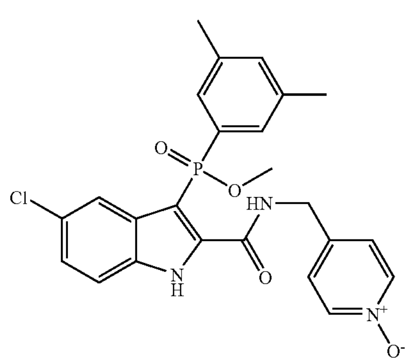 | Off-white solid, $^1$H NMR (d$_6$-DMSO, 300 MHz) δ 2.25 (s, 6H), 3.74 (d, J = 11.7 Hz, 3H), 4.55 (dd, J = 5.4 and 15.9 Hz, 1H), 4.65 (dd, J = 5.4 and 15.9 Hz, 1H), 7.23 (brs, 1H), 7.28 (brs, 1H), 7.31-7.35 (m, 2H), 7.38-7.4 (m, 2H), 7.59 (dd, J = 1.8 and 6.9 Hz, 2H), 8.19 (d, J = 6.9 Hz, 1H), 11.36 (t, J = 5.4 Hz, 1H), 12.86 (brs, 1H), $^{31}$P NMR (d$_6$-DMSO, 121.49 MHz) δ 32.83, MS (ES$^+$) m/z = 484.19 (MH$^+$). |

TABLE 2-continued

| Compound | structure | Description |
| --- | --- | --- |
| 22p | 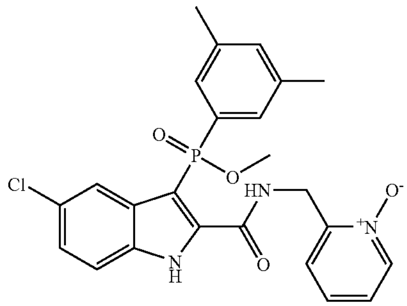 | Off-white solid, $^1$H NMR (d$_6$-DMSO, 300 MHz) δ 2.28 (s, 6H), 3.77 (d, J = 11.7 Hz, 3H), 4.64-4.74 (m, 2H), 7.24-7.47 (m, 7H), 7.57-7.64 (m, 2H), 8.34-8.36 (m, 1H), 11.32-11.37 (m, 1H), 12.86 (brs, 1H), $^{31}$P NMR (d$_6$-DMSO, 121.49 MHz) δ 32.67, MS (ES$^+$) m/z = 484.5 (MH$^+$). |
| 22q | 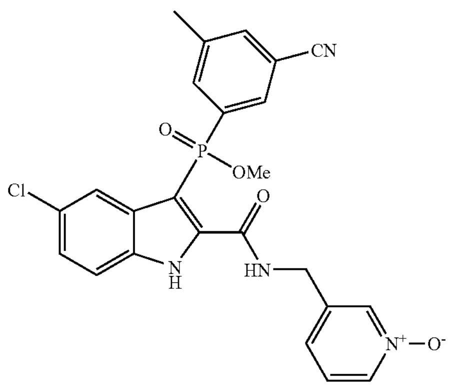 | |
| 22r | 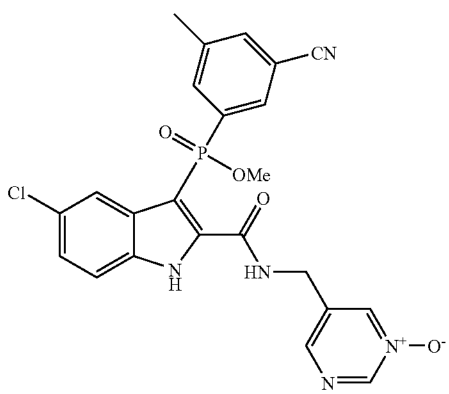 | |
| 22s | 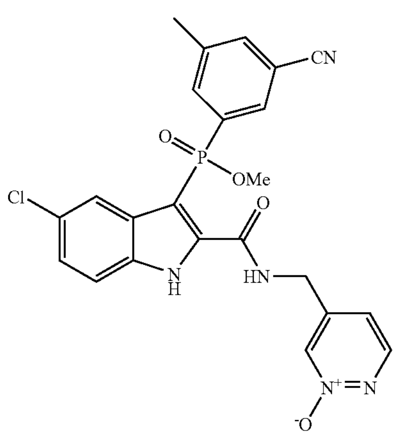 | |

TABLE 2-continued

| Compound | structure | Description |
|---|---|---|
| 22t | 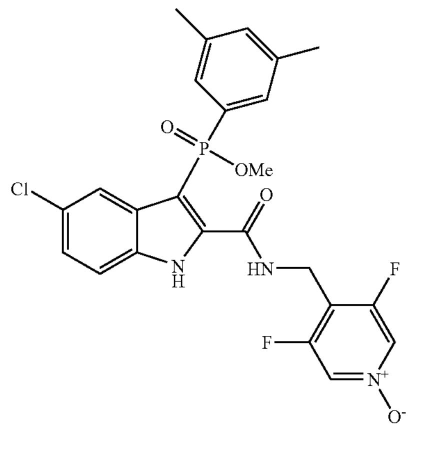 | |
| 22u | 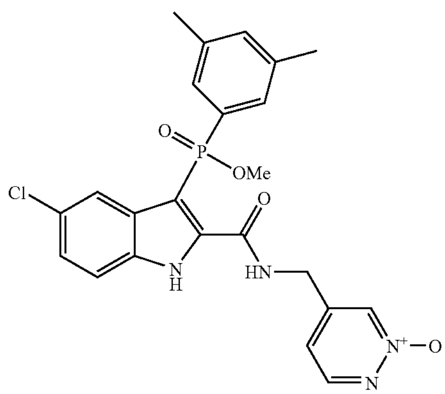 | |
| 22v | 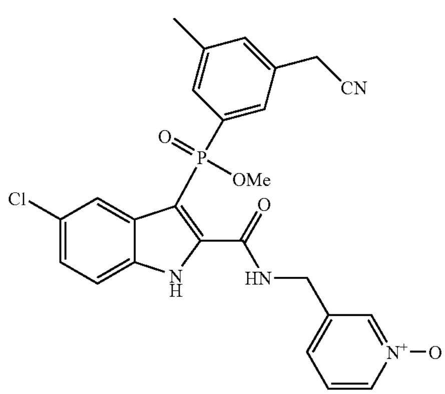 | |
| 22w | 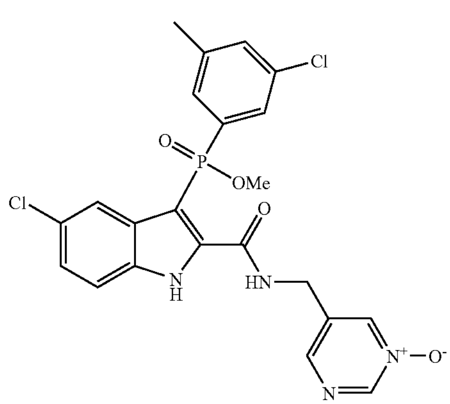 | |

TABLE 2-continued

| Compound | structure | Description |
|---|---|---|
| 22x | 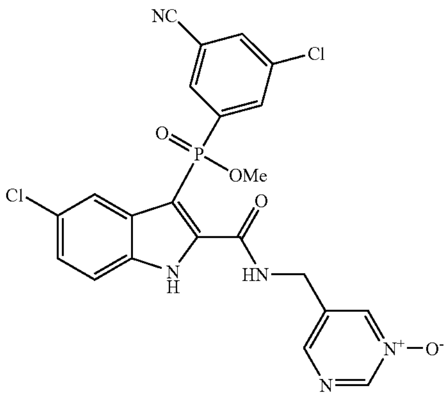 | |
| 22y | 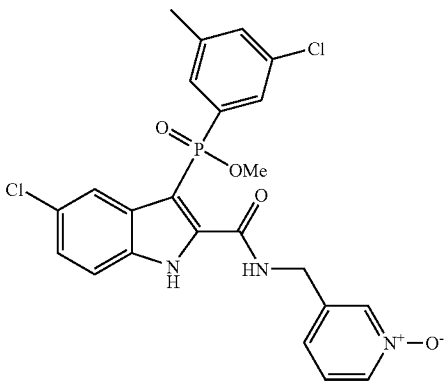 | |
| 22z | 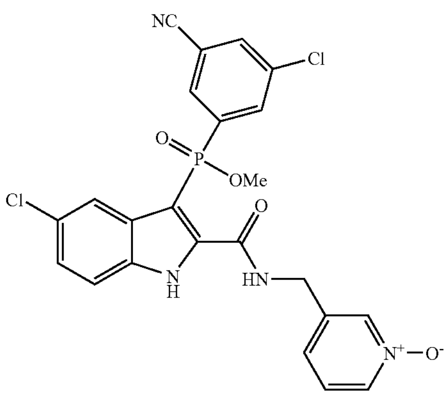 | |
| 22aa | 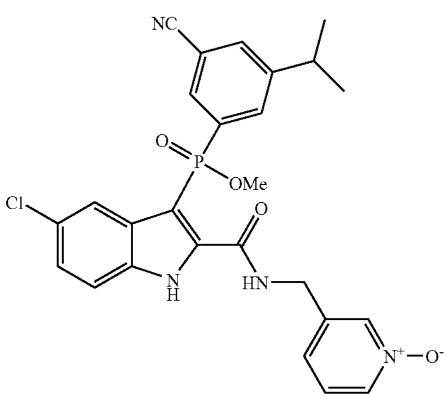 | |

TABLE 2-continued
| Compound | structure | Description |
| --- | --- | --- |
| 22ab | 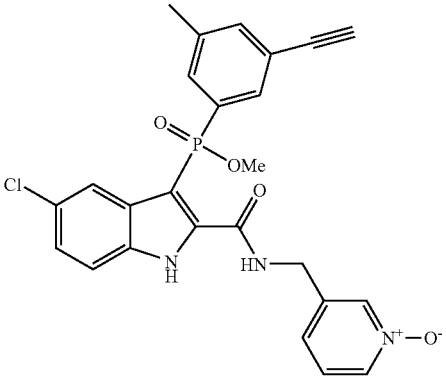 | |
| 22ac | 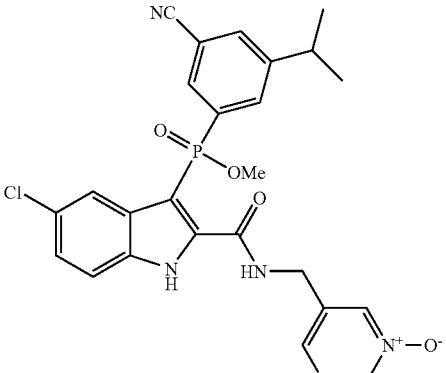 | |
| 22ad | 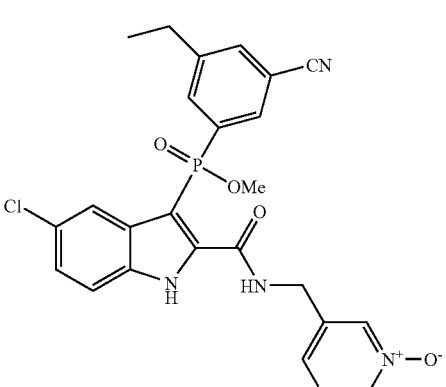 | |
| 22ae | 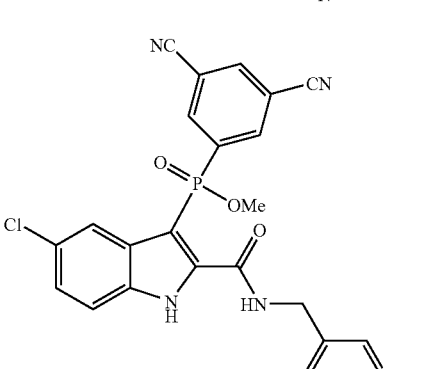 | |

TABLE 2-continued

| Compound | structure | Description |
|---|---|---|
| 22af | 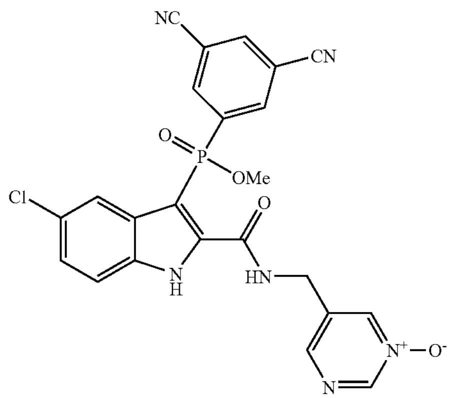 | |
| 22ag | 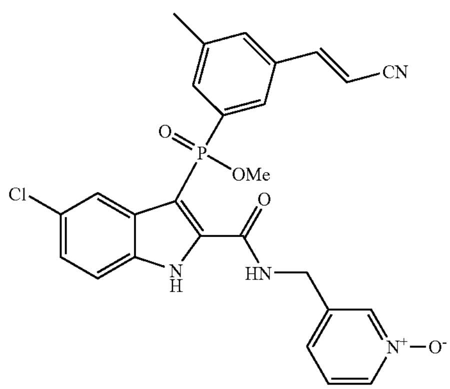 | |
| 22ah | 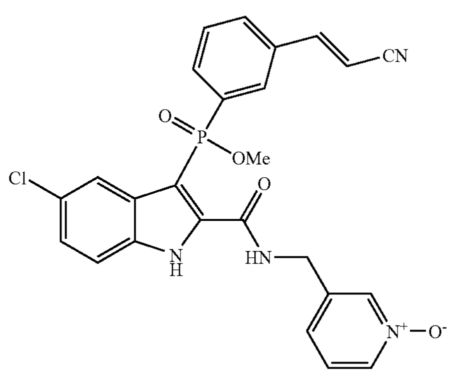 | |
| 22ai | 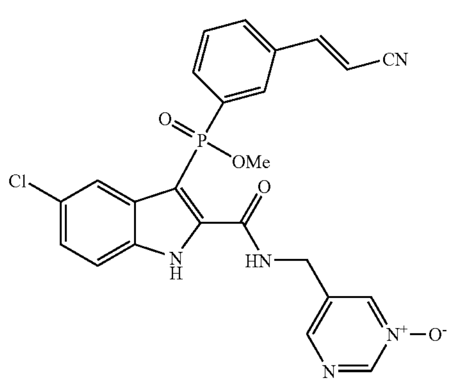 | |

| Compound | structure | Description |
|---|---|---|
| 22aj | 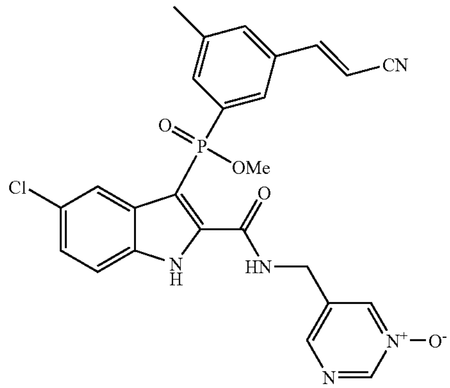 | |
| 22ak | 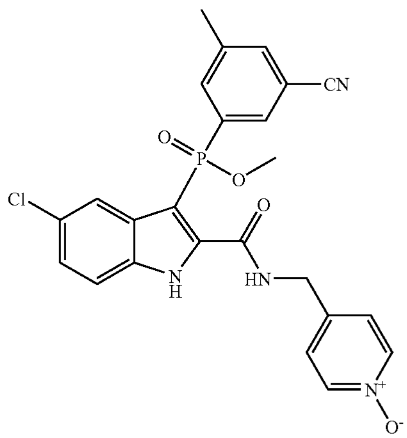 | Yellow powder, $^1$H NMR (CDCl$_3$, 300 MHz) δ 2.4 (s, 3H), 3.86 (d, J = 12 Hz, 3H), 4.58 (dd, J = 5.4 and 15.6 Hz, 1H), 4.73 (dd, J = 5.4 and 15.6 Hz, 1H), 7.33-7.35 (m, 3H), 7.53-7.60 (m, 3H), 7.7-7.8 (m, 2H), 8.27-8.3 (m, 2H), 11.55 (t, J = 5.4 Hz, 1H), 11.61 (brs, 1H), $^{31}$P NMR (CDCl$_3$, 121.49 MHz) δ 31.62, MS (ES$^+$) m/z = 495.4 (MH$^+$). |
| 22al | 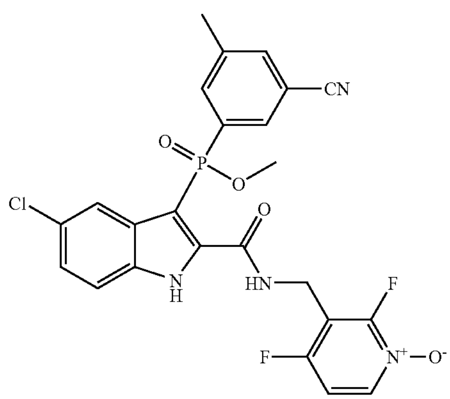 | |
| 22am | 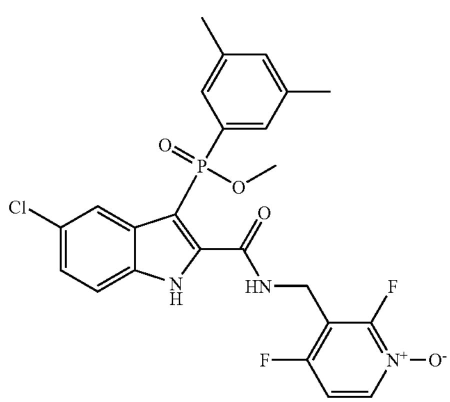 | |

TABLE 2-continued

| Compound | structure | Description |
|---|---|---|
| 23a | Phenyl-P(=O)(H)-OBn | Colorless oil, $^1$H NMR (CDCl$_3$, 300 MHz) δ 5.03-5.2 (m, 2H), 7.3-7.47 (m, 5H), 7.48-7.63 (m, 3H), 7.64 (d, J = 565.8 Hz, 1H), 7.75-7.83 (m, 2H), $^{31}$P NMR (CDCl$_3$, 101.256 MHz) δ 25.55, MS (ESI, EI$^+$) m/z = 233 (MH$^+$). |
| 23b | Phenyl-P(=O)(H)-OtBu | Colorless oil, $^1$H NMR (CDCl$_3$, 250 MHz) δ 1.59 (s, 9H), 7.76 (d, J = 552 Hz, 1H), 7.5-7.82 (m, 5H), $^{31}$P NMR (CDCl$_3$, 121.49 MHz) δ 15.27, MS (ESI, EI$^+$) m/z = 198 (MH$^+$). |
| 23c | 4-methylphenyl-P(=O)(H)-OMe | Colorless oil, $^1$H NMR (d$_6$-DMSO, 300 MHz) δ 2.38 (s, 3H), 3.68 (d, J = 12 Hz, 3H), 7.49 (d, J = 566 Hz, 1H), 7.4 (dd, J = 3 and 7.8 Hz, 2H), 7.62 (d, J = 13.8 Hz, 1H), 7.64 (d, J = 13.5 Hz, 1H) |
| 25a | 5-Cl-3-[P(=S)(Ph)]-3-OCH$_3$-2-CO$_2$Et-1-SO$_2$Ph-indoline | White oil, $^1$H NMR (CDCl$_3$, 300 MHz) δ 1.46 (t, J = 7.2 Hz, 3H), 3.74 (d, J = 14.4 Hz, 3H), 4.46-4.57 (m, 2H), 7.33 (dd, J = 1.95 Hz and 8.7 Hz, 1H), 7.43-7.56 (m, 5H), 7.62-7.67 (m, 1H), 7.93-8.01 (m, 4H), 8.09-8.13 (m, 2H), $^{31}$P NMR (CDCl$_3$, 121.49 MHz) δ 73.28, MS (ESI, EI$^+$) m/z = 534 (MH$^+$). |
| 25b | 5-Cl-3-[P(=S)(Ph)]-3-OMe-2-CONH$_2$-indole | White powder, $^1$H NMR (CDCl$_3$, 300 MHz) δ 3.80 (d, J = 14.4 Hz, 3H), 5.92 (brs, 1H), 7.32 (dd, J = 1.95 Hz and 9 Hz, 1H), 7.42-7.58 (m, 4H), 7.8-7.9 (m, 3H), 9.24 (brs, 1H), 10.15 (brs, 1H), $^{31}$P NMR (CDCl$_3$, 121.49 MHz) δ 80.48, MS (ESI, EI$^+$) m/z = 365 (MH$^+$). |
| 25'a | 5-Cl-3-[P(=O)(Ph)]-3-OMe-2-CSNH$_2$-indole | Yellow powder, $^1$H NMR (CDCl$_3$, 400 MHz) δ 3.86 (d, J = 11.6 Hz, 3H), 7.31 (dd, J = 1.95 Hz and 8.8 Hz, 1H), 7.42-7.47 (m, 3H), 7.52-7.56 (m, 1H), 7.69-7.78 (m, 3H), 8.05 (brs, 1H), 10.63 (brs, 1H), 12.5 (brs, 1H), $^{31}$P NMR (CDCl$_3$, 101.256 MHz) δ 34.54, MS (ESI, EI$^+$) m/z = 365 (MH$^+$). |
| 25'b | 5-Cl-3-[P(=O)(Ph)]-3-OEt-2-CSNH$_2$-indole | Yellow powder, $^1$H NMR (CDCl$_3$, 300 MHz) δ 1.45 (t, J = 7.2 Hz, 3H), 4.03-4.13 (m, 1H), 4.25-4.36 (m, 1H), 7.3 (dd, J = 1.95 Hz and 8.85 Hz, 1H), 7.41-7.47 (m, 3H), 7.51-7.56 (m, 1H), 7.72-7.79 (m, 3H), 8.01 (brs, 1H), 10.59 (brs, 1H), 12.59 (brs, 1H), $^{31}$P NMR (CDCl$_3$, 121.49 MHz) δ 32.32, MS (ESI, EI$^+$) m/z = 379 (MH$^+$). |

TABLE 2-continued

| Compound | structure | Description |
| --- | --- | --- |
| 26a | 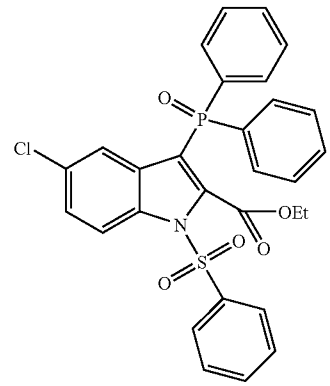 | White solid, $^1$H NMR (CDCl$_3$., 300 MHz) δ 1.18 (t, J = 7.2 Hz, 3H), 3.78 (q, J = 7.2 Hz, 2H), 7.33 (dd, J = 2.1 and 9 Hz, 1H), 7.45-7.75 (m, 14H), 7.93-7.97 (m, 1H), 8-8.04 (m, 2H), $^{31}$P NMR (CDCl$_3$, 101.256 MHz) δ 22.23, MS (ESI, EI$^+$) m/z = 564 (MH$^+$). |
| 27a | 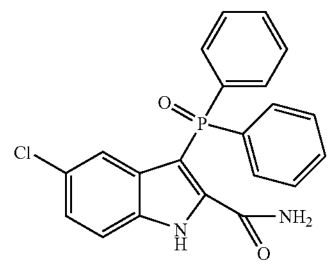 | White solid, $^1$H NMR (d$_6$-DMSO, 300 MHz) δ 6.13 (d, J = 1.8 Hz, 1H), 7.22 (dd, J = 2.1 and 8.7 Hz, 1H), 7.53-7.72 (m, 11H), 7.92 (brs, 1H), 10.37 (brs, 1H), 12.84 (brs, 1H), $^{31}$P NMR (d$_6$-DMSO, 101.256 MHz) δ 26.61, MS (ESI, EI$^+$) m/z = 395 (MH$^+$). |
| 28a | 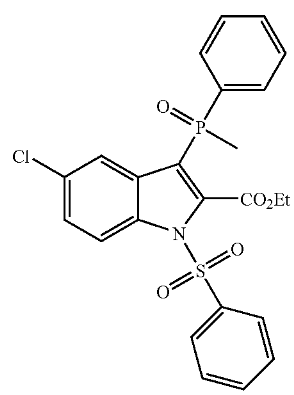 | Yellow thick oil, $^1$H NMR (CDCl$_3$, 300 MHz) δ 1.36 (t, J = 7.2 Hz, 3H), 4.2-4.41 (m, 2H), 7.32-7.35 (dd, J = 2.1 Hz and 9 Hz, 1H), 7.47-7.65 (m, 6H), 7.74-7.81 (m, 2H), 7.88-7.93 (m, 2H), 8-8.03 (m, 2H), $^{31}$P NMR (CDCl$_3$, 101.256 MHz) δ 25.04, MS (ESI, EI$^+$) m/z = 502 (MH$^+$). |
| 29a | 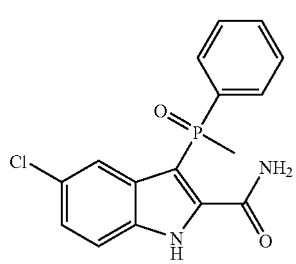 | White solid, $^1$H NMR (d$_6$-DMSO, 300 MHz) δ 2.24 (d, J = 13.5 Hz, 3H), 7.1 (m, 1H), 7.25 (dd, J = 1.2 and 8.7 Hz, 1H), 7.51-7.64 (m, 4H), 7.74-7.8 (m, 2H), 7.83-7.86 (m, 1H), 10.53 (brs, 1H), 12.62 (brs, 1H), $^{31}$P NMR (d$_6$-DMSO, 101.256 MHz) δ 30.62, MS (ESI, EI$^+$) m/z = 333 (MH$^+$). |

TABLE 2-continued

| Compound | structure | Description |
|---|---|---|
| 30a | (structure) | Yellow oil, $^1$H NMR (CDCl$_3$, 300 MHz) δ 1.44 (t, J = 6.5 Hz, 3H), 2.66 (d, J = 11.1 Hz, 6H), 4.48 (q, J = 6.7 Hz, 2H), 7.34 (d, J = 9.9 Hz, 1H), 7.45-7.52 (m, 5H), 7.60 (m, 1H), 7.85-7.95 (m, 4H), 8.07-8.09 (m, 2H), $^{31}$P NMR (CDCl$_3$, 101 MHz) δ 25.11, MS (ESI, EI$^+$) m/z = 531 (MH$^+$). |
| 31a | (structure) | Pale orange powder, $^1$H NMR (d$_6$-DMSO, 300 MHz) δ 2.64 (d, J = 11.7 Hz, 6H), 7.32 (dd, J = 2.1 and 8.7 Hz, 1H), 7.5-7.59 (m, 4H), 7.72-7.79 (m, 3H), 7.86 (brs, 1H), 10.85 (brs, 1H), 12.61 (brs, 1H), MS (ESI, EI$^+$) m/z = 384 (M + Na). |
| 32a | (structure) | Slight yellow solid; $^1$H NMR (CDCl$_3$, 300 MHz) δ 1.38-1.49 (m, 6H), 4.1-4.24 (m, 2H), 4.55 (q, J = 7.2 Hz, 2H), 5.97 (d, J = 16.8 Hz, 1H), 7.16-7.68 (m, 7H), 7.86-8.12 (m, 6H), $^{31}$P NMR (CDCl$_3$, 121.49 MHz) δ 22.82, MS (ES$^+$) m/z = 582.88 (MH$^+$). |
| 32b | (structure) | Slight yellow solid; $^1$H NMR (CDCl$_3$, 300 MHz) δ 1.38-1.49 (m, 6H), 4.1-4.24 (m, 2H), 4.55 (q, J = 7.2 Hz, 2H), 5.56 (d, J = 12 Hz, 1H), 7.16-7.68 (m, 7H), 7.86-8.12 (m, 6H), $^{31}$P NMR (CDCl$_3$, 121.49 MHz) δ 22.82, MS (ES$^+$) m/z = 582.88 (MH$^+$). |
| 33a | (structure) | White solid, $^1$H NMR (CDCl3, 300 MHz) δ 3.90 (d, J = 11.7 Hz, 3H), 5.80 (brs, 1H), 5.93 (d, J = 16.5 Hz, 1H), 7.39-7.92 (m, 5.93, 8H), 10.16 (brs, 1H), 10.85 (brs, 1H), $^{31}$P NMR (CDCl$_3$, 121.49 MHz) δ 31.53, MS (ES$^+$) m/z = 400 (MH$^+$). |

TABLE 2-continued

| Compound | structure | Description |
| --- | --- | --- |
| 38a | 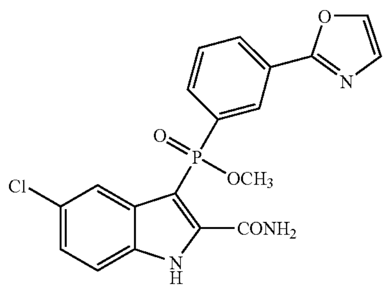 | |
| 38b | 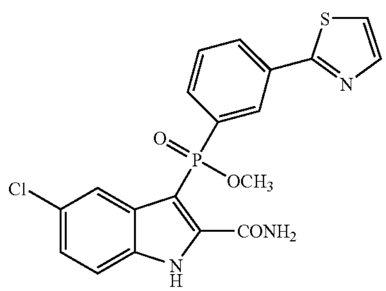 | |
| 38c | 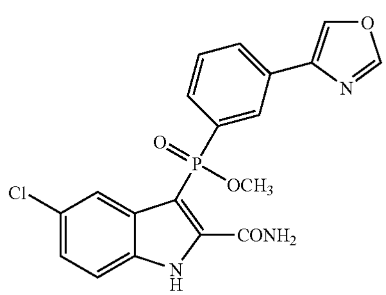 | |
| 38d | 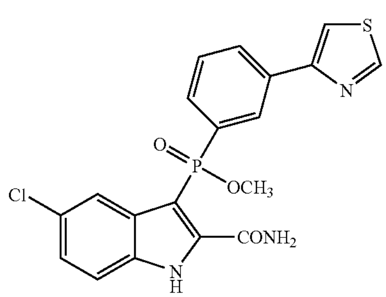 | |
| 38e | 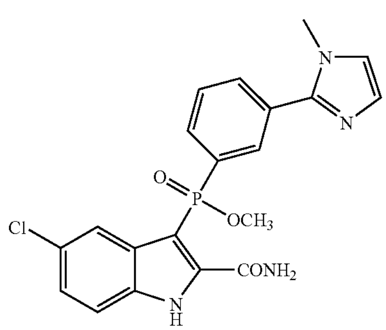 | |

TABLE 2-continued

| Compound | structure | Description |
| --- | --- | --- |
| 38f | 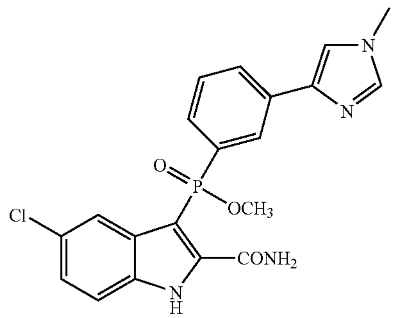 | |
| 38g | 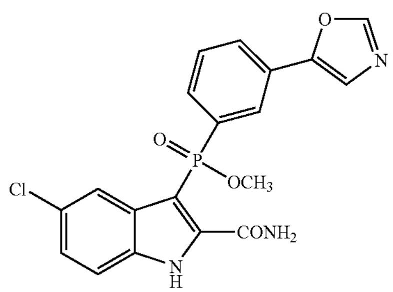 | |
| 38h | 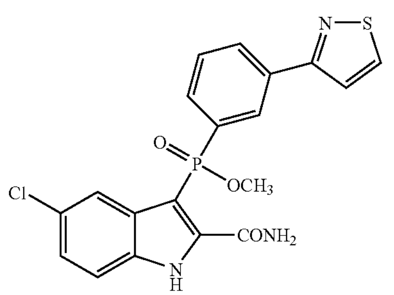 | |
| 38i | 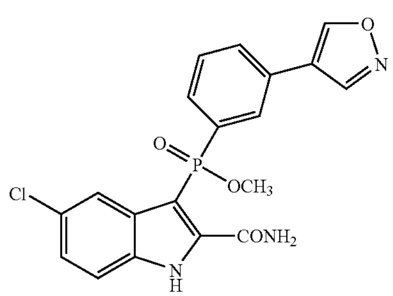 | |
| 38j | 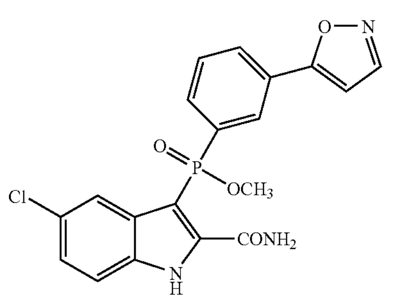 | |

TABLE 2-continued

| Compound | structure | Description |
|---|---|---|
| 38k | 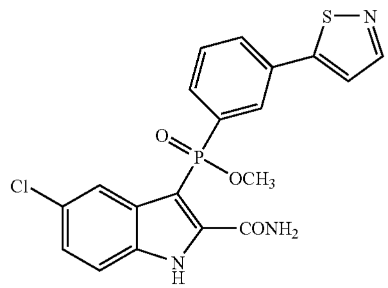 | |
| 43a | 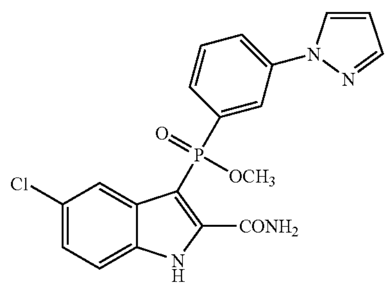 | |
| 43b | 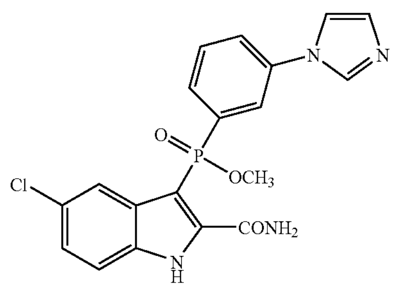 | |
| 43c | 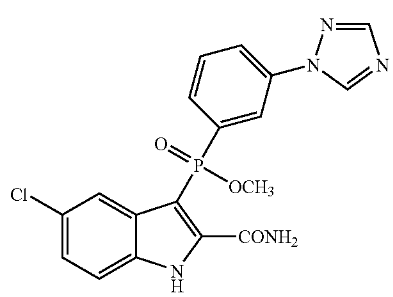 | |
| 47a | 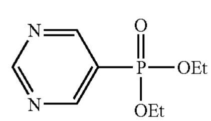 | Yellow oil, $^1$H NMR (CDCl$_3$, 300 MHz) δ 1.32 (t, J = 6.9 Hz, 6H), 420-4.10 (m, 4H), 9.01 (d, J = 6.6 Hz, 2H), 9.31 (d, J = 3.3 Hz, 1H), $^{31}$P NMR (CDCl$_3$, 121.49 MHz) δ 12.37, MS (ESI, EI$^+$) m/z = 217 (MH$^+$). |
| 47b | 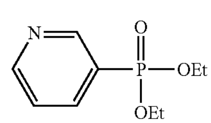 | Yellow oil, $^1$H NMR (CDCl$_3$, 300 MHz) δ 1.2 (t, J = 7.2 Hz, 6H), 3.95-4.1 (m, 4H), 7.25-7.3 (m, 1H), 7.93-8 (m, 1H), 8.62-8.64 (m, 1H), 8.83-8.85 (m, 1H) $^{31}$P NMR (CDCl$_3$, 121.49 MHz) δ 15.72. |
| 47c | 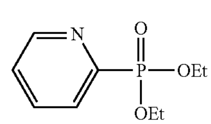 | Yellow oil, $^1$H NMR (CDCl$_3$, 300 MHz) δ 1.36 (t, J = 7.2 Hz, 6H), 4.16-4.31 (m, 4H), 7.41-7.46 (m, 1H), 7.77-7.85 (m, 1H), 7.96-8.01 (m, 1H), 8.8-8.82 (m, 1H) $^{31}$P NMR (CDCl$_3$, 121.49 MHz) δ 7.16, MS (ESI, EI$^+$), m/z = 216 (MH$^+$). |

TABLE 2-continued

| Compound | structure | Description |
|---|---|---|
| 47d | pyridin-4-yl-P(=O)(OEt)(OEt) | Brown oil, ¹H NMR (CDCl₃, 300 MHz) δ 1.27 (t, J = 6.9 Hz, 6H), 4.01-4.16 (m, 4H), 7.56-7.62 (m, 2H), 8.67-8.71 (m, 2H), ³¹P NMR (CDCl₃, 121.49 MHz) δ 14.63, MS (ESI, EI⁺) m/z = 216 (MH⁺). |
| 47e | thiophen-3-yl-P(=O)(OEt)(OEt) | Oil, ¹H NMR (CDCl₃, 300 MHz) δ 1.33 (t, J = 7.2 Hz, 6H), 4.04-4.19 (m, 4H), 7.32-7.35 (m, 1H), 7.41-7.45 (m, 1H), 7.97-8.01 (m, 1H), ³¹P NMR (CDCl₃, 121.49 MHz) δ 13.35, MS (ESI, EI⁺) m/z = 221.11 (MH⁺). |
| 47f | thiophen-2-yl-P(=O)(OEt)(OEt) | Yellow pale oil, ¹H NMR (CDCl₃, 300 MHz) δ 1.34 (t, J = 7.05 Hz, 6H), 4.06-4.22 (m, 4H), 7.16-7.20 (m, 1H), 7.65-7.72 (m, 2H), ³¹P NMR (CDCl₃, 121.49 MHz) δ 12.05, MS (ESI, EI⁺) m/z = 221.11 (MH⁺). |
| 48a | thiophen-3-yl-P(=O)(OEt)(OH) | Yellow oil, ¹H NMR (CDCl₃, 300 MHz) δ 1.27 (t, J = 7.05 Hz, 3H), 4.01-4.07 (m, 2H), 7.31-7.4 (m, 2H), 7.91-7.95 (m, 1H), 12.73 (s, 1H), ³¹P NMR (CDCl₃, 101.256 MHz) δ 14.67. |
| 48b | thiophen-2-yl-P(=O)(OEt)(OH) | Yellow oil, ¹H NMR (CDCl₃, 300 MHz) δ 1.31 (t, J = 7.05 Hz, 3H), 4.04-4.14 (m, 2H), 7.12-7.16 (m, 1H), 7.61-7.68 (m, 2H), 9.12 (brs, 1H), ³¹P NMR (CDCl₃, 121.49 MHz) δ 14.7. |
| 50a | 5-chloro-3-[(thiophen-2-yl)(ethoxy)phosphoryl]-1-(phenylsulfonyl)-1H-indole-2-carboxylic acid ethyl ester | Yellowish powder, ¹H NMR (CDCl₃, 300 MHz) δ 1.41 (t, J = 7.05 Hz, 3H), 1.49 (t, J = 7.05 Hz, 3H), 4.13-4.28 (m, 2H), 4.57 (qd, J = 1.8 Hz and 7.05 Hz, 2H), 7.16-7.19 (m, 1H), 7.36 (dd, J = 2.4 Hz and 9 Hz, 1H), 7.50-7.56 (m, 2H), 7.61-7.73 (m, 3H), 7.9-7.96 (m, 2H), 8.1-8.14 (m, 2H), MS (ESI, EI⁺) m/z = 537 (MH⁺). |
| 50b | 5-chloro-3-[(pyridin-2-yl)(ethoxy)phosphoryl]-1-(phenylsulfonyl)-1H-indole-2-carboxylic acid ethyl ester | Yellowish powder, ¹H NMR (CDCl₃, 300 MHz) δ 1.38 (t, J = 7.05 Hz, 3H), 1.42 (t, J = 7.05 Hz, 3H), 4.08-4.26 (m, 2H), 4.52 (q, J = 7.05 Hz, 2H), 7.34 (dd, J = 2.1 Hz and 9 Hz, 1H), 7.35-7.41 (m, 1H), 7.47-7.53 (m, 2H), 7.58-7.64 (m, 1H), 7.77-7.84 (m, 1H), 7.88-7.92 (m, 1H), 8.03-8.15 (m, 4H), 8.72-8.74 (m, 1H), ³¹P NMR (CDCl₃, 121.49 MHz) δ 19.72. |
| 50c | 5-chloro-3-[(thiophen-3-yl)(ethoxy)phosphoryl]-1-(phenylsulfonyl)-1H-indole-2-carboxylic acid ethyl ester | Oil, ¹H NMR (CDCl₃, 300 MHz) δ 1.37 (t, J = 7.05 Hz, 3H), 1.45 (t, J = 7.2 Hz, 3H), 4.05-4.22 (m, 2H), 4.52 (q, J = 7.2 Hz, 2H), 7.34 (dd, J = 2.1 and 8.7 Hz, 1H), 7.39 (dd, J = 2.1 and 3.3 Hz, 2H), 7.48-7.54 (m, 2H), 7.6-7.65 (m, 1H), 7.88 (d, J = 1.8 Hz, 1H), 7.92 (dd, J = 1.8 and 9 Hz, 1H), 8.02-8.1 (m, 3H), ³¹P NMR (CDCl₃, 121.49 MHz) δ 18.36. |

TABLE 2-continued

| Compound | structure | Description |
|---|---|---|
| 51 | 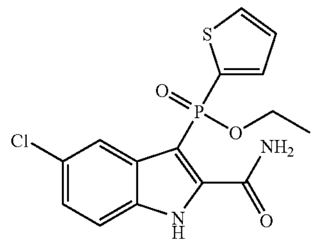 | White powder, ¹H NMR (d₆-DMSO, 300 MHz) δ 1.33 (t, J = 7.05 Hz, 3H), 4.03-4.09 (m, H), 4.15-4.24 (m, 1H), 7.21-7.23 (m, 1H), 7.34 (dd, J = 2.1 and 8.7 Hz, 1H), 7.55-7.61 (m, 2H), 7.7 (d, J = 2.1 Hz, 1H), 8-8.03 (m, 2H), 10.12 (brs, 1H), 12.76 (brs, 1H), ³¹P NMR (d₆-DMSO, 121.49 MHz) δ 23.46, MS (ES⁺) m/z = 368.8 (MH⁺). |
| 52a | 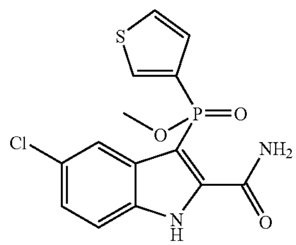 | Beige powder, ¹H NMR (CDCl₃, 300 MHz) δ 3.83 (d, J = 12 Hz, 3H), 5.93 (brs, 1H), 7.3-7.34 (m, 2H), 7.39-7.42 (m, 1H), 7.47 (dd, J = 1.8 Hz and 8.7 Hz, 1H), 7.7 (d, J = 1.8 Hz, 1H), 7.91 (ddd, J = 1.2 Hz and 2.7 Hz and 8.1 Hz, 1H), 10.44 (brs, 1H), 10.95 (brs, 1H), MS (ES⁺) m/z = 353.06 (MH⁺). |
| 53b | 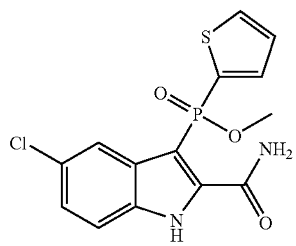 | White powder, ¹H NMR (d₆-DMSO, 300 MHz) δ 3.77 (d, J = 12 Hz, 3H), 7.22-7.24 (m, 1H), 7.34 (dd, J = 1.8 and 8.7 Hz, 1H), 7.56-7.61 (m, 2H), 7.66 (d, J = 1.8 Hz, 1H), 8.01-8.05 (m, 2H), 10.1 (brs, 1H), 12.81 (brs, 1H), MS (E5) m/z = 354.7 (MH⁺). |
| 53a | 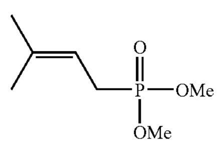 | Colorless oil, ¹H NMR (CDCl₃, 300 MHz) δ 1.66 (d, J = 3.9 Hz, 3H), 1.76 (d, J = 5.4 Hz, 3H), 2.57 (dd, J = 7.65 and 21.75 Hz, 2H), 3.74 (d, J = 10.5 Hz, 6H), 5.12-5.21 (m, 1H), ³¹P NMR (CDCl₃, 121.49 MHz) δ 7.32, MS (ESI, EI⁺) m/z = 179 (MH⁺). |
| 56a | 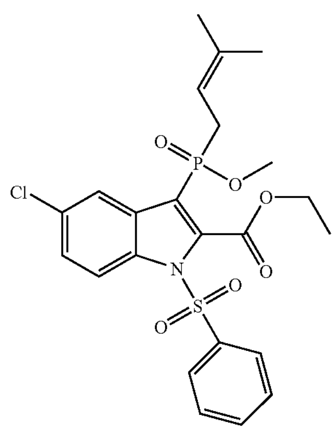 | Thick yellow oil, ¹H NMR (CDCl₃, 300 MHz) δ 1.24 (d, J = 3.9 Hz, 3H), 1.5 (t, J = 7.2 Hz, 3H), 1.54 (d, J = 6 Hz, 3H), 2.78 (dd, J = 8.1 and 19.5 Hz, 2H), 3.7 (d, J = 11.1 Hz, 3H), 4.57 (q, J = 7.2 Hz, 2H), 5.07-5.1 (m, 1H), 7.37 (dd, J = 2.1 and 8.7 Hz, 1H), 7.5-7.55 (m, 2H), 7.63-7.67 (m, 1H), 7.87 (d, J = 1.8 Hz), 7.96 (dd, J = 1.2 and 9 Hz, 1H), 8.1-8.13 (m, 2H), ³¹P NMR (CDCl₃, 121.49 MHz) δ 8.68, MS (ESI, EI⁺) m/z = 511 (MH⁺). |
| 57a | 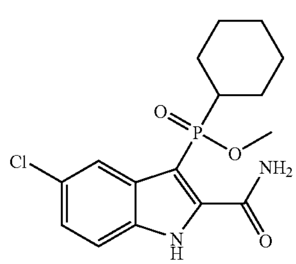 | White solid, ¹H NMR (d₆-DMSO, 300 MHz) δ 1.03-1.38 (m, 4H), 1.49-1.75 (m, 4H), 1.87-1.98 (m, 2H), 3.59 (d, J = 11.1 Hz, 3H), 7.33 (dd, J = 1.95 and 8.7 Hz, 1H), 7.59 (d, J = 8.7 Hz, 1H), 7.67 (brs, 1H), 7.87 (brs, 1H), 10.23 (brs, 1H), 12.69 (brs, 1H), ³¹P NMR (d₆-DMSO, 101.256 MHz) δ 48.93, MS (ESI, EI⁺) m/z = 355 (MH⁺). |

TABLE 2-continued

| Compound | structure | Description |
| --- | --- | --- |
| 57b | 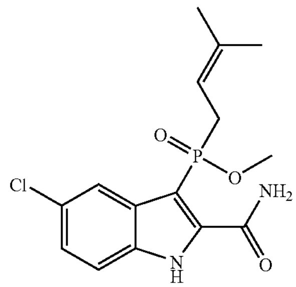 | Pale yellow solid, ¹H NMR (d₆-DMSO, 300 MHz) δ 1.17 (d, J = 3.6 Hz, 3H), 1.55 (d, J = 5.7, Hz, 3H), 2.81 (m, 2H), 3.62 (d, J = 11.1 Hz, 3H), 5.0 (m, 1H), 7.33 (dd, J = 2.0 and 8.7 Hz, 1H), 7.57 (d, J = 8.7 Hz, 1H), 7.68 (d, J = 2.0 Hz, 1H), 7.85 (brs, 1H), 7.87 (brs, 1H), 10.10 (brs, 1H), 12.64 (brs, 1H), MS (ESI, EI⁺) m/z = 341 (MH⁺). |
| 59a | 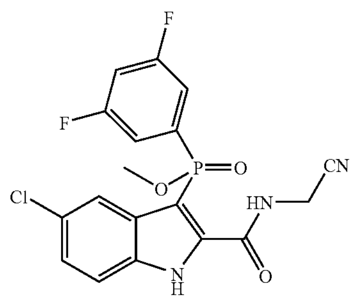 | Yellow powder, ¹H NMR (CDCl₃, 300 MHz) δ 3.88 (d, J = 12 Hz, 3H), 4.4 (d, J = 5.4 Hz, 2H), 6.98 (tt, J = 2.4 Hz and 8.7 Hz, 1H), 7.26-7.31 (m, 2H), 7.38 (dd, J = 1.8 Hz and 8.7 Hz, 1H), 7.59 (d, J = 1.5 Hz, 1H), 7.46 (dd, J = 1.8 Hz and 8.7 Hz, 1H), 11.24 (brs, 1H), 11.79 (t, J = 5.4 Hz, 1H), ³¹P NMR (CDCl₃, 121.49 MHz) 630.82 (t, J = 8.6 Hz, 1P), ¹⁹F NMR (CDCl₃, 282.40 MHz) δ −106.22 (m, 2F), MS (ES⁺) m/z = 424.04 (MH⁺). |
| 59b | 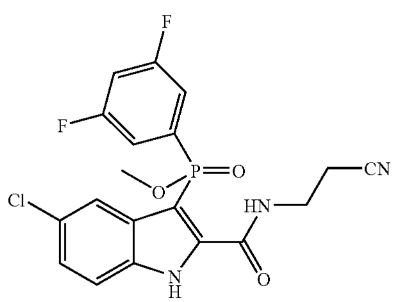 | Yellow powder, ¹H NMR (CDCl₃, 300 MHz) δ 2.8 (t, J = 6.9 Hz, 2H), 3.79-3.85 (m, 2H), 3.87 (d, J = 11.7 Hz, 3H), 6.96 (tt, J = 2.4 Hz and 8.7 Hz, 1H), 7.25-7.33 (m, 2H), 7.36 (d, J = 1.8 Hz, 1H), 7.53 (dd, J = 1.8 Hz and 8.7 Hz, 1H), 7.60 (d, J = 1.8 Hz, 1H), 11.13 (brs, 1H), 11.46 (t, J = 5.4 Hz, 1H), ¹⁹F NMR (CDCl₃, 282.40 MHz) δ −106.25 (m, 2F), MS (ES⁺) m/z = 437.96 (MH⁺). |
| 60a | 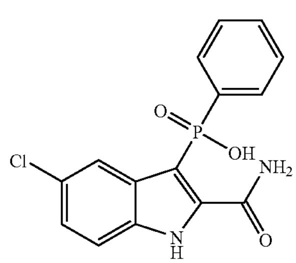 | White solid, ¹H NMR (d₆-DMSO, 300 MHz) δ 7.14-7.17 (m, 1H), 7.32-7.73 (m, 7H), 8.16 (brs, 1H), 11.78 (brs, 1H), 12 (brs, 1H), MS (ESI, EI⁺) m/z = 335 (MH⁺). |

TABLE 2-continued

| Compound | structure | Description |
| --- | --- | --- |
| 60b | 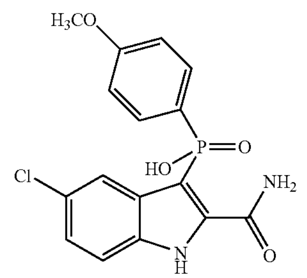 | White powder, $^1$H NMR ($d_6$-DMSO, 300 MHz) δ 3.72 (s, 3H), 6.9-6.93 (m, 2H), 7.19 (dd, J = 1.5 Hz and 8.7 Hz, 1H), 7.43-7.46 (m, 1H), 7.58-7.69 (m, 3H), 8-8.03 (m, 1H), 11.25 (brs, 1H), 12.15 (brs, 1H), $^{31}$P NMR ($d_6$-DMSO, 121.49 MHz) δ 31.44, MS (ESI, EI$^+$) m/z = 365 (MH$^+$). |
| 60d | 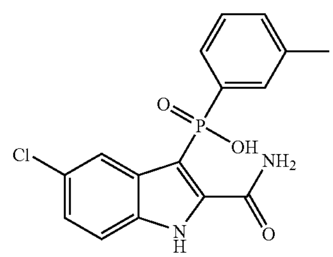 | Off white powder, $^1$H NMR ($d_6$-DMSO, 400 MHz) δ 2.3 (s, 3H), 7.26 (dd, J = 2 and 8.8 Hz, 1H), 7.3-7.37 (m, 2H), 7.46-7.54 (m, 3H), 7.82 (brs, 1H), 7.88 (brs, 1H), 10.69 (brs, 1H), 12.49 (brs, 1H), $^{31}$P NMR ($d_6$-DMSO, 101.256 MHz) δ 23.81, MS (ESI, EI$^+$) m/z = 349 (MH$^+$). |
| 60f | 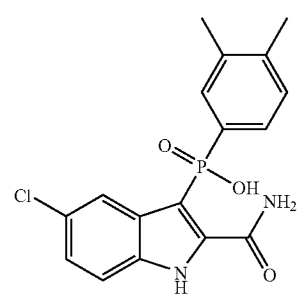 | Off white powder, $^1$H NMR ($d_6$-DMSO, 300 MHz) δ 2.21 (s, 6H), 7.2-7.28 (m, 2H), 7.37-7.53 (m, 3H), 7.79 (brs, 1H), 7.87 (brs, 1H), 10.68 (brs, 1H), 12.47 (brs, 1H), MS (ESI, EI$^+$) m/z = 363 (MH$^+$). |
| 60g | 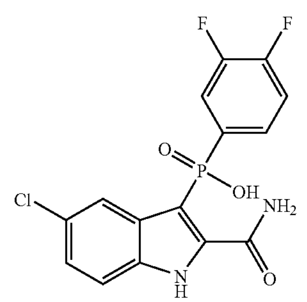 | Orange powder, $^1$H NMR ($d_6$-DMSO, 300 MHz) δ 7.27 (dd, J = 1.95 and 8.87 Hz, 1H), 7.48-7.54 (m, 3H), 7.61-7.71 (m, 1H), 7.85 (d, J = 1.8 Hz, 1H), 7.9 (brs, 1H), 10.54 (brs, 1H), 12.53 (brs, 1H), $^{31}$P NMR ($d_6$-DMSO, 101 MHz) δ 20.39, $^{19}$F NMR ($d_6$-DMSO, 282.4 MHz) δ −133.8 (m, 1F), −137.3 (m, 1F), MS (ESI, EI$^+$) m/z = 371 (MH$^+$). |

The following examples are provided to illustrate the present invention, and are in no way intended to limit the scope of the invention.

EXAMPLES

X. Compound Synthesis

---
General Synthetic Method
---

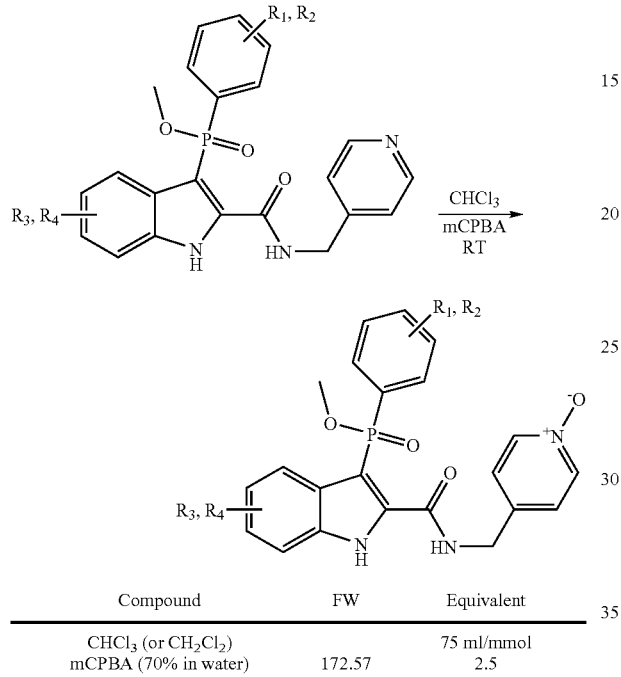

| Compound | FW | Equivalent |
|---|---|---|
| CHCl$_3$ (or CH$_2$Cl$_2$) | | 75 ml/mmol |
| mCPBA (70% in water) | 172.57 | 2.5 |

Experimental:

The pyridine precursor was dissolved in chloroform (or in CH$_2$Cl$_2$) under stirring at room temperature; m-chloroperoxybenzoic acid was added and the reaction allowed to stir overnight (~15H).

The mixture was diluted with dichloromethane and extracted with a mixture of saturated K$_2$CO$_3$/H$_2$O (1/3).

The aqueous layer was extracted three times with dichloromethane. The combined organic layer was dried over sodium sulphate, filtered and concentrated under reduced pressure. (TLC:dichloromethane/methanol=9/1). The crude product was then purified by chromatography.

Compounds Synthesised:

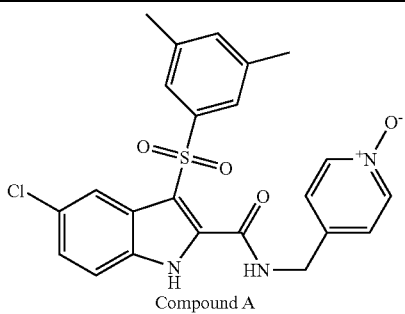

Compound A

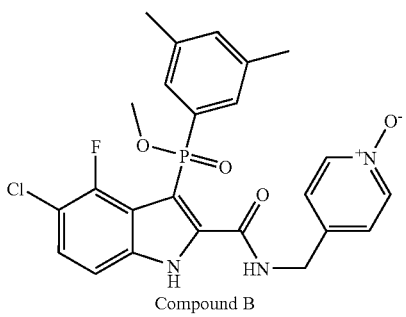

Compound B

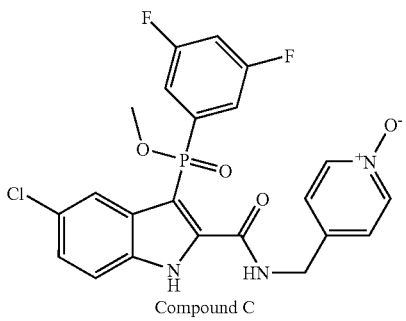

Compound C

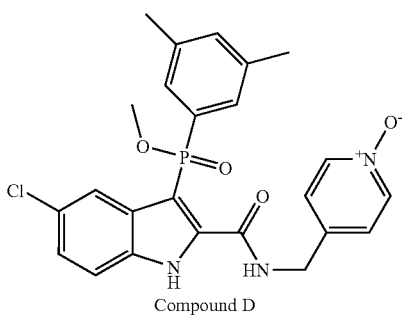

Compound D

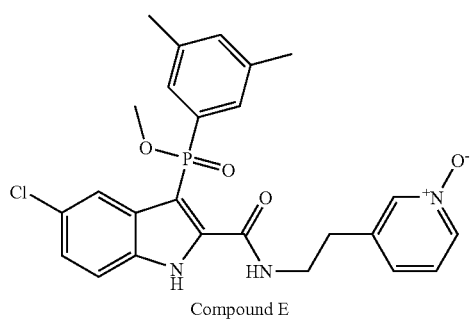

Compound E

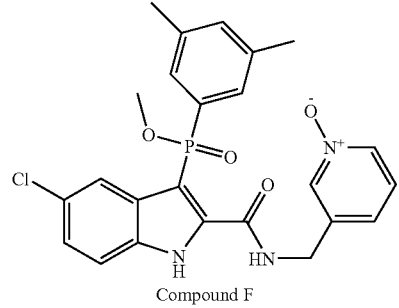

Compound F

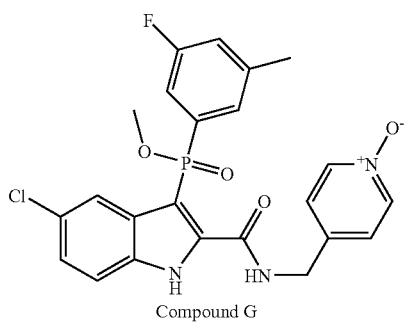
Compound G
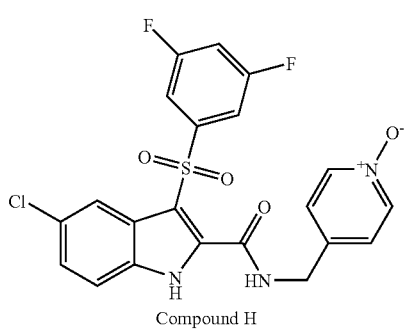
Compound H
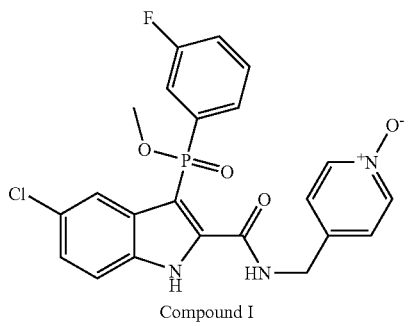
Compound I
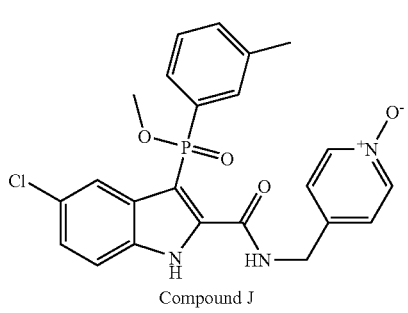
Compound J
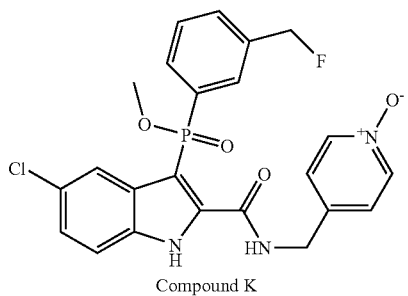
Compound K
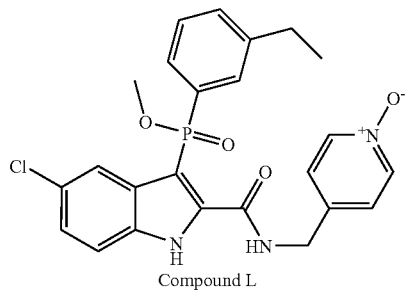
Compound L
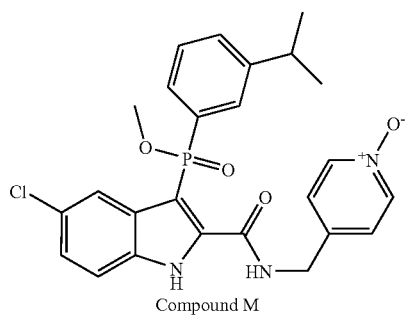
Compound M
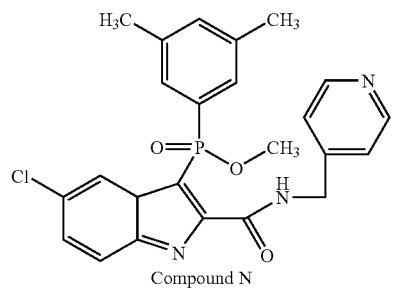
Compound N
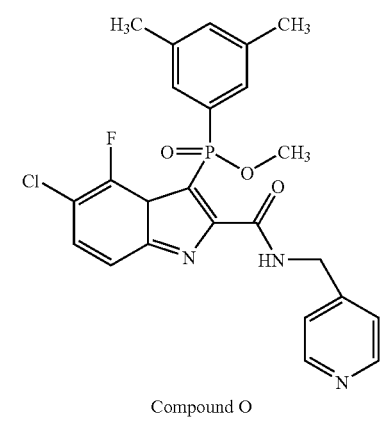
Compound O
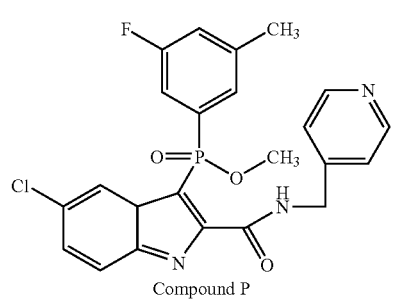
Compound P

Example 1

Ethyl 3-bromo-5-chloro-1-(phenylsulfonyl)-1H-indole-2-carboxylate a) Synthesis of ethyl 5-chloro-1-(phenylsulfonyl)-1H-indole-2-carboxylate as starting material (based on work of Silvestri R., De Martino G., La Regina G., Artico M., Massa S., Vargiu L., Mura M., Loi A.-G., Marceddu T., La Colla P. *J. Med. Chem.* 2003, 46:2482-2493):

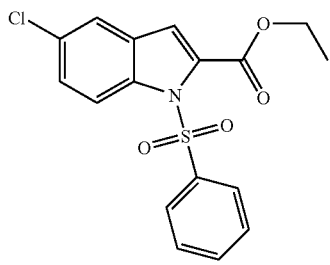

To a stirred and cooled (0° C.) solution of ethyl-5-chloroindole-2-carboxylate (1.052 g, 4.70 mmol) in DMF (25 mL) under $N_2$, was added NaH (60% in oil, 230 mg, 5.64 mmol) portionwise. After the end of gas evolution, phenylsulfonyl chloride (0.72 mL, 5.64 mmol) was added. The reaction mixture was stirred for 1H (TLC monitoring, eluant dichloromethane). A little amount of water was added carefully and DMF was evaporated. Crude residue was dissolved in EtOAc and washed with water and brine. After drying and evaporation of solvents the compound was purified by chromatography on silica gel (eluant:cyclohexane/EtOAc 9/1 to 7/3) to afford protected indole (1.547 g, 90% yield. Off-white solid; $^1$H NMR ($d_6$-DMSO) δ 1.30 (t, J=7.2 Hz, 3H), 4.35 (q, J=7.2 Hz, 2H), 7.37 (s, 1H), 7.53 (dd, J=2.2 and 9.1 Hz), 7.62-7.77 (m, 3H), 7.80 (d, J=2.2 Hz, 1H), 7.99 (m, 2H), 8.06 (d, J=9.1 Hz); MS (ESI, El$^+$) m/z=364 (MH$^+$).

b) Synthesis of ethyl 3-bromo-5-chloro-1-(phenylsulfonyl)-1H-indole-2-carboxylate intermediate:

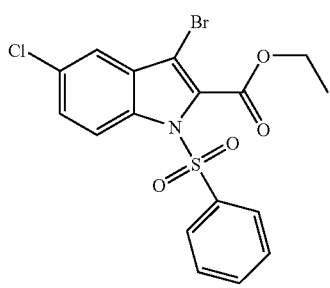

To a stirred solution of ethyl 5-chloro-1-(phenylsulfonyl)-1H-indole-2-carboxylate (4.83 g, 13.27 mmol) in DMF (40 mL) under $N_2$, was added a solution of bromine (1.3 mL, 26.54 mmol) in DMF (10 mL). Reaction media was stirred at RT 4H, water was added (150 mL) and was extracted with dichloromethane (3×100 mL). Organic layer was washed with a saturated solution of $Na_2SO_5$, dried and evaporated to give a crude yellow oil. Purification by chromatography on silica gel (eluant:cyclohexane/EtOAc 9/1) afforded 3-brominated indole (5.548 g, 93% yield). Off white solid; $^1$H NMR ($d_6$-DMSO) δ 1.37 (t, J=7.2 Hz, 3H), 4.48 (q, J=7.2 Hz, 2H), 7.59-7.68 (m, 4H), 7.77 (m, 1H), 7.96-8.09 (m, 3H); MS (ESI, El$^+$) m/z=442-444 (MH$^+$).

Method A: Typical Procedure for the Synthesis of Ethyl 5-chloro-3-(dialkoxyphosphoryl)-1-(phenylsulfonyl)-1H-indole-2-carboxylate and Ethyl 5-chloro-3-[alkoxy(phenyl)phosphoryl]-1-(phenylsulfonyl)-1H-indole-2-carboxylate To a stirred and cooled (−90° C.) solution of ethyl 3-bromo-5-chloro-1-(phenylsulfonyl)-1H-indole-2-carboxylate (0.50 mmol) in anhydrous THF (2.5 mL) under $N_2$, was added n-BuLi (2.5M in hexanes, 0.24 mL, 0.60 mmol) dropwise. After 5 min at −90° C., appropriate chorophosphus reagent (0.60 mmol) was added dropwise at the same temperature. The reaction was allowed to warm up to RT over 3H (TLC monitoring, eluant dichloromethane/ETOAc 9/1). Water was then added (5 mL). Extraction with EtOAc (3×20 mL) drying and evaporation led to a crude oil that was purified by chromatography on silica gel.

Example 2

Ethyl 5-chloro-3-(diethoxyphosphoryl)-1-(phenylsulfonyl)-1H-indole-2-carboxylate

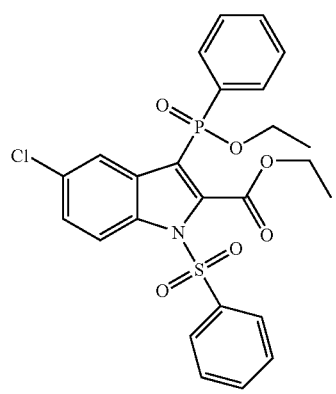

Method A: Purification by chromatography on silica gel (eluant:dichloromethane/EtOAc 9/1 to 8/2) afforded desired indole (176 mg, 71% yield). White solid; $^1$H NMR ($d_6$-DMSO, 300 MHz) δ 1.19 (t, J=7.1 Hz, 6H), 1.39 (t, J=7.1 Hz, 3H), 3.99-4.09 (m, 4H), 4.46 (q, J=7.1 Hz, 2H), 7.77 (dd, J=2.1 and 8.7 Hz, 1H), 7.67-7.82 (m, 4H), 8.07-8.12 (m, 2H); $^{31}$P NMR ($d_6$-DMSO, 101 MHz) δ 9.7; MS (ESI, El$^+$) m/z=500 (MH$^+$).

Example 3

Ethyl 5-chloro-3-[ethoxy(phenyl)phosphoryl]-1-(phenylsulfonyl)-1H-indole-2-carboxylate a) Synthesis of ethyl hydrogen phenylphosphonochloridate intermediate was synthesized according to Smith A. B. III, Ducry L., Corbett, R. M., Hirschmann R. *Org. Lett.* 2000, 2:3887-3890:

i) Synthesis of Diethyl Phenylphosphonate:

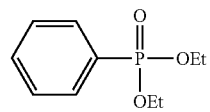

Colorless oil; ¹H NMR (CDCl₃, 250 MHz) δ 1.33 (t, J=7.1 Hz, 6H), 4.05-4.25 (m, 4H), 7.46-7.57 (m, 3H), 7.78-7.87 (m, 2H); ³¹P NMR (CDCl₃, 101 MHz) δ 19.3.

ii) Synthesis of Ethyl Hydrogen Phenylphosphonate:

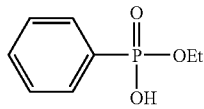

Colorless oil; ¹H NMR (CDCl₃, 300 MHz) δ 1.32 (t, J=7.3 Hz, 3H), 4.08 (q, J=7.3 Hz, 2H), 7.42-7.56 (m, 3H), 7.79-7.86 (m, 2H), 10.67 (brs, 1H); ³¹P NMR (CDCl₃, 101 MHz) δ 21.3;

iii) Synthesis of Ethyl Hydrogen Phenylphosphonochloridate having the Following Physical Characteristics:

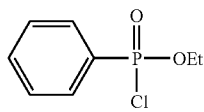

³¹P NMR (CDCl₃, 101 MHz) δ 10.20 and 10.24.

b) Synthesis of Final Product Ethyl 5-chloro-3-[ethoxy(phenyl)phosphoryl]-1-(phenylsulfonyl)-1H-indole-2-carboxylate:

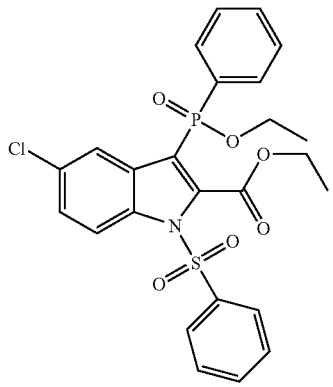

Method A: Purification by chromatography on silica gel (eluant:dichloromethane/EtOAc 9/1) afforded debrominated indole (318 mg) and then desired indole (326 mg, 41% yield). Colorless oil; ¹H NMR (d₆-DMSO, 300 MHz) δ 1.27 (t, J=7.1 Hz, 3H), 1.36 (t, J=7.1 Hz, 3H), 4.03 (m, 2H), 4.38 (q, J=7.1 Hz, 2H), 7.51-7.83 (m, 11H), 8.05-8.11 (m, 3H); ³¹P NMR (d₆-DMSO, 101 MHz) δ 23.3; MS (ESI, EI⁺) m/z=532 (MH⁺).

Example 4

Ethyl 5-chloro-3-[ethoxy(3,5-dimethylphenyl))phosphoryl]-1-(phenylsulfonyl)-1H-indole-2-carboxylate a) Synthesis of diethyl 3,5-dimethylphenylphosphonate intermediate according to method described by Hirao T., Masunaga T., Oshiro Y., Agawa T. *Synthesis* 1981, 56-57.

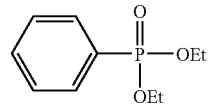

Purification by chromatography on silica gel (eluant:cyclohexane/EtOAc 6/4) afforded product (1.625 g, 61% yield) as a colorless oil; ¹H NMR (CDCl₃, 300 MHz) δ 1.33 (t, J=7.0 Hz, 6H), 2.35 (s, 6H), 4.02-4.18 (m, 4H), 7.18 (s, 1H), 7.40 (s, 1H), 7.45 (s, 1H); ³¹P NMR (CDCl₃, 101 MHz) δ 20.3.

Other intermediates are synthesized according to Example 3 (i, ii and iii).

b) Synthesis of Ethyl 5-chloro-3-[ethoxy(3,5-dimethylphenyl))phosphoryl]-1-(phenylsulfonyl)-1H-indole-2-carboxylate:

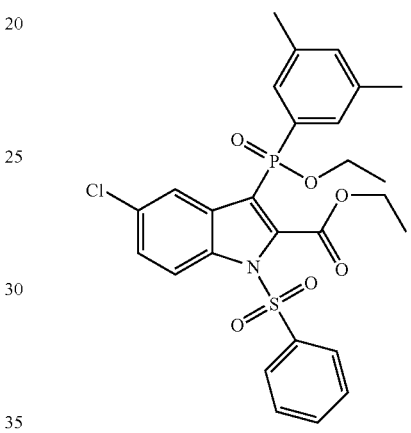

Method A: Purification by chromatography on silica gel (eluant:dichloromethane/EtOAc 95/5) afforded product (750 mg, 56% yield) as a light yellow solid. ¹H NMR (d₆-DMSO, 300 MHz) δ 1.27 (t, J=7.1 Hz, 3H), 1.36 (t, J=7.1 Hz, 3H), 2.30 (s, 6H), 3.94-4.06 (m, 2H), 4.44 (q, J=7.1 Hz, 2H), 7.25 (s, 1H), 7.39 (s, 1H), 7.42 (s, 1H), 7.53 (dd, J=2.1 and 9.0 Hz, 1H), 7.65-7.71 (m, 2H), 7.77-7.82 (m, 2H), 8.05-8.11 (m, 3H); ³¹P NMR (d₆-DMSO, 101 MHz) δ 23.6; MS (ESI, EI⁺) m/z=560 (MH⁺).

Example 5

Ethyl 5-chloro-3-[methoxy(phenyl)phosphoryl]-1-(phenylsulfonyl)-1H-indole-2-carboxylate a) Synthesis of Dimethyl Phenylphosphonate:

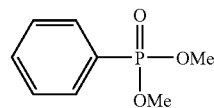

To a solution of benzenephosphonyl dichloride (1 mL, 6.35 mmol) in anhydrous dichloromethane (25 mL) was added dropwise at 0° C. ethanol (1.12 mL, 19.04 mmol) following by triethylamine (2.65 mL, 19.04 mmol). The reaction mixture was stirred at RT 2 h. The reaction mixture was washed with a solution of HCl 1N (50 mL). Aqueous layer was extracted with dichoromethane. Combined organic phases were dried and concentrated under reduce pressure. The crude oil was purified by chromatography on silica gel (Eluant:cyclohexane/EtOAc 6/4) to afford dimethyl phenylphosphonate as colorless oil (1,110 g, 82% yield). $^1$H NMR (CDCl$_3$, 300 MHz) δ 3.76 (d, J=11.1 Hz, 3H), 7.44-7.58 (m, 3H), 7.76-7.84 (m, 2H); $^{31}$P NMR (CDCl$_3$, 101 MHz) δ 22.2. Other intermediates are synthesised according to example 3 (i, ii and iii).

b) Synthesis of Final Product Ethyl 5-chloro-3-[methoxy(phenyl)phosphoryl]-1-(phenylsulfonyl)-1H-indole-2-carboxylate:

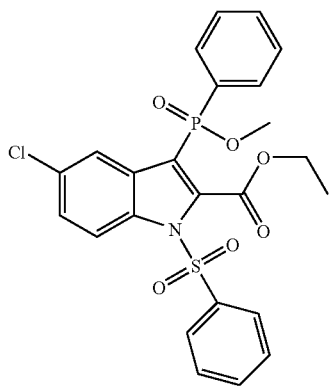

Method A: Colorless oil; $^1$H NMR (CDCl$_3$, 300 MHz) δ 1.45 (t, J=7.2 Hz, 3H), 3.80 (d, J=11.4 Hz, 3H), 4.54 (q, J=7.2 Hz, 2H), 7.36 (dd, J=2.1 and 9.0 Hz, 1H), 7.47-7.67 (m, 6H), 7.84-7.96 (m, 4H), 8.09-8.12 (m, 2H); $^{31}$P NMR (CDCl$_3$, 101 MHz) δ 26.7; MS (ESI, EI$^+$) m/z=518 (MH$^+$).

Example 6

Ethyl 2-(aminocarbonyl)-5-chloro-1H-indol-3-yl-(phenyl)phosphinate

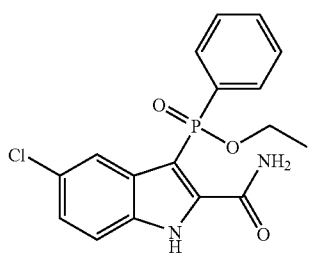

Ethyl-5-chloro-3-[ethoxy(phenyl)phosphoryl]-1-(phenylsulfonyl)-1H-indole-2-carboxylate (268 mg, 0.50 mmol) was dissolved in a saturated solution of ammonia in methanol (5 mL) in a pressure tube. The tube was heated under microwave irradiation under pressure at 65° C. (Maximum power input 100 W, CEM discover apparatus) for 2H. After evaporation of solvents, purification by chromatography on silica gel (eluant:dichloromethane/MeOH 95/5 to 9/1) afforded desired carboxamide indole (107 mg, 81% yield). White solid; $^1$H NMR (d$_6$-DMSO, 300 MHz) δ 1.34 (t, J=7.1 Hz, 3H), 4.05 (m, 1H), 4.20 (m, 1H), 7.32 (dd, J=2.1 and 8.7 Hz, 1H), 7.49-7.61 (m, 5H), 7.68-7.75 (m, 2H), 8.02 (brs, 1H), 10.27 (brs, 1H), 12.77 (brs, 1H); $^{31}$P NMR (d$_6$-DMSO, 101 MHz) δ 31.1; MS (ESI, EI$^+$) m/z=363 (MH$^+$).

Example 7

Ethyl 2-(aminocarbonyl)-5-chloro-1H-indol-3-yl-(3,5-dimethylphenyl)phosphonate

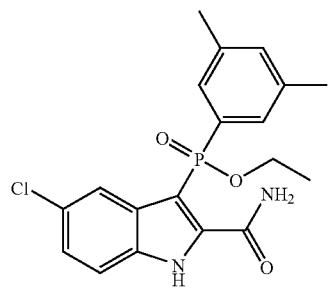

Same procedure as described in example 5. white solid; $^1$H NMR (d$_6$-DMSO, 300 MHz) δ 1.32 (t, J=7.0 Hz, 3H), 2.26 (s, 6H), 3.90-4.03 (m, 1H), 4.09-4.22 (m, 1H), 7.21 (s, 1H), 7.29-7.33 (m, 3H), 7.57 (dd, J=1.8 and 9.0 Hz, 1H), 7.60 (dd, J=1.8 Hz, 1H), 7.99 (brs, 1H), 10.3 (brs, 1H), 12.7 (brs, 1H); $^{31}$P NMR (d$_6$-DMSO, 101 MHz) δ 31.3; MS (ESI, EI$^+$) m/z=391 (MH$^+$).

Example 8

Methyl 2-(aminocarbonyl)-5-chloro-1H-indol-3-yl-(phenyl)phosphinate

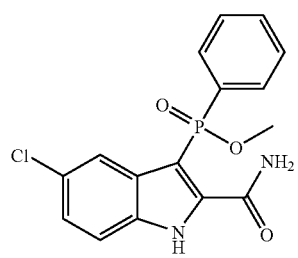

Same procedure as described in example 5. Pale yellow powder; $^1$H NMR (CDCl$_3$, 300 MHz) δ 3.85 (d, J=11.4 Hz, 3H), 6.08 (broad s, 1H), 7.30 (dd, J=2.0 and 9.0 Hz, 1H), 7.36-7.56 (m, 4H), 7.68 (d, J=1.8 Hz, 1H), 7.73-7.81 (m, 2H), 10.78 (broad s, 1H), 10.03 (broad s, 1H); $^{31}$P NMR (CDCl$_3$, 101 MHz) δ 33.3; MS (ESI, EI$^+$) m/z=349 (MH$^+$).

Example 9

Biological Activity Against Drug Resistant Strains of HIV

In one embodiment, the efficacy of an anti-HIV compound is measured in vitro by a rapid, sensitive, and automated assay that involves the reduction of 3-(4,5-dimethylthiazol-2-yl)-2,5-diphenyltetrazolium bromide (MTT). An HIV-transformed cell line that is highly permissive and selective for HIV infection, such as, for example, the T-4 cell line, MT-4, is chosen as the target cell line (Koyanagi et al., *Int. J. Cancer*, 1985, 36:445-451). In situ reduction of 3-(4,5-dimethylthiazol-2-yl)-2,5-diphenyl-tetrazolium bromide (MTT) as assessed spectrophotometrically is the standard by which the viability of both mock-infected cells and HIV-infected cells is measured. Inhibition of the HIV-induced cytopathic effect serves as the end-point. A 50% cytotoxic concentration ($CC_{50}$ in $\mu M$) is defined as the concentration of compound that reduces the absorbance of the mock-infected control sample by 50%. The percent efficacy of an anti-HIV compound is calculated by the formula (expressed as a %):

$$(OD_{HIV\,test\,compound}) - (OD_{control}) / (OD_{mock\,infected\,cells}) - (OD_{control})$$

Here, ($OD_{HIV\,test\,compound}$) is the optical density measured for a specific amount of a test compound in HIV-infected cells; ($OD_{control}$) is the optical density measured for untreated HIV-infected, control cells; and ($OD_{mock\,infected\,cells}$) is the optical density measured for control, mock-infected cells that are untreated. Optical density values typically are assessed at 540 nm. The dosage of an anti-HIV test compound that provides 50% protection according to the preceding formula is defined as the 50% inhibitory concentration ($IC_{50}$ in $\mu M$). The selectivity index (SI) is defined as the ratio of the $CC_{50}$ to the $IC_{50}$.

In another embodiment, the p24 ELISA assay is used to determine the efficacy of an anti-HIV compound. This viral replication immunoassay measures the amount of p24 viral capsid (core) antigen present, and is available commercially from sources such as, for example, Coulter Corporation/Immunotech, Inc.® (Westbrook, Mich.).

Still other embodiments include a reverse trancriptase assay in which the amount of viral replication is measured by utilizing a homopolymer poly rA:oligo dT template primer system that quantifies the incorporation into cells of tritiated thymidine monophosphate by scintillation counting methods (Southern Research Institute, University of Alabama, Birmingham, Ala.); a syncytial inhibition assay that employs CEM-SS, HeLa-CD4, or HeLa-CD4-LTR-b-galactosidase cells having an immuno-fluorescent, chemiluminescent, or colorimetric endpoint; and an attachment- and fusion-inhibition assay that utilizes indicator cell lines and quantitation by chemiluminescent, colorimetric or microscopic evaluation (Southern Research Institute, University of Alabama, Birmingham, Ala.).

In one embodiment the indole compounds of the present invention do not exhibit cross resistance with other non-nucleoside reverse transcriptase inhibitors (NNRTIs), in that the compounds of the present invention display an $EC_{50}$ (in molar concentration) in a mutant HIV strain of less than approximately 50, 25, 10 or 1 $\mu M$ concentration. In a typical embodiment, the NNRTIs display an $EC_{50}$ in a mutant HIV strain of less than approximately 5, 2.5, 1 or 0.1 $\mu M$ concentration. The degree of cross-resistance against a drug resistant strain of HIV is measured by assessing the $EC_{50}$ of the desired oxo-pyrimidine compound in the target mutated, i.e., drug resistant, virus.

Therefore, in another important embodiment of this invention, a method for treating a patient with a cross-resistant HIV is provided that includes administering an effective HIV-treatment amount of an indole compound, a salt, prodrug, stereoisomer or tautomer thereof.

Biological Activity Against Drug Resistant Strains of HIV

In one embodiment the phenylindoles of the present invention do not exhibit cross resistance with other non-nucleosides reverse transcriptase inhibitors (NNRTI), in that it displays an $EC_{50}$ (in molar concentrations) in a mutant HIV strain of less than approximately 50, 25, 10 or 1 micromolar concentration. In a typical embodiment, the non-nucleosides reverse transcriptase inhibitors (NNRTI) displays an $EC_{50}$ (in molar concentrations) in a mutant HIV strain of less than approximately 5, 2.5, 1 or 0.1 micromolar concentration. The degree of cross-resistance against a drug resistant strain of HIV can easily be measured by assessing the $EC_{50}$ of the desired indole in the target mutated i.e., drug resistant, virus.

Therefore, in another important embodiment of this invention, a method for treating a patient with a cross-resistant HIV is provided that includes administering an effective HIV-treatment amount of a phenylindole or its prodrug or salt.

TABLE 3

ENZYME ASSAY DATA

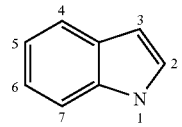

| Compound Number | Indole Substituent Position | | | | | | | $IC_{50}$ WT ($\mu M$) | $IC_{50}$ Y181C ($\mu M$) | $IC_{50}$ K103N ($\mu M$) | $IC_{50}$ K103N/ Y181C ($\mu M$) |
|---|---|---|---|---|---|---|---|---|---|---|---|
| | 1 | 2 | 3 | 4 | 5 | 6 | 7 | | | | |
| 7ah | H | CONH2 | P(O)(Ph)OMe | H | Cl | H | H | 0.309 | 0.349 | 0.389 | 6.75 |
| 6a | H | CONH2 | P(O)(Ph)OEt | H | Cl | H | H | 0.722 | 1.968 | 1.634 | >5 |
| 6b | H | CONH2 | P(O)(Ph:3,5-di-Me)Oet | H | Cl | H | H | 1.641 | 4.311 | 2.607 | >5 |
| 18ar | H | CONHCH2(4-pyridine) | P(O)(Ph)OMe | H | H | H | H | 0.156 | 0.489 | 0.93 | 1.662 |
| 9a | H | CONHCH2(4-pyridine) | P(O)(Ph:3,5-di-Me)OEt | H | Cl | H | H | 3.413 | 4.489 | 3.356 | >5 |
| 27a | H | CONH2 | P(O)Ph2 | H | Cl | H | H | >5 | >5 | >5 | >5 |
| 7ai | H | CONH2 | P(O)(Ph)OMe | H | Cl | H | H | 0.393 | 5.606 | 6.587 | >5 |
| 60a | H | CONH2 | P(O)(Ph)OH | H | Cl | H | H | >5 | >5 | >5 | >5 |
| 29a | H | CONH2 | P(O)(Ph)CH3 | H | Cl | H | H | 0.233 | 2.524 | >5 | >5 |
| 31a | H | CONH2 | P(O)(Ph)N(Me)2 | H | Cl | H | H | 1.401 | >5 | >5 | >5 |

TABLE 3-continued

ENZYME ASSAY DATA

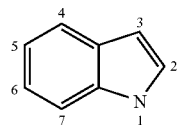

| Compound Number | \_\_\_Indole Substituent Position\_\_\_ | | | | | | | IC$_{50}$ WT (µM) | IC$_{50}$ Y181C (µM) | IC$_{50}$ K103N (µM) | IC$_{50}$ K103N/ Y181C (µM) |
|---|---|---|---|---|---|---|---|---|---|---|---|
| | 1 | 2 | 3 | 4 | 5 | 6 | 7 | | | | |
| 6c | H | CONH2 | P(O)(Ph:4-F)OEt | H | Cl | H | H | 3.62 | >5 | >5 | >5 |
| 6ac | H | CONH2 | P(O)(Ph:3,5-di-F)OEt | H | Cl | H | H | 0.726 | 3.5 | 12.72 | >5 |
| 6ad | H | CONH2 | P(O)(Ph:2-F)OEt | H | Cl | H | H | 0.433 | 4.346 | 3.293 | >5 |

TABLE 4

CELL-BASED ASSAY DATA USING BH-10 CELLS

| Compound No. | \_\_\_Indole Substituent Position\_\_\_ | | | | | | | EC$_{50}$ WT///B (µM) | EC$_{50}$ Y181C (µM) | EC$_{50}$ K103N/Y181C (µM) |
|---|---|---|---|---|---|---|---|---|---|---|
| | 1 | 2 | 3 | 4 | 5 | 6 | 7 | | | |
| 7ah | H | CONH2 | P(O)(Ph)OMe | H | Cl | H | H | 0.0004 | 0.0049 | 0.0034 |
| 6a | H | CONH2 | P(O)(Ph)OEt | H | Cl | H | H | 0.0012 | 0.0137 | 0.0164 |
| 6b | H | CONH2 | P(O)(Ph: 3,5-di-Me)OEt | H | Cl | H | H | 0.003 | 0.028 | 0.0517 |
| 18ar | H | CONHCH2(4-pyridine) | P(O)(Ph)OMe | H | Cl | H | H | 0.001 | 0.0056 | 0.0039 |
| 9a | H | CONHCH2(4-pyridine) | P(O)(Ph: 3,5-di-Me)OEt | H | Cl | H | H | 0.011 | 0.0577 | 0.008 |
| 27a | H | CONH2 | P(O)Ph2 | H | Cl | H | H | >1.25 | >1.25 | >1.25 |
| 7ai | H | CONH2 | P(O)(Ph)OMe | H | H | H | H | 0.001 | 1.1091 | 0.7056 |
| 60a | H | CONH2 | P(O)(Ph)OH | H | Cl | H | H | >1.25 | >1.25 | >1.25 |
| 29a | H | CONH2 | P(O)(Ph)CH3 | H | Cl | H | H | 0.0008 | 0.2664 | 1.3828 |
| 31a | H | CONH2 | P(O)(Ph)N(Me)2 | H | Cl | H | H | 0.0139 | 0.4668 | >1.25 |
| 6c | H | CONH2 | P(O)(Ph: 4-F)OEt | H | Cl | H | H | 0.0345 | >1.25 | >1.25 |
| 6ac | H | CONH2 | P(O)(Ph: 3,5-di-F)OEt | H | Cl | H | H | 0.0037 | 0.9862 | >1.25 |
| 6ad | H | CONH2 | P(O)(Ph: 2-F)OEt | H | Cl | H | H | 0.0009 | 0.0583 | 0.017 |
| 6ae | H | CONH2 | P(O)(Ph: 3-F)OEt | H | Cl | H | H | 0.0005 | 0.0616 | 0.011 |
| 7ak | H | CONH2 | P(O)(Ph: 4-F)OMe | H | Cl | H | H | 0.0055 | 0.0345 | 0.468 |
| 7aj | H | CONH2 | P(O)(Ph: 3,5-di-F)OMe | H | Cl | H | H | 0.0006 | 0.0177 | 0.0091 |
| 6ab | H | CONH2 | P(O)(Ph: 3-Me)OEt | H | Cl | H | H | 0.0005 | 0.0348 | 0.0196 |
| 6m | H | CONH2 | P(O)(Ph: 3-OMe)OEt | H | Cl | H | H | 0.0023 | | 0.0664 |
| 6w | H | CONH2 | P(O)(Ph: 4-Me)OEt | H | Cl | H | H | 0.0072 | | >1.25 |
| 6f | H | CONH2 | P(O)(Ph: 3-CF3)OEt | H | Cl | H | H | 0.0067 | | 0.498 |
| 6g | H | CONH2 | P(O)(Ph: 3-C≡N)OEt | H | Cl | H | H | 0.0095 | | 0.1951 |
| 6x | H | CONH2 | P(O)(Ph: 2-Me)OEt | H | Cl | H | H | 0.0213 | | 0.4483 |
| 7l | H | CONH2 | P(O)(Ph: 3-OMe)OMe | H | Cl | H | H | 0.0006 | 0.0385 | 0.0218 |
| 7ac | H | CONH2 | P(O)(Ph: 3-Me)OMe | H | Cl | H | H | 0.0013 | 0.0096 | 0.0055 |
| 6s | H | CONH2 | P(O)(Ph: 3-F,5-Me)OEt | H | Cl | H | H | 0.0014 | | 0.0207 |
| 57a | H | CONH2 | P(O)(CH(CH2)5)OMe | H | Cl | H | H | 0.0017 | | 0.1615 |
| 6y | H | CONH2 | P(O)(Ph: 3,4-di-Me)OEt | H | Cl | H | H | 0.0026 | | >1.25 |
| 7r | H | CONH2 | P(O)(Ph: 3-F,5-Me)OMe | H | Cl | H | H | 0.0004 | 0.0005 | 0.0004 |
| 25b | H | CONH2 | P(S)(Ph)OMe | H | Cl | H | H | 0.0004 | 0.0414 | 0.0899 |
| 7s | H | CONH2 | P(O)(Ph: 3,5-di-CF3)OMe | H | Cl | H | H | 0.0128 | 0.0683 | 0.0479 |
| 7q | H | CONH2 | P(O)(Ph: 3-F,5-CF3)OMe | H | Cl | H | H | 0.0011 | 0.0166 | 0.0029 |
| 6d | H | CONH2 | P(O)(Ph: 3-Cl)OEt | H | Cl | H | H | 0.0014 | 0.0166 | 0.0158 |
| 7n | H | CONH2 | P(O)(Ph: 2-OMe)OMe | H | Cl | H | H | 0.0017 | 0.066 | 0.0015 |
| 6t | H | CONH2 | P(O)(1-naphthalene)OEt | H | Cl | H | H | 0.0325 | >1.25 | >1.25 |
| 6e | H | CONH2 | P(O)(Ph: 3-Et)OEt | H | Cl | H | H | 0.002 | 0.0341 | 0.0012 |
| 7ad | H | CONH2 | P(O)(Ph: 2-Me)OMe | H | Cl | H | H | 0.0013 | 0.032 | 0.0047 |
| 7ae | H | CONH2 | P(O)(Ph: 3,4-di-Me)OMe | H | Cl | H | H | 0.0005 | 0.0111 | 0.0011 |
| 6ai | H | CONH2 | P(O)(Ph: 2-Cl)OEt | H | Cl | H | H | 0.0012 | 0.1456 | 0.0173 |
| 7am | H | CONH2 | P(O)(Ph: 2,5-di-F)OMe | H | Cl | H | H | 0.0003 | 0.0149 | 0.0012 |
| 7al | H | CONH2 | P(O)(Ph: 2-F)OMe | H | Cl | H | H | 0.0005 | 0.0139 | 0.0026 |
| 7c | H | CONH2 | P(O)(Ph: 3-Cl)OMe | H | Cl | H | H | 0.0004 | 0.0087 | 0.0026 |
| 7d | H | CONH2 | P(O)(Ph: 3-Et)OMe | H | Cl | H | H | 0.0006 | 0.0065 | 0.0014 |
| 7e | H | CONH2 | P(O)(Ph: 3-CF3)OMe | H | Cl | H | H | 0.0009 | 0.0032 | 0.0012 |
| 7ao | H | CONH2 | P(O)(Ph: 2-Cl)OMe | H | Cl | H | H | 0.0004 | 0.002 | 0.0014 |
| 7t | H | CONH2 | P(O)(1-naphthalene)OMe | H | Cl | H | H | 0.0006 | 0.0057 | 0.0026 |
| 7a | H | CONH2 | P(O)(Ph: 3,5-di-Me)OMe | H | Cl | H | H | 0.0002 | 0.0012 | 0.001 |
| 6ah | H | CONH2 | P(O)(Ph: 2-Et)OEt | H | Cl | H | H | 0.0162 | 0.211 | 0.3072 |
| 18at | H | CONHCH2(2-furan) | P(O)(Ph)OMe | H | Cl | H | H | 0.0018 | 0.0015 | 0.0005 |
| 7an | H | CONH2 | P(O)(Ph: 2-Et)OMe | H | Cl | H | H | 0.0029 | 0.0505 | 0.0013 |

TABLE 4-continued

CELL-BASED ASSAY DATA USING BH-10 CELLS

| Compound No. | \multicolumn{7}{c}{Indole Substituent Position} | EC$_{50}$ WT///B (μM) | EC$_{50}$ Y181C (μM) | EC$_{50}$ K103N/Y181C (μM) |
| --- | --- | --- | --- | --- | --- | --- | --- | --- | --- | --- |
| | 1 | 2 | 3 | 4 | 5 | 6 | 7 | | | |
| 6aa | H | CONH2 | P(O)(Ph: 2,5-di-Me)OEt | H | Cl | H | H | 0.0002 | 0.0019 | 0.0016 |
| 18as | H | CONHCH2(5-imidazole: 1-Me) | P(O)(Ph)OMe | H | Cl | H | H | 0.0003 | 0.0099 | 0.0006 |
| 7ag | H | CONH2 | P(O)(Ph: 2,5-di-Me)OMe | H | Cl | H | H | 0.0003 | 0.0407 | 0.001 |
| 7-Aza | H | CONH2 | P(O)(Ph)OMe | - | Cl | H | N7 | 0.0147 | >1.25 | 0.1929 |
| 7b | H | CONH2 | P(O)(Ph: 3,5-di-Cl)OMe | H | Cl | H | H | 0.0012 | 0.0053 | 0.0168 |
| 57b | H | CONH2 | P(O)(CH2CH=CMe2)OMe | H | Cl | H | H | 0.0008 | 0.0131 | 0.1743 |
| 18a | H | CONHCH2(4-pyridine) | P(O)(Ph: 3-Me)OMe | H | Cl | H | H | 0.001 | 0.0101 | 0.0031 |
| 18b | H | CONHCH2(2-furan) | P(O)(Ph: 3-Me)OMe | H | Cl | H | H | 0.0036 | 0.0101 | 0.004 |
| 18av | H | CONHCH2(4-pyridine) | P(O)(Ph: 3-F)OMe | H | Cl | H | H | 0.0007 | 0.0013 | 0.0024 |
| 18av | H | CONHCH2(4-pyridine) | P(O)(Ph: 3-OMe)OMe | H | Cl | H | H | 0.0008 | 0.0033 | 0.0014 |
| 18au | H | CONHCH2(2-furan) | P(O)(Ph: 3-OMe)OMe | H | Cl | H | H | 0.0008 | 0.0033 | 0.006 |
| 6i | H | CONH2 | P(O)(Ph: 3-iPr)OEt | H | Cl | H | H | 0.0012 | 0.0091 | 0.0035 |
| 7g | H | CONH2 | P(O)(Ph: 3-iPr)OMe | H | Cl | H | H | 0.0025 | 0.0088 | 0.0077 |
| 51 | H | CONH2 | P(O)(2-thiophene)OEt | H | Cl | H | H | 0.0022 | 0.0529 | 0.0656 |
| 52b | H | CONH2 | P(O)(2-thiophene)OMe | H | Cl | H | H | 0.0005 | 0.0087 | 0.0025 |
| 7af | H | CONH2 | P(O)(Ph: 2,3-di-Me)OMe | H | Cl | H | H | 0.0022 | 0.1156 | 0.033 |
| 18aab | H | CONHCH2(Ph: 2-F) | P(O)(Ph)OMe | H | Cl | H | H | 0.0038 | 0.0335 | 0.0102 |
| 18ax | H | CONHCH2(4-pyridine) | P(O)(Ph: 3,5-di-Me)OMe | H | Cl | H | H | 0.003 | 0.0072 | 0.0023 |
| 18aan | H | CONHCH(Ph)CONH2 (S) | P(O)(Ph)OMe ("R") | H | Cl | H | H | 0.015 | 0.3044 | 0.6004 |
| 18aao | H | CONHCH(Ph)CONH2 (S) | P(O)(Ph)OMe ("S") | H | Cl | H | H | 0.0381 | 0.287 | 0.1177 |
| 7z | H | CONH2 | P(O)(Ph: 3,5-di-Me)OMe | F | Cl | H | H | 0.0021 | 0.0085 | 0.0022 |
| 7h | H | CONH2 | P(O)(Ph: 3-CH2F)OMe | H | Cl | H | H | 0.0009 | 0.0061 | 0.0025 |
| 18c | H | CONHCH2(4-pyridine) | P(O)(Ph: 3-CH2F)OMe | H | Cl | H | H | 0.002 | 0.0029 | 0.0047 |
| 18ap | H | CONHCH2(4-pyridine) | P(O)(Ph: 3-Et)OMe | H | Cl | H | H | 0.0058 | 0.0037 | 0.0058 |
| 18aac | H | CONHCH2N(CH2CH2)2O | P(O)(Ph)OMe | H | Cl | H | H | 0.0005 | 0.0101 | 0.014 |
| 7ap | H | CONH2 | P(O)(Ph: 3-CH2OCH2Ph)OMe | H | Cl | H | H | 0.1528 | 1.1352 | >1.25 |
| 18r | H | CONHCH2(4-pyridine) | P(O)(Ph: 3,5-di-Me)OMe | F | Cl | H | H | 0.0038 | 0.0165 | 0.0036 |
| 7f | H | CONH2 | P(O)(Ph: 3-C≡N)OMe | H | Cl | H | H | 0.0009 | 0.0105 | 0.0153 |
| 18ay | H | CONHCH2N(CH2CH2)2O | P(O)(Ph: 3,5-di-Me)OMe | H | Cl | H | H | 0.0035 | 0.0198 | 0.0093 |
| 7aq | H | CONH2 | P(O)(Ph: 3-CH2OH)OMe | H | Cl | H | H | 0.0025 | 0.0831 | 0.1265 |
| 18d | H | CONHCH2(4-pyridine) | P(O)(Ph: 3-F,5-Me)OMe | H | Cl | H | H | 0.0023 | 0.0094 | 0.0037 |
| 18aq | H | CONHCH2(4-pyridine) | P(O)(Ph: 3-iPr)OMe | H | Cl | H | H | 0.012 | 0.0317 | 0.0186 |
| 18aaq | H | CONHCH2(Ph) | P(O)(Ph)OMe | H | Cl | H | H | 0.0072 | 0.0184 | 0.0276 |
| 52a | H | CONH2 | P(O)(3-thiophene)OMe | H | Cl | H | H | 0.0005 | 0.0015 | 0.0063 |
| 22m | H | CONHCH2(4-pyridine: 4-O) | P(O)(Ph: 3,5-di-Me)OMe | F | Cl | H | H | 0.0021 | 0.0026 | 0.0019 |
| 7aa | H | CONH2 | P(O)(Ph: 3-cPr)OMe | H | Cl | H | H | 0.0022 | 0.007 | 0.0037 |
| 18aad | H | CONHCH2(Ph: 2-F) | P(O)(Ph: 3,5-di-F)OMe | H | Cl | H | H | 0.011 | 0.0382 | 0.0125 |
| 7ar | H | CONH2 | P(O)(Ph: 3-tBu)OMe | H | Cl | H | H | 0.0029 | 0.0193 | 0.0306 |
| 59a | H | CONHCH2C≡N | P(O)(Ph: 3,5-di-F)OMe | H | Cl | H | H | 0.0014 | 0.0473 | 0.0084 |
| 59b | H | CONH(CH2)2C≡N | P(O)(Ph: 3,5-di-F)OMe | H | Cl | H | H | 0.0035 | 0.0693 | 0.0215 |
| 18e | H | CONHCH2(4-pyridine) | P(O)(Ph: 3,5-di-F)OMe | H | Cl | H | H | 0.0035 | 0.0148 | 0.012 |
| 22a | H | CONHCH2(4-pyridine: 4-O) | P(O)(Ph: 3,5-di-F)OMe | H | Cl | H | H | 0.0031 | 0.0524 | 0.0113 |
| 18q | H | CONHCH2(Ph: 4-C≡N) | P(O)(Ph: 3,5-di-Me)OMe | H | Cl | H | H | 0.003 | 0.0357 | 0.0542 |
| 22n | H | CONHCH2(4-pyridine: 4-O) | P(O)(Ph: 3,5-di-Me)OMe | H | Cl | H | H | 0.002 | 0.0088 | 0.0045 |
| 7i | H | CONH2 | P(O)(Ph: 3-Ph)OMe | H | Cl | H | H | 0.0099 | 0.3983 | 0.3801 |
| 18aae | H | CONHCH2(5-imidazole: 1-Me) | P(O)(Ph: 3,5-di-F)OMe | H | Cl | H | H | 0.0026 | 0.0105 | 0.0027 |
| 18az | H | CONHCH2(Ph: 2-F) | P(O)(Ph: 3,5-di-Me)OMe | H | Cl | H | H | 0.003 | 0.0167 | 0.0085 |
| 18aaa | H | CONHCH2(5-imidazole: 1-Me) | P(O)(Ph: 3,5-di-Me)OMe | H | Cl | H | H | 0.0032 | 0.0064 | 0.0033 |
| 22l | H | CONHCH2(4-pyridine: 4-Me•I⁻) | P(O)(Ph: 3,5-di-Me)OMe | H | Cl | H | H | 0.0061 | 0.2693 | 0.0774 |
| 18f | H | CONHCH2(3-pyridine) | P(O)(Ph: 3,5-di-Me)OMe | H | Cl | H | H | 0.0023 | 0.0059 | 0.0034 |
| 18g | H | CONH(CH2)2(4-pyridine) | P(O)(Ph: 3,5-di-Me)OMe | H | Cl | H | H | 0.0116 | 0.0306 | 0.0098 |
| 22c | H | CONH(CH2)2(4-pyridine: 4-O) | P(O)(Ph: 3,5-di-Me)OMe | H | Cl | H | H | 0.0028 | 0.0101 | 0.0268 |
| 18aah | H | CONHCH2(Ph: 2,6-di-F) | P(O)(Ph: 3,5-di-Me)OMe | H | Cl | H | H | 0.007 | 0.0228 | 0.0169 |
| 7v | H | CONH2 | P(O)(Ph: 3-F,5-Cl)OMe | H | Cl | H | H | 0.0008 | 0.0149 | 0.0023 |
| 18aai | H | CONHCH2(Ph: 2,5-di-F) | P(O)(Ph: 3,5-di-Me)OMe | H | Cl | H | H | 0.0036 | 0.0156 | 0.0183 |
| 22b | H | CONHCH2(3-pyridine: 3-O) | P(O)(Ph: 3,5-di-Me)OMe | H | Cl | H | H | 0.0035 | 0.0187 | 0.0032 |
| 18n | H | CONHCH2(Ph: 2-NH2) | P(O)(Ph: 3,5-di-Me)OMe | H | Cl | H | H | 0.0195 | 0.0878 | 0.0231 |
| 18k | H | CONHCH2(Ph: 4-Br) | P(O)(Ph: 3,5-di-Me)OMe | H | Cl | H | H | 0.0393 | 0.1023 | 0.0504 |
| 18aaj | H | CONHCH2(Ph: 2,4-di-F) | P(O)(Ph: 3,5-di-Me)OMe | H | Cl | H | H | 0.0316 | 0.1089 | 0.0416 |
| 7as | H | CONH2 | P(O)(Ph: 3-Me,5-C≡N)OMe | H | Cl | H | H | 0.0014 | 0.0048 | 0.0029 |
| 7x | H | CONH2 | P(O)(Ph: 3-nPr)OMe | H | Cl | H | H | 0.003 | 0.0138 | 0.0087 |
| 18aaj | H | CONHCH2(Ph: 2-Cl) | P(O)(Ph: 3,5-di-Me)OMe | H | Cl | H | H | 0.0155 | 0.0214 | 0.0258 |
| 18aak | H | CONHCH2(Ph: 2-CF3) | P(O)(Ph: 3,5-di-Me)OMe | H | Cl | H | H | >1.25 | >1.25 | 0.9067 |
| 18aaf | H | CONHCH2(4-pyridine) | P(O)(Ph: 3-Me,5-C≡N)OMe | H | Cl | H | H | 0.0018 | 0.0039 | 0.0011 |
| 18aag | H | CONHCH2(5-imidazole: 1-Me) | P(O)(Ph: 3-Me,5-C≡N)OMe | H | Cl | H | H | 0.0031 | 0.0188 | 0.0029 |
| | H | CONHCH2(Ph: 2,3,6-tri-F) | P(O)(Ph: 3,5-di-Me)OMe | H | Cl | H | H | 0.0179 | 0.0171 | 0.0228 |
| 22ak | H | CONHCH2(4-pyridine: 4-O) | P(O)(Ph: 3-Me,5-C≡N)OMe | H | Cl | H | H | 0.007 | 0.0067 | 0.011 |
| 18aal | H | CONHCH2(2-pyridine) | P(O)(Ph: 3,5-di-Me)OMe | H | Cl | H | H | 0.0301 | 0.0197 | 0.0218 |
| 18aam | H | CONHCH2(3-pyridine) | P(O)(Ph: 3,5-di-Me)OMe | F | Cl | H | H | 0.0173 | 0.0068 | 0.0225 |
| 22j | H | CONHCH2(3-pyridine: 3-O) | P(O)(Ph: 3,5-di-Me)OMe | F | Cl | H | H | 0.0068 | 0.0099 | 0.006 |
| 22p | H | CONHCH2(2-pyridine: 2-O) | P(O)(Ph: 3,5-di-Me)OMe | H | Cl | H | H | 0.0019 | 0.0513 | 0.0179 |
| 7at | H | CONH2 | P(O)(Ph: 3-F,5-C≡N)OMe | H | Cl | H | H | 0.0057 | 0.0221 | 0.0103 |
| 18l | H | CONHCH2(4-pyrimidine) | P(O)(Ph: 3,5-di-Me)OMe | H | Cl | H | H | 0.0017 | 0.0025 | 0.0022 |

TABLE 4-continued

CELL-BASED ASSAY DATA USING BH-10 CELLS

| Compound No. | Indole Substituent Position | | | | | | | $EC_{50}$ WT///B (μM) | $EC_{50}$ Y181C (μM) | $EC_{50}$ K103N/Y181C (μM) |
|---|---|---|---|---|---|---|---|---|---|---|
| | 1 | 2 | 3 | 4 | 5 | 6 | 7 | | | |
| 7w | H | CONH2 | P(O)(Ph: 3-Me,5-Et)OMe | H | Cl | H | H | 0.0004 | 0.0055 | 0.0012 |
| 22i | H | CONHCH2(4-pyrimidine: 1-O) | P(O)(Ph: 3,5-di-Me)OMe | H | Cl | H | H | 0.0014 | 0.0062 | 0.0079 |
| 22h | H | CONHCH2(3-pyridine: 3-O) | P(O)(Ph: 3-Me,5-Et)OMe | H | Cl | H | H | 0.0016 | 0.0058 | 0.0036 |
| 18h | H | CONHCH2(4-pyridine: 3-F) | P(O)(Ph: 3,5-di-Me)OMe | H | Cl | H | H | 0.0017 | 0.0143 | 0.0043 |
| 22d | H | CONHCH2(4-pyridine: 3-F,4-O) | P(O)(Ph: 3,5-di-Me)OMe | H | Cl | H | H | 0.0029 | 0.0015 | 0.0067 |
| 18i | H | CONHCH2(2-pyrazine) | P(O)(Ph: 3,5-di-Me)OMe | H | Cl | H | H | 0.003 | 0.0168 | 0.0018 |
| 18j | H | CONHCH2(5-pyrimidine) | P(O)(Ph: 3,5-di-Me)OMe | H | Cl | H | H | 0.0036 | 0.0051 | 0.0019 |
| 22g | H | CONHCH2(5-pyrimidine: 1-O) | P(O)(Ph: 3,5-di-Me)OMe | H | Cl | H | H | 0.0021 | 0.0107 | 0.003 |
| 33a | H | CONH2 | P(O)(Ph: 3-CH=CHC=N)OMe | H | Cl | H | H | 0.0032 | 0.002 | 0.0034 |
| 7j | H | CONH2 | P(O)(Ph: 3-F,5-Br)OMe | H | Cl | H | H | 0.0018 | 0.003 | 0.0041 |

Ph is phenyl; Me is methyl; and Et is ethyl. Relative solubilities (at OD 600 nm) for the compounds ranged from about 75 μM/mL for Compound No. 5 to >1000 μM/ml for Compound Nos. 7-11. A cytochrome-P450 binding assay completed for Compound No. 3 indicated binding of 15.87 μM, and MDRC4 and CNDO cell-based assays for this same compound versus other mutant forms such as, for example, K103N/M184V/NAMS and K103N/Y181C/M184V/NAMS, gave $EC_{50}$ values of from 0.0013-0.4466 μM.

Toxicology 1. pH Dependent Aqueous Solubility

The aqueous solubility of each compound was determined by the conventional shake-flask method at a saturated concentration of 1 mM. The flask (vial) was shaken for 3 hrs at ambient temperature, and then centrifuged. The supernatant was analyzed by HPLC with UV detection for solubility determination. In general, a higher aqueous solubility is more desirable for drug candidates.

2. Human Plasma Protein Binding

The human plasma protein binding was determined using the Equilibrium Dialysis method. Dialysis was conducted with pooled human plasma at 37° C. for approximately 6 hours at a drug concentration of 1 μM. At the end of the dialysis, buffer samples from the buffer-side of the dialysis cell were collected and analyzed by LC/MS/MS for free drug concentration. For NNRTIs, a lower protein binding is more desirable.

3. Bi-directional CACO-2 Permeability

The objective of this assay is to determine the bi-directional permeability classification and efflux-limited absorption potential of a test compound in a Caco-2 cell monolayer system. Typically, the assay involves the measurement of non-specific binding to the Transwell apparatus in a pH7.4 assay buffer, the bi-directional permeability assessment of a test compound across Caco-2 cell monolayers, apical-to-basolateral transport assessment, basolateral-to-apical transport assessment, and monolayer integrity. High permeability and no efflux suggest that intestinal permeability is not expected to be a limiting factor for oral absorption in humans.

4. CYP450 Inhibition

In vitro CYP450 inhibition screening allows for the prediction of potential drug-drug interactions. To determine whether a test compound inhibits a particular P450 enzyme activity, changes in the metabolism of a P450-specific substrate by human liver microsomes are monitored with varying concentrations of the test compound. Potency and rank order of the inhibition can be assessed by determination of the IC50 values for a particular isozyme. For NNRTIs, higher IC50 values would suggest less inhibition, and thus less potential for drug-drug interaction in patients.

CYP3A4 inhibition was screened using the CYP3A4/BFC high throughput inhibitor screening kit (BD Biosciences), CYP2D6 inhibition was screened using the CYP2D6/AMMC high throughput inhibitor screening kit (BD Biosciences), and CYP2C9 inhibition was screened using the P450-Glo™ Assay kit (Promega).

5. In Vitro Metabolic Stability in Liver Microsomes

The metabolic stability assay is to evaluate the stability of test compound in biological matrices. Data are useful in terms of understanding and predicting the elimination mechanisms of the test compound. CYP450-dependent metabolism of drugs can also vary widely from one species to another. Evaluating in vitro metabolism of a drug by liver microsomes from multiple species allows the comparison of metabolism in animal species to that of humans. This can help identify the most relevant animal model for PK and toxicology studies. The metabolic stability of a test compound was evaluated in vitro in liver microsomes of the rat, dog, monkey, and human. 10 μM of the test compound was pre-incubated for 5 min at 37° C. with 1 mg/mL liver microsomes in 0.1M Tris buffer, pH 7.4 containing 5 mM $MgCl_2$ and 0.1 mM EDTA. Following pre-incubation, NADPH (final concentration of 3 mM) was added to start the reaction and samples incubated for 0 and 1 or 2 hours. After terminating the reaction, the supernatant was analyzed by HPLC-UV or LC/MS/MS for the disappearance of the parent and formation of metabolite(s). The % parent remaining was the peak area ratio of the 1 or 2 hr sample to the time 0 sample. In general, less metabolism (higher % parent values) is more desirable.

6. In Vitro Metabolism in Liver Microsomes—Metabolic Pathway

Phase I biotransformation of a test compound is evaluated in this assay. Samples from the metabolic stability experiment were analyzed by LC/MS/MS for metabolite profiling and identification. Structures of metabolites were elucidated based on multiple MS/MS experiments such as full scan, neutral loss scan, and product ion scan. Metabolic pathways were then postulated based on the structures of major metabolites. For compounds from the phosphinate series, N-oxidation of the terminal pyridine ring is the predominant pathway, followed by the oxidation of the dimethyl-phenyl group, where the methyl group(s) is hydroxylated, further oxidized to an aldehyde, and finally to a carboxylic acid. The elucidation of metabolic pathways is important in terms of understanding the elimination mechanism of a test compound and assisting the design of new molecules with improved DM-PK profiles.

7. PK and oral bioavailability in the rat and dog.

| Cat. | Cmpd | Aqueous solubility (uM) | | | | Protein binding (human plasma) | CYP450 inhibition, human (IC50, uM) | | | CYP3A4 induction, human hepatocytes |
|---|---|---|---|---|---|---|---|---|---|---|
| | | pH 1 | pH 3 | pH 7 | pH 9 | % Free | CYP3A4 | CYP2D6 | CYP2C9 | (mRNA) |
| Parent | N | >1000 | 231 | 2.1 | 1.7 | 0.2% | 0.66 | 2.04 | | weak to moderate |
| N-Oxide | D | 52 | 74.2 | 50.6 | 66.8 | 1.6% | 1.07 | >10 | >10 | |
| Parent | O | 820 | 590 | 9.1 | 10.1 | 0.9% | 0.81 | 1.35 | 5.35 | |
| N-Oxide | B | 190 | 170 | 200 | 190 | 3.8% | 1.04 | >10 | >10 | |
| Parent | P | >1000 | 724.3 | 24 | 33.8 | <0.5% | 0.77 | 2.01 | 1.68 | |
| N-Oxide | G | | | | | 1.6% | 1.14 | >10 | 8.85 | |

| Cat. | Cmpd | Metabolic stability in liver microsomes % Parent after 2 hrs | | | | Metabolic pathway (in vitro) |
|---|---|---|---|---|---|---|
| | | Human | Rat | Dog | Monkey | |
| Parent | N | 22%* | 1%* | 24%* | 1%* | N-oxidation, hydroxylation to CH3OH— to CHO— to COOH— |
| N-Oxide | D | 76% | 1% | 82% | 24% | Hydroxylation to CH3OH— to CHO— to COOH— |
| Parent | O | 15% | 2% | 29% | 1% | N-oxidation, hydroxylation to CH3OH— to CHO— to COOH— |
| N-Oxide | B | 94% | 1% | 85% | 63% | Hydroxylation to CH3OH— to CHO— to COOH— |
| Parent | P | 3% | 0% | 20% | 3% | N-oxidation, hydroxylation to CH3OH— to CHO— to COOH— |
| N-Oxide | G | 85% | 24% | 77% | 41% | Hydroxylation to CH3OH— to CHO— to COOH— |

*% Parent after 1 hr incubation

The pharmacokinetics of a test compound was evaluated in Sprague-Dawley rats and Beagle dogs. A typical PK study involved dosing of 2 to 3 animals via a single IV bolus injection at 1 mg/kg and another 3 animals via a single oral gavage at 5 mg/kg. Blood samples were collected at various time points over a 24-hr period. Plasma was separated and analyzed for test compound and its metabolite(s) by LC/MS/MS. PK parameters were calculated from the plasma concentration - time profile using a noncompartmental method. Oral bioavailability (F) was calculated based on dose-normalized AUC values from oral and IV administration. Higher oral bioavailability values are better.

| Cmpd | Cat. | Species | Route | Dose (mg/kg) | Vehicle | (MEAN PK PARAMETERS (N = 3 OR 2)) | | | | | | | | |
|---|---|---|---|---|---|---|---|---|---|---|---|---|---|---|
| | | | | | | Cmax (ng/mL) | Tmax (hr) | T½ (hr) | AUClast (hr*ng/mL) | AUCinf (hr*ng/mL) | AUCinf/Dose | Cl (mL/kg/hr) | Vss (mL/kg) | F (%) |
| D | N-Oxide | Rat | IV | 1.0 | PEG400 | 165.7 | | 0.9 | 174.3 | 188.3 | 188.3 | 5417.8 | 6368.6 | |
| D | N-Oxide | Rat | PO | 5.0 | PEG400 | 45.0 | 0.5 | 2.2 | 132.0 | 150.9 | 30.2 | | | 16.0% |
| N | Parent | Rat | IV | 1.0 | PEG400 | 118.8 | | 0.9 | 108.3 | 125.9 | 125.9 | 7992.2 | 9587.9 | |
| N | Parent | Rat | PO | 5.0 | PEG400 | NC | NC | NC | NC | NC | NC | NC | NC | NC |
| N | Parent | Dog | IV | 1.0 | PEG400 | 407.0 | | 4.2 | 923.5 | 970.1 | 970.1 | 1192.3 | 4079.3 | |
| N | Parent | Dog | PO | 5.0 | PEG400 | 60.9 | 0.7 | 2.8 | 116.4 | 138.6 | 27.7 | | | 2.9% |
| D | N-Oxide | Dog | IV | 1.0 | PEG400 | 429.7 | | 3.2 | 1007.0 | 1220.5 | 1220.5 | 821.8 | 3715.7 | |
| D | N-Oxide | Dog | PO | 5.0 | 0.5% MC | 116.2 | 2.7 | 2.6 | 696.1 | 746.7 | 149.3 | | | 12.4% |

We claim:

1. A compound of Formula (B):

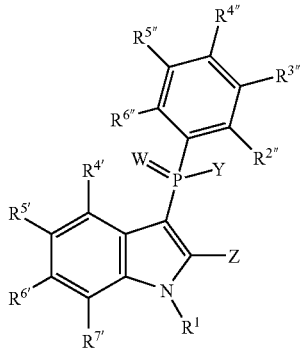

or a pharmaceutically acceptable salt, prodrug, N-oxide, quaternary amine, stereochemical isomer or tautomer thereof, wherein:

Y is O-alkyl;

W is O;

$R^1$ is selected from the group consisting of H, $R^2$, C(=O)$R^2$, C(=O)—O—$R^2$, C(=O)—S—$R^2$, C(=O)—NH—$R^2$, C(=O)—$NR^2R^2$, C(=O)—NH-A-(amino acid residue), A-(amino acid residue)-$R^2$, $S(O)_n$—$R^3$, $S(O)_2$—$NR^2R^2$, any of which may optionally be substituted by one or more $C_{1-6}$ alkyl, OH, alkoxy, aryl, halo, CN, $NO_2$, or $NR^2R^2$;

each $R^2$ is independently H; OH; halogen; optionally substituted, branched or unbranched alkyl; optionally substituted, branched or unbranched alkenyl; optionally substituted, branched or unbranched alkynyl; 3-14 membered carbocycle; alkylheterocycle; acyl; carboxamido; carbamoyl; alkoxy; optionally substituted aryl; optionally substituted aralkyl; optionally substituted alkylaryl; O-alkyl; O-alkenyl; O-alkynyl; O-alkaryl; O-aralkyl; O-carbocycle; O-heterocycle; O-aryl; $CF_3$; CN; $S(O)_n$—$R^3$; $N(R^3)(R^3)$; NH—$S(O)_n$—$R^3$; NHC(=W)-aryl; NHC(=W)-alkyl; NHC(=W)-heterocycle; $CH_2$—$S(O)_n$—$R^3$; C(=W)$R^3$; C(=W)$NR^3R^3$; $C(alkyl)_2$-$S(O)_nR^3$; CH(alkyl)-$S(O)_nR^3$; $C(alkyl)_2$-$NH_2$; CH(alkyl)-N(alkyl)$R^3$; $CR^3R^2$—$NR^3R^3$; $CH_2N(alkyl)R^3$; CH(alkyl)-$NHR^3$; $C(alkyl)_2$-$NHR^3$; $C(alkyl)_2$-N(alkyl)$R^3$; $CH_2$—C(=W)H; $CH_2$—C(=W)alkyl; $CR^3R^3$—C(=W)$R^3$; A-$R^3$; $C(R^3)_2$—C(=W)$R^3$; $CH_2$—C(=W)H; $CH_2$—C(=W)alkenyl; CH(alkenyl)-C(=W)H; A-$S(O)R^3$; CH(NH)—$S(O)_nR^3$; or A-N(NH)$R^3$; wherein said optional substitution comprises one or more of: a substituted or unsubstituted heterocycle; C(=W)O-aryl; C(=W)O-alkyl; C(=W)$NH_2$; C(=W)NH-alkyl; C(=W)NH-aryl; C(=W)N-di-alkyl; C(=W)N(alkyl)-aryl; α-amino acid; α-amino ester; α-amino-carboxamide; β-amino acid; β-amino ester; or β-amino-carboxamide;

each $R^3$ is independently H; OH; $C_{1-6}$ alkyl; $C_{2-6}$ alkenyl; $C_{2-6}$ alkynyl; alkoxy; $CF_3$; CN; amino; $NR^2R^2$; O-alkyl; O-alkenyl; O-alkynyl; $C(R^2)(R^2)$—$S(O)_nNH_2$; $C(R^2)(R^2)$—$S(O)_nCF_3$; $C(R^2)(R^2)$—$NH_2$; A-heterocycle; $C(R^2)(R^2)$—$NR^2R^2$; $C(R^2)(R^2)$—C(=W)$R^2$; aryl; carbocycle; heterocycle; cycloalkyl; alkaryl; alkylheterocycle; aralkyl; or heterocycle-alkyl; any of which may be unsubstituted or substituted with one or more of the following taken in any combination: halo; OH; $OR^2$; $SR^2$; COOH; carboxylic acid ester; C(=W)$R^2$; C(=W)OR^2$; C(=W)$OR^3$; C(=W)$SR^2$; A-C(=W)$NH_2$; C(=W)$NR^2R^3$; $NR^2R^2$; $NR^2R^3$; $NR^2$—$S(O)_nR^3$; $NR^2$—C(=W)—$C_{1-6}$alkyl; $S(O)_nR^3$; $C_{1-6}$alkoxy; $C_{1-6}$ thioether; amino acid residue; NH-A-(amino acid residue); C(=W)NH-A-(amino acid residue); and wherein when said optional substitution comprises a substituted heterocycle, then substitution is selected from the group consisting of: C(=W)O-aryl; C(=W)O-alkyl; C(=W)$NH_2$; C(=W)NH-aryl; C(=W)NH-alkyl; C(=W)N-di-alkyl; C(=W)N(alkyl)-aryl; α-amino acid; α-amino ester; α-amino-carboxamide; β-amino acid; β-amino ester; β-amino-carboxamide; halo; or cyano, taken alone or in any combination;

each n is independently 0, 1 or 2;

A is a disubstituted spacer selected from the group consisting of: $C_{1-6}$ alkylene, branched or unbranched, and optionally having one or more heteroatoms, aryl, cycloalkyl or heterocyclyl functions in or attached to the chain; $C_{2-12}$ alkenylene, branched or unbranced, and optionally having one or more heteroatoms, aryl, cycloalkyl or heterocyclyl functions in or attached to the chain; $C_{2-12}$ alkynylene, branched or unbranced, and optionally having one or more heteroatoms, aryl, cycloalkyl or heterocyclyl functions in or attached to the chain; optionally substituted arylene; O-alkylene, branched or unbranched, and optionally having one or more heteroatoms, aryl, cycloalkyl or heterocyclyl functions in or attached to the chain; aralkylene, branched or unbranched, and optionally having one or more heteroatoms, aryl, cycloalkyl or heterocyclyl functions in or attached to the chain; optionally substituted cycloalkyl; and optionally substituted heterocycle; wherein "A" may be joined by any desired linkage or any combination of desired linkages;

$R^{6'}$ and $R^{7'}$ are each independently H;

$R^{4'}$ and $R^{5'}$ are each independently Cl, F, Br, I, methyl, ethyl or $CF_3$;

Z is —C(=O)$NH_2$; and $R^{2''}$, $R^{3''}$, $R^{4''}$, $R^{5''}$, and $R^{6''}$ are each independently selected from the group consisting of hydrogen, halogen, $NO_2$, CN, $OR^2$, $SR^2$, $NH_2$, $NR^2R^3$, $N(R^2)$—C(=W)—$C_{1-4}$alkyl, $N(R^2)$—$SO_2$—$C_{1-4}$alkyl, $C_{1-6}$alkyl, $C_{2-6}$ alkenyl, $C_{2-6}$ alkynyl, aryl, $CF_3$, $CR^2R^2$—$S(O)_n$—$R^3$, $CR^2R^2NR^2R^3$, C—OH, $CR^2R^2$—C(=W)$R^2$, acyl, C(=W)$R^2$, C(=W)$OR^2$, C(=W)$SR^2$, C(=W)—$NR^2R^3$, C(=W)NH$(CH_2)_p$-(amino acid residue), amino residue, and A-(amino acid residue), any of which optionally may be substituted.

2. The compound of claim 1 wherein
each $R^{2''}$, $R^{4''}$, and $R^{6''}$ is independently hydrogen, and
each $R^{3''}$ and $R^{5''}$ is independently halogen; $NO_2$; CN; $OR^2$; NH—CO—$C_{1-4}$ alkyl; oxime; hydrazine; —N(OH)$C_{1-6}$ alkyl; $C_{1-6}$ alkoxy; OH; $NR^2R^3$; or $C_{1-6}$ alkyl, $C_{2-6}$ alkenyl, or $C_{2-6}$ alkynyl optionally substituted with one or more of —OH, —SR, —CN, —C(=W)H, —C(=W)OH, halogen, $NR^2R^3$, —$C_{1-6}$ thioether, or —$C_{1-6}$ alkoxy.

3. The compound of claim 1 that is:

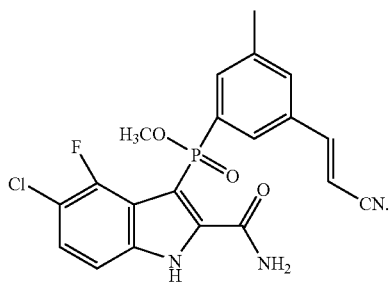

4. A pharmaceutical composition comprising an effective anti-HIV treatment amount of a compound of any of claims 1-3, or its pharmaceutically acceptable salt, prodrug, stereoisomer, tautomer, N-oxide or quaternary amine, optionally with a pharmaceutically acceptable carrier or diluent.

5. A pharmaceutical composition comprising an effective anti-HIV treatment amount of a compound of any of claims 1-3, or its pharmaceutically acceptable salt, prodrug, stereoisomer, tautomer, N-oxide or quaternary amine, in combination with at least one other anti-HIV agent, optionally with a pharmaceutically acceptable carrier or diluent.

6. The pharmaceutical composition of claim 5 wherein the other anti-HIV agent is a reverse transcriptase inhibitor.

7. The pharmaceutical composition of claim 6 wherein the reverse transcriptase inhibitor induces a mutation lysine 103→ asparagine and/or tyrosine 181→ cysteine in HIV reverse transcriptase.

8. A method for the treatment of an HIV-infection in a host comprising administering to said host an anti-HIV effective treatment amount of a compound of any of claims 1-3, or its pharmaceutically acceptable salt, prodrug, stereoisomer, tautomer, N-oxide or quaternary amine, optionally with a pharmaceutically acceptable carrier or diluent.

9. The method of claim 8 wherein the host is human.

10. A method for the treatment of an HIV-infection in a host comprising administering to said host an anti-HIV effective treatment amount of a compound of any of claims 1-3, or its pharmaceutically acceptable salt, prodrug, stereoisomer, tautomer, N-oxide or quaternary amine, in combination and/or alternation with at least one other anti-HIV agent, optionally with a pharmaceutically acceptable carrier or diluent.

11. The method of claim 10 wherein the host is human.

12. The method of claim 10 wherein the other anti-HIV agent is a reverse transcriptase inhibitor.

13. The method of claim 12 wherein the reverse transcriptase inhibitor induces a mutation lysine 103→ asparagine and/or tyrosine 181→ cysteine in HIV reverse transcriptase.

14. A method for the treatment of an HIV-infection in a host, wherein the HIV has a mutation at lysine 103→ asparagine and/or tyrosine 181→ cysteine in HIV reverse transcriptase, comprising administering to said host an effective anti-HIV treatment amount of a compound according to any of claims 1-3, or its pharmaceutically acceptable salt, prodrug, stereoisomer, tautomer, N-oxide or quaternary amine, optionally with a pharmaceutically acceptable carrier or diluent.

15. The method of claim 14 wherein the host is a human.

16. A method for the treatment of an HIV-infection in a host, wherein the HIV has a mutation at lysine 103→ asparagine and/or tyrosine 181→ cysteine in HIV reverse transcriptase, comprising administering to said host an effective anti-HIV treatment amount of a compound according to any of claims 1-3, or its pharmaceutically acceptable salt, prodrug, stereoisomer, tautomer, N-oxide or quaternary amine, in combination and/or alternation with at least one other anti-HIV agent, optionally with a pharmaceutically acceptable carrier or diluent.

17. The method of claim 16 wherein the host is a human.

18. A method for the treatment of an HIV-infection in a host wherein the HIV is resistant to one or more reverse transcriptase inhibitor(s), comprising administering to said host an anti-HIV effective treatment amount of a compound of any of claims 1-3, or its pharmaceutically acceptable salt, prodrug, stereoisomer, tautomer, N-oxide or quaternary amine, optionally with a pharmaceutically acceptable carrier or diluent.

19. The method of claim 18 wherein the host is a human.

20. A method for the treatment of an HIV-infection in a host wherein the HIV is resistant to one or more reverse transcriptase inhibitor(s), comprising administering to said host an anti-HIV effective treatment amount of a compound of any of claims 1-3, or its pharmaceutically acceptable salt, prodrug, stereoisomer, tautomer, N-oxide or quaternary amine, in combination and/or alternation with at least one other anti-HIV agent, optionally with a pharmaceutically acceptable carrier or diluent.

21. The method of claim 20 wherein the host is a human.

22. A method for salvage therapy in the treatment of an anti-HIV infection in a host comprising administering to said host an anti-HIV effective treatment amount of a compound of any of claims 1-3, or its pharmaceutically acceptable salt, prodrug, stereoisomer, tautomer, N-oxide or quaternary amine, optionally with a pharmaceutically acceptable carrier or diluent.

23. The method of claim 22 wherein the host is a human.

24. A method for salvage therapy in the treatment of an anti-HIV infection in a host comprising administering to said host an anti-HIV effective treatment amount of a compound of any of claims 1-3, or its pharmaceutically acceptable salt, prodrug, stereoisomer, tautomer, N-oxide or quaternary amine, in combination and/or alternation with at least one other anti-HIV agent, optionally with a pharmaceutically acceptable carrier or diluent.

25. The method of claim 24 wherein the host is a human.

* * * * *